US012011326B2

(12) United States Patent
Gregg, II et al.

(10) Patent No.: US 12,011,326 B2
(45) Date of Patent: Jun. 18, 2024

(54) LASER APPARATUS AND METHOD OF USE FOR DENTAL SURGERY

(71) Applicant: MILLENNIUM HEALTHCARE TECHNOLOGIES, INC., Cerritos, CA (US)

(72) Inventors: Robert H. Gregg, II, Huntington Beach, CA (US); Dawn M. Gregg, Huntington Beach, CA (US)

(*) Notice: Subject to any disclaimer, the term of this patent is extended or adjusted under 35 U.S.C. 154(b) by 0 days.

(21) Appl. No.: 17/588,598

(22) Filed: Jan. 31, 2022

(65) Prior Publication Data

US 2022/0151731 A1    May 19, 2022

Related U.S. Application Data

(63) Continuation of application No. 15/011,441, filed on Jan. 29, 2016, now Pat. No. 11,273,006.

(51) Int. Cl.
*A61C 1/00* (2006.01)
*A61B 5/00* (2006.01)
(Continued)

(52) U.S. Cl.
CPC .......... *A61C 1/0046* (2013.01); *A61B 5/4547* (2013.01); *A61B 18/22* (2013.01); *A61B 34/25* (2016.02); *A61C 1/0015* (2013.01); *A61C 8/0006* (2013.01); *A61C 17/0202* (2013.01); *A61C 17/036* (2013.01);
(Continued)

(58) Field of Classification Search
CPC ... A61C 1/0046; A61C 1/0015; A61C 8/0006; A61C 17/0202; A61C 17/036; A61C 19/043; A61C 19/063; A61B 5/4547; A61B 18/22; A61B 2018/22853; A61B 2018/0023; A61B 2018/00565; A61B 2018/00577; A61B 2018/00589; A61B 2018/00595; A61B 2018/00601; A61B 2018/00625; A61B 2018/00642; A61B 2018/00708; A61B 2018/00779; A61B 2018/00815; A61B 2018/00863; A61B 2018/00988; A61B 2018/202; A61B 2017/004829; A61B 2218/002; A61M 19/00; A61N 5/062; A61N 5/0624; A61N 2005/0606; A61N 2005/063;
(Continued)

(56) References Cited

U.S. PATENT DOCUMENTS 4,169,984 A   10/1979 Parisi
4,398,129 A   8/1983 Logan
(Continued)

FOREIGN PATENT DOCUMENTS

DE   2020100001369   5/2010

OTHER PUBLICATIONS

Gkogkos AS, Karoussis IK, Prevezanos ID, Marcopoulou KE, Kyriakidou K, Vrotsos IA, "Effect of Nd:YAG low level laser therapy on human gingival fibroblasts", Int. J. Dent. Oct. 4, 2015,2015:258941.

(Continued)

*Primary Examiner* — Cris L. Rodriguez
*Assistant Examiner* — Drew S Folgmann
(74) *Attorney, Agent, or Firm* — Cotman IP Law Group

(57) ABSTRACT

A laser and a minimally invasive dental surgical procedure using the laser to stimulate periodontal tissue formation.

8 Claims, 74 Drawing Sheets

(51) Int. Cl.

| | | |
|---|---|---|
| *A61B 17/00* | (2006.01) | |
| *A61B 18/00* | (2006.01) | |
| *A61B 18/20* | (2006.01) | |
| *A61B 18/22* | (2006.01) | |
| *A61B 34/00* | (2016.01) | |
| *A61C 8/02* | (2006.01) | |
| *A61C 17/00* | (2006.01) | |
| *A61C 17/02* | (2006.01) | |
| *A61C 19/04* | (2006.01) | |
| *A61C 19/06* | (2006.01) | |
| *A61M 19/00* | (2006.01) | |
| *A61N 5/06* | (2006.01) | |
| *A61N 5/067* | (2006.01) | |

(52) U.S. Cl.
CPC .......... *A61C 19/043* (2013.01); *A61C 19/063* (2013.01); *A61M 19/00* (2013.01); *A61N 5/062* (2013.01); *A61N 5/0624* (2013.01); *A61B 2017/00482* (2013.01); *A61B 2018/00023* (2013.01); *A61B 2018/00565* (2013.01); *A61B 2018/00577* (2013.01); *A61B 2018/00589* (2013.01); *A61B 2018/00595* (2013.01); *A61B 2018/00601* (2013.01); *A61B 2018/00625* (2013.01); *A61B 2018/00642* (2013.01); *A61B 2018/00708* (2013.01); *A61B 2018/00779* (2013.01); *A61B 2018/00815* (2013.01); *A61B 2018/00863* (2013.01); *A61B 2018/00988* (2013.01); *A61B 2018/202* (2013.01); *A61B 2018/22853* (2017.05); *A61B 2034/252* (2016.02); *A61B 2034/254* (2016.02); *A61B 2034/256* (2016.02); *A61B 2218/002* (2013.01); *A61M 2210/0631* (2013.01); *A61N 2005/0606* (2013.01); *A61N 2005/063* (2013.01); *A61N 2005/0651* (2013.01); *A61N 2005/0662* (2013.01); *A61N 2005/0663* (2013.01); *A61N 5/067* (2021.08)

(58) Field of Classification Search
CPC .... A61N 2005/0651; A61N 2005/0663; A61N 2005/067
See application file for complete search history.

(56) References Cited

U.S. PATENT DOCUMENTS

| | | |
|---|---|---|
| 4,764,114 A | 8/1988 | Jeffcoat |
| 5,055,048 A | 10/1991 | Vassiliadis |
| 5,123,845 A | 1/1992 | Vassiliadis |
| 5,090,908 A | 2/1992 | Teumim-Stone |
| 5,194,005 A | 3/1993 | Levy |
| 5,230,621 A | 7/1993 | Jacoby |
| 5,255,277 A | 10/1993 | Carvalho |
| 5,275,564 A | 1/1994 | Vassiliadis |
| 5,292,253 A | 3/1994 | Levy |
| 5,300,067 A | 4/1994 | Nakajima |
| 5,328,365 A | 7/1994 | Jacoby |
| 5,455,837 A | 10/1995 | Negus |
| 5,497,051 A | 3/1996 | Langhans |
| 5,570,182 A | 10/1996 | Nathel |
| 5,585,698 A | 12/1996 | Langhans |
| 5,642,997 A | 7/1997 | Gregg |
| 5,895,984 A | 4/1999 | Renz |
| 5,897,509 A | 4/1999 | Toda |
| 6,019,605 A | 2/2000 | Myers |
| 6,039,565 A | 3/2000 | Chou |
| 7,090,497 B1 | 8/2006 | Harris |
| 7,310,466 B2 | 12/2007 | Fink |
| 8,240,312 B2 | 8/2012 | Feuerstein |
| 8,738,116 B2 | 5/2014 | Liu |
| 8,998,616 B2 | 4/2015 | Cao |
| 2003/0059379 A1 | 3/2003 | Andersen |
| 2003/0108078 A1 | 6/2003 | McCarthy |
| 2005/0226287 A1 | 10/2005 | Shah |
| 2008/0058908 A1 | 3/2008 | Bornstein |
| 2008/0276192 A1 | 11/2008 | Jones |
| 2009/0225060 A1 | 10/2009 | Rizoiu |
| 2010/0167226 A1 | 7/2010 | Altshuler |
| 2010/0216088 A1 | 8/2010 | Bierbaum |
| 2011/0207075 A1 | 8/2011 | Altshuler |
| 2014/0141389 A1 | 5/2014 | Kalmeta |
| 2014/0272771 A1 | 9/2014 | Boutoussov |
| 2014/0363784 A1 | 12/2014 | Monty |
| 2015/0268803 A1* | 9/2015 | Patton .................. G16H 20/40 715/771 |
| 2017/0027647 A1 | 2/2017 | DiVito |

OTHER PUBLICATIONS

Ronay V, Belibaskakis GN, Altin T, Schmidlin PR, Boastanci N, "Expression of embryonic stem cell markers and osteogenic differentiation potential in cells derived from periodontal granulation tissue", Cell. Biol. Int. Feb. 2014;28(2):179-186.

Kao RT, Nares S, Reynolds MA, "Periodontal regeneration—intrabony defects: A systematic review from the AAP Regeneration Workshop", J. Periodontol. Feb. 2015;86(2 Suppl):S77-S104.

Harris DM, Gregg RH 2nd, McCarthy DK, Colby LE, Tilt LV, "Laser-assisted new attachment procedure in private practice", Gen. Dent. Sep.-Oct. 2004;52(5):396-403.

Yukna RA, Carr RL, Evans GH, "Histologic evaluation of an Nd:YAG laser-assisted new attachment procedure in humans", Int. J. Periodontics Restorative Dent. Dec. 2007;27(6):577-587.

Tilt LV, "Effectiveness of LANAP over time as measured by tooth loss", Gen. Dent. Mar.-Apr. 2012,60(2);143-146.

Nevins ML, Camelo M, Schupbach P, Kim S-W, Kim DM, Nevins M., "Human clinical and histologic evidence of laser-assisted new attachment procedure", Int. J.Periodontics Restorative Dent. Oct. 2012;32(5):497-507.

Brown IS, "Current advances in the use of lasers in periodontal therapy: A laser-assisted new attachment procedure case series", Clin. Adv. Periodontics May 2013;3(2):96-104.

Nevins M, Kim S-W, Camelo M, Martin IS, Kim 0, Nevins M., "A prospective 9-month human clinical evaluation of Laser-Assisted New Attachment Procedure (LANAP) therapy", Int. J. Periodontics Restorative Dent. Jan.-Feb. 2014;34(1):21-27.

Tezel A, Kara C, Balkaya V, Orbak R., "An evaluation of different treatments for recurrent aphthous stomatitis and patient perceptions: Nd:YAG laser versus medication", Photomed. Laser Surg. Feb. 2009;27(1):101-106.

Arcoria CJ, Vttasek-Arcoria BA, "The effects of low-level energy density Nd:YAG irradiation on calculus removal", J. Clin. Laser Med. Surg. Oct. 1992;10(5):343-347.

Gomez C, Costela A, Garcia-Moreno I, Garcia JA, "In vitro evaluation of Nd:YAG laser radiation at three different wavelengths (1064, 532, and 355 nm) on calculus removal in comparison with ultrasonic scaling", Photomed. Laser Surg. Jun. 2006;24(3):366-376.

Krishna R, De Stefano JA, "Ultrasonic vs. hand instrumentation in periodontal therapy: Clinical outcomes", Periodontal. Jun. 2000 2016;71(1):113-127.

Crea A, Deli G, Uttarru C, Lajolo C, Orgeas GV, Tatakin DN, "Infrabony defects, open-flap debridement, and decortication: A randomized clinical trial", J. Periodontol. Jan. 2014;85(1):34-42.

Soh LL, Newman HN, Strahan JD, "Effects of subgingival chlorhexidine irrigation of peridontal inflammation", J. Clin. Periodontol. Jan. 1982;9(1):66-74.

Chebath-Taub D, Steinberg D, Featherstone JDB, Feuerstein O,. "Influence of blue light on *Steptococcus mutans* reorganization in biofilm", J. Photochem. Photobiol. B Nov. 2012; 116:75-78.

Henry CA, Dyer B, Wagner M, Judy M, Matthews JL., "Phototoxicity of argon laser eradication on biofilms of Porphyromonas and *Prevotella* species", J. Photochem. Photobiol. B Jul. 1996; 34(2-3):123-128.

(56) References Cited

OTHER PUBLICATIONS

Powell GL, Whisenant BK., "Comparison of three lasers for dental instrument sterilization", Lasers Surg. Med 1991;11(1):69-71.
Xiang X, Sowa MG, Iacopino AM, Maev RG, Hewko MD, Man A, Liu K-Z, "An update on novel non-invasive approaches for periodontal diagnosis", J. Periodontal. Feb. 2010;81(2):186-198.
Nicholson K et al., "Pulsed Nd:YAG laser treatment for failing dental implants due to peri-implantitis", In: Rechmann P, Fried D, eds. Lasers in Dentistry XX, Feb. 2, 2014, San Francisco, CA Proc. SPIE 8929. Bellingham, WA:SPIE—The International Society of Optical Engineering, 2014:89290H-1-89290H-14.
Giannini R, Vassalli M, Chellini F, Polidori L, Dei R, Giannelli M., "Neodymium:yttrium aluminum garnet laser irradiation with low pulse energy: A potential tool for the treatment of peri-implant disease", Clin. Oral implants Res. Dec. 2006;17(6):638-643.
Goncalves F, Zanetti AL, Zanetti RV, Martelli FS, Avila-Campos MJ, Tomazinho LF, Granjeirp JM, "Effectiveness of 980-nm diode and 1064-nm extra-long pulse neodymium-doped yitrium aluminum garnet lasers in implant disinfection", Photomed. Laser Surg. Apr. 2010;28(2):273-280.
Giannelli F, Bani D, Tani A, Pini A, Margheri M, Zecchi-Orlandini S, Tonelli P, Formigli L., "In vitro evaluation of the effects of low-intensity Nd:YAG laser irradiation on the inflammatory reaction elicited by bacterial lipopolysaccharide adherent to titanium dental implants", J. Periodontol. Jun. 2009:80(6):977-984.
Vassalli M, Giannelli M., "Effect of Nd:YAG laser on titanium dental implants studied by AFM", Ital. J. Anat. Embryol. Oct.-Dec. 2003;108(4):195-203.
Kawashima H, Sato S, Kishida M, Yagi H, Matsumoto K, Ito K, "Treatment of titanium :dental implants with three piezoelectric ultrasonic scalers: An in vivo study", J. Periodontal. Sep. 2007;78(9):1689-1694.
Seol K-Y, Kim S-G, Kim H-K, Moon S-Y, Kim B-O, Ahn J-M, Jang H-S, Kim H-J, Min J-B, Lee B-J, Lim S-C., "Effects of decortication in the treatment of bone defect around particulate dentin-coated implants: An experimental pilot study", Oral Surg. Oral Med. Oral Pathol. Oral Radiol. Endod. Oct. 2009;108(4):529-536.
Mombelli A, Lang NP, "Antimicrobial treatment of peri-implant infections", Clin. Oral Implants Res. Dec. 1992;3(4):162-168.
Felo A, Shibly O, Ciancio SG, Lauciello FR, Ho A, "Effects of subgingival irrigation on peri-implant maintenance", Am. J. Dent. Apr. 1997;10(2):107-110.
Merin RL., "Repair of peri-implant bone loss after occlusal adjustment: A case report", J. Am. Dent. Assoc. Oct. 2014;145(10):1058-1062.
Abraham CM, "A brief historical perspective on dental implants, their surface coatings and treatments", Open Dent. J. May 16, 2014;8(Suppl 1-M2):50-55.
Aziz-Gandour IA, Newman HN, "The effects of a simplified oral hygiene regime plus supragingival Irrigation with chlorhexidine or metronidazole on chronic inflammatory periodontal disease", J. Clin. Periodontal. Mar. 1986;13(3):228-236.
Nunn ME, Harrel SK, "The effect of occlusal discrepancies on periodontitis. I Relationship of initial occlusal discrepancies to initial clinical parameters", J. Periodontol. Apr. 2001;72(4):485-494.
Harrel SK, Nunn ME, "The effect of occlusal discrepancies on periodontitis. II Relationship of occlusal treatment to the progression of periodontal disease", J. Periodontol. Apr. 2001;72(4):495-505.
Gutknecht N, Moritz A. Dercks HW. Lampert F., "Treatment of hypersensitive teeth using neodymium:ytbium-aluminum-gamet lasers: A comparison of the use of various settings in an in vivo study", J. Clin. Laser Med. Surg. 1997;15(4):171-174.
Dilsiz A, Aydin T, Canakci V, Gungormus M., "Clinical evaluation of Er:YAG, Nd:YAG, and diode laser therapy for desensitization of teeth with gingival recession", Photomed Laser Surg. Oct. 2010;28 Suppl 2:S11-S17.
Usumez A, Cengiz B, Oztuzcu S, Demir T, Aras MH, Gutknecht N., "Effects of laser irradiation at different wavelengths (660, 810,980, and 1,064 nm) on mucositis in an animal model of wound healing", Lasers Med. Sci. Nov. 2014;29(6):1807-1813.
Ankri R, Lubart R, Taitelbaum H., "Estimation of the optimal wavelengths for laser-induced wound healing", Lasers Surg. Meet Oct. 2010;42(8):760-764.
Feuerstein O,Persman N, Weiss EL, "Phototoxic effect of visible light on Porphyromonas gingivalis and fusobacterium nucleatum: An in vitro study", Photochem. Photobiol. Nov.-Dec. 2004;80(3):412-415.
Song H-H, Lee J-K, Urn H-S, Chang B-S, Lee S-Y, Lee M-K., "Phototoxic effect of blue light on the planktonic and biofilm state of anaerobic periodontal pathogens", J. Periodontal Implant Sci. Apr. 2013;43(2):72-78.
Enwemeka CS, Williams D, Hollosi S, Yens D, Enwemeka SK., "Visible 405 nm SLD light photo-destroys methicillin-resistant *Staphylococcus aureus* (MRSA) in vitro", Lasers Surg. Med. Dec. 2008;40(10):734-737.
Maclean M, Murdoch LE, MacGregor SJ, Anderson JG.,"Sporicidal effects of high-intensity 405 nm visible light on endospore-forming bacteria", Photochem. Photobiol. Jan.-Feb. 2013;89(1):120-126.
Tomb RM, Maclean M, Herron PR, Hoskisson PA, MacGregor SJ, Anderson JG., "Inactivation of Streptomyces phage pC31by 405 nm light", Bacteriophage.Jul. 2014;4:e32129-1-e32129-6.
Moorhead S, Maclean M, MacGregor SJ, Anderson JG., "Comparative sensitivity of Trichophyton and Aspergillus conidia to inactivation by violet-blue light exposure", Photomed. Laser Surg. Jan. 2016;34(1):36-41.
Masson-Meyers OS, Bumah W, Biener G, Raicu V, Enwemeka CS.,"The relative antimicrobial effect of blue 405 nm LED and blue 405 nm laser on methicillin-resistant *Staphylococcus aureus* in vitro", Lasers Med. Sci. Dec. 2015;309):2265-2271.
Kim S, Kim J, Lim W, Jeon S, Kim 0, Koh J-T. Kim C-S, Choi H, Kim 0., "In vitro bactericidal effects of 625, 525,and 425 nm wavelength (red, green, and blue) light-emitting diode irradiation", Photomed. Laser Surg. Nov. 2013;31(11):554-562.
Tsen S-WD, Wu TC, Kiang JG, Tsen K-T., "Prospects for a novel ultrashort pulsed laser technology for pathogen inactivation", J. Biomed. Sci. 2012;19:62.
De Sousa NTA, Santos MF, Gomes RC, Brandino HE, Martinez R, de Jesus Guirro RR., "Blue laser inhibits bacterial growth of *Staphylococcus aureus, Escherichia coli*, and Pseudomonas aeruginosa", Photomed. Laser Surg. May 2015;33(5):278-282.
Fontana CR, Song X, Polymeri A, Goodson JM, Wang X, Soukos NS., "The effect of blue light on periodontal biofilm growth in vitro", Lasers Med. Sci. Nov. 2015;30(8):2077-2086.
Mussi MA, Gaddy JA, Cabruja M, Arivett BA, Viale AM, Rasia R, Actis LA., "The opportunistic human pathogen Acinetobacter baumannii senses and responds to light", J. Bacteriol. Dec. 2010;192(24):6336-6345.
Bumah VV, Whelan HT, Masson-Meyers OS, Quirk B, Buchmann E, Enwemeka CS., "The bactericidal effect of 470 run light and hyperbaric oxygen on methicillin-resistant *Staphylococcus aureus* (MRSA)", Lasers Med. Sci. Apr. 2015;30(3):1153-1159.
Israel,M., et al., "Use of the Carbon Dioxide Laser in Retarding Epithelial Migration: A Pilot Histological Human Study Utilizing case Reports", Journal of Periodontology, Mar. 1995, vol. 66, No. 3, pp. 197-204, 00110.1902/Op.1995.66.3.197 (doi:10.1902/jop.1995.66.3.197).
Israel, M. "Use of the C02 laser in soft tissue and periodontal surgery", Practical Periodontics and Aesthetic Dentistry :PPAD [1994,6(6):57-64; quiz 64].
Golub,L. M. et al., Journal of Clinical Periodontology,Feb. 1995, 22(2):100-9 entitled; "Doxycycline inhibits neutrophil (PMN) type matrix mealloproteinases in human adult periodontitis gingiva".
Siedentop KH, et al,(1985),"Autologous fibrin tissue adhesive", Laryngoscope 95:1074-1076.
Siedentop KH, et al,(1986),"Extended experimental and preliminary surgical findings with autologous fibrin tissue adhesive made from patient's own blood", Laryngoscope 96:1062-1064.
Kimmel D., "LANAP-Laser-Assisted New Attachment Procedure", Can J Restorative Dent Prosthodont, Fall 2009, vol. 2, No. 4, pp. 28-30.

(56) References Cited

OTHER PUBLICATIONS

Gregg Robert H. II, Introduction to the LANAP protocol for the traetment of periodontitis, Laser 2012, vol. 3, pp. 8-9.
Gregg Robert H. II, et al., "Laser Periodontal Therapy for Bone Regeneration", Dentistry Today No. 5, May 2002, vol. 21, pp. 54-59.
Deas DE, et al., "Scaling and root planing vs. conservative surgery in the treatment of chronic periodontitis", Periodontology 2000, Jun. 2016, vol. 71, No. 1,pp. 128-139.
Braga CR, "Using a Variable Pulsed Nd:YAG Laser to Treat Periodontal Disease", Inside Dentistry, Jul. 2013, vol. 9, No. 7, pp. 96-97.
Mizutani K, et al., "Lasers in minimally invasive periodontal and peri-implant therapy", Periodontology 2000, Jun. 2016, vol. 71, No. 1, pp. 185-212.
Kimmel D, "Laser Assisted New Attachment Procedure", Laser Dentistry, CJRDP 2011, vol. 3, No. 3, pp. 6-8.
Chebath-Taub D, Steinberg D, Featherstone JDB, Feuerstein 0., "Influence of blue light on *Streptococcus mutans* reorganization in biofilm", J. Photochem. Photobiol. B Nov. 2012;116:75-78.
Henry CA. Dyer B, Wagner M, Judy M, Matthews JL, "Phototoxicity of argon laser irradiation on biofilms of *Porphyromonas* and *Prevotella* species", J. Photochem. Photobiol. B Jul. 1996;34(2-3):123-128.
Nicholson K, et al., "Pulsed Nd:YAG laser treatment for failing dental implants due to peri-implantitis", In: Rechmann P, Fried D., eds. Laser Dentistry XX, Feb. 2, 2014, San Fancisco, CA. Proc. SPIE 8929. Bellingham, WA:SPIE—The International Society for Optical Engineering, 2014:89290H-1-89290H-14.
Giannini R, Vassalli M, Chellini F, Polidori L, Dei R, Gianneli M., "Neodymium:yttriumn aluminum garnet laser irradiation with low pulse energy: A potential tool for the treatment of peri-implant disease", Clin. Oral Implants Res. Dec. 2006;17(6):638-643.
Goncalves F, Zanetti AL, Zanetti RV, Martelli FS, Avila-Campos MJ, Tomazinho LF, Granjeiro JM.,"Effectiveness of 980-nm diode and 1064-nm extra-long-pulse neodymium-doped yttrium aluminum garnet lasers in implant disinfection", Photomed. Laser Surg. Apr. 2010,28(2):273-280.
Giannelli M, et al., "In vitro evaluation of the effects of low-intensity Nd:YAG laser irradiation on the inflammatory reaction elicited by bacterial lipopolysaccaride adherent to titanium dental implants", J. Periodontal. Jun. 2009;80(6):977-984.
Vassalli M, Giannelli M., "Effect of Nd:YAG laser on titanium dental implants studied by AFM", Ital. J. Anal. Embryol. Oct.-Dec. 2003;108(4):195-203.
Seol K-Y, Kim S-G, Kim H-K, Moon S-Y, Kim B-0, Ahn J-M, Jang H-S, Kim H-J, Min J-B, Lee B-J, Lim S-C., "Effects of decortication in the treatment of bone defect around particulate dentin-coated implants: An experimental pilot study", Oral Surg. Oral Med. Oral Pathol. Oral Radiol. Endod. Oct. 2009;108(4):529-536.
Mombelli A, Lang NP, "Antimicrobial treatment of peri-implant infections", Clin. Oral Impaints Res. Dec. 1992;3(4):162-168.
Felo A, et al, "Effects of subgingival irrigation on peri-implant maintenance", Am. J. Dent. Apr. 1997;10(2):107-110.
American Academy of Periodontology. Glossary of periodontal terms. 4th edition. Chicago: The American Academy of Periodontology, 2001:27.
Ryu JJ, Shrotriya P., "Synergistic mechanisms of bio-tribocorrosion in medical implants" Chapter 2 in: Yan Y, ed. Bio-tribocorrosion in biomaterials and medical implants. Oxford: Woodhead Publishing, 2013:25-44.
Wilson TG Jr, et al., "Foreign bodies associated with peri-implantitis human biopsies", J. Periodontol. Jan. 2015;86(1):9-15.
Golub LM, et al., "Doxycycline inhibits neutrophil (PMN) type matrix mealloproteinasas in human adult periodontitis gingiva", Journal of Clinical Periodontology, Feb. 1995,22(2):100-109.
Schwarz F, et al., "Traetment of periodontitis and peri-implantitis with an Er.YAG laser. Experimnetal and clinical studies", Medical Laser Application 20 (2005), 47-59.

\* cited by examiner

PerioLase with eGUI Serial Communication Description
9600 Baud No Parity, 8 data Bits, 1 Stop Bit
RS485 to USB 2 via Galaxy Interface Box (GIB)
General Communications Protocol: Described Below Data Packages:
Command Tablet Processor to PerioLase Main Controller

601

| Packet Location | Name | Bytes | |
|---|---|---|---|
| 0 | Address | 1 | Always 0 for Master (0x00) |
| 1 | Packet Length to Follow | 1 | Always 11 (0x0B) |
| 2 | Pulse Width | 1 | Index into Pulse Width Selections 0-6 (0x00-0x06) |
| 3 | Millijoules | 1 | Index into Energy Selections 0-25 (0x00-0x19) |
| 4 | Frequency, Hz | 1 | Index into Pulse Rate Selections 0-10 (0x00-0x0A) |
| 5 | Mode: Standby/Ready/Service | 1 | Operating Mode 0-6,10,11,14,15 |
| 6 | Parameter 1 | 1 | See Descriptions |
| 7 | Parameter 2 | 1 | See Descriptions |
| 8 | Aiming Beam Intensity | 1 | Aiming Beam Intensity Setting 0-5 |
| 9 | Tube Start Current | 1 | Tube Starting Current 10-80, Default 15 |
| 10 | Calibration Factor Value | 1 | Calibration Factor 0-99 |
| 11, 12 | CRC, 16-bit | 2 | |

FIG. 6A

Response PerioLase Main Computer to Tablet Processor (Short, Returned when Status <> 14)

| Packet Location | Name | Bytes | |
|---|---|---|---|
| 0 | Address | 1 | Always 1 for Slave (0x01) |
| 1 | Packet Length to follow | 1 | Always 17 (0x11) for This Reply Structure |
| 2 | Pulse Width | 1 | Index into Pulse Width Selections 0-6 (0x00-0x06) |
| 3 | Millijoules | 1 | Index into Energy Selections 0-25 (0x00-0x19) |
| 4 | Frequency, Hz | 1 | Index into Pulse Rate Selections 0-10 (0x00-0x0A) |
| 5 | Status (Operating Mode) | 1 | Operating Mode 0-6,10,11,15 |
| 6 | Error Mode (code) | 1 | Error Code when in Error Mode (15) |
| 7, 8 | Molectron Reading | 2 | Molectron Reading in ADC Counts 0-10000, 0-10 Volts |
| 9,10 | Energy Meter Reading | 2 | Energy Monitor Per Pulse Average in mJ |
| 11,12 | Calibration Factor | 2 | Energy Meter Calibration Factor 0-99 |
| 13-16 | Total Energy Delivered | 4 | Total mJ Delivered at All Pulse Widths |
| 17,18 | CRC, 16-bit | 2 | |

FIG. 6B

Response PerioLase Main Computer to Tablet Processor (Long, Returned when Status = 14[Status Mode])

| Packet Location | Name | Bytes | |
|---|---|---|---|
| 0 | Address | 1 | Always 1 for Slave (0x01) |
| 1 | Packet Length to follow | 1 | Always 34 (0x22) for This Reply Structure |
| 2 | Status (Operating Mode) | 1 | Operating Mode Always 14 for This Reply Structure |
| 3 | Firmware Major | 1 | Firmware Version Major Number |
| 4 | Firmware Minor | 1 | Firmware Version Minor Number |
| 5 | Firmware Build | 1 | Firmware Version Build Number |
| 6-9 | Total Energy Delivered at 100 μsec PW | 2 | Total mJ delivered at 100 μsec Pulse Width |
| 10-13 | Total Energy Delivered at 150 μsec PW | 2 | Total mJ delivered at 150 μsec Pulse Width |
| 14-17 | Total Energy Delivered at 250 μsec PW | 2 | Total mJ delivered at 250 μsec Pulse Width |
| 18-21 | Total Energy Delivered at 350 μsec PW | 2 | Total mJ delivered at 350 μsec Pulse Width |
| 22-25 | Total Energy Delivered at 450 μsec PW | 2 | Total mJ delivered at 450 μsec Pulse Width |
| 26-29 | Total Energy Delivered at 550 μsec PW | 2 | Total mJ delivered at 550 μsec Pulse Width |
| 30-33 | Total Energy Delivered at 650 μsec PW | 2 | Total mJ delivered at 650 μsec Pulse Width |
| 34, 35 | CRC 16-bit | 2 | |

FIG. 6C

Pulse Width Selections 604

| Ind | Pulse Width |
|---|---|
| 0 | 100 µsec |
| 1 | 150 µsec |
| 2 | 250 µsec |
| 3 | 350 µsec |
| 4 | 450 µsec |
| 5 | 550 µsec |
| 6 | 650 µsec |

FIG. 6D

Mode Descriptions 605

| Mode | Description |
|---|---|
| 0 | Initializing |
| 1 | Standby |
| 2 | Ready |
| 3 | Laser On |
| 4 | HVPS On |
| 5 | Footswitch |
| 6 | Firing Laser |
| 10 | Service Mode 1 |
| 11 | Service Mode 2 |
| 14 | Status Mode |
| 15 | Error |

FIG. 6E

Energy Selections 606

| Index | Energy mJ |
|---|---|
| 0 | 20 mJ |
| 1 | 30 mJ |
| 2 | 40 mJ |
| 3 | 60 mJ |
| 4 | 80 mJ |
| 5 | 100 mJ |
| 6 | 110 mJ |
| 7 | 120 mJ |
| 8 | 130 mJ |
| 9 | 140 mJ |
| 10 | 150 mJ |
| 11 | 160 mJ |
| 12 | 170 mJ |
| 13 | 180 mJ |
| 14 | 190 mJ |
| 15 | 200 mJ |
| 16 | 210 mJ |
| 17 | 220 mJ |
| 18 | 230 mJ |
| 19 | 240 mJ |
| 20 | 250 mJ |
| 21 | 260 mJ |
| 22 | 270 mJ |
| 23 | 280 mJ |
| 24 | 290 mJ |
| 25 | 300 mJ |

FIG. 6F

Parameter 1 Values 607

| Value | Purpose |
|---|---|
| 237 (0xED) | (0xE Exit Service Mode 1 Flag, Only Valid if Mode = Standby (1) |
| 0-250 | Calibration Current in Service Mode 1 (10) |
| Bit 0 | HVPS State in Service Mode 2 (11), Set Bit to Turn HVPS on |

FIG. 6G

Parameter 2 Values 608

| Value | Purpose |
|---|---|
| 0x80 | Save Cal Factor on Service Mode 1 Exit, Only Valid with Service Mode 1 |
| | Flag (0xED) in cParam1 |

FIG. 6H

Error Code Contains Bit Flags When in Service Mode 2 (11) 609

| Value | Purpose | |
|---|---|---|
| Bit 0 | HVPS On | 1- High Voltage Power Supply On |
| Bit 1 | CC450 | 1 - Cap Charged to 450V |
| Bit 2 | SIMMER | 1 - Simmer Supply On |

FIG. 6I

Pulse Rate Selections 610

| Index | Pulse Rate |
|---|---|
| 0 | 10 Hz |
| 1 | 15 Hz |
| 2 | 20 Hz |
| 3 | 30 Hz |
| 4 | 40 Hz |
| 5 | 50 Hz |
| 6 | 60 Hz |
| 7 | 70 Hz |
| 8 | 80 Hz |
| 9 | 90 Hz |
| 10 | 100 Hz |

| Patients | | | | | | | Reporting | | | |
|---|---|---|---|---|---|---|---|---|---|---|
| Treatment Interval 2012-04-14 | | | | | | | | | | |
| Chronological ▽ Filter Patients | | | | | | | | | | |
| Patient Name(Last,First) | Date | Time | | | | | mJ | Hz | dia | Proc Name |
| Undefined | 2015-04-14 | 14:49 | | | | | 180 | 20 | 360 | Undefined |
| Undefined | 2015-04-14 | 14:49 | | | | | 180 | 20 | 360 | Undefined |
| Undefined | 2015-04-14 | 14:49 | Select Report Options | | | | 180 | 20 | 360 | Undefined |
| Undefined | 2015-04-14 | 14:49 | | | | | 180 | 20 | 360 | Undefined |
| Undefined | 2015-04-14 | 14:48 | Clinician Options — 5403 | | | | 180 | 20 | 360 | Undefined |
| Undefined | 2015-04-14 | 14:48 | ⦿ Self ○ All | | | | 180 | 20 | 360 | Undefined |
| Undefined | 2015-04-14 | 14:48 | Grouping Options — 5404 | | | | 180 | 20 | 360 | Undefined |
| Undefined | 2015-04-14 | 14:47 | ⦿ None ○ PtChron ○ Pt:Tx Site | | | | 180 | 40 | 360 | Undefined |
| Undefined | 2015-04-14 | 14:47 | Report Detail Options — 5405 | | | | 60 | 30 | 360 | Undefined |
| Undefined | 2015-04-14 | 12:01 | ⦿ Detail ○ Summary ○ Both | | | | 60 | 80 | 360 | Undefined |
| Undefined | 2015-04-14 | 10:36 | | | | | 60 | 60 | 360 | Undefined |
| Undefined | 2015-04-14 | 10:35 | | 5406 | | | 60 | 60 | 360 | Undefined |
| Undefined | 2015-04-14 | 10:35 | | OK | | | 180 | 20 | 360 | LPT Hemostasis |
| Atwood,Brian | 2015-04-14 | 10:34 | | | | | 180 | 20 | 360 | LPT Hemostasis |
| Atwood,Brian | 2015-04-14 | 10:08 | | | | | 180 | 20 | 360 | LPT Hemostasis |
| Atwood,Brian | 2015-04-14 | 10:08 | | | | | | | | |
| Atwood,Brian | 2015-04-14 | 10:08 | | | | | | | | |

PROCEDURES    HOME    PATIENTS    ADMIN

LASER APPARATUS AND METHOD OF USE FOR DENTAL SURGERY

PRIORITY CLAIM AND INCORPORATION BY REFERENCE

This application is a continuation of U.S. patent application Ser. No. 15/011,441 filed Jan. 29, 2016. This application incorporates by reference in its entirety and for all purposes the disclosure of U.S. patent application Ser. No. 15/011,441.

FIELD OF INVENTION

The present disclosure relates to laser-assisted periodontal procedures, and more particularly relates to laser-assisted dental procedures utilizing a dynamic user interface.

DISCUSSION OF THE RELATED ART

In the field of dentistry, it is common to use a laser to perform dental procedures such as ablation. By using a laser to perform such functions instead of, for example, mechanical tools, it is ordinarily possible to reduce the occurrence of complications and to improve therapeutic outcomes.

SUMMARY

Periodontal diseases are caused by certain types of bacteria in plaque and calculus (concrements). These bacteria create toxins which irritate the gums, cause deep pockets, and result in a breakdown of the periodontal tissues that support the teeth. Over time, these toxins can destroy gum tissues, and allowing the infection to progress, can result in bone loss.

Accordingly, there is a need for a minimally invasive surgical method for the removal of a deep pocket, elimination of disease, reattachment of the gingiva to the tooth surface and true regeneration of the attachment apparatus (new cementum, new periodontal ligament, and new alveolar bone) on a previously diseased root surface.

Therefore, according to one example embodiment described herein, periodontal disorders associated with teeth are treated. An average power for a laser is selected via a user interface on a display, along with a set of permissible laser parameters provided in response to the selected average power. A gingival trough or flap is created around the tooth with the laser. Infected tissue is selectively ablated or denatured via selective photo thermolysis, and a pocket is lased around the affected tooth. Steps are performed to create and maintain angiogenesis. Marginal tissues are compressed against the tooth and occlusal interferences are removed.

By virtue of this arrangement, it is ordinarily possible to treat gingivitis and periodontitis in both adult and young patients while reducing periodontal pocket defects, by establishing a new cementum-mediated periodontal ligament attachment to the root surface in the absence of long junctional epithelium.

According to an example embodiment described herein, a laser-assisted periodontal device includes a laser head and a controller, and the controller performs the steps of accepting a dosimetry amount via a user interface on a display device, and controlling the laser head to apply dosimetry in accordance with the dosimetry amount. The display device displays when a predetermined portion of dosimetry has been applied.

According to another example embodiment described herein, a method for laser treatment includes controlling a laser-assisted periodontal device including a laser head and a controller to perform steps including accepting a dosimetry amount via a user interface on a display device, and applying dosimetry in accordance with the dosimetry amount.

According to one aspect, a selection of an average power for a laser is received via a user interface on a display device, and a set of permissible laser parameters is provided to the display device and laser head in response to the selected average power. The laser head is controlled in accordance with the laser parameters to create a gingival trough or flap around a tooth, ablate or denature infected tissue via selective photo thermolysis, and lase a pocket around the affected tooth.

According to another example aspect, there is an acceptance from a set of permissible laser parameters via a user interface on a display device, and in a case that there is a selection to override an already-fixed parameter, the controller calculates changes to other parameters in the set to fit a new value of the overridden parameter.

According to still another example aspect, a selection is received from a set of permissible laser parameters via a user interface on a display device, and a user can fix one parameter and view permissible values of other parameters based on the fixed parameter.

According to yet another aspect, a change to a fiber diameter on the laser head is detected, and laser parameters are changed in accordance with the changed fiber diameter.

According to another example aspect, a method for control of a laser-assisted periodontal device includes selecting from a set of permissible laser procedures via a user interface on a display device. The set of permissible procedures corresponds to a level of training stored in the display device for a user, and the selected procedure is performed with the laser-assisted periodontal device.

According to yet another example aspect, data associated with the treatment is transmitted to a data appliance, and a treatment recommendation is received from the data appliance based on the transmitted data.

According to another example aspect, a running total of the energy applied by the laser head is transmitted to a display device.

According to still another example aspect, a selection of a tooth or group of teeth is received via a user interface on a display device, and data associated with operation of the laser head and the selected tooth or group of teeth is stored based on the selection on the user interface. In another aspect, the selection is of a tooth or a group of teeth via the user interface on the display device.

According to another example aspect, a selection of a time interval, a patient, or a treatment site is received via a user interface on a display device, and data associated with operation of the laser head is stored based on the selection on the user interface.

According to still another example aspect, the laser head includes a bendable fiber.

According to another example aspect, the laser-assisted periodontal device is a laser periodontal, periodontitis, gingivitis treatment device for both adult and young patients.

According to one example aspect, creating a gingival trough or flap around a tooth includes creating a circumferential and radial soft tissue, gingival, or mucosal trough or flap around a tooth.

According to still another example aspect, photothermally rupturing, disassociating, separating, ablating, denaturing and vaporizing the infected tissue includes ablating or denaturing inflamed, infected, erythematous, edematous, hyperplastic, bacteria-invaded, ulcerated, degenerated, bleeding, suppurative, or sloughing periodontal soft tissue, including sulcular epithelium, junctional epithelium, and keratinized tissue, via selective photo thermolysis.

According to another example aspect, the method includes using a blue light device with wavelength emission in the range of 400 to 520 nm, such as a diode laser, argon ion laser, light-emitting diode, super luminescent diode, or other light source to simultaneously, sequentially, or singularly irradiate the tissues for lethal effect on bacteria.

According to yet another example aspect, there is control to perform a step of circumferentially and radially irradiating surfaces of the tooth and root to denature or ablate bioactive bacterial products including lipopolysaccharide endotoxins.

According to another example aspect, the method includes diagnosing and assessing the effectiveness of treatment over time by such means as clinical examination, laboratory tests, noninvasive tools (including optical coherence tomography, infrared spectroscopy, acoustic microscopy), and other techniques.

This brief summary has been provided so that the nature of this disclosure may be understood quickly. A more complete understanding can be obtained by reference to the following detailed description and to the attached drawings.

BRIEF DESCRIPTION OF THE DRAWINGS

FIGS. 6A to 6J are views for explaining a communication protocol according to an example environment.

FIGS. 8 to 67 are views for explaining an electronic graphical user interface (eGUI) according to example embodiments.

DETAILED DESCRIPTION

I. LANAP (Laser-Assisted New Attachment Procedure)

Figure 1:
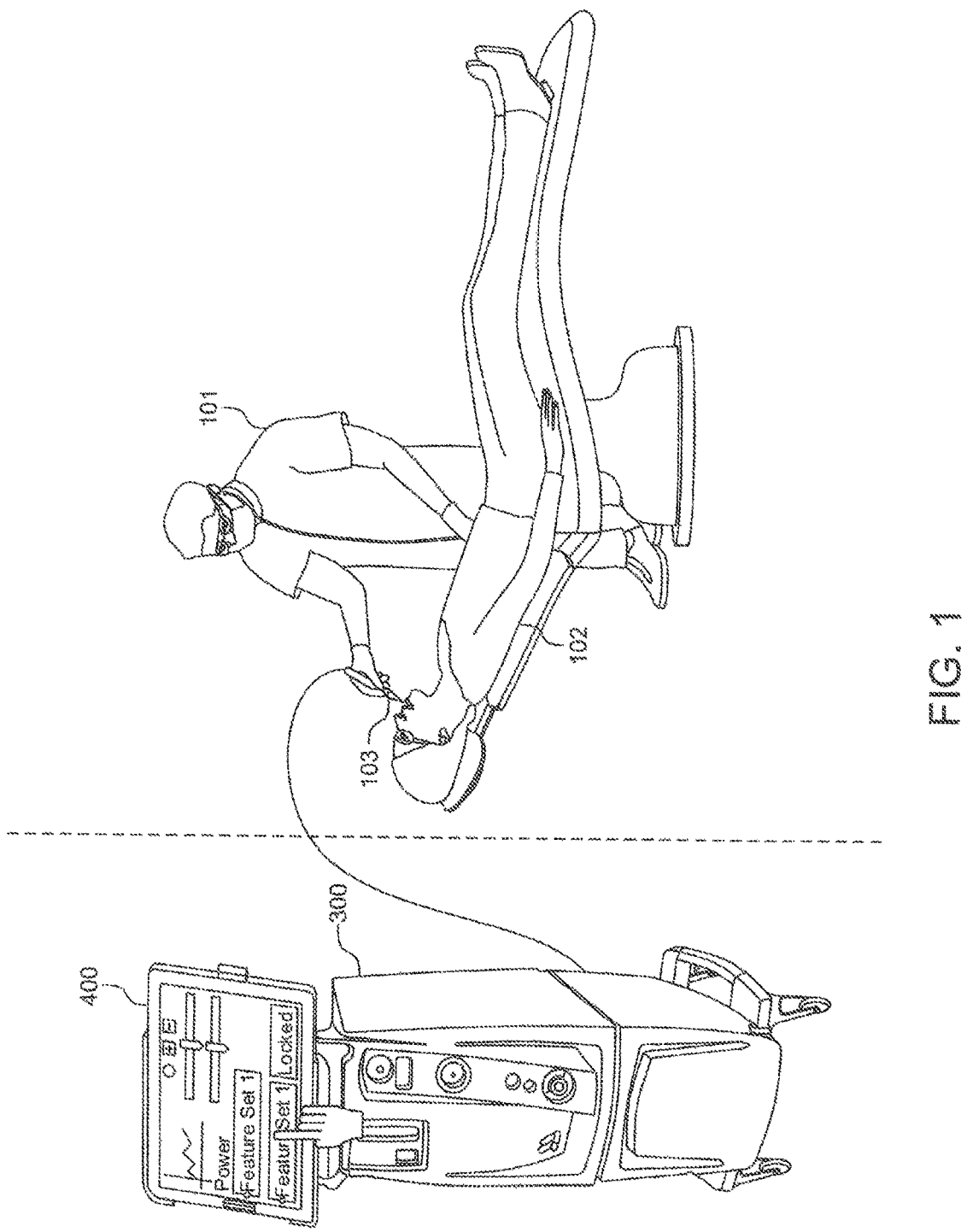
FIG. 1 is a representative view of an environment in which aspects of example embodiments may be practiced.

FIG. 1 is a representative view of an environment in which aspects of example embodiments may be practiced. In that regard, although this procedure is described with respect to a specific device (PerioLase® MVP-7™ including eGUI), it should be understood that the procedure is not limited to this device, and can be performed by other devices capable of periodontal laser dosimetry, even devices without the eGUI, such as an original MVP-7™ type laser without the eGUI.

In particular, FIG. 1 depicts an example environment in which a dentist 101 (or another clinician) inputs touch commands on a displayed eGUI of a display control subsystem 400, which in an example embodiment herein is a tablet 400. The commands are transmitted to a main laser computer 300 and/or a laser delivery system 103 in order to control laser delivery system 103. In the context of FIG. 1, tablet 400 is used to control laser delivery system 103, which is held by dentist 101, to perform laser therapy on a patient 102. In that regard, laser delivery system 103 is also referred to as "laser 103" below for conciseness, or as "handpiece 103" below for differentiation from other hardware associated with the laser. Feedback data and other responses may be transmitted from main laser computer 300 and/or laser 103 back to tablet 400, and displayed on the eGUI. These processes will be described more fully below.

In that regard, while a tablet is shown in FIG. 1, it should be understood that the display control subsystem may in other embodiments be implemented by numerous other types of devices to view the eGUI and communicate with main laser computer 300. More generally, a display control subsystem according to this disclosure, of which a tablet is merely an example, includes at least a display, an input for accepting user input, a processor or processing independent of that of main laser computer 300, a communication interface to laser computer 300, and storage capability. The display and the input are preferably combined into a touch-sensitive display.

For example, it should be understood that computing equipment or devices for implementing a display control subsystem and practicing aspects of the present disclosure can be implemented in a variety of embodiments, such as a laptop, mobile phone, ultra-mobile computer, portable media player, game console, personal device assistant (PDA), netbook, or set-top box, among many others. In still another example, the device for communicating with main laser computer 300 might be attached to or communicatively coupled physically in a common housing with main laser computer 300.

For conciseness in the description that follows, the display control subsystem will hereinafter be referred to as simply a "tablet".

Main laser computer 300 contains hardware and/or software for controlling laser 103 via a wired or wireless interface. For example, main laser computer 300 may be a free-standing computing device including a hard disk and one or more processors dedicated to control of laser 103.

Laser 103 is a handheld laser for performing laser therapy including laser dentistry (e.g., ablation of bacteria in gum tissue). For example, laser 103 might correspond to a "PerioLase® MVP7™", manufactured by Millennium Dental Technologies, Inc. In that regard, the PerioLase® MVP- 7™ is a 6-Watt FR (Free Running) Nd:YAG (Neodymium: Yttrium Aluminum Garnet) laser with features necessary to perform soft tissue procedures, and includes operator-selectable pulse durations from, e.g., 100 to 650 microseconds (μsec) to allow optimum ablation and hemostasis.

Hardware Elements

Figure 2:
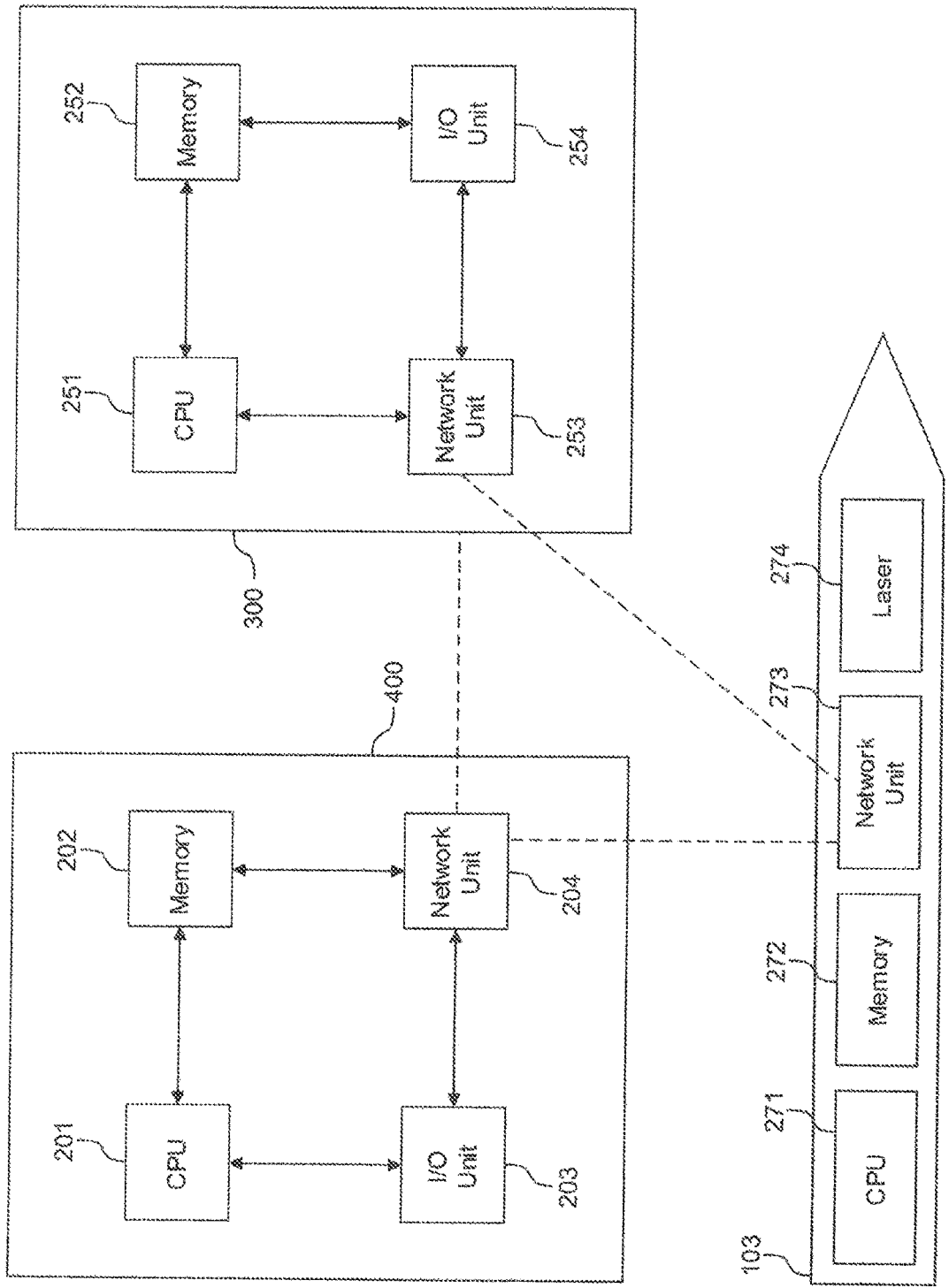
FIG. 2 is a simplified block diagram depicting the internal architecture of the hardware shown in FIG. 1.

FIG. 2 is a simplified block diagram depicting the internal architecture of the hardware shown in FIG. 1.

In particular, as shown in FIG. 2, tablet 400 includes central processing unit (CPU) 201, memory 202, I/O unit 203 and network unit 204.

Central Processing Unit (CPU) 201 is a computer processor such as a single core or multi-core central processing unit or micro-processing unit (MPU), which is constructed to realize the functionality described below. CPU 201 might comprise multiple computer processors which are constructed to work together to realize such functionality. CPU 201 executes a computer-executable program (sometimes referred to as computer-executable instructions or computer-executable code) to perform some or all of the above-described functions.

Memory 202 may be any of a wide variety of tangible storage devices which are constructed to retrievably store data, including, for example, any of a flexible disk (floppy disk), a hard disk, an optical disk, a magneto-optical disk, a compact disc (CD), a digital versatile disc (DVD), microdrive, a read-only memory (ROM), random-access memory (RAM), erasable programmable read-only memory (EPROM), electronically erasable programmable read-only memory (EEPROM), dynamic random-access memory (DRAM), video RAM (VRAM), a magnetic tape or card, optical card, nanosystem, molecular memory integrated circuit, redundant array of independent disks (RAID), a non-volatile memory card, a flash memory device, a storage of distributed computing systems and the like. Memory 202 is constructed to store computer-readable information, such as computer-executable process steps or a computer-executable program for causing CPU 201 to communicate inputs on tablet 400 to main laser computer 300 and/or laser 103 and to receive and display data, as described more fully below.

I/O unit 203 includes hardware and/or software for interfacing tablet 400 with other devices or a user, such as receiving input and transmitting or displaying output. In the context of tablet 400, I/O unit 203 might include hardware and software for, e.g., recognizing a touch input on the face of tablet 400 (or other input via hardware on tablet 400 such as a pressable button or voice input), and for displaying output to a user via a display on tablet 400. For example, I/O unit 203 might control display of an eGUI, as described more fully below with respect to FIG. 3.

Network unit 204 includes hardware and/or software for communicating with other devices across a wired or wireless network (not shown). As shown in FIG. 2, network unit 204 communicates with corresponding network unit 273 at laser 103, and network unit 253 at main laser computer 300. For example, network unit 204 may communicate control commands to network unit 253 at main laser computer 300, and may receive feedback from network unit 273 at laser 103. Of course, communication is not limited to the devices shown in FIG. 2, and network unit 204 may be used to transmit various data across various networks. In that regard, the implementation, scale and hardware of the network may vary according to different embodiments. Thus, for example, the network could be the Internet, a Local Area Network (LAN), Wide Area Network (WAN), Metropolitan Area Network (MAN), or Personal Area Network (PAN), among others. The network can be wired or wireless, and can be implemented, for example, as an Optical fiber, Ethernet, or Wireless LAN network. In addition, the network topology may vary.

As shown in FIG. 2, main laser computer 300 includes CPU 251, memory 252, network unit 253, and I/O unit 254, and laser 103 includes CPU 271, memory 272, and network unit 273. In that regard, the general nature of these elements corresponds to the description above of similar elements in tablet 400, and for purposes of conciseness will not be repeated again. Nevertheless, it should be understood that each element (e.g., memory, CPU) would be tailored to the corresponding device. Thus, for example, CPU 251 in main laser computer 300 might execute programs to implement functionality for receiving input from tablet 400 and transmitting commands to laser 103, whereas CPU 271 in laser 103 might execute programs to implement functionality for emitting a laser beam and recording feedback.

Laser 103 also includes laser 274, which is hardware for performing laser therapy as described above.

Figure 3A:
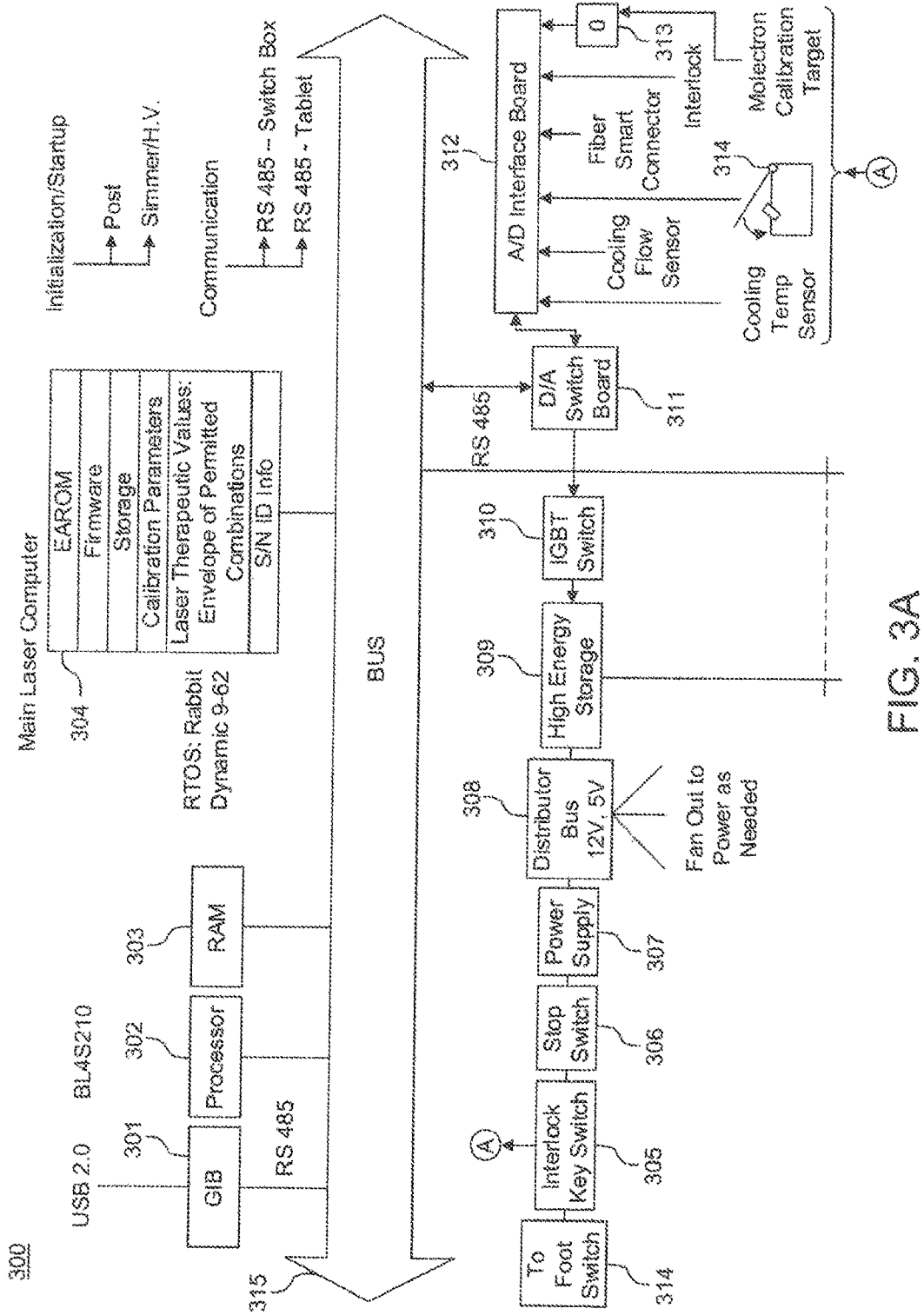
FIGS. 3A and 3B are a detailed block diagram of a main laser computer and a laser head assembly according to an example embodiment.
Figure 3B:
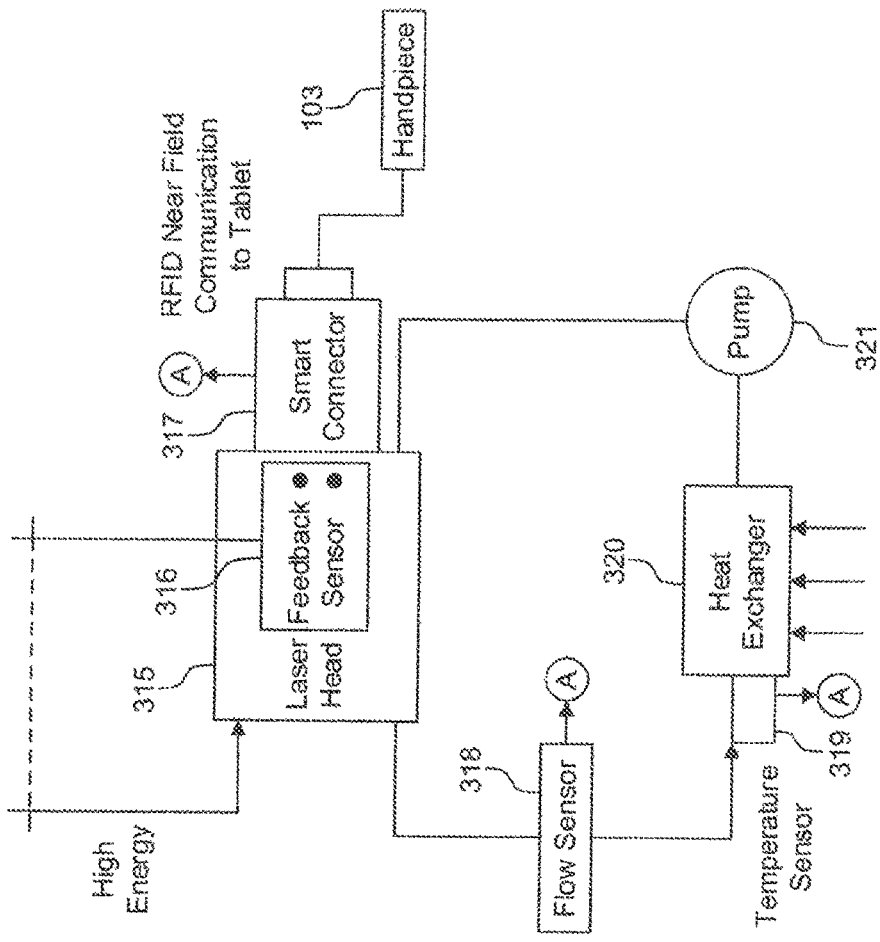

FIG. 3 is a detailed block diagram of a main laser computer and a laser head assembly according to an example embodiment.

In particular, as shown in FIG. 3, a main laser computer 300 includes a bus 315, a Galaxy Interface Box™ (GIB) 301, a processor 302, RAM 303, an electronically alterable read-only memory (EAROM) or other memory functioning as a storage 304, an interlock/key switch 305, a stop switch 306, a power supply 307, a distributor bus 308, a high energy storage 309, an insulated-gate bipolar transistor (IGBT) switch 310, a digital/analog (D/A) switchboard 311, an analog/digital (AID) interface board 312, a Molectron (calibration target) 313 and a footswitch 314. Meanwhile, a laser head assembly includes laser head 315, feedback sensor 316, smart connector 317, laser delivery system 103, flow sensor 318, thermistor temperature sensor 319, heat exchanger 320, and pump 321.

As a general matter, main laser computer 300 directs energy pulses having energy into laser delivery system 103. Thus, electrical energy (electrons) is converted into laser energy (photons). The laser pulse (and therefore energy supplied) may vary based on a pulse duration (in μs), an amount of instantaneous energy (in mJ), or a pulse repetition rate (in Hz), each independently selectable under software control of main laser computer 300, as described more fully below. The control to vary the pulse is important from a therapeutic perspective, as different durations, energies and the like may be beneficial under different circumstances or during different treatments. Under control of the main laser computer 300, IGBT 310 switches capacitance and inductance in order to store pulses. As far as the laser head, the use of an Nd:YAG laser is acceptable. Thus, an Nd:YAG crystal (not shown) sends out a series of pulses, directed through lenses, to a bendable optical fiber in laser delivery system 103. Fibers with different diameters can be used to, for example, specialize for certain procedures, although parameters must be recalculated to ensure that they are within acceptable limits after a fiber is switched. In order to cause the main laser computer 300 to create pulses, it is directed by a user interface on tablet 400, as described in more detail below.

Standby Mode

In standby mode, the controller sets the mains relay, capacitor board relay, simmer circuitry, and an aiming beam off. The user can select parameters at the control panel, but the footswitch will not activate the laser.

Ready Mode

When the ready button is pressed, and if no faults are present, processor 302 closes an on-board relay which powers the pump and the mains relay. The capacitor relay is still open, so the capacitor is not charged. The aiming beam is turned on after two seconds.

Firing Mode

When the footswitch is pressed in ready mode, the system enters firing mode. Processor 302 closes a second on-board relay, which provides 12V to the simmer circuitry and the capacitor relay control. Within 250 ms, the capacitor has charged and the lamp is lit. Processor 302 then fires laser pulses at the parameters set on the control panel. Processor 302 stores the lamp current required for each energy level in non-volatile memory, and uses this current again when that energy is next selected. During firing, the current is continually adjusted to match the measured laser energy to the selected energy. A calibration factor, set during calibration procedures, provides the conversion. When the footswitch is released, the laser stops firing. The lamp remains lit for a short period, however, to allow rapid tapping of the footswitch without frequent lamp starts. After a period of inactivity, the system returns to standby.

In one example, when the 12V power supply comes on, processor 302 powers up and performs system tests, does a display lamp test for 2 seconds, displays the software version number, and enters the standby mode.

Thus, main laser computer 300 produces pulsed Nd:YAG laser output from a fiber-optic delivery system. Laser parameters are set by the user on a touch screen 408 (see FIG. 4) on tablet 400, and output is actuated by footswitch 314.

Processor 302 is a computer processor such as a single core or multi-core central processing unit or micro-processing unit (MPU), which is constructed to realize the functionality described below. Processor 302 might comprise multiple computer processors which are constructed to work together to realize such functionality. Processor 302 executes a computer-executable program (sometimes referred to as computer-executable instructions or computer-executable code) to perform some or all of the above-described functions. Processor 302 manages the general operation of main laser computer 300, including controls and displays, the cooling system, the laser electronics, the laser energy feedback, interlocks and sensors, and retrieving or saving data. In that regard, processor 302 executes data stored in a memory, e.g., RAM 303, in order to perform required functions. In some cases, processor 302 might comprise a single core or multi-core central processing unit (CPU) or micro-processing unit (MPU). In one example, processor 302 comprises a BL4S210 single-board computer.

RAM 303 is random-access memory which allows data items to be read and written in approximately the same amount of time, regardless of the order in which data items are accessed. In addition to serving as temporary storage and working space for the operating system and applications, RAM is used in numerous other ways, which for purposes of conciseness are not described here in further detail.

In one example, communication from the tablet is via a USB interface, whereas main laser computer 300 uses an RS485 interface. To that end, GIB 301 is a Galaxy Interface Box™ for converting between USB and RS485. In particular, GIB 301 may include a USB hub so that tablet 400 can become a client and charge, i.e., a "kiosk mode" in which the hub allows fast data while also charging. In one example, GIB 301 includes a 9600 baud serial interface and is bidirectional, and charges itself from a regulated power supply via distribution bus 308.

In one brief example, upon pressure of a footswitch 314, power is directed from AID interface board 312 to D/A switchboard 311 to IGBT switch 310 to high energy storage 309 to laser head 315. Thus, D/A switchboard 311 powers IGBT switch 310.

Bus 315 is a communication system that transfers data between components inside main laser computer 300. In that regard, the internal structure of bus 315 may vary.

In one example, D/A switchboard 311 provides lamp start and simmer functions, and converts low voltage controller signals to isolated IGBT signals. To start the lamp, 12V is applied to the input of a DC-to-DC converter, which applies a voltage (e.g., 1100 V) across the lamp. At the same time, 300 V pulses are applied to the trigger transformer primary, generating 15 kV pulses to start the lamp. Once the lamp is lit, simmer current is drawn from the pulse capacitor, and is ballasted by a bank of external simmer resistors. The lamp pulse current is set by a serial signal from processor 302, which controls the output of a serial digital-to-analog converter (DAC). The actual lamp current is monitored by a shunt resistor, and compared to the DAC output. Switching circuits modulate the IGBT 310 to set the current. The pulse width is set by a gating signal from the processor 302, which does not pass through the interface board.

In one example embodiment, laser head assembly 350 contains the pump chamber with flashlamp, Nd:YAG rod, and trigger transformer; laser cavity optics, an energy monitor, a fiber lens cell, and a diode laser aiming beam. All are supported by an aluminum and graphite/epoxy resonator structure. The flashlamp output is absorbed by the Nd ions in the YAG rod, and provides the gain which supports laser oscillation. The laser pulse shape closely matches the lamp electrical pulse, except for some smoothing caused by the fluorescent lifetime of the gain medium. The energy monitor contains a beam sampler, which splits off 4% of the output beam. This sampled beam is spatially integrated by a pair of opal diffusers, then converted to electrical current by a reverse-biased germanium PIN photodiode. Circuitry on the energy monitor board converts this current into a stream of digital pulses, which are counted by the controller. After subtraction of a background count, the total number of pulses is proportional to the laser energy.

High energy storage 309 is a high-energy power supply, i.e., is a storage device configured to store a relatively large amount of energy and is switched by IGBT switch 310. The amount of energy supplied may be dependent on a switchable mode and/or input via independently selectable parameters, e.g., duration (in µs), an amount of instantaneous energy (in mJ), or a pulse repetition rate (in Hz). The switch between the modes/parameters above (e.g., between different modes corresponding to different amounts of energy or between different laser parameters such as duration and instantaneous energy) may be digital. In one example, energy for the laser flashlamp is stored in a pulse capacitor. The capacitor is charged to 600 V through a step-up toroidal transformer powered from the mains relay, and a bridge rectifier on the capacitor board. The capacitor board also contains a high voltage solid state relay, which controls the charge timing and regulates the voltage.

Molectron 313 is a hardware power meter which acts as a calibration target. In particular, a user can aim the laser at the window of Molectron 313, and see if the laser is performing as requested. For example, Molectron 313 measures the output power, and verifies whether the average power requested or expected from a set of parameters is what is actually being output by the laser. To that end, Molectron 313 is connected to A/D interface board 312, which routes the measured power/information back to the main laser computer 300, specifically processor 302. Firmware in Molectron 313 may support such a calibration mode and provide feedback to the user via an eGUI on the tablet. Calibration in Molectron 313 works in tandem with feedback sensor 316 in laser head assembly 350, which detects the flow of energy through the laser head. In one example, ordered pairs/sets of parameters may be stored as calibration factors/best fits for an input value, e.g., average power.

A/D interface board 312 collects and converts (if necessary) various analog values and transmits information corresponding thereto to processor 302. For example, as shown in FIG. 3, A/D interface board collects data from Molectron 313, flow sensor 318, thermistor temperature sensor 319, smart connector 317, interlock/key switch 305, and footswitch 314. Accordingly, A/D interface board 312 measures, e.g., power, cooling and other housekeeping data, and processor 302 can inquire with A/D interface board 312 (or A/D interface board 312 may push information thereto) in order to verify that the laser is performing within specifications.

Thus, A/D interface board 312 monitors and receives analog or digital signals from various parts of the main laser computer 300 and laser head assembly 350, converts the information to digital data, and forwards the digital data on for processing (e.g., to processor 302). In one example embodiment, the only digital communication between the system and A/D interface board 312 is via the D/A switchboard 311. Put another way, A/D interface board 312 is responsible for taking in analog inputs and converting them to digital information, but the D/A switchboard 311 acts as a messenger to forward that information from A/D interface board 312 to other components in main laser computer 300. Accordingly, in such an example embodiment, A/D interface board 312 does not directly communicate with other components such as processor 302.

Footswitch 314 is a physical pedal or other foot-actuated hardware which sends a signal upon being pressed, such as a signal indicating to fire the laser. Of course, the physical element for activating the laser is not limited to a footswitch, and other hardware elements and control are possible. Footswitch 314 is connected to A/D interface board 312 in order to transmit signals to the main laser computer 300.

Interlock key switch 305 is the physical connection to an external main power supply (e.g., via a plug), and is connected to stop switch 306. Together, these elements perform line filtering, as well as acting as a two-step fail-safe for providing or cutting power and are connected to power supply 307.

Power supply 307 is a regulated power supply, and acts as an embedded circuit to input unregulated energy into a stable power supply, e.g., a stable voltage or current within set limits. In one example, AC mains enters at the back panel, and is fused and filtered. The front panel key switch controls AC input to the 12V power supply, which powers the controller and all low voltage components.

Distribution bus 308 fans power out to elements of main laser computer 300 as needed. To that end, distribution bus includes a 5V output and a 12V output, among others as necessary. For example, parallel circuits allow distribution bus 308 to transmit power to high energy storage 309.

IGBT switch ("IGBT") 310 is a solid-state switch which acts as an amplifier of signals from D/A switchboard 311. In one example, IGBT 310 is essentially a large transistor, acting as an amplifier. D/A switchboard 311 acts together with the IGBT to control high energy storage 309 to drive the laser head assembly 350. The laser may need to "simmer" prior to usage, in which a certain lower amount of power is used to get the laser ready for firing. In one example, the shape of the current pulse is controlled by the IGBT 310 and a smoothing inductor. The IGBT 310 allows control of both the amplitude and width of the pulse.

EAROM 304 for main laser computer 300 stores firmware programs for controlling the operation of main laser computer 300, as well as data corresponding thereto. In one example embodiment, a software architecture stored in EAROM 304 includes a real-time operating system (RTOS) based on dynamic C programming (e.g., version 9.62), a monitoring module, an initialization/startup module (such as for controlling a "simmer" mode for warming up the laser), a firing module for controlling firing of the laser, and a communication module for performing, e.g., RS485 communication to D/A switchboard 311 (for internal communications) and to GIB 301 (for external communications). EAROM 304 also stores calibration factors and calibration values in a persistent manner, and can return appropriate signals for the IGBT 310 and AID interface board 312 in accordance with requested signal parameters. EAROM 304 may also store permissible values or a "permissible therapeutic window" which includes combinations of laser parameter values. Examples can be seen in U.S. Publication No. 2003/0108078. EAROM 304 may also store other housekeeping information, such as a serial number of the laser.

In the laser head assembly 350, a cooling system includes flow sensor 318, thermistor temperature sensor 319, and heat exchanger 320. Cooling includes both primary and secondary systems. The primary system may include distilled water conduction (flow) through the laser head 315, and a secondary system may use forced convection (a fan). Flow detection sensor 318 issues an analog signal indicating whether the amount of flow through the laser head is acceptable or not, and interfaces to AID interface board 312. Heat exchanger 320 is a forced convection heat exchange, e.g., a small control loop for the fan which monitors temperature through thermistor temperature sensor 319, transfers heat as necessary, and reports temperature to A/D interface board 312.

In one example, the cooling system consists of a 12V brushless DC pump, a heat exchanger, a 12V brushless DC temperature-sensing fan, a flow switch, a thermistor sensor, and connecting corrugated Teflon tubing. The coolant is approximately 400 ml of de-ionized or distilled water. The fan is powered directly from the 12V supply, but includes temperature sensing circuits to monitor the coolant temperature. If the coolant reaches 40° C., the fan speed increases gradually. The controller board contains a relay which drives the pump 321. The controller also monitors the coolant temperature via the thermistor.

Smart connector 317 is connected to laser head 315, laser delivery system 103 and A/D interface board 312, and acts to transfer information such as analog feedback to A/D interface board 312 (which is then converted to digital information for processor 302), as well as to detect certain conditions on its own. For example, smart connector 317 can detect the fiber diameter in laser delivery system 103, and then relay this information to main laser computer 300 or tablet 400. As mentioned above, parameters must be recalculated to ensure that they are within acceptable limits after a fiber is switched. Error codes may be transmitted from smart connector in accordance with a mismatch between fiber and parameters, or in accordance with any other conditions that are out of specification. A non-limiting example of error codes is described below with respect to FIG. 15.

In one aspect, analog feedback from smart connector 317 to A/D interface board 312 may be sent via near-field communication (NFC), radio-frequency identification (RFID) transmissions, and the like. For example, analog feedback may be sent to confirm the laser fiber diameter if the user has changed the fiber, but wants to keep the same power density, as well as to confirm that the laser parameters meet safety requirements.

Feedback sensor 316 detects the flow of energy through laser head 315, and tells processor 302 the status of the laser, including parameters such as, e.g., average power. Feedback sensor may also be configured to transmit an error message to stop the laser, as a fail-safe for when the laser appears to be operating incorrectly.

Figure 4:
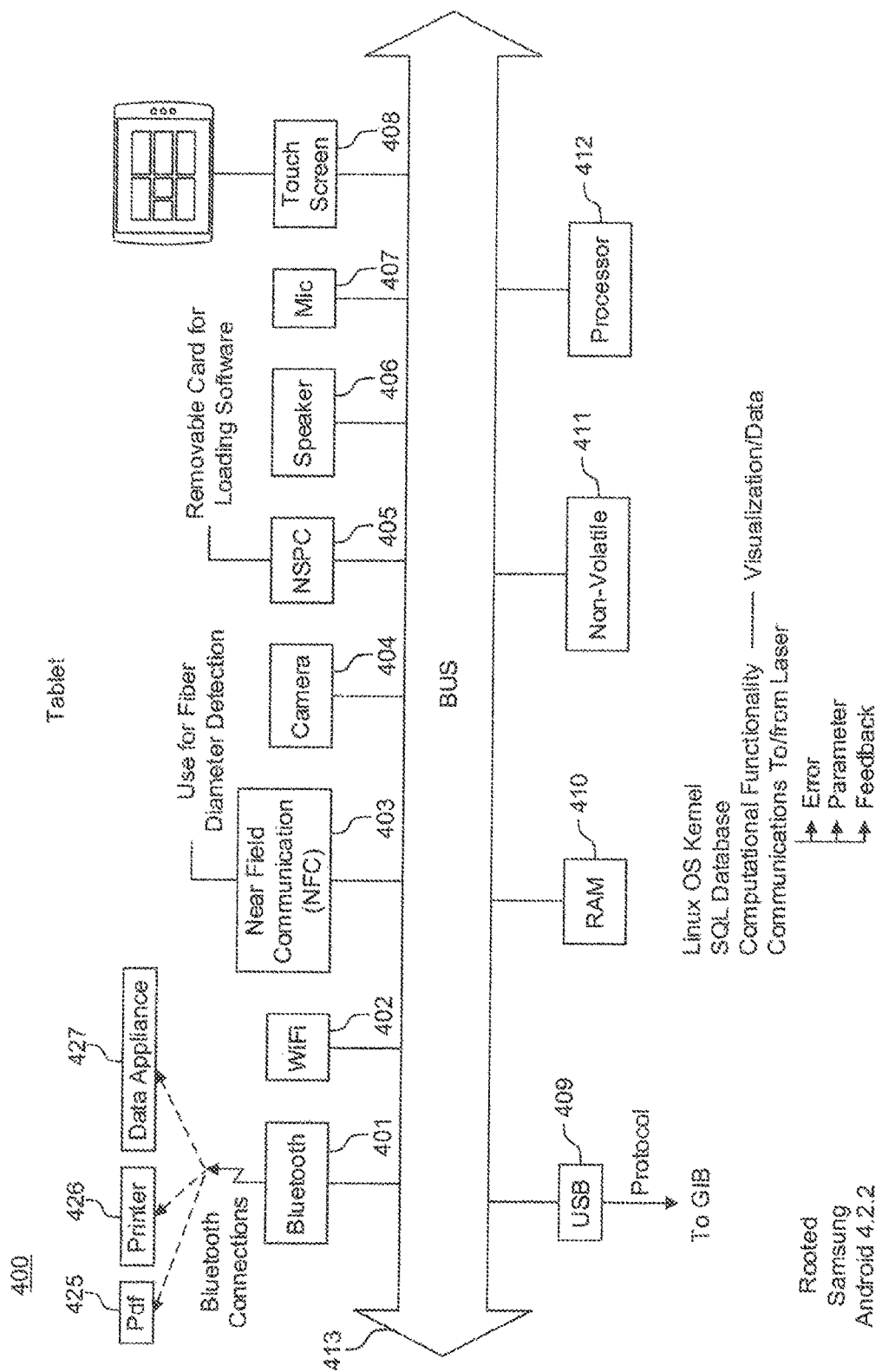
FIG. 4 is a detailed block diagram of a display control subsystem in the form of a tablet according to an example embodiment.

FIG. 4 is a detailed block diagram of a tablet according to an example embodiment.

As shown in FIG. 4, tablet 400 includes bus 413, Bluetooth unit 401 connecting to pdf element 425, printer 426 and data appliance 427, WiFi unit 402, near-field communication (NFC) unit 403, camera 404, nonparametric statistical process control (NSPC) unit 405, speaker 406, microphone 407, touch screen 408, USB 409, RAM 410, non-volatile memory 411 and processor 412.

Generally, tablet 400 may run on a Linux/Unix-based Operating System (OS). For example, tablet 400 may be an Android™ tablet running OS version 4.2.2. Of course, numerous other variations on hardware and software are possible.

According to one embodiment, default safeguards are modified or eliminated to allow for direct calls to the OS (e.g., from main laser computer 300), thereby allowing the tablet 400 to be used as an effective control system. In another example, variants of Linux allowing such calls may be used.

The main functionality of tablet 400 covers a variety of aspects. In one aspect, functionality is computational, such as receiving calls to a relational database in non-volatile memory 411, e.g., recording data for a particular patient or user, including a location of the mouth and observations related thereto, as well as computing a new set of laser parameters in accordance with a user request on touch screen 408 to change a different parameter, and forwarding such parameters to main laser computer 300 for verification. In another aspect, tablet 400 functions as a communication medium between a user and main laser computer 300 and performs functions such as transmitting data to and from main laser computer 300, including commands, feedback, error codes, and input laser parameters.

Insofar as the eGUI is concerned, it should be understood that various display and control arrangements are possible. In addition, numerous aspects of different eGUI screens and controls will be described more fully below with respect to FIGS. 8 to 67.

Nevertheless, for purposes of clarity, an example embodiment will be described which includes four main "control surfaces" on the displayed eGUI which can be switched between using, e.g., a "swipe" on touch screen 408.

First, a "home screen" provides main command and control functionality, including control of patient management and of main functionality of the laser. For example, the home screen allows a user to view information concerning a patient selected from a patient management surface (described below), to select and vary clinical laser parameters, to select a quadrant of the mouth, tooth or tooth group for treatment, and the like. In addition, the home screen allows for monitoring and control of the laser itself. For example, the home screen may display "standby", "ready" or "FIRE" as the status of the laser, in accordance with the operation of the laser in response to a press of footswitch 314.

In one example aspect, when the footswitch 314 is actuated, information including the patient, tooth, etc. selected or displayed on the tablet eGUI is saved to non-volatile memory 411 in the tablet, along with a running total of energy, pulses, parameters, dosimetry and the like for the period in which the footswitch is held, and an editable name for the current treatment period, e.g., "First Pass On Bicuspid".

In one example embodiment, the recorded data may be used to recommend new laser parameters. For example, treatment feedback may be fed to a data apparatus, and may be used to calculate new recommended laser parameters for the current patient and procedure.

In another example, a manual power measurement mode may allow for laser data to be saved without being tied to a patient. For example, if a threshold energy is reached, recording may stop and measurement of power may begin, even if the user is not currently using Molectron 313.

Second, a "patient management screen" allows for access and display of information from a database of up to thousands of patients or more, as well as providing manipulation of such information, such as adding, deleting, or selecting a patient.

In one example, information about a patient is displayed (e.g., name, ID number, dental history), along with, e.g., dental records or links thereto. Thus, the patient management screen can integrate electronic dental records, as required in some instances by Federal law. For example, the patient management screen can provide digital reports in a HIPAA-compliant manner, which can be readily integrated with patient data files. In that regard, additional security measures may prevent unauthorized persons from offloading the information gathered.

Third, a "procedures control surface" allows for selection and control of laser procedures, and may include, for example, a table with preset laser parameters (e.g., in sets or "triplets" comprising three parameters) for sample procedures, as shown more fully below.

In one aspect, the procedures control surface is used to provide training procedures for users such as a dentist and clinician. For example, a user may log into the home screen, after which the eGUI depicts information about the currently logged-in dentist or other user, such as name, ID number, and, for example, an indication of training or certification and what corresponding service modes are available. In that regard, the term "dentist" is used here for purposes of conciseness, but it should be understood that "clinician" and the like could also be used. In addition, service modes may allow, e.g., operation of the laser at fixed current and pulse width, while monitoring the internal energy monitor, and changing a calibration factor, to match the laser output to an external power meter testing of the capacitor charge, whereas another service mode might allow testing of lamp start and simmer circuits, setting of the initial lamp current, and display of the coolant temperature. Yet another service mode might restore default parameters, display energy monitor counts, or the like.

The procedures control surface may provide advanced features and capabilities for control of laser as user training and certification permit. Thus, in one example, procedures control surface allows for training, in which additional features or options are made available only after the user has completed a training course. For example, while a control box may be shown for selection of one feature set, another feature set may be displayed with a lock icon indicating that the feature set is currently unavailable (e.g., because of insufficient training). The procedures control surface may also display icons indicating levels of training which have been completed.

In one embodiment, a database (e.g., SQL) or table stores a correspondence between each user and authorized procedures and corresponding laser parameters. For example, a value of 0, 1, or 2 may be assigned for a user for certain procedures, with 0 indicating that the user can see the procedure but not use it, a 1 indicating that the user has access to that procedure/parameters and can use them, and a 2 indicating that the user can see, use, and even overwrite the parameters for a given procedure. In that regard, the corresponding eGUI may be more simple than the stored table values. In addition, controls such as overriding parameters for a procedure may require transfer to the home screen (with or without a corresponding warning), since the home screen governs more basic controls.

In a real-world example, controls on the procedures control surface can be integrated with a training program from, e.g., the Institute for Advanced Laser Dentistry (IALD). The IALD is an American Dental Association Continuing Education Recognition Program (ADA CERP®) Recognized Provider that administers a CE training program that includes a standard proficiency course along with four days of hands-on, live-patient clinical instruction to ensure success by the practitioners.

Thus, features in the procedures control surface can be synthesized from impactful portions of the IALD training continuum. Accordingly, the procedures control surface can be designed to reflect the training, rather than altering training to fit a device design.

In one example, the procedures control surface is configured so that the clinician who is in the midst of completing his/her training will have access to only the features of the laser for the LANAP® and LAPIP™ protocols that they have learned at that point in training, commensurate with their level of clinical proficiency as certified by the IALD. In addition, these clinicians will also learn additional value-added procedures (VAPs™), based on their level of training. In one example, a unique password is issued to each dentist at the completion of each level of training, which reveals the features that are appropriate. For example, in the context of IALD certifications, clinicians might receive new passwords after they complete Laser BootCamp®, after they complete Evolution 4™, and after they complete Evolution 5™. With such control of access to laser control, the IALD can give LANAP®-clinicians-in-training the access to only what they have learned. This will increase safety of LANAP® patients and will guide the clinicians toward techniques and therapeutic settings, encouraging them to use only the techniques that they have mastered up to that point.

In addition to the above, the procedures screen may also display a light dose chart, showing an amount of laser dosimetry over time, as well as a line indicating the maximum dosage allowed for that tissue/procedure. For example, the procedures screen may, using information from the patient records, determine a disease being treated and a dosage administered thus far, and display a "max" line on a graph, with a dosage line which increases in real time toward the maximum as further laser dosage is applied.

An "Admin" maintenance/settings screen may allow for general housekeeping and maintenance control, such as setting a time zone or date, adjusting display settings such as selecting between a simplified and more complex display, control icons, and the like.

In one example, the tablet eGUI may show which combinations of laser parameters (e.g., duration (in µs), an amount of instantaneous energy (in mJ), or a pulse repetition rate (in Hz) as discussed above) are allowed and/or within safe limits. Put another way, the tablet eGUI may use rules to keep parameters within specified therapeutic "windows" and prevent control of parameter values outside such windows. For example, a user or administrator might be able to unlock a locked parameter (e.g., instantaneous energy), but the system may force the other two parameters to safe boundaries in accordance with the newly selected instantaneous energy, and display information as such to the user.

Such control may be enforced from main laser computer 300, and then transmitted to the tablet 400 to display on the eGUI. In another example, having received a recalculation of a locked (or unlocked) parameter, tablet 400 may perform a recalculation of other parameters at its end, and then transmit the new parameters to main laser computer 300 for validation or refusal (e.g., as indicated by an error message, grayed-out parameter values, etc.). Generally, main laser computer 300 will not send an illogical choice of parameters to the laser, whereas the tablet will not allow selection of an illogical combination at the user end on the display. The tablet 400 may store default combinations of parameters.

Turning to the hardware of tablet 400, in one example, RAM 410 is random-access memory which allows data items to be read and written in approximately the same amount of time, regardless of the order in which data items are accessed. In addition to serving as temporary storage and working space for the operating system and applications, RAM is used in numerous other ways, which for purposes of conciseness are not described here in further detail.

Bluetooth 401, WiFi 402 and NFC 403 variously act as wireless network units for wirelessly interfacing with main laser computer 300 or other devices, whereas USB 409 acts as a physical connection to other devices. Bluetooth 401 is hardware/software for exchanging data over short distances (using short-wavelength UHF radio waves in the Industrial, Scientific and Medical (ISM) bands from 2.4 to 2.485 GHz) from fixed and mobile devices, WiFi 402 is hardware/software for local area wireless communications, and NFC 403 is hardware/software for NFC-protocol-based radio communication with nearby devices or elements.

In some examples, these units interface with a data appliance 427, shown in FIG. 4. Data appliance 427 is, e.g., a physically and electronically secure data server with hardwired digital electronic interfaces and wireless digital electronic interfaces. Data appliance 427 may act as a more secure storage for data such as patient records, including HIPAA reports. In some cases, the tablet 400 may first transmit such data to data appliance 427 using Bluetooth, which then offloads the data to another computer such as a PC (not shown). Such a transfer can also be two-way, in that information such as recommendations can be transmitted back to the tablet, with treatment progress and recommendations re-synchronized again with the PC after new treatment, etc. In some cases, WiFi may be used to transmit data from the tablet if, under the circumstances, it is more secure (or HIPAA compliant).

Camera 404 is an optical instrument for recording images, which may be stored locally, transmitted to another location, or both. The images may be individual still photographs or sequences of images constituting videos or movies.

NSPC 405 is hardware/software for monitoring and controlling processes in tablet 400 to ensure that it operates at or near its full potential. Speaker 406 is an electromechanical element which produces sound. Microphone ("Mic") 407 is an acoustic-to-electric transducer or sensor that converts sound into an electrical signal.

Touch screen 408 is a hardware/software input device normally layered on the top of an electronic visual display, by which user can give input or control the information processing system through simple or multi-touch gestures by touching the screen with a special stylus/pen and/or one or more fingers. As described above, touch screen 408 displays several eGUis and controls, along with various data.

USB 409 is a connector for communicating via the Universal Serial Bus protocol, and in particular, is used to communicate from tablet 400 to main laser computer 300 via GIB 301.

Non-volatile memory 411 is computer memory that can retrieve stored information even after having been power-cycled. Examples of non-volatile memory include read-only memory, flash memory, ferroelectric RAM (F-RAM), most types of magnetic computer storage devices (e.g. hard disks, floppy disks, and magnetic tape), and optical discs.

Processor 412 is a computer processor such as a single core or multi-core central processing unit or micro-processing unit (MPU), which is constructed to realize the functionality described below. CPU 201 might comprise multiple computer processors which are constructed to work together to realize such functionality. CPU 201 executes a computer-executable program (sometimes referred to as computer-executable instructions or computer-executable code) to perform some or all of the above-described functions.

Figure 5:
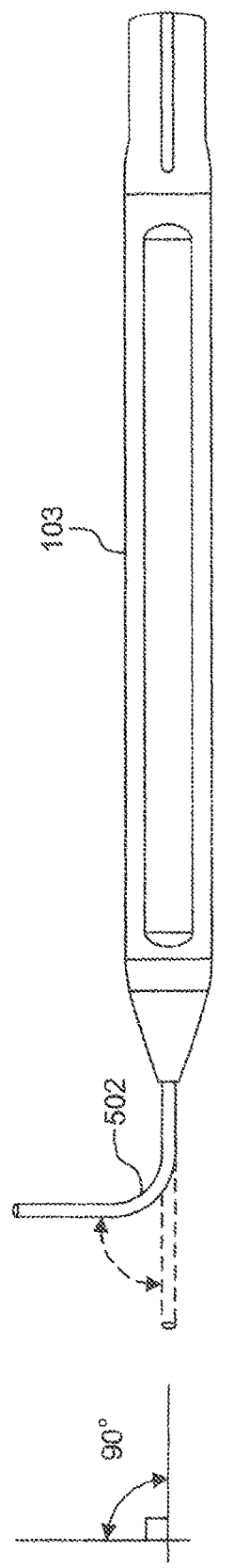
FIG. 5 is a representative view of hardware of a laser delivery system according to an example embodiment.

FIG. 5 is a view for explaining a laser delivery system 103 with a bendable cannula 502 containing a bendable laser fiber according to an example embodiment. The laser delivery system 103 is held by the dentist (or clinician, etc.), and is the physical implement used to administer laser energy to a patient through the bendable cannula 502. As shown in FIG. 5, the bendable cannula 502 can bend up to 90°, which allows for better access to parts of the mouth which might otherwise be obscured or difficult to reach. Thus, according to one example embodiment, a laser delivery angle may be adjusted.

Communications Protocol

FIG. 6A and FIG. 6B are views for explaining the protocol for transferring data between tablet 400 and main laser computer 300 via, e.g., GIB 301. Of course, it should be understood that this arrangement is merely an example, and other arrangements and data combinations are possible.

In one example, tablet 400 issues command packets over the USB/RS485 communications link via GIB 301 and expects an appropriate reply packet to be returned by main laser computer 300 as slave device. All communications are initiated by the GIB 301 and GIB 301 performs a timing check to make sure the tablet 400 is periodically communicating. In the event that the tablet 400 stops communicating with main laser computer 300 for a predetermined period of time, e.g. a couple of seconds, main laser computer 300 will drop out of any active mode and return to the standby mode. This prevents the system from being operated without tablet 400 attached and communicating. In this context the tablet 400 is essentially the user interface controlled by the operator and the main laser computer 300, and specifically processor 302 is the embedded controller that handles the laser power control and the operator footswitch.

The communications packets include a 16-bit cyclic redundancy check (CRC) to prevent badly formed packets or packets containing bit errors from being used to set laser operating modes and operating power setpoints. In one example, upon start-up, tablet 400 sets a status mode, packet position 5 to 14, requesting a long word response from the main laser computer 300 to determine a firmware revision. Tablet 400 communicates with main laser computer 300 periodically. In one example, the period is 4 Hz.

Communication between tablet 400 and main laser computer 300 (also referred to as PerioLase® Main Controller or PerioLase® Main Computer) comprises serial communication and is converted between USB and RS485 using GIB 301. As shown in FIG. 6A, a communication 601 from the processor in tablet 400 to the main laser computer 300 may comprise a packet with 13 bytes: a one-byte address (which can, e.g., always be 0 or 0x00 for a master in a master-slave communication), a one-byte packet length (e.g., the packet length to follow, which might always be 11, or 0x0B), a one-byte pulse duration (e.g., an index into pulse width selections such as "0-6", or 0x00-0x06), a one-byte energy in millijoules such as the energy expended during a footswitch period (e.g., an index into energy selections 0-25 or 0x00x00-0x19), a one-byte frequency in Hz (e.g., an index into pulse rate selections such as "0-10", or 0x00-0x0A), a mode (e.g., standby/ready/service), other one-byte parameters (generically referred to here as "Parameter 1" and "Parameter 2"), a one-byte aiming beam intensity (e.g., an intensity setting value from 0-5), a one-byte tube start current (e.g., an start current value from 10-80, and a default value of 15), a one-byte calibration factor value (e.g., 0-99) used to scale and display average power, and two cyclic redundancy check (CRC) bytes. Such a packet might be sent, for example, every time the laser mode changes from "standby" to "ready", i.e., when the user is ready to take action.

A short response 602 from main laser computer 300 to tablet 400 might be 17 bytes: a one-byte address (which can, e.g., always be 1 or 0x0 1 for a slave in the master-slave communication), a one-byte packet length to follow (e.g., always 17 or 0x 1 1 for this reply structure), a one-byte pulse width (e.g., an index into pulse width selections such as "0-6", or 0x00-0x06), a one-byte energy in millijoules (e.g., an index into energy selections 0-25 or 0x00-0x 19), a one-byte frequency in Hz (e.g., an index into pulse rate selections such as "0-10", or px00-0x0A), a one-byte status code for an operating mode (e.g., an operating mode such as 0-6, 10, 11 or 15, described below), a one-byte error mode (or error mode code, discussed above, which may be, e.g., an error code such as 15 when in an error mode), two bytes of Molectron reading outputs (e.g., two values, in analog-to-digital converter (ADC) counts 0-10000, 0-10 volts), two bytes of joule count energy meter reading values (e.g., two energy monitor per pulse average values in mJ), two calibration factor bytes for energy meter calibration factors (two values, e.g., from 0-99), four bytes of total energy delivered (e.g., the total mJ delivered at all pulse widths), and two CRC bytes.

In one example, the Molectron reading contains a temperature sensor reading in Service Mode 2. Moreover, in one example, an energy monitor value incorporates the calibration factor to convert energy meter pulses to mJ, and readings greater than 2*a mJ setpoint result in an error code. For example, the calibration factor value 0-99 gets an offset of 50 added to it to produce 50-149, and the energy monitor value=pulses*200 I Calibration Factor (50-149). In still another example, the total energy delivered values get cleared in the status mode after a reply.

A longer response 603 from main laser computer 300 to tablet 400 might include additional bytes indicating firmware (major and minor) and a firmware build and values representing an energy array which indicates the total running energy (joules) so far during one footswitch press.

These response packets might be sent at start-up, or in case of an error code, or at another timing.

For example, as shown in FIG. 6C, response 603 might include a one-byte address (e.g., always 1 for Slave (0x01)), a one-byte packet length to follow (e.g., always 34 (0x22) for this reply structure), a one-byte status/operating mode (e.g., which might always be a value such as 14 for this reply structure), a one-byte firmware major value indicating the firmware version major number and a one-byte firmware minor value indicating the firmware version minor number, a one-byte firmware build value indicating the firmware version build number, and two CRC bytes. Moreover, as shown in FIG. 6C, response 603 might include 14 bytes of total energy values delivered at various pulse widths. These values may be cleared after a reply.

FIG. 6D shows example pulse duration selections which may range from, for example, 100 μsec to 650 μsec, along with corresponding indexes. FIG. 6E depicts example modes (e.g. those included in short response 602) which may include standby, ready, laser on, and the like. FIG. 6F depicts example indexes and corresponding energy selections (in mJ). FIGS. 6G and 6H depict example parameter 1 and parameter 2 values, respectively, and may store, for example, calibration currents or calibration factors in a service mode. FIG. 6I depicts example error code values, and FIG. 6J depicts example pulse rate selections and corresponding indexes.

It should be understood that the foregoing are merely examples of data and data formatting according to the communication protocol, and that various other data elements and arrangements are possible.

Periodontitis Procedure

Figure 7:
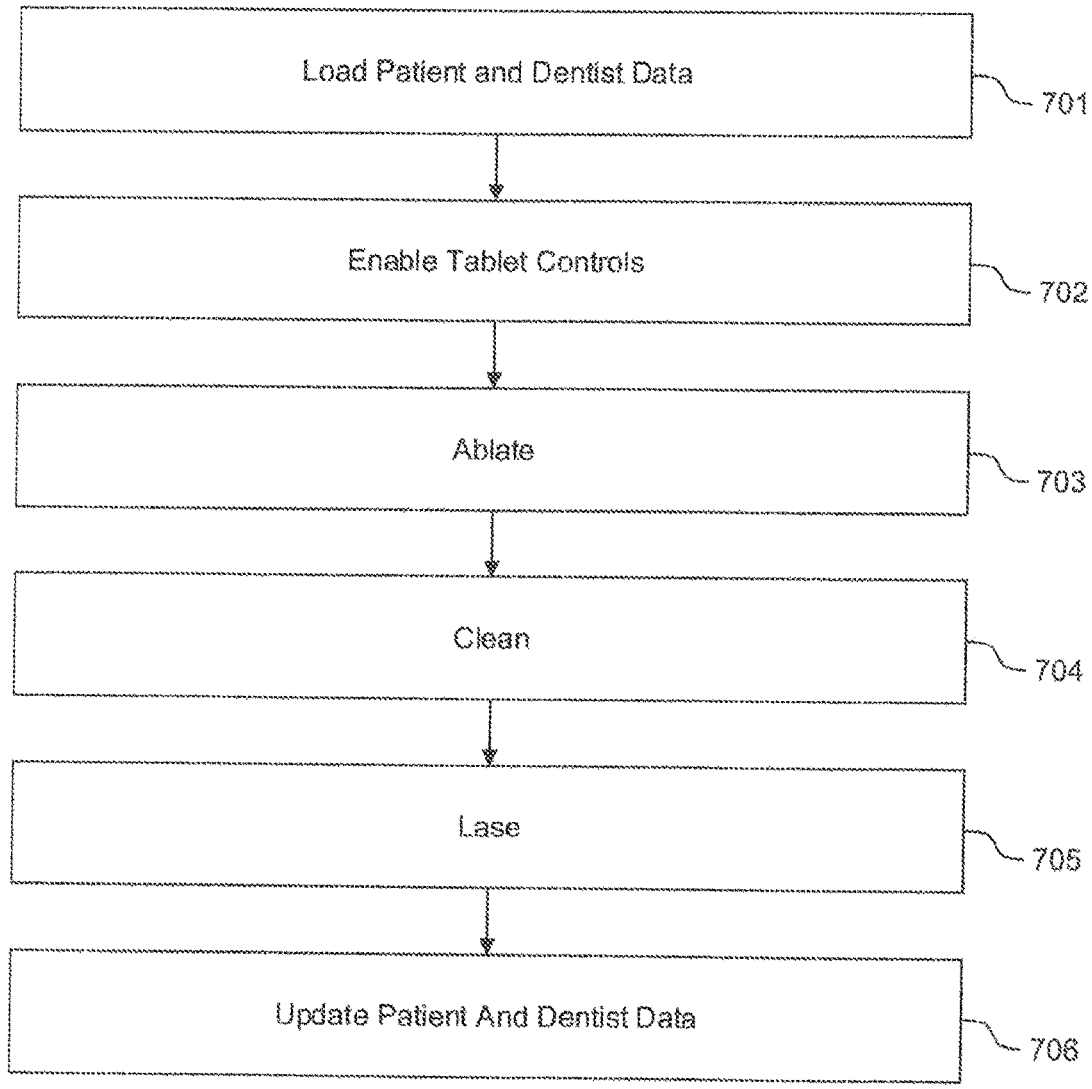
FIG. 7 is a flow diagram for explaining a laser-assisted periodontitis procedure according to an example embodiment.

FIG. 7 is a flow diagram for explaining a LANAP® Procedure according to an example embodiment.

Periodontal infection and inflammation and periodontal diseases are caused by certain types of bacteria in plaque and calculus (concrements). These bacteria create toxins which irritate the gums and result in a breakdown of the periodontal tissues that support the teeth. Over time, these toxins can destroy gum tissues, and allowing the infection to progress can result in bone loss. There are many forms of periodontal diseases, the most common types being gingivitis and periodontitis. Gingivitis is the earliest stage, and affects only the gum tissue. At this stage, the disease is still reversible.

If not treated, however, this disease may lead to more severe conditions called periodontitis. The gums, bone and other structures that support the teeth become damaged. Teeth can become loose and may have to be removed. At this stage, the disease may require more complex treatment to prevent tooth loss. With healthy gingiva (gum tissue), the teeth are firmly anchored in bone. Gingivitis develops as toxins in plaque irritate the gums, making them red, tender, swollen and likely to bleed easily. Periodontitis occurs when toxins destroy the tissues and bone. Gums become detached from the teeth, forming pockets that fill with more plaque. Advanced periodontitis is present when the teeth lose the supporting bone. Unless treated, the affected tooth frequently becomes loose and may fall out.

The method of treatment of periodontal diseases depends upon the type of disease and how far the condition has progressed. Conventionally, the first step is usually a thorough cleaning which may include scaling to remove plaque and calculus deposits beneath the gum line. Surgery may be required when deeper pockets, usually over 4 to 6 mm, are found. It is difficult for the dentist or hygienist to thoroughly remove plaque and calculus from deep pockets. Patients can seldom keep them clean and free of plaque. Allowing pockets to remain may invite infection and bone destruction. When pockets are deep and bone has been destroyed, flap surgery may be necessary to provide access to the surfaces of the tooth roots in order to thoroughly remove calculus, plaque and any diseased tissue, and to recontour the bone to a more favorable architecture. In this technique, the gum is lifted away and is then sutured back into place or into a new position that will be easier to keep clean. Conventionally, surgical debridement of the tooth root surface and the removal of granulation and granulomatous tissue are performed following the resection of the soft tissue flap. Aesthetic modifications of this approach have been reported under the title of open flap curettage, reverse bevel flap surgery, Widman flap surgery and modifications of Widman flap surgery, apically positioned flap osseous surgery, and guided tissue regeneration.

Nevertheless, conventional methods do not appear to provide an appropriate minimally invasive surgical method for the reduction of the deep pocket, elimination of disease, reattachment of the gingiva to the tooth root surface and true regeneration of the attachment apparatus (new cementum, new periodontal ligament, and new alveolar bone) on a previously diseased root surface.

Therefore, an example embodiment for addressing these concerns will now be described, with respect to FIG. 7.

Briefly, in FIG. 7, gingivitis and periodontitis are treated in both adult and young patients. Reducing early, shallow and deep bony pockets provides for removal of diseased tissue, periodontal pathogens, pathologic proteins, and calculus and other concrements on the tooth surface. This provides for true regeneration of the attachment apparatus. The process includes creating a gingival trough or flap around the tooth with a contact laser fiber, and photothermally rupturing, disassociating, separating, ablating, denaturing and vaporizing the diseased, inflamed, infected, bacteria-invaded, ulcerated pocket epithelium via selective photothermolysis. The process further includes vaporizing or denaturing the inner marginal gum tissues and pocket epithelium and granulomatous tissue fully around the targeted tooth to the accessible depth of the defect without breaking through the soft tissue attachment apparatus above the depth of the bony defect, ultrasonic debridement of the tooth and root surfaces, transitioning to the full depth of the bony defect via blunt dissection through any soft tissue attachment and perforating into the bony defect, modifying the bone through osteoplasty and/or ostectomy below the level of the mucoperiosteum as needed, creating angiogenesis, lasing the pocket to disinfect and decontaminate the soft and hard tissues, assisting in hemostasis, cauterizing free nerve endings, sealing lymphatics, preparing the coronal soft tissue for approximation against the tooth and root, and compressing the soft marginal tissues against the tooth and root, adhesion is achieved, and a stabilized fibrin clot has formed. In one example, elimination of occlusal interferences and occlusal traumatic forces is typically achieved by occlusal adjustment.

By virtue of this arrangement, it is ordinarily possible to treat gingivitis and periodontitis periodontal pocket defects in both adult and young patients by establishing a new cementum-mediated periodontal ligament attachment to the root surface in the absence of long junctional epithelium and achieving true regeneration of the attachment apparatus (new cementum, new periodontal ligament, and new alveolar bone) on a previously diseased root surface. Moreover, the inflamed pocket epithelium is selectively separated via photothermolysis, ordinarily without substantially removing any connective tissue.

The procedure may be indicated when, for example, there is a moderate-to-deep probed pocket depth of five mm or greater, as measured from the coronal aspect of the tissues to the extent of the probable pocket, or when there is the presence of bony defects, or when there is infection in the gingival tissue, notably presence of bleeding and/or suppuration, or mobility of the teeth, or other aesthetic considerations.

In more detail, in step 701, patient and dentist (clinician) data is loaded into tablet 400. For example, a dentist may enter login credentials into a eGUI to identify his/herself, and may further enter an ID number, name, or other identification information to load data corresponding to a patient.

In step 702, tablet controls are enabled, corresponding to the dentist data. As mentioned above, an eGUI on tablet 400 may be configured such that the dentist who is in the midst of completing his/her training will have access to only the features of the main laser computer 300/laser 103 for the LANAP® protocol that he/she learned at that point in training, commensurate with the dentist's level of clinical proficiency.

At this point, a number of preliminary procedural steps may be performed. For example, gingival tissue of a patient corresponding to a targeted tooth can be anesthetized.

In that regard, a topically placed anesthetic is used to anesthetize the area. In one example, the dentist may begin with 4% Prilocaine Plain™, using a 30-gauge needle. This anesthetic is perceived by the patient as painless, due to its unique ability to anesthetize soft tissue without stinging. The anesthetic is injected very slowly into the area, allowing several minutes for the Prilocaine Plain™ to take effect. The dentist may then continue using a 30-gauge needle and follow this procedure with a suitable longer-acting anesthetic. However, an exception would be made if health reasons caused the anesthetic to be contraindicated. The area of concern usually involves LANAP® Protocol treatment of two opposing quadrants and then the other two opposing quadrants some days later, or alternatively, full-mouth treatment in one appointment. Anesthesia is routinely used in every procedure, in order to: aid in bone-sounding (discussed below) for accurate measurement of the full depth of the diseased pocket and bony defects; allow aggressive debridement of soft and hard tissues around the surfaces of the tooth; allow the patient to be as comfortable as possible during the treatment, thereby minimizing the patient's endogenous adrenaline production, and in turn achieve the optimal therapy results; maximize the doctor's ability to concentrate on the procedure; and optimize the use of ultrasonic probes at frequencies between one hertz and fifty thousand hertz.

As another preliminary step, bone sounding and pocket depth measurement can be performed using a periodontal probe, recording the depths of all bony defects in the soft tissue around the tooth and root, from an upper gingival margin to the extent of the accessible bony defect. In one example, pocket depths can be recorded with a periodontal probe with six areas recorded around each tooth root. This will allow a determination of the full depth of the diseased pocket. The dentist uses the sum total of all 6 probe depths/bone soundings and multiplies that number by 1 to 40, depending on soft tissue phenotype (biotype), LANAP® Periodontal Disease Case Type Classification I-V, and LANAP® Tooth Mobility Score 0-4 (or other periodontal disease classifications or tooth mobility measures), to compute a "light dose" of 1 to 40/Joules per millimeter pocket depth. Such tooth mobility measures may, for example, include modifications to the Miller Index of Tooth Mobility or other measures. Such periodontal disease classifications may, for example, include the classifications specified by the 1999 International Workshop for a Classification of Periodontal Diseases and Conditions or any future updates thereto: gingival diseases (dental plaque-induced gingival diseases, non-plaque-induced gingival lesions; chronic periodontitis (localized, generalized); aggressive periodontitis (localized, generalized); periodontitis as a manifestation of systemic diseases (associated with hematological disorders, associated with genetic disorders, not otherwise specified); necrotizing periodontal diseases (necrotizing ulcerative gingivitis, necrotizing ulcerative periodontitis); abscesses of the periodontium (gingival abscess, periodontal abscess, pericoronal abscess); periodontitis associated with endodontic lesions (combined periodontic-endodontic lesions); developmental or acquired deformities and conditions (localized tooth-related factors that modify or predispose to plaque-induced gingival diseases/periodontitis, mucogingival deformities and conditions around teeth, mucogingival deformities and conditions on edentulous ridges, occlusal trauma). (For example: 6 probe depths of 10 mm each=60 mm total×1=60 Joules of total light dose.) The summation number of the probe depth represents the TOTAL Joules to be delivered. The majority of the total light dose is applied during the 1st Step of laser application in LANAP® Ablation, while the remaining amount of the energy is delivered during the 2nd laser application in the LANAP® Hemostasis setting. (In the example above, 40 Joules are delivered during the LANAP® Ablation Step, and 20 Joules are delivered during the LANAP® Hemostasis Step). Thus, a light dose computation is made in conjunction with the surgical treatment.

In that regard, tooth mobility measures may, for example, include modifications to the Miller Index of Tooth Mobility or other measures. Such periodontal disease classifications may, for example, include those classifications specified by the 1999 International Workshop for a Classification of Periodontal Diseases and Conditions or any future updates thereto:

Gingival diseases (dental plaque-induced gingival diseases, non-plaque-induced gingival lesions)

Chronic periodontitis (localized, generalized);

Aggressive periodontitis (localized, generalized);

Periodontitis as a manifestation of systemic diseases (associated with hematological disorders, associated with genetic disorders, not otherwise specified);

Necrotizing periodontal diseases (necrotizing ulcerative gingivitis, necrotizing ulcerative periodontitis);

Abscesses of the periodontium (gingival abscess, periodontal abscess, pericoronal abscess);

Periodontitis associated with endodontic lesions (combined periodontic-endodontic lesions); and Developmental or acquired deformities and conditions (localized tooth-related factors that modify or predispose to plaque-induced gingival diseases/periodontitis, mucogingival deformities and conditions around teeth, mucogingival deformities and conditions on edentulous ridges, occlusal trauma).

In one example, defect measurements (mm pocket depth) are provided to tablet 400 for computation and recommendation of light dose and are stored by patient name and tooth location at data appliance 427. In one embodiment, the defect measurements are gathered by interfacing with electronic medical (dental) record systems where the defect measurements have been previously recorded, such as data appliance 427. In one example, the light dose recommendations are further modulated (adjusted) based on examples of the physical characteristics of the tissue (phenotypes) presented visually on the tablet 400 and selected by the clinician to indicate the tissue characteristics presented by the patient. These phenotype selections can be used to compute the recommended light dose in the tablet 400.

In step 703, selective ablation is performed. In this regard, ablation of the free gingival margin with the laser energy via selective photothermolysis removes pathogens and pathologic proteins within the tissue of the free margin, which otherwise would not be removable, whereas lasing the pocket tissue surface around the affected tooth (step 705) is used to, e.g., remove only granulomatous tissue, intentionally leaving the disinfected granulation tissue in place, and to disinfect, assist in hemostasis, cauterize free nerve endings, and seal lymphatics of the pocket tissue surface.

Thus, using laser delivery system 103, there is selective rupturing, disassociating, separating, ablating, denaturing and vaporizing of an interior diseased epithelial lining of the pocket, to the soft tissue extent of the pocket on all sides of the tooth, to establish a new cementum-mediated periodontal ligament attachment to the root surface in the absence of long junctional epithelium and achieving true regeneration of the attachment apparatus (new cementum, new periodontal ligament, and new alveolar bone) on a previously diseased root surface. In one example, ablating, denaturing and vaporizing is completed with not more than 6.00 Watts of average output power from the laser, as measured at the distal end of a laser fiber, and with a lasing frequency of not more than 100 Hz.

Laser delivery system 103, such as manufactured by Millennium Dental Technologies, Inc., for their model number "PerioLase® MVP-7™" operating at a wavelength in the near-infrared of, e.g., 1000 to 2000 nanometers, is used to create the initial trough or flap at the marginal gingiva using between, e.g., one and six Watts of average fiber output power (measured at the distal end of the fiber), and frequencies between one and one hundred hertz. A contact laser fiber (e.g., the fiber in cannula 502) with a fiber diameter of between 200 (microns) and 1000 (microns) can be used, in an orientation parallel to the surface of the tooth root, to create a gingival trough or flap by ablating the free gingival margin and the internal diseased epithelial lining of the pocket, thus exposing the tooth root surface and removing all internal epithelial lining from the periodontal pocket.

An appropriately cleaved contact laser fiber is used for the precise control of the laser energy, the physical placement of the laser energy, and the determination of the desired orientation of the laser to the tissue desired to be removed. Orientation parallel to the surface of the tooth root defines the direction of the laser fiber for the proper initial tissue selective ablation. The tooth root surface is then exposed for viewing by a gingival trough or flap.

Ablation of the free gingival margin with the laser energy via selective photothermolysis removes pathogens and pathologic proteins within the tissue of the free margin, which otherwise would not be removable. Lasing the tooth and root surface destroys the lipopolysaccharides (LPS) of gram-negative bacteria. Additionally, this procedure provides hemostasis, and further defines the tissue margins preceding piezo-electric instrumentation. The integrity of the mucosa is also preserved prior to mechanical manipulation, thereby dissecting the separation between the free gingival margin and the fibrous collagen matrix, which holds the gingiva in position. Maintenance of the crest of the gingival margin is aided in that the healing of the fibrous collagen matrix will maintain the gingival crest at, or apical to, the presurgical level.

By use of the "hot-tip" effect (accumulated tissue proteins heated via conductivity secondary to the passage of laser energy through the fiber), the dentist may continue to excise the inner pocket epithelium around the entire tooth and root to the depth of the probed reading, but not using the laser or the optical fiber to break through the mucogingival junction. This effect provides the selective removal of sulcular, pocket epithelium and granulomatous tissues without removing any substantial connective fibrous tissue and does so circumferentially and radially. As necessary, the dentist may remove the excised tissue that accumulates on the tip of the laser fiber.

Using the quartz optical fiber oriented less than 30 degrees to the tooth root surface, the clinician may lase the tooth and root surface to destroy lipopolysaccharides (LPS). Greater than 30 degrees risks the possibility that the Nd:YAG laser pulse may interact with the surface of the tooth root. A few pulses of Nd:YAG laser energy are not injurious to a tooth root as long as the irradiation is immediately discontinued so that heat does not accumulate within the tooth. The nature of a quartz optical "bare" fiber is such that it has a 27-degree beam divergence. Therefore, even parallel to the root surface, the Nd:YAG laser radiation can reach the surface by "side-firing" scatter.

Thus, there is separation of the inner pocket diseased epithelium around the entire tooth root to a depth equal to an initial probe reading of the inner pocket, followed by an ultrasonic scaling of fixture surfaces and blunt dissection of any soft tissue adhesions or attachments through to the bony defect.

In step 704, cleaning is performed with, e.g., an ultrasonic handpiece, along with further cleaning by laser delivery system 103. In particular, the tooth and root surface is cleaned of all foreign matter, to the full depth of the pocket on all sides of the tooth from crestal margin to bony base. For example, the dentist may use an ultrasonic handpiece to ultrasonically scale all tooth and root surfaces to the depth of the pocket, with the intent to remove all foreign structures and substances from the tooth and root surface (including the bacterial smear layer covering and included in soft and hard tissue calcification, calculus, concrements and cement), thereby allowing adhesion of the lased soft tissue to the clean tooth and root surface. Bone modification, as appropriate with osteotomy and/or ostectomy, may be undertaken. Then, using laser delivery system 103, between one and six Watts of laser fiber output power and a frequency between one hertz and one hundred hertz may be used in the deep periodontal pockets for optimal bacterial destruction without causing bacterial injection into the periodontal tissues. This will minimize the occurrence of soft tissue cellulitis.

In step 705, lasing is performed with laser delivery system 103, to remove only granulomatous tissue, intentionally leaving the disinfected granulation tissue in place, and to disinfect, assist in hemostasis, cauterize free nerve endings, and seal lymphatics of the pocket tissue surface, and to prepare the pocket tissue surface for adhesion. Laser delivery system 103 may also be used to stop blood flow as needed.

Therefore, as described above, the procedure further includes cleaning and lasing of the pocket in preparation for soft tissue adhesion.

In one example, the ablating, vaporizing, and lasing are completed with a laser fiber oriented parallel to the surface of the tooth root. In a further example, the laser fiber diameter is between, e.g., approximately 200 and 1000 microns.

In one specific example, although the disclosure is not hereby limited, laser delivery system 103 might comprise a FiberFlex™ 360-micron diameter quartz optical fiber fed through a handpiece such as an anodized aluminum True-Flex® handpiece and bendable cannula. The dentist activates the laser to intentionally irradiate the bone at the base of the bony defect in the 6 separate pocket depth measurement locations to initiate hemostasis from the medullary bone, stimulate and upregulate the release of growth factors (e.g., IGF-I and IGF-11, TGF-beta 1, TGF-beta 2, BMP-2), stimulate and upregulate fibroblasts and stem cells, warm the blood in the pocket to thermolytically cleave fibrinogen thereby converting the blood into fibrin (thrombin catalyzes the conversion of fibrinogen to fibrin), the body's first connective tissue, create a stable fibrin clot, and to create angiogenesis (new vascularization); to remove and/or denature any remaining, residual granulomatous tissue, and inflamed, infected and diseased epithelial lining, intentionally leaving granulation tissue in place (stem cells, capillaries, fibroblasts), but disinfected; and to, e.g., cauterize free nerve endings and seal lymphatics of the pocket tissue surface, and to prepare the pocket tissue surface for adhesion.

Following the lasing, a number of follow-up steps may be performed. In particular, the pocket may be irrigated with a bactericidal solution, occlusal interferences may be eliminated, and the pocket tissue may also be lased, to adapt the pocket tissue surface for tissue adhesion. In one example, all treatment sites are irrigated to the deepest depth of the periodontal pockets with a bactericidal solution of a high tissue substantivity (e.g., chlorhexidine gluconate 0.12%). The irrigation aids the laser in the reduction of bacteria in the pocket and in removing debris. In one example, a high-speed handpiece for occlusal adjustment is used to eliminate occlusal prematurities and interferences and occlusal traumatic forces. In some instances, an anterior deprogrammer and dis-occluding occlusal splint may be necessary when trauma-induced periodontal disease is manifest, i.e., occlusal trauma in the absence or presence of bacteria-induced periodontal disease. The splint is designed to provide anterior guidance, e.g., a "LANAP Splint", or anterior "jig".

The pocket tissue surface can be approximated with the tooth and root surface and the pocket tissue surface can be maintained in contact with the tooth and root surface to advance adhesion.

In addition, the process can include applying firm pressure to hold the pocket tissue surface in contact with the tooth and root surface for one to three minutes, allowing a thin clot to form between the pocket tissue surface and the tooth and root surface. Put another way, the tissues should be compressed with firm pressure for one to three minutes against the tooth and root from both a facial and lingual direction, permitting only a thin clot to form between the tissue and the tooth and root. In addition, follow-up steps can include prescribing medications for outpatient use in preventing infection, providing ongoing occlusal equilibration examination, and enhancing the patient's natural immune system (e.g., through medication) to protect against infection and reduce inflammation.

In step 706, the patient and dentist data is updated to reflect the performance and outcome of the procedure.

The procedure can be categorized as a Surgical Flap Procedure and "Laser-Assisted Regeneration", with limited or complete occlusal adjustment. In some examples, a time of 45 minutes is reasonable to treat a quadrant. As suggested above, treatment can be followed by a coronal polishing/prophylaxis and an occlusal equilibration follow-up and a postoperative check of the area treated.

Thus, as described above, the laser-assisted periodontal device is a laser periodontal, periodontitis, gingivitis, treatment device for use on both adult and young patients.

According to one example aspect, creating a gingival trough or flap around a tooth includes creating a circumferential and radial soft tissue, gingival, or mucosal trough or flap around a tooth.

According to still another example aspect, photothermally rupturing, disassociating, separating, ablating, denaturing and vaporizing the infected tissue comprises ablating or denaturing inflamed, infected, erythematous, edematous, hyperplastic, bacteria-invaded, ulcerated, degenerated, bleeding, suppurative, or sloughing periodontal soft tissue, including sulcular epithelium, junctional epithelium and keratinized tissue, via selective photothermolysis.

According to another example aspect, the method can be accomplished using a blue light device with wavelength emission in the range of 400 to 520 nm (e.g., 405, 420, 425, 470 nm), such as a diode laser, Ti:sapphire laser, argon ion laser, light-emitting diode, superluminescent diode, halogen, plasma-arc curing (PAC), or other light source to simultaneously, sequentially, or singularly irradiate the tissues to kill or inactivate bacteria, spores, fungi, viruses, and bacteriophages and to suppress biofilm formation.

In one aspect, the blue light device irradiation is co-axial with an aiming light for guiding the laser. In another example, the blue light device comprises a separate energy source and a separate handpiece from that of the laser. Thus, the blue light device can be combined with, or completely independent from, the hardware comprising the laser.

According to yet another example aspect, there is control to perform a step of circumferentially and radially irradiating surfaces of the tooth and root to denature or ablate bioactive bacterial products including lipopolysaccharide endotoxins.

According to another example aspect, the method includes diagnosing and assessing the effectiveness of treatment over time by such means as clinical examination, laboratory tests, noninvasive tools (including optical coherence tomography, infrared spectroscopy, acoustic microscopy), and other techniques.

Graphical User Interface

Figure 8:
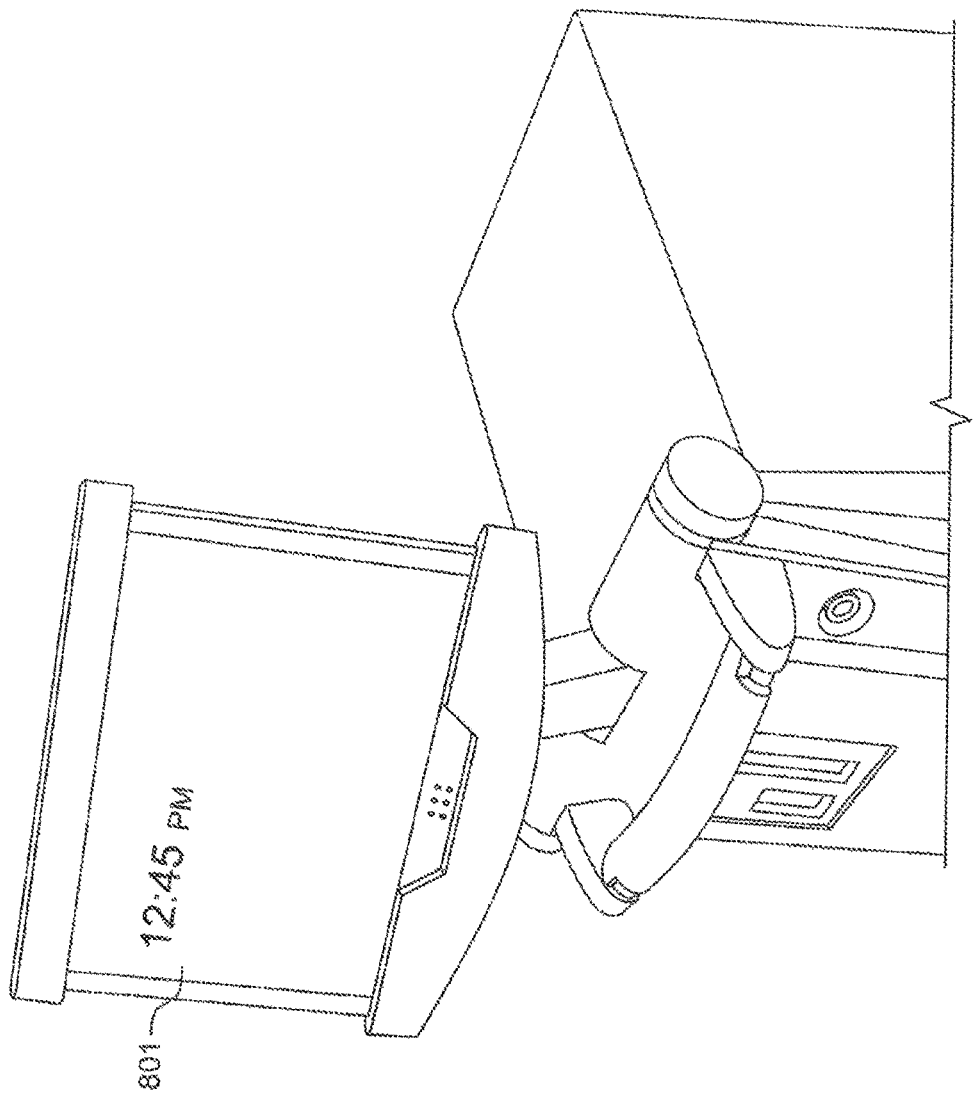
Figure 67:
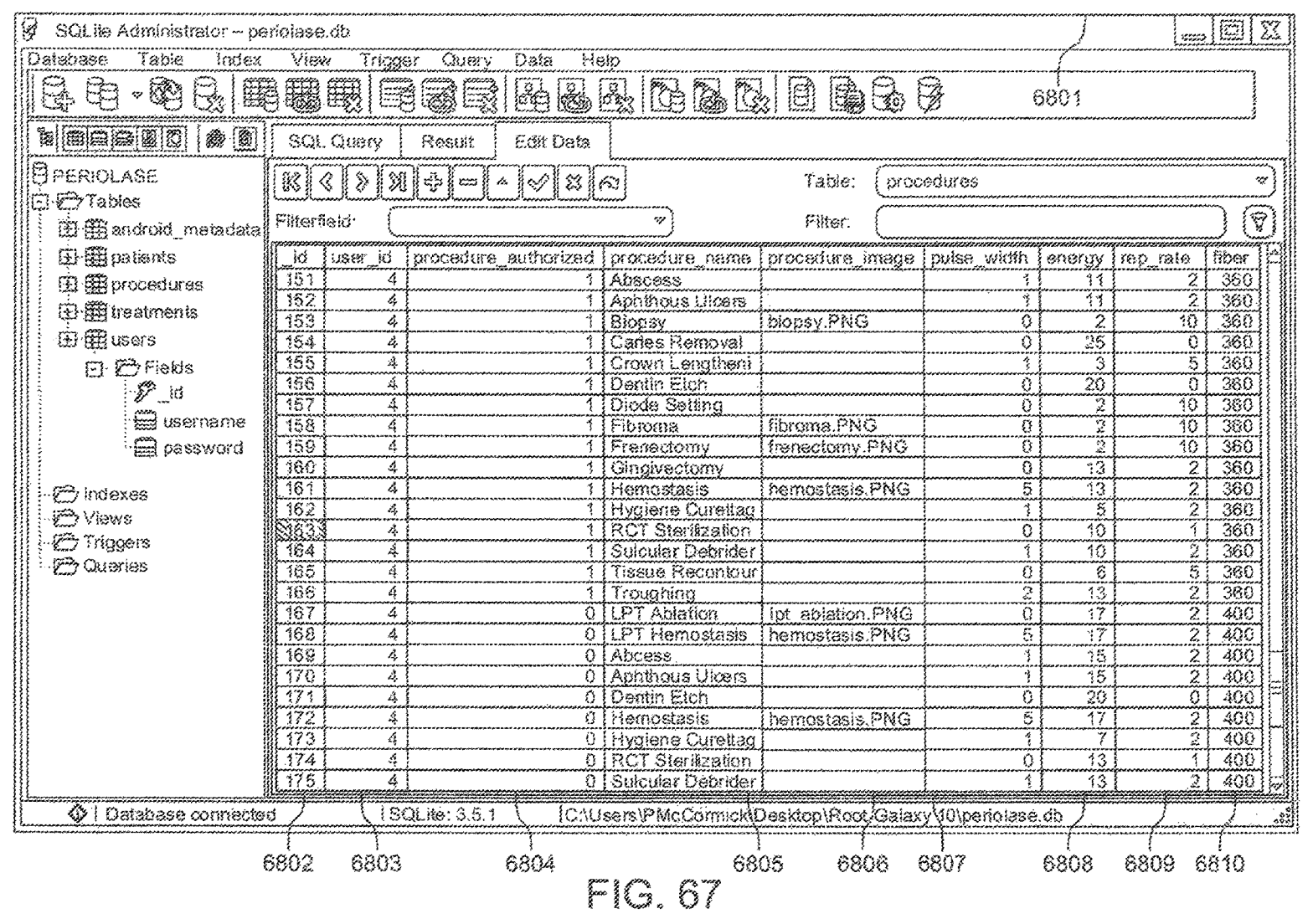

FIGS. 8 to 67 are views for explaining a graphical user interface (eGUI) according to example embodiments.

Figure 9:
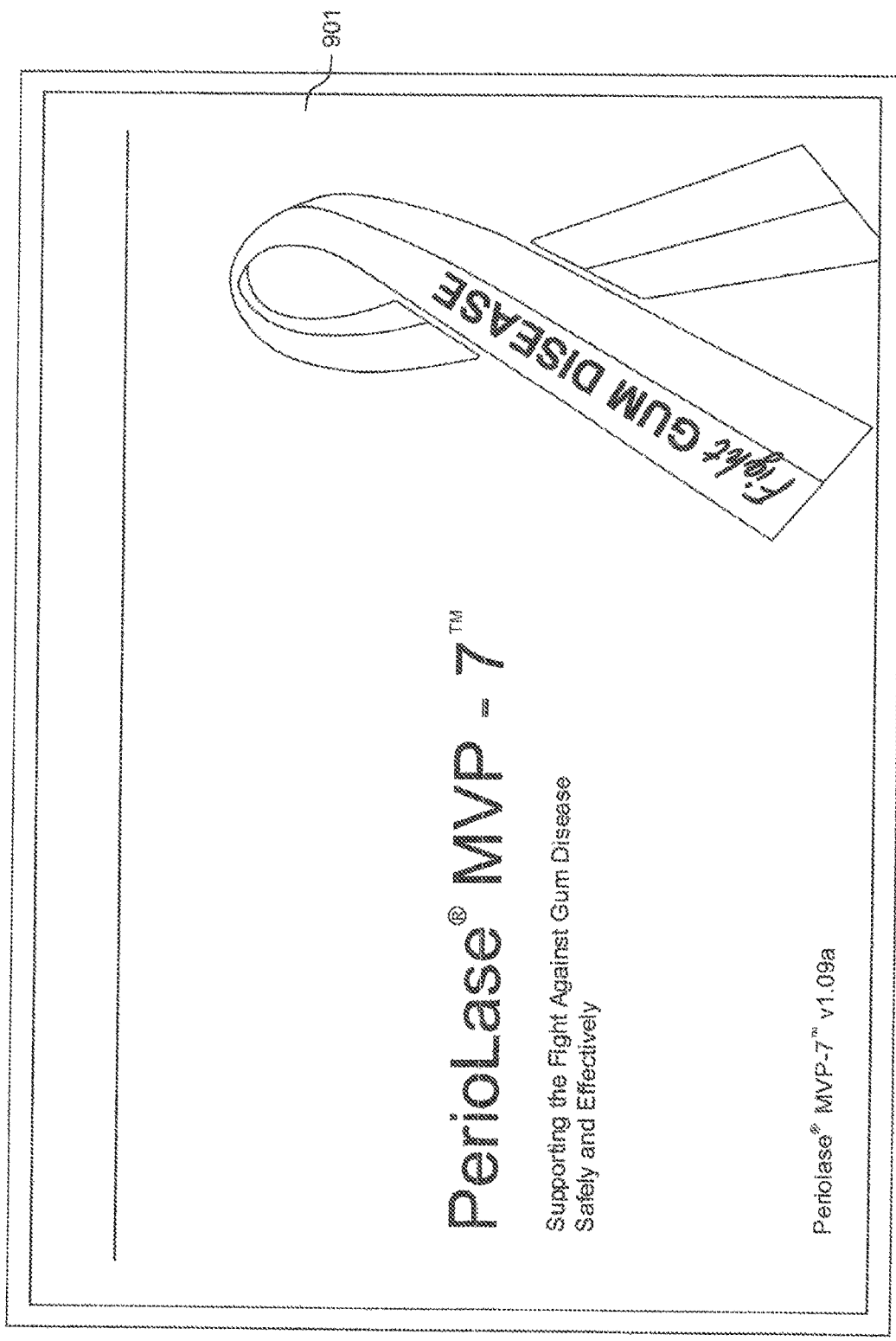
Figure 10:
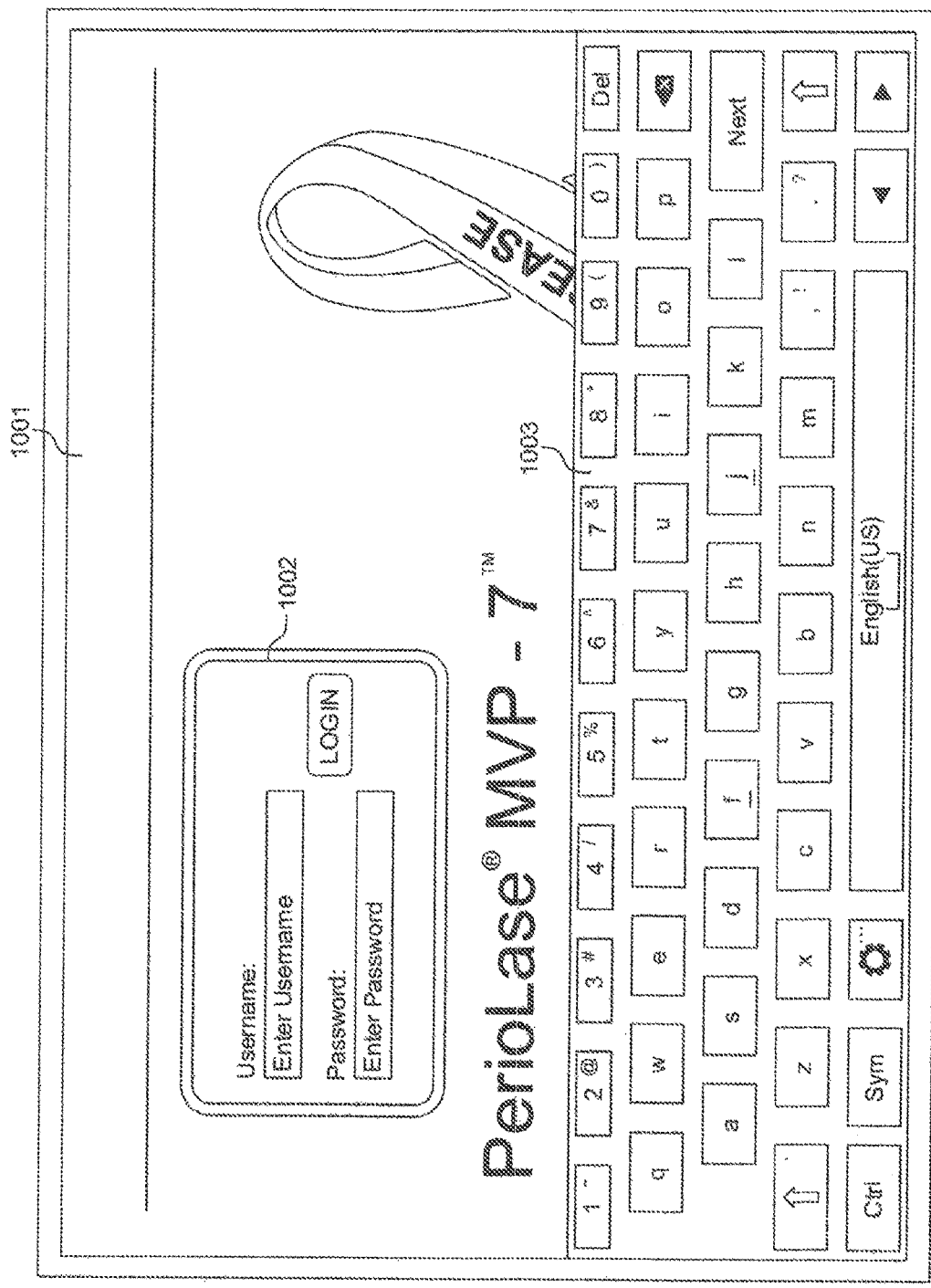

In that regard, FIGS. 8, 9 and 10 depict screens associated with a start-up procedure.

In one example start-up procedure, a main breaker switch (not shown), which is at the rear of main laser computer 300, should be in the OFF (0) position. A key is inserted and left in the OFF or vertical position (I), and a power cord is plugged into 120 VAC main power and to the rear of the main laser computer 300. Footswitch 314, fiber cannula 502, and an interlock plug (not shown) are manually connected. In one example embodiment, a wireless footswitch 314 may not have a cable connector attached like a standard footswitch. If so equipped, the wireless footswitch 314 can be activated using, e.g., a selector toggle switch on the back of the main laser computer 300 that indicates WIRELESS.

In the example start-up procedure, tablet 400 is powered on by pressing and holding a tablet power button on the upper left side of the tablet 400, until a start-up image 801 (shown in FIG. 8) begins to appear and tablet 400 initiates a boot-up process. At this time, main laser computer 300's main breaker (rear) can be turned to ON (I).

The main laser computer 300 splash screen 901, shown in FIG. 9, may automatically appear. A key switch can be turned to the horizontal (−) position, and a loading icon may momentarily appear at the upper right of the screen. The procedure then proceeds to a LOGIN screen 1001, shown in FIG. 10. As can be seen in FIG. 10, LOGIN screen 1001 includes a login window 1002 for a user to enter a username and password (e.g., as shown below), as well as a keyboard 1003 by which to enter this information. In one example, a user may select a username bar with a finger on touch screen 408, and keyboard 1003 may appear at that time. The user then uses keyboard 1003 to enter username and password. After that, the user may select the LOGIN button on login window 1002 to submit the information for verification. After a logout or switch users procedure, the LOGIN screen 1001 can be displayed again.

In one embodiment, the login credentials for the user may fall into four main categories: "Clinician" (e.g., a dentist or other user of the machine), "demo" (e.g., a demonstration mode for showing features of the product), "BootCamp" (a training mode in which user rights are limited), and a "service" mode for maintenance and other administrative procedures. Example usernames, password attributes, and rights for each are as follows:

LOGIN CREDENTIALS

| USERNAME | PASSWORD | RIGHTS |
| --- | --- | --- |
| Clinician | As Assigned | Access as trained |
| demo | password | all procedures |
| BootCamp | password | 360-μ procedures only no overrides |
| service | service | access to SERVICE MODES 1&2 |

As mentioned above, tablet 400 displays four primary control surfaces. These control surfaces include (in order from left to right): Procedures, Home, Patients, and Admin.

For first-time users, tablet 400 may allow the user to set up certain HOME screen features according to one's preference(s). This may include, for example, going to the Admin screen to select the time zone, auto power measurement mode, and start-up configuration check box options. Initial home Screen setup may include adding Patient data such as the patient name (first and last), and patient case number.

Figure 11:
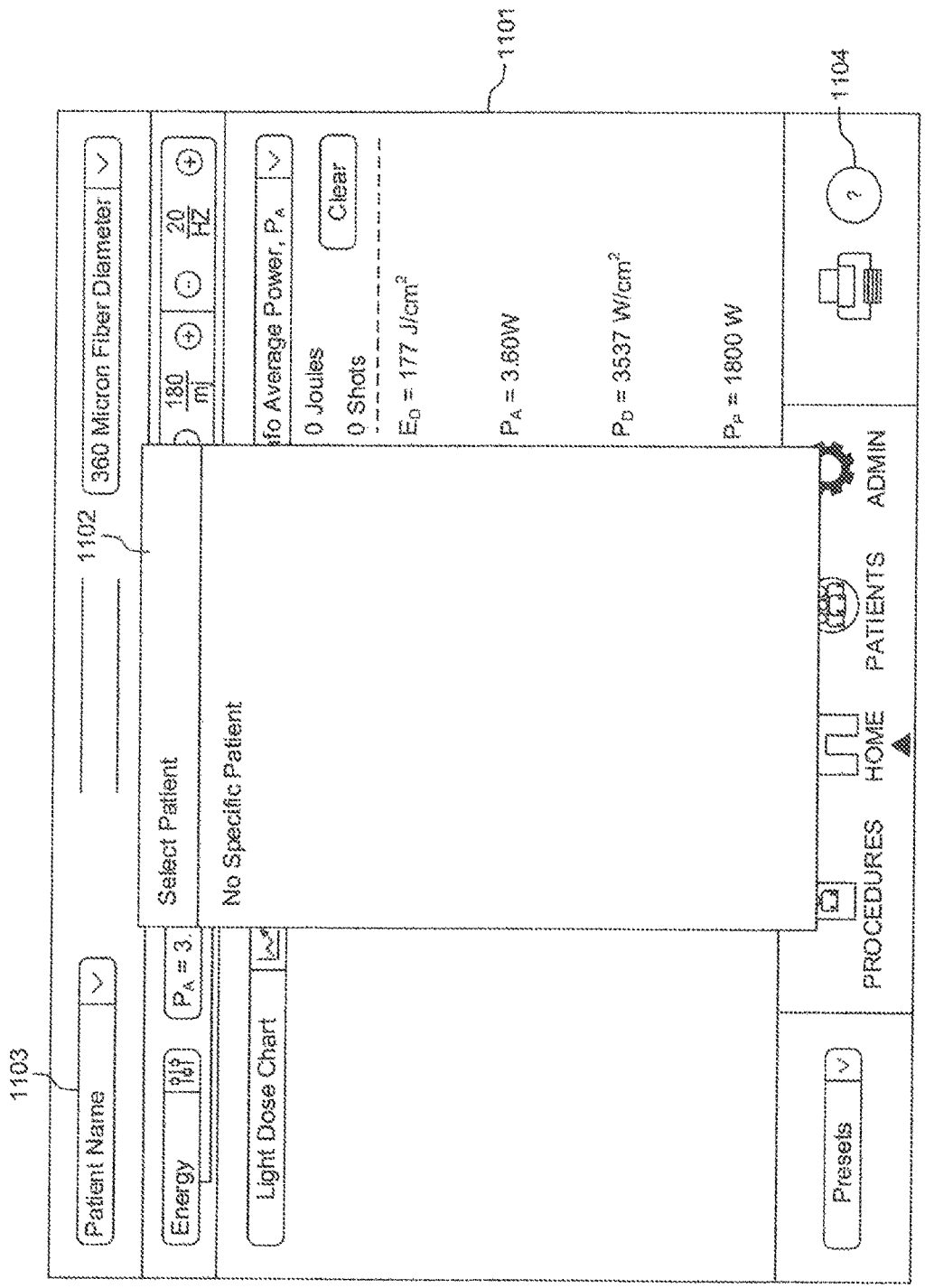

FIG. 11 is a view for explaining operations on a "Home" screen control surface 1101. As mentioned above, a home screen allows main command and control functionality, including control of patient management and of main functionality of the laser. As shown in FIG. 11, control surface 1101 allows a user to select a patient name. In that regard, the eGUI records treatment data which can be assigned to specific patients. The user can select a Patient Name icon bar 1103, and a separate pop-up box 1102 will appear with a drop-down list of selectable patient names. Upon selecting the Patient Name icon bar 1103, the user has a choice between two options. The first option is the default setting which is labeled as No Specific Patient and is listed as the first option in the drop-down list.

In addition, a help icon 1104 is accessible to the user on all 4 main screens of the eGUI. By selecting this icon, the user is displayed a pdf attachment of all the functions and features of all the 4 main eGUI screens.

Figure 12:
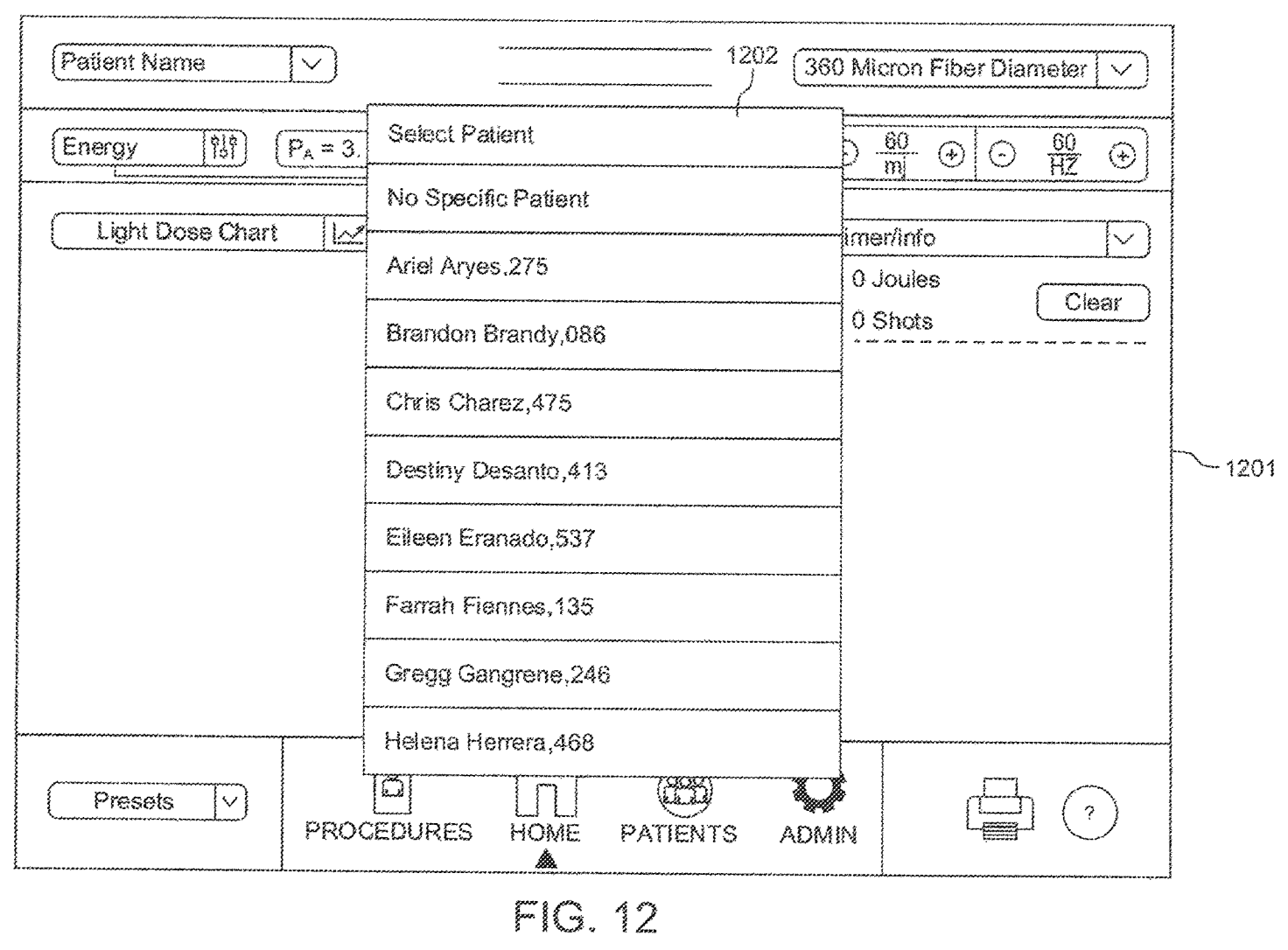

FIG. 12 shows another home screen control surface 1201, with a second option for selecting a patient. In particular, as shown in FIG. 12, the second option is a list of patient names that will appear in alphabetical order on the drop-down list 1202. The patient names that are displayed here are designated from the Patient Management/Reporting control surface.

Figure 13:
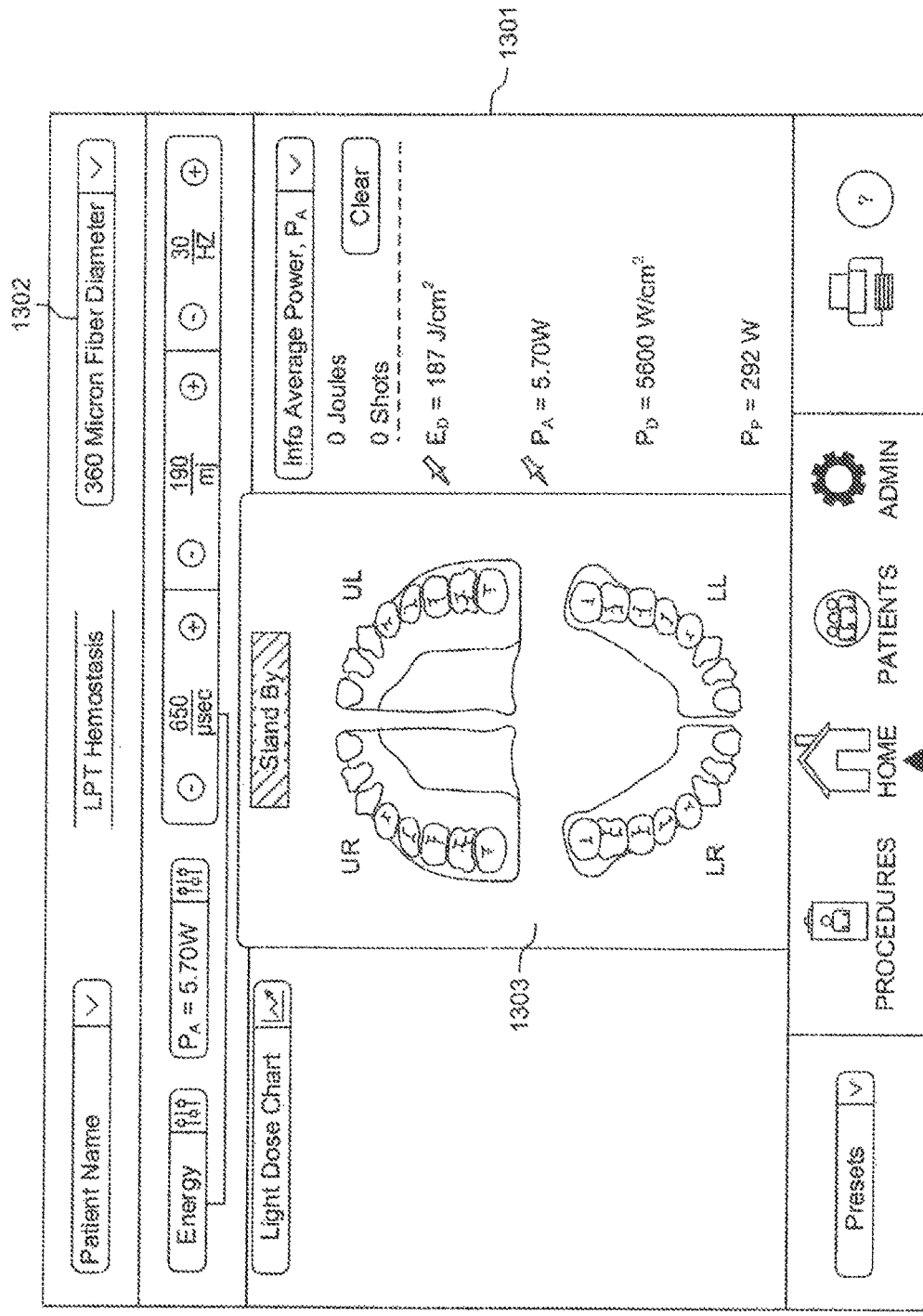

FIG. 13 is a view for explaining a control surface 1301 for procedure names and error messages. In particular, when a user selects a preset procedure from a Preset Procedures screen (which can be accessed by a right swipe from the home screen and is depicted in, e.g., FIGS. 14 and 49), the procedure the user has selected from this screen will be able to be seen on the home screen to the right of the Patient Name Icon Bar (here, "LANAP Hemostasis"). Control surface 1301 also includes a drop-down display of fiber diameters for laser delivery system 103, and an image of quadrants of the mouth 1303 which might be subject to the selected procedure. In addition, fiber diameter icon bar 1302, located at the upper right side of the home screen, is selectable so that a drop-down list of selectable fiber diameters in microns will appear, as discussed more fully below.

Figure 14:
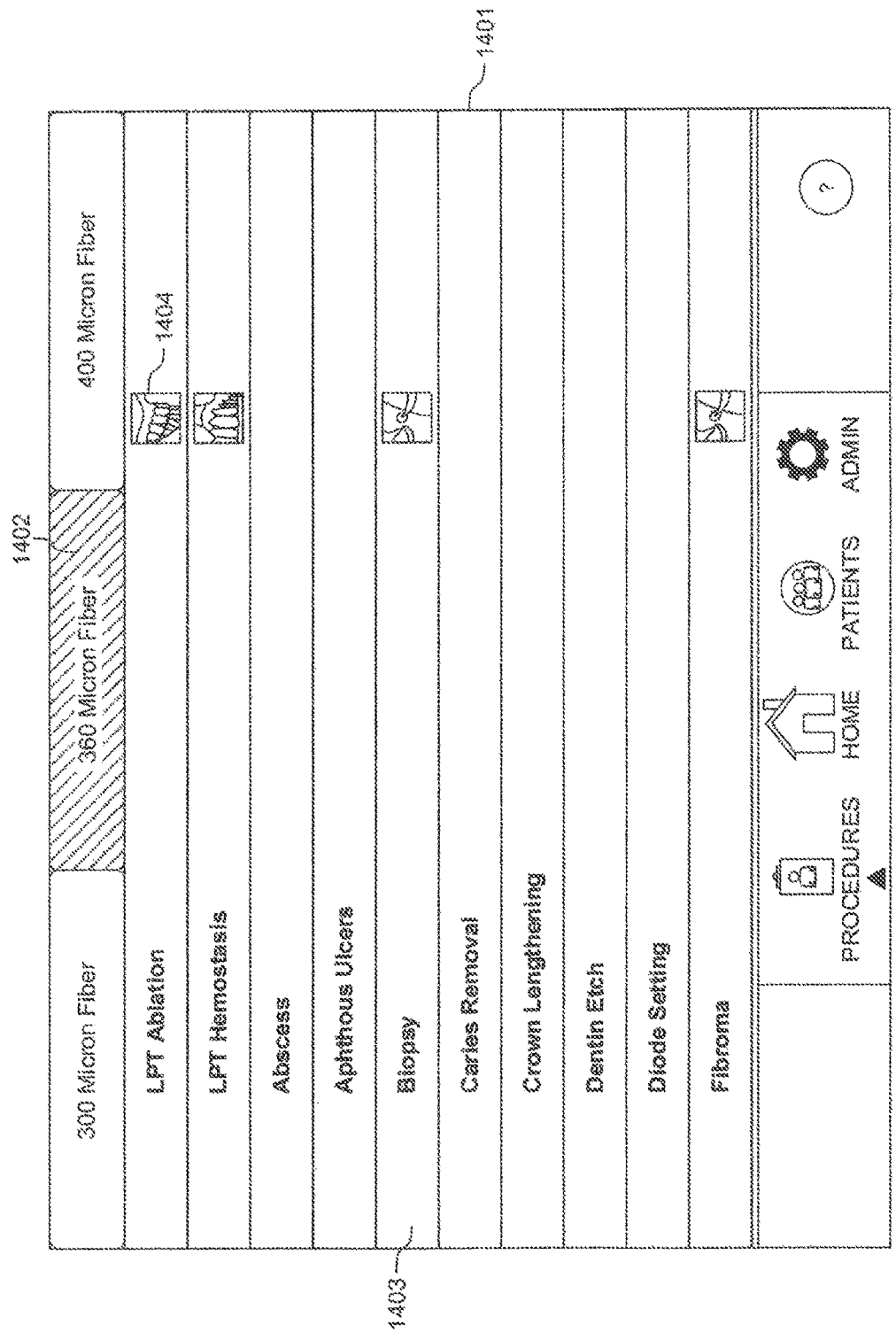

In another example, if the user has selected a LANAP® First Pass from the Preset Procedures screen, then that procedure will appear between the Patient Name icon bar and the Fiber Diameter icon bar. In that regard, FIG. 14 is a view of an example preset procedures screen 1401. As shown in FIG. 14, a selected fiber diameter 1402 corresponds to a list of preset procedures 1403 for that fiber diameter, which can then be selected by, e.g., tapping on the procedure. Certain procedures may have associated video or photos depicted by icons such as icon 1404, to assist in performing the procedure.

Figure 15:
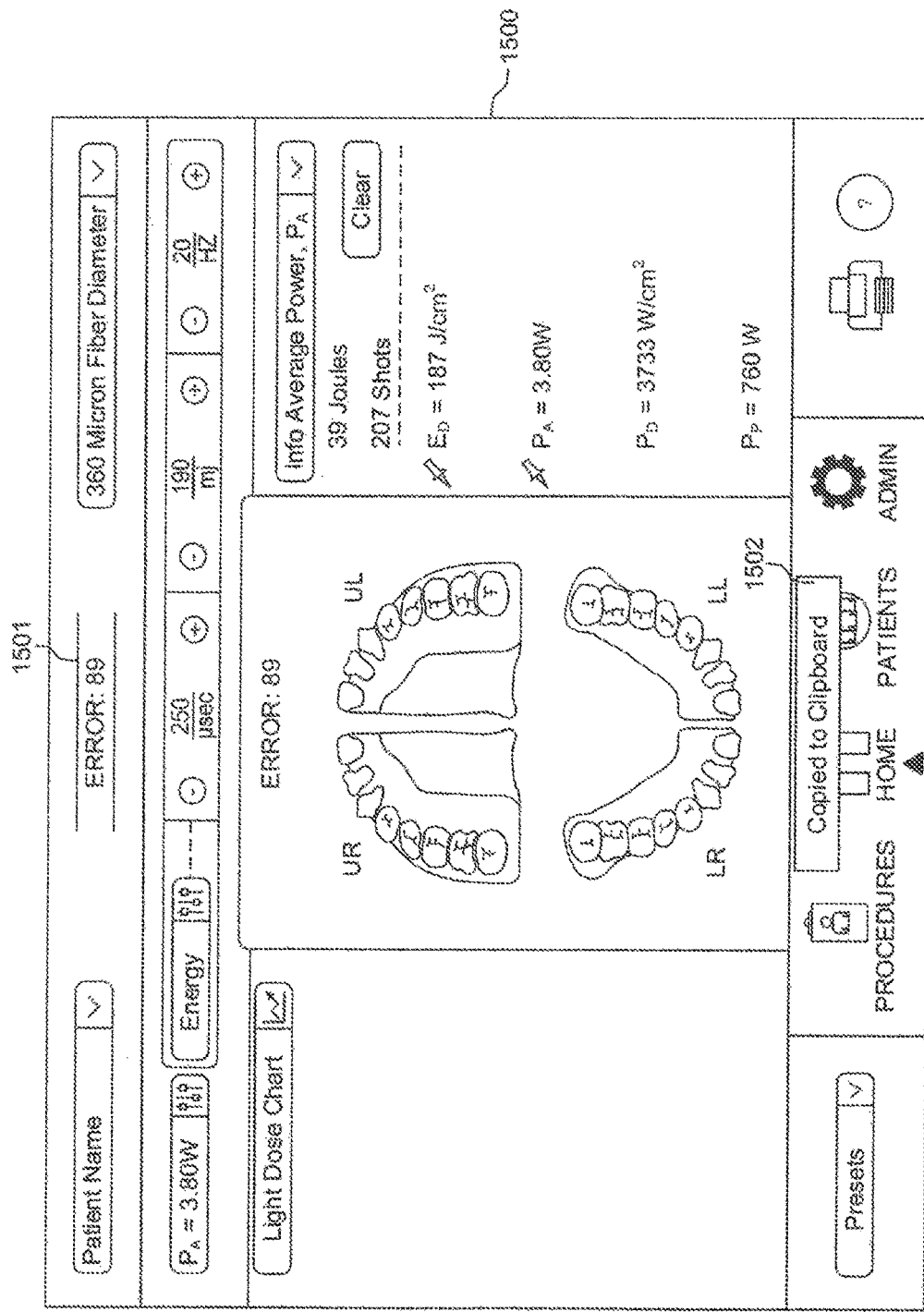

FIG. 15 is another view of the home screen, indicating a home screen control surface 1500 displaying an error code. Specifically, at location 1501, home screen control surface 1500 displays an error code 89. Thus, error messages appear in this location on the Home Control surface. A pop-up indication 1502 indicates that the error message is also being copied to a clipboard for later access. Examples of error codes are shown below, although it should be understood that these are merely examples, and other error codes or error conditions may be used:

| CODE | MEANING |
| --- | --- |
| "INT" | Interlock circuit is open (Standby Mode) |
| "TEM" | Temperature is >70 degrees C. (Standby Mode) |
| "FSW" | Footswitch is partially or fully active (Standby Mode) |
| "FIB" | Fiber is missing (Standby Mode) |
| "INTERLOCK" | Interlock circuit is open (non-Standby Mode) |
| "TEMPERATURE" | Temperature is >70 degrees C. (non-Standby Mode) |
| "FIBER" | Fiber is missing (non-Standby Mode) |
| E81 | Fiber sensor is stuck in the ON state |
| E82 | Temperature sensor indicates <2 degrees C. |
| E83 | Temperature sensor indicates >80 degrees C. |
| E84 | Coolant flow switch is closed when the pump should be off |
| E85 | Coolant flow switch is open when the pump should be on |
| E88 | Insufficient energy detected during firing |
| E89 | Excessive energy detected during firing |
| E90 | High voltage present when it should not be |
| E93 | Energy detector calibration factor corrupted |

FIGS. 16 to 20 are views for explaining a preset procedure overwrite, which allows the user to overwrite the therapeutic parameters of the Preset Procedures listed on the Preset Procedures Screen. To enable this feature, the user must select a Preset Procedure from the Preset Procedures Screen. The Preset Procedures screen can be accessed by a right swipe from the home screen. A user may select a preset procedure by, e.g., "clicking" or tapping on it, and be automatically brought back to the home screen after the desired preset procedure has been selected.

Figure 16:
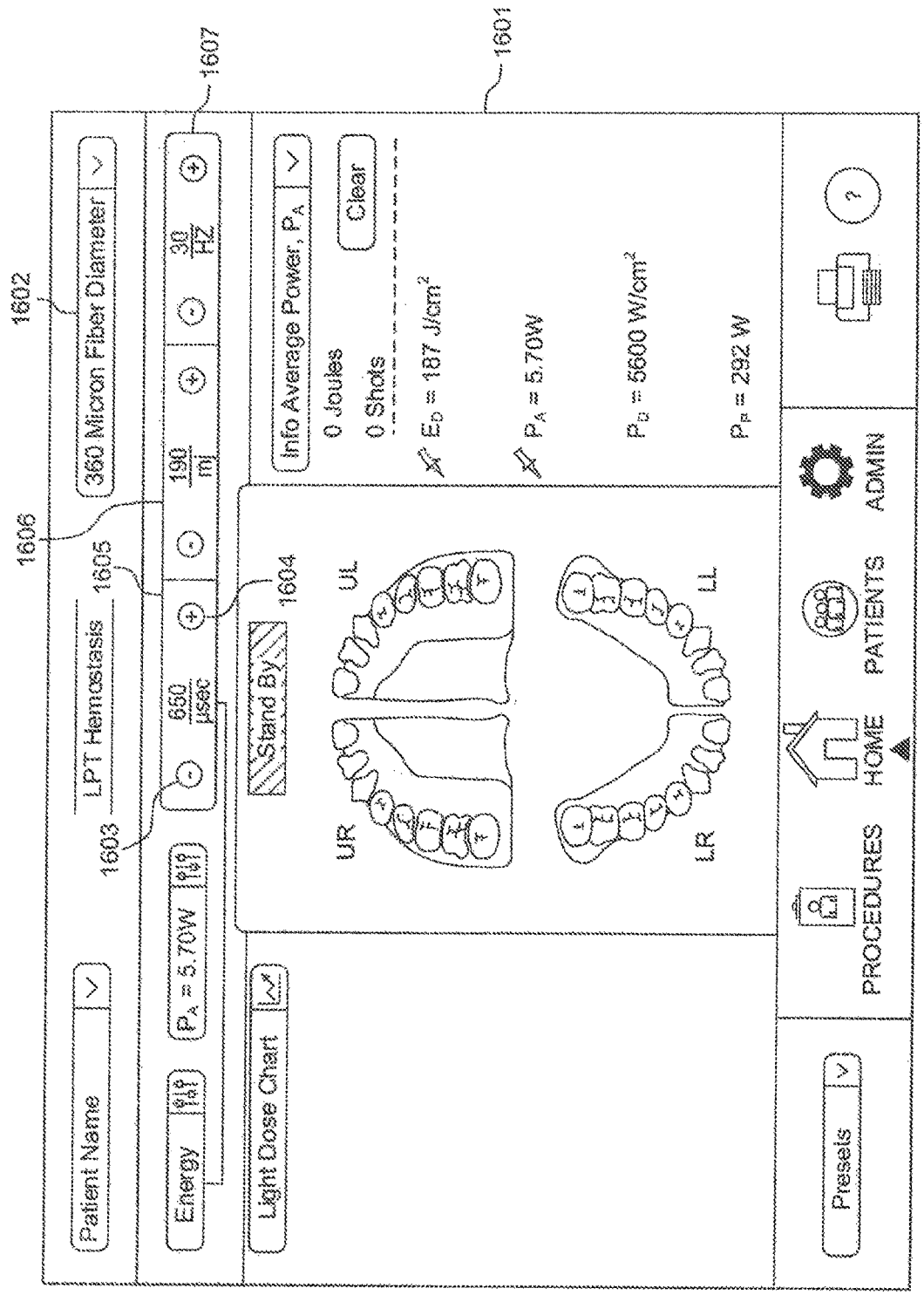
Figure 17:
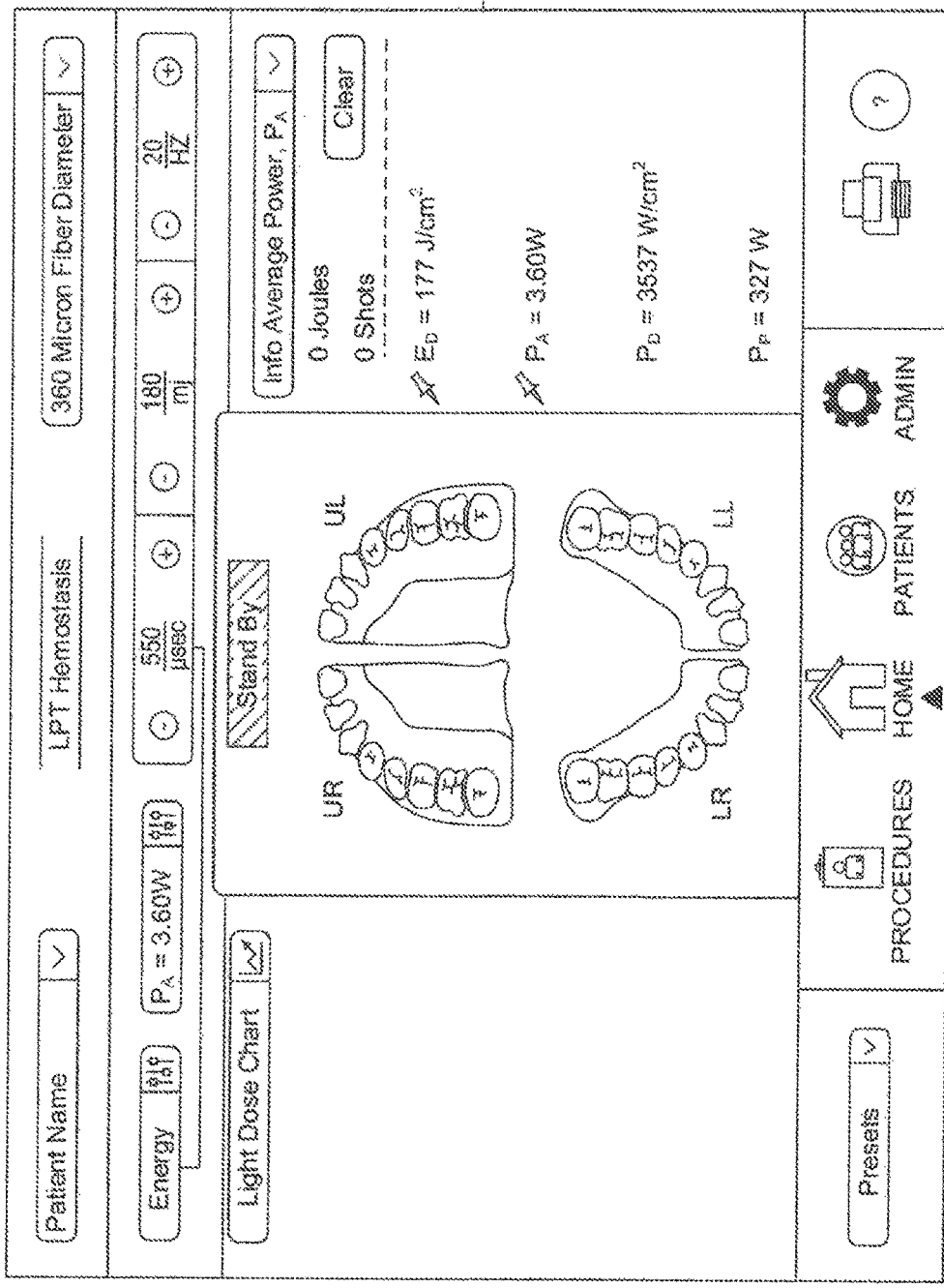

As shown in FIG. 16, a control surface 1601 for the home screen in the preset procedure overwrite depicts icons showing the therapeutic parameters or the energy settings: pulse duration in μsec 1605, instantaneous energy in mJ 1606, and pulse repetition rate in Hz 1607 of the Preset Procedure, which can then be manipulated by using the (+) and (−) symbols (e.g., 1603 and 1604) next to each parameter. In addition, fiber diameter icon bar 1602, located at the upper right side of the home screen, is selectable so that a drop-down list of selectable fiber diameters in microns will appear, as discussed more fully below. FIG. 17 depicts a control screen 1701, where the therapeutic parameter settings of LANAP Hemostasis, namely, 550 μsec, 180 mJ, and 20 Hz have been changed to 650 μsec, 190 mJ and 30 Hz as shown in FIG. 18.

Figure 18:
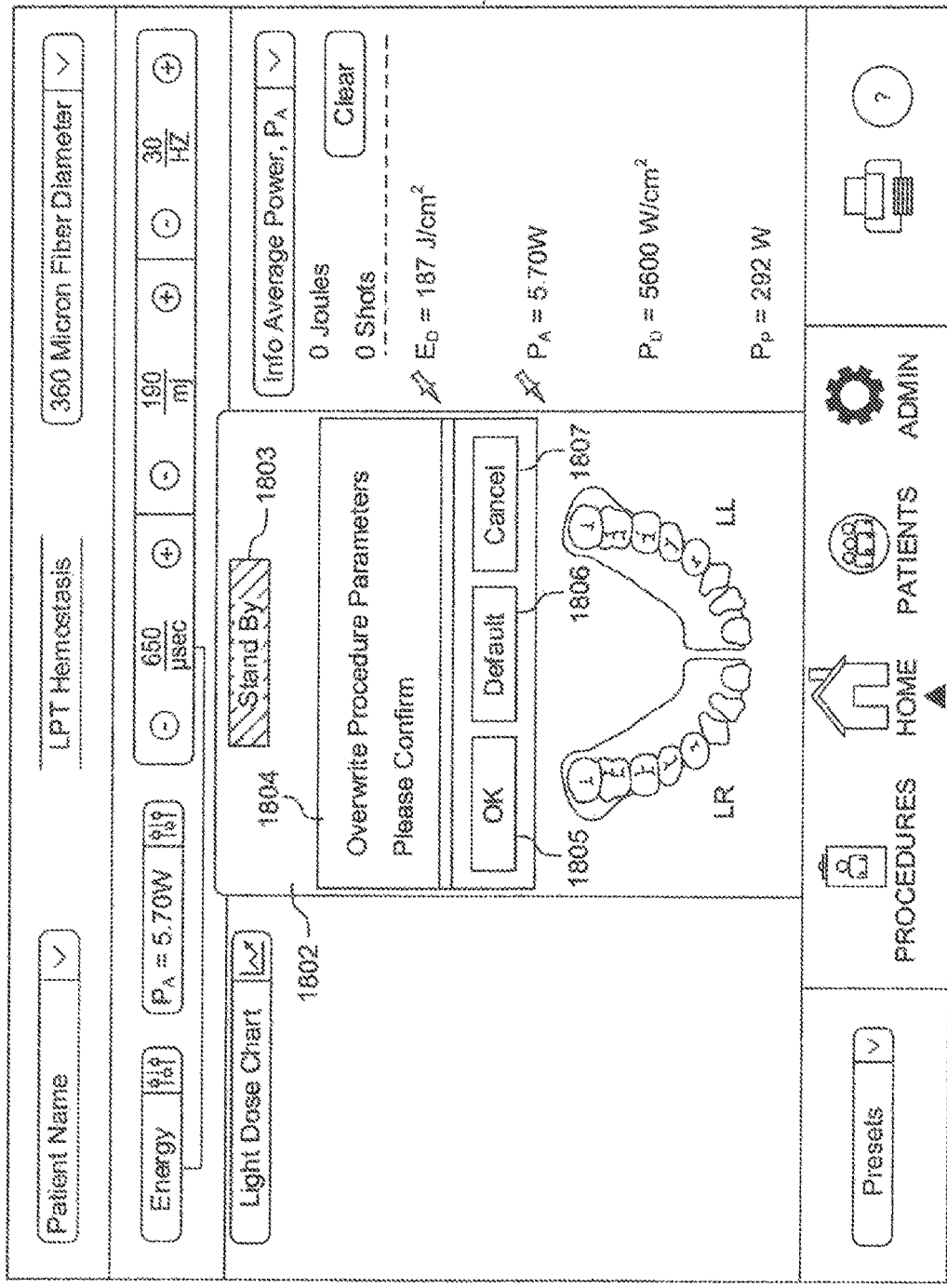

In one example, as shown in FIG. 18, after the user makes a change in the therapeutic parameters and performs a long press on the Preset Procedure (located in between the Patient Name and Fiber Diameter icon bars), a separate pop-up box 1802 will appear on a control screen 1801 that includes a "Stand By" indication 1803 and a message box 1804 stating: "Overwrite Procedure Parameters, Please Confirm." The user is provided with icons 1805, 1806 and 1807 to select to proceed, return to default parameters, or cancel, respectively. If the user selects the Ok icon 1805, the therapeutic parameters or corresponding energy settings are saved in accordance with the changes selected.

Figure 19:
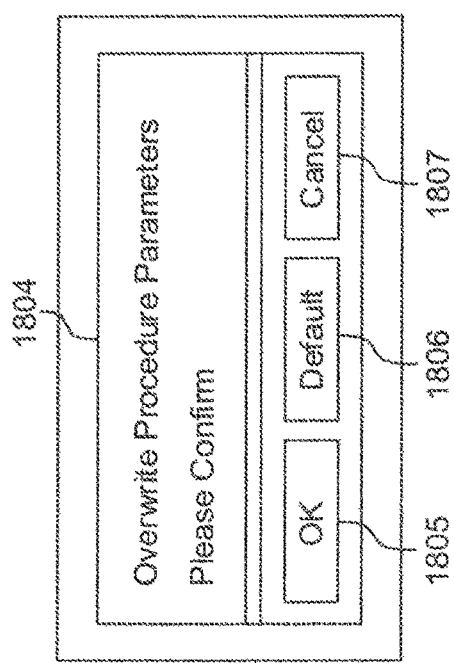

FIG. 19 is another view for explaining a preset procedures restore. In that regard, there are two ways that the user can restore the treatment preset procedure(s) back to their original default settings. The first option is to restore the preset procedure individually, from the home screen surface. To initiate a preset procedure restore, the user selects the preset procedure to restore to factory default settings from the procedures screen, and is brought back to the home screen. In one example, a long press on the Preset Procedure (located in between the Patient Name and Fiber Diameter icon bars) causes the message box 1804 stating "Overwrite Procedure Parameters, Please Confirm" to appear as a separate pop-up box, again. The user is again provided with icons 1805, 1806 and 1807 to select to proceed, return to default parameters, or cancel, respectively. If the user selects the icon 1806, the therapeutic settings are restored to their default settings.

Figure 20:
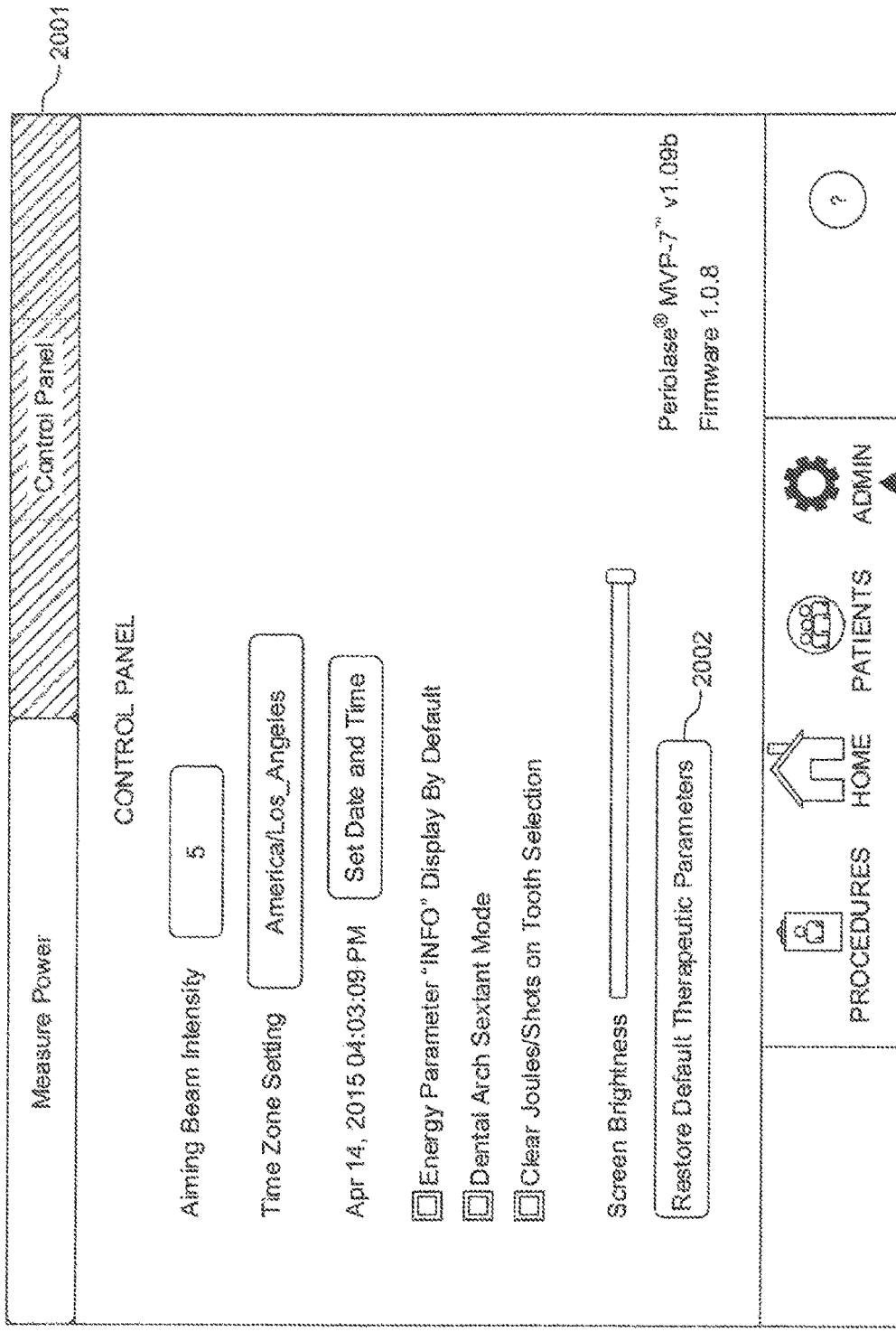

FIG. 20 is a view for explaining another option for restoring default settings. In particular, FIG. 20 depicts a control surface 2001 which is obtained by swiping to the "Admin" screen (explained above) and selecting a Control Panel tab. At the bottom of the surface 2001 is an icon bar 2002 that displays "Restore Default Therapeutic Parameter Settings". Upon selection of this feature, all the therapeutic parameter settings that have been previously overwritten will go back to their original default settings.

Figure 21:
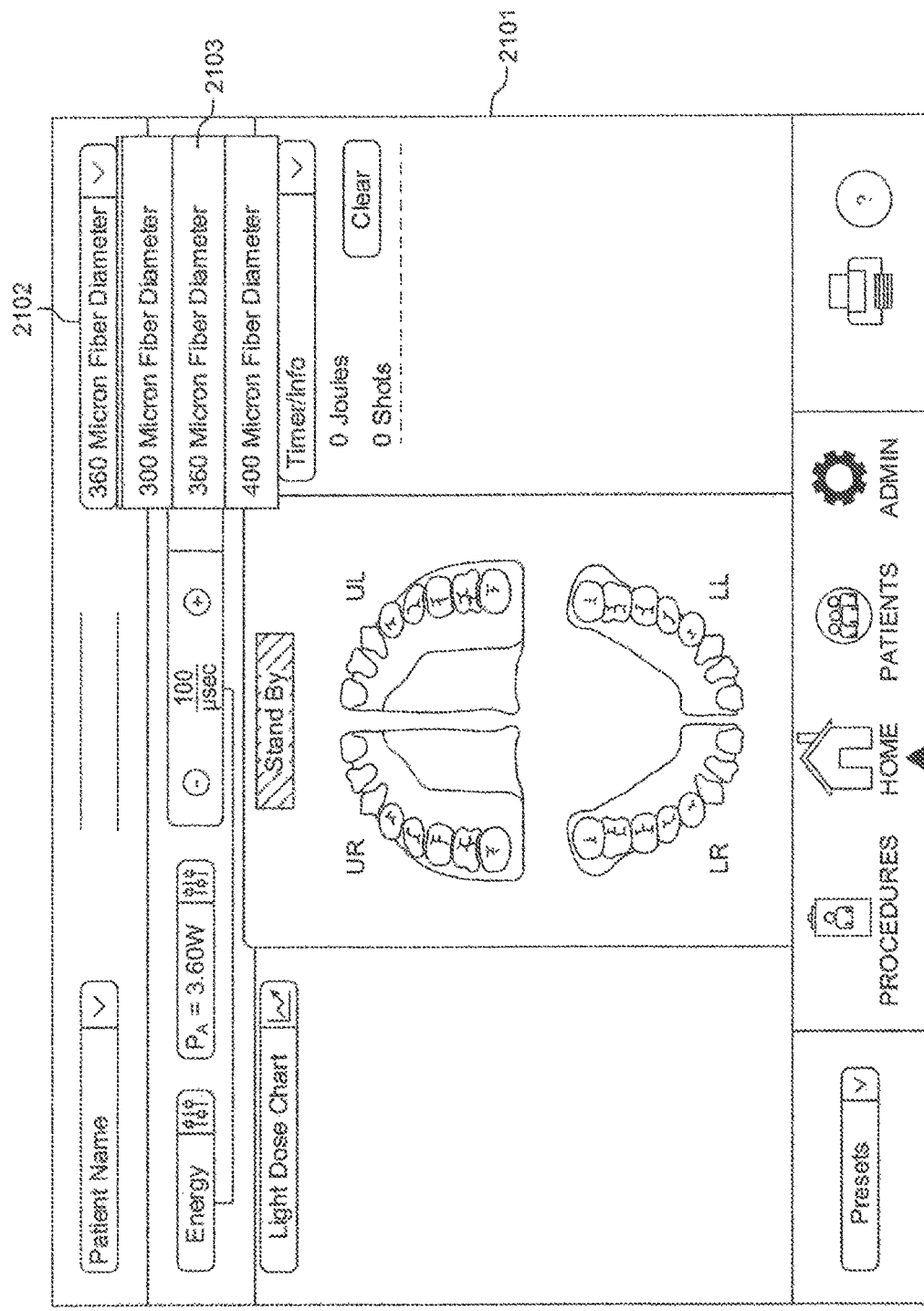

FIG. 21 is a view for explaining selection of a fiber diameter. In particular, in the updated home screen 2101, the user has selected the Fiber Diameter icon bar 2102 which is located at the upper right side of the home screen. A drop-down list 2103 of fiber diameter in microns will appear: 300μ, 360μ, 400μ (in some examples, fiber diameters are color-coded on the home screen). The user may then select the fiber that corresponds with the one presently installed. In that regard, in certain embodiments, only certain login credentials can access certain fiber diameters.

FIGS. 22 to 29 are views for explaining control of energy settings.

Figure 22:
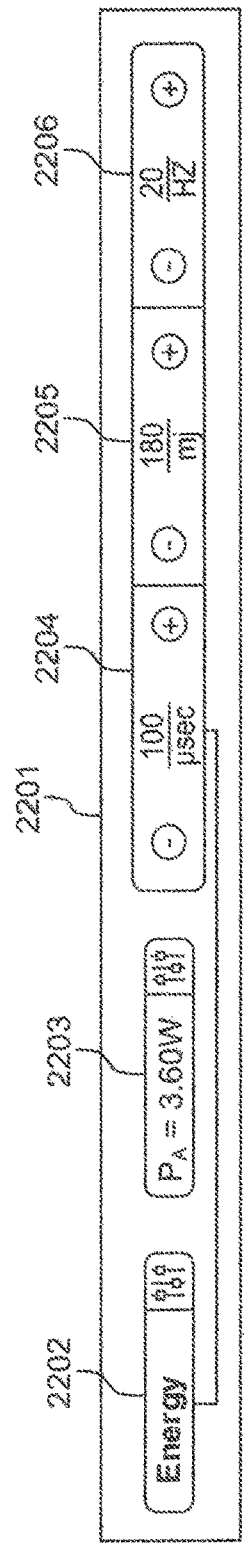

In particular, FIG. 22 is a view individually showing an Energy icon bar 2201 which is included on the various home screens (e.g., FIG. 11, FIG. 13, etc.). Energy icon bar 2201 is a control grouping which changes the therapeutic parameter settings. The fundamental therapeutic parameters are average power (PA) 2203, Pulse Duration in microseconds (μsec) 2204, Energy in millijoules (mJ) 2205, and pulse repetition rate 2206, in pulses per second (Hz). The user can change the primary therapeutic parameter settings individually by selecting μsec, mJ, and Hz by pressing the adjacent (+) and (−) icons. In addition, by selecting the stand-alone icons for energy 2202 or PA 2203 with corresponding images depicting sliders for various parameters, the user can access sets of the different parameters at the same time and scroll through to see their relationships and allowed/disallowed values for each parameter, depending on the settings of the other parameters.

Figure 23:
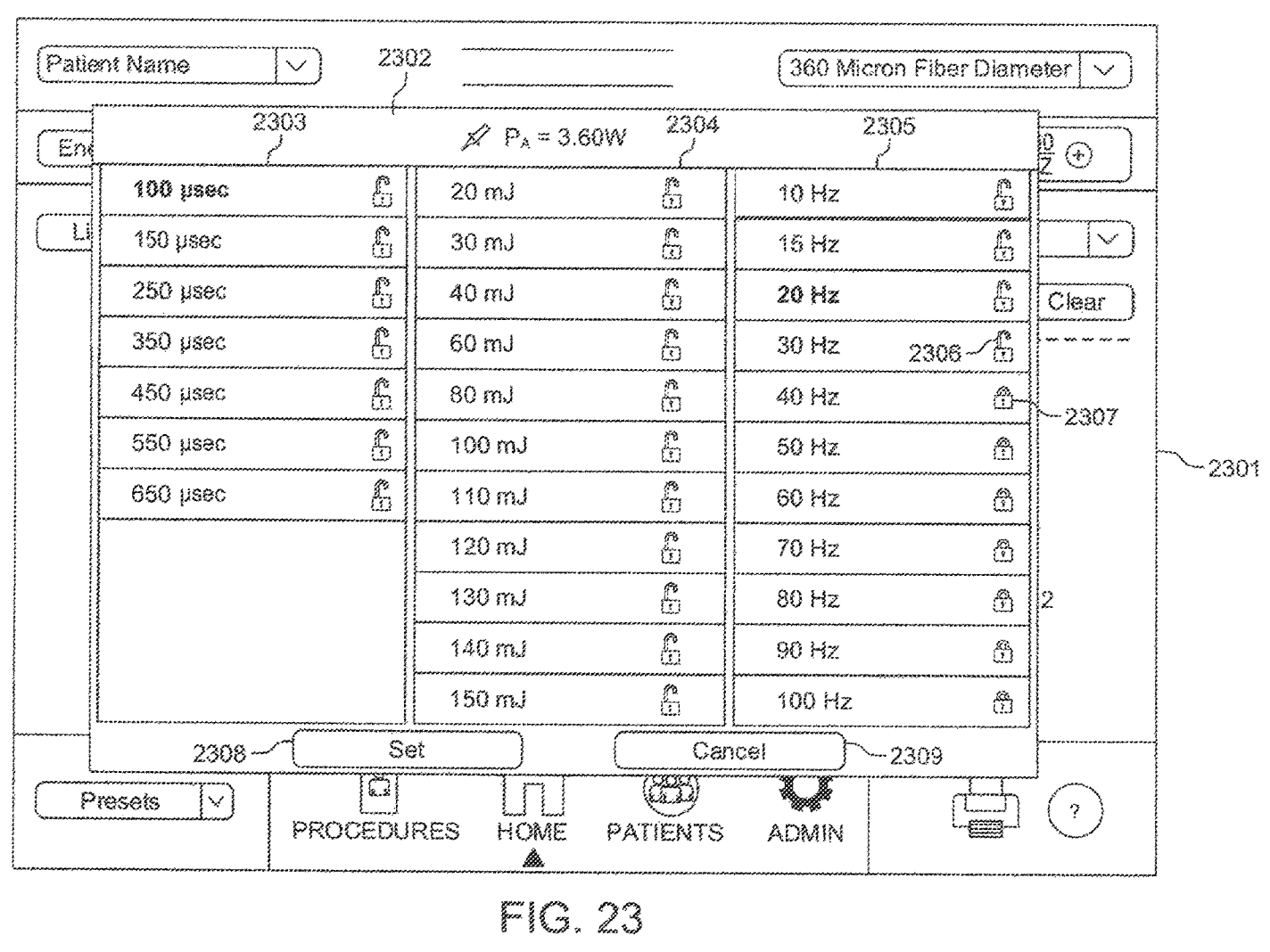

Specifically, as shown in FIG. 23, to visualize the relationships between the fundamental therapeutic parameters after selecting the Energy icon bar, a pop-up box 2302 will appear on the control surface 2301 with three different columns from left to right: μsec column 2303, mJ column 2304, and Hz column 2305. Settings that have an "unlocked" lock icon 2306 (which may be colored, e.g., green) next to them indicate those parameters which are available to be selected, whereas parameters with a "locked" lock icon 2307 (which may be colored, e.g., red) indicate that those values are currently prohibited, at least with the other parameters at their current settings. Using a finger, the user may scroll up and down within a parameter column to observe values above or below those presently displayed. A user may change from among the three fundamental therapeutic parameters and observe the corresponding average Power, PA, values. A user may also select a set button 2308 to accept designated set of therapeutic parameters, or a cancel button 2309 to return without changes.

Figure 24:
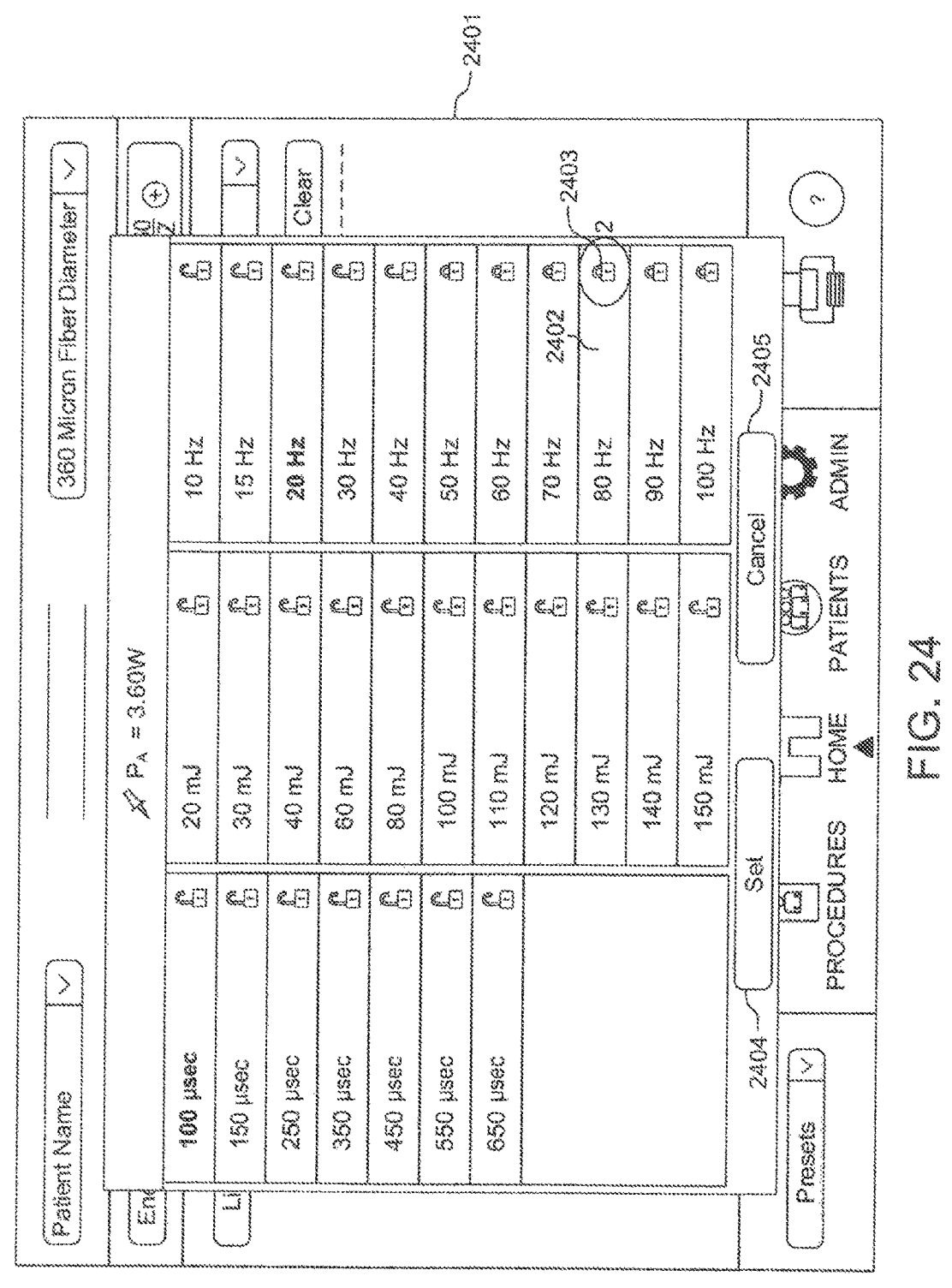

FIG. 24 is a view for explaining a control surface 2401 for providing an override feature of energy settings (therapeutic parameter settings) with a red lock icon (e.g., lock icon 2403 for Hz setting 2402) that may be selected using an override procedure. To initiate the override feature, the user must select the therapeutic parameter (whether it is mJ, or Hz) that has the red locked icon. Once selected, the therapeutic parameter with the red locked icon may change display (e.g., turn "unlocked" and green). Meanwhile, other therapeutic parameters allowed using this override condition will be designated with a revised set of green unlocked icons. A user may also select a set button 2404 to accept a designated set of therapeutic parameters, or a cancel button 2405 to return without changes.

Figure 25:
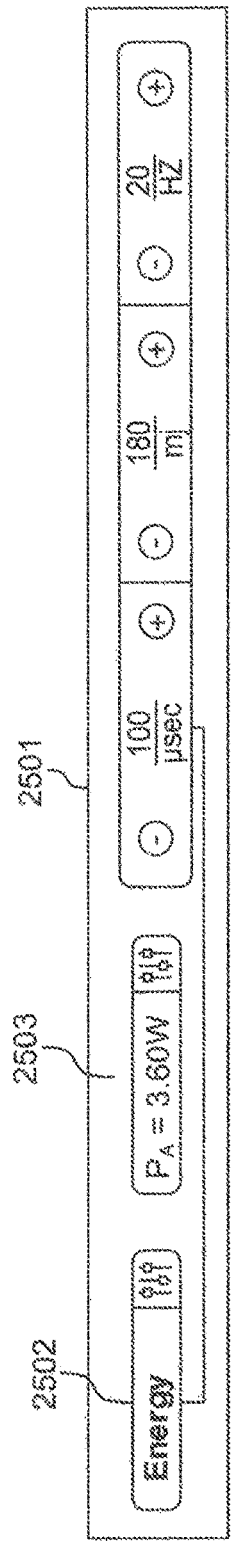
Figure 26:
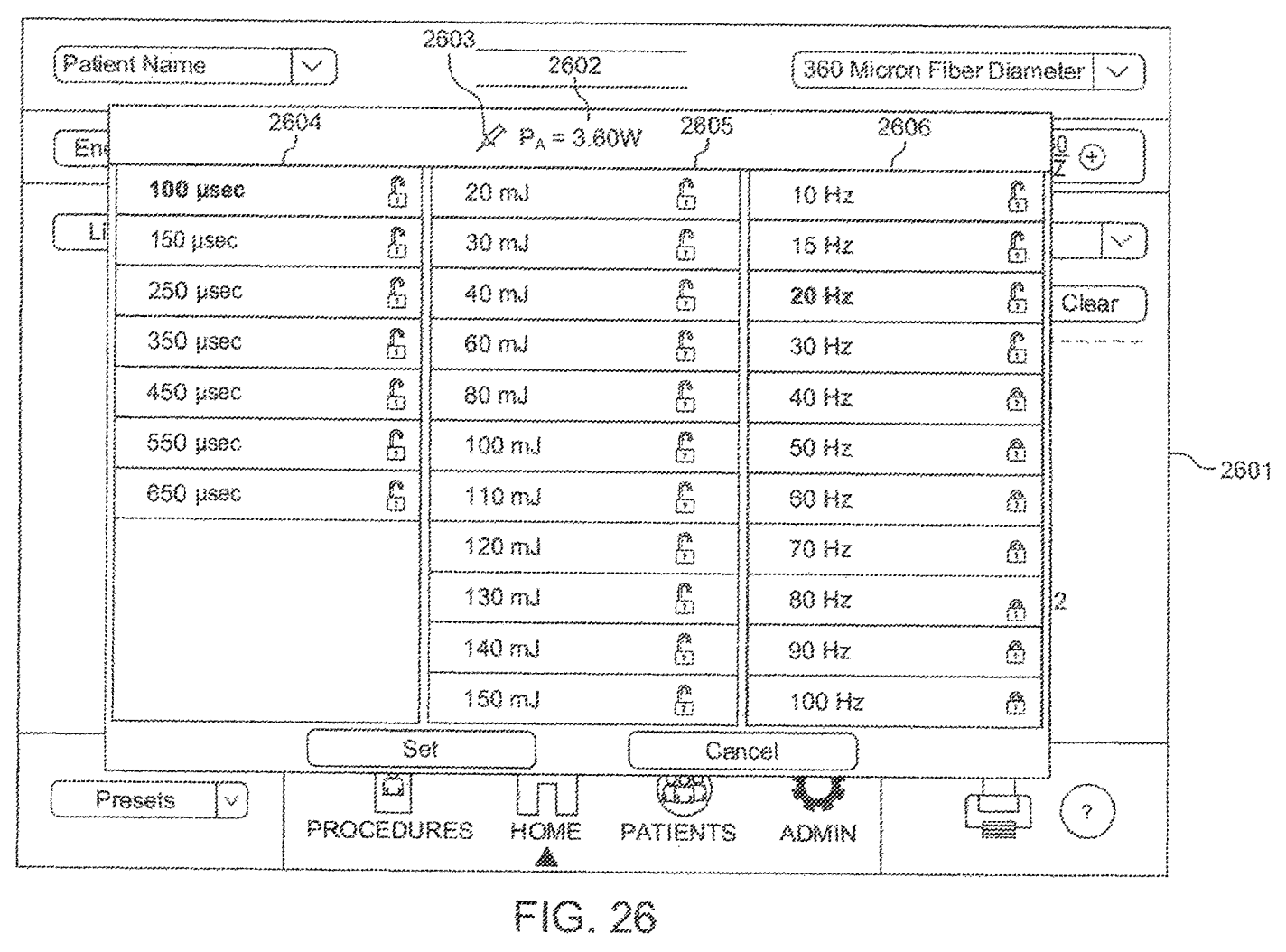
Figure 27:
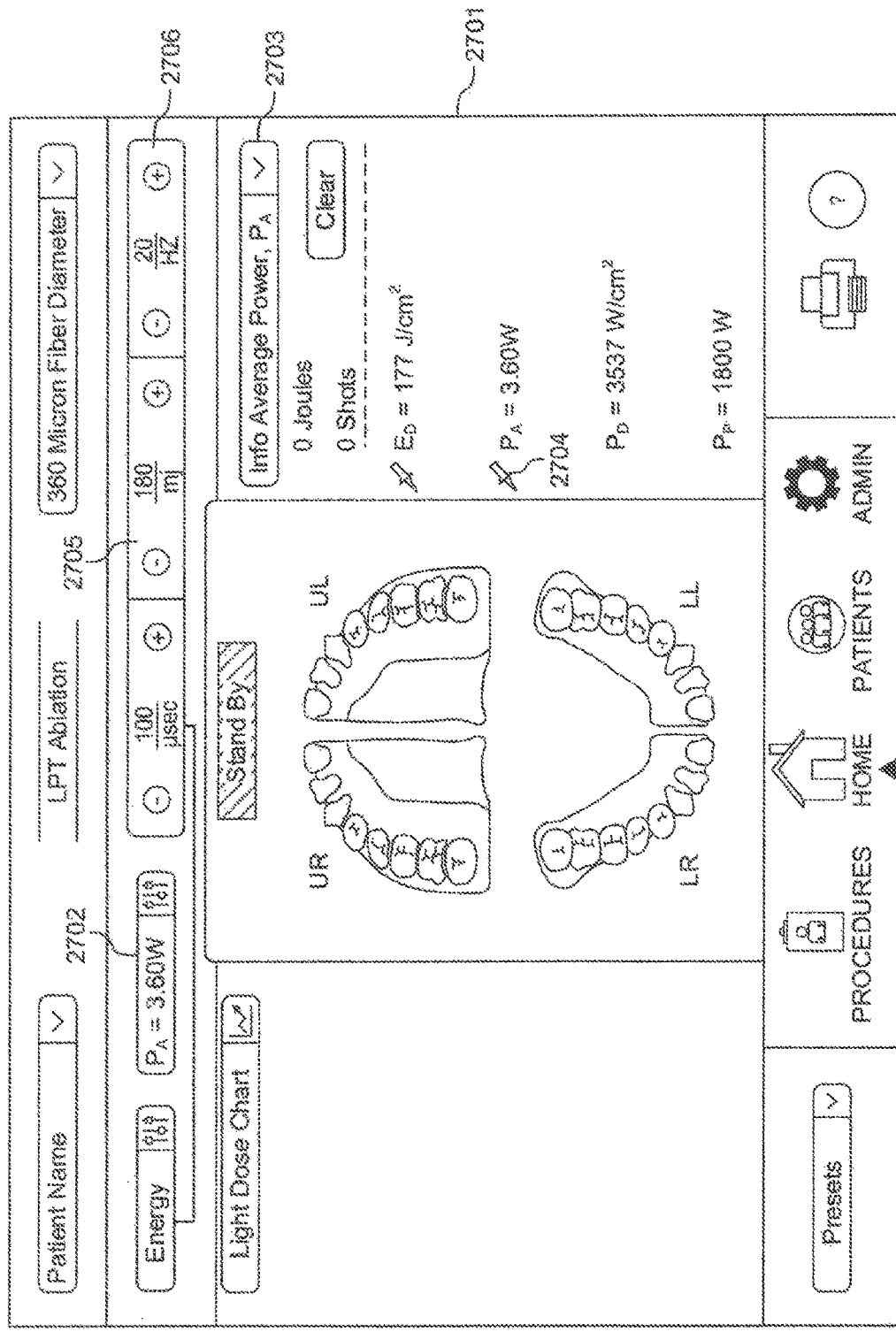

FIGS. 25, 26 and 27 are views for explaining another feature called average power hold, which can be accessed in the Energy icon bar (e.g., by selecting icon 2502 or icon 2503 on bar 2501 in FIG. 25).

Turning to FIG. 26, at the top of the pop-up box on control screen 2601, the Average Power 2602, PA, value can be seen along with an icon 2603 that looks like a thumbtack next to it.

Selecting the thumbtack icon 2603 next to the PA will fix the average power value. Selecting another Pulse Repetition, Hz, from list 2606 will change to a corresponding energy value in millijoules, mJ, which will maintain this average power value. Likewise, after the user changes an energy value, mJ, from list 2605, or changes a duration value in μsec from list 2604, the system will select the corresponding pulse repetition, Hz, to maintain the designated PA value.

The Average Power Hold feature is also available on another part of the home screen, as shown on control screen 2701 in FIG. 27. Specifically, under the Timer/Info icon bar, the user is provided with the option of selecting Info Average Power PA icon 2703 on the drop-down list next to PA and can also see the Average Power hold thumbtack feature icon 2704. If the user fixes the PA value by selecting the thumbtack icon 2704 the user may thereafter change either Hz or mJ using the +/− icon bars 2705 and 2706, and the system maintains the PA value fixed by the thumbtack. This value may also be shown on the same screen by PA icon 2702.

Figure 28:
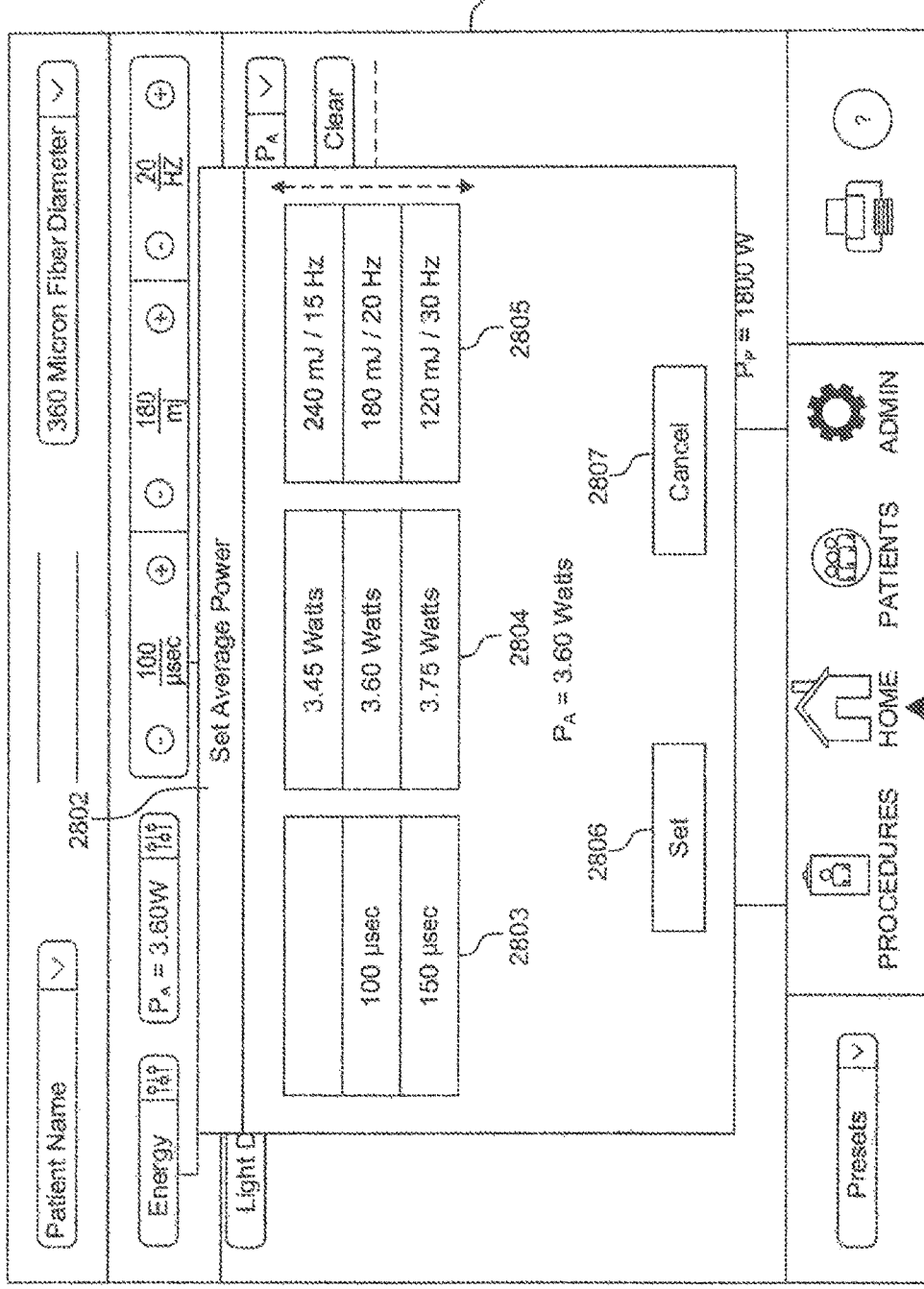
Figure 29:
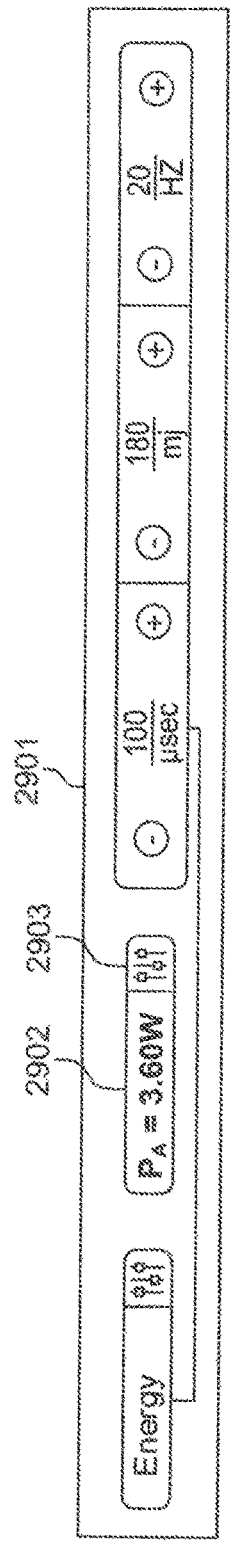

Turning to FIGS. 28 and 29, the Average Power, PA, can also be directly designated when the clinician selects the icon PA, e.g., either PA numerical display 2902 or parameter shift image 2903 on the energy icon bar 2901. Turning to FIG. 28, the pop-up window 2802 correspondingly displayed on a screen 2801 has a thumbwheel control using a rolling up-and-down motion. The first step is to select the desired Average Power, Watts, using the center thumbwheel 2804. Available combinations of mJ and Hz can now be selected for this PA using the thumbwheel 2805 on the right. The user may also use the left side thumbwheel 2803 to select from the available pulse durations, μsec, to complete the selection. The user is also provided with a set button 2806 to set the parameters, and a cancel button 2807 to cancel the operation.

Thus, the thumbwheel visual allows for a convenient visualization of parameters and their relationship. For example, having set one parameter (or a separate value such as PA), the user is provided with another thumbwheel by which to choose other parameters. In addition, in one example, the user may set an average power for the laser via a user interface on the tablet, and then select from a set of permissible laser parameters provided in response to the selected average power. Accordingly, it is ordinarily possible for a user to, for example, work backward to select laser parameters from the average power, rather than relying on trial and error.

FIGS. 30 to 33 are views for explaining light dose tracking and display according to example embodiments. As mentioned above, a light dose chart may show an amount of laser dosimetry over time, as well as a line indicating the maximum dosage allowed for that tissue/procedure. For example, the procedures screen may, using information from the patient records, determine a disease being treated and a dosage administered thus far, and display a "max" line on a graph, with a dosage line which increases in real time toward the maximum as further laser dosage is applied.

Figure 30:
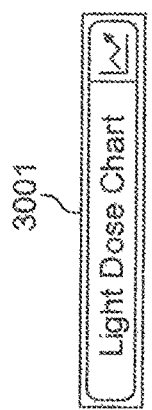
Figure 31:
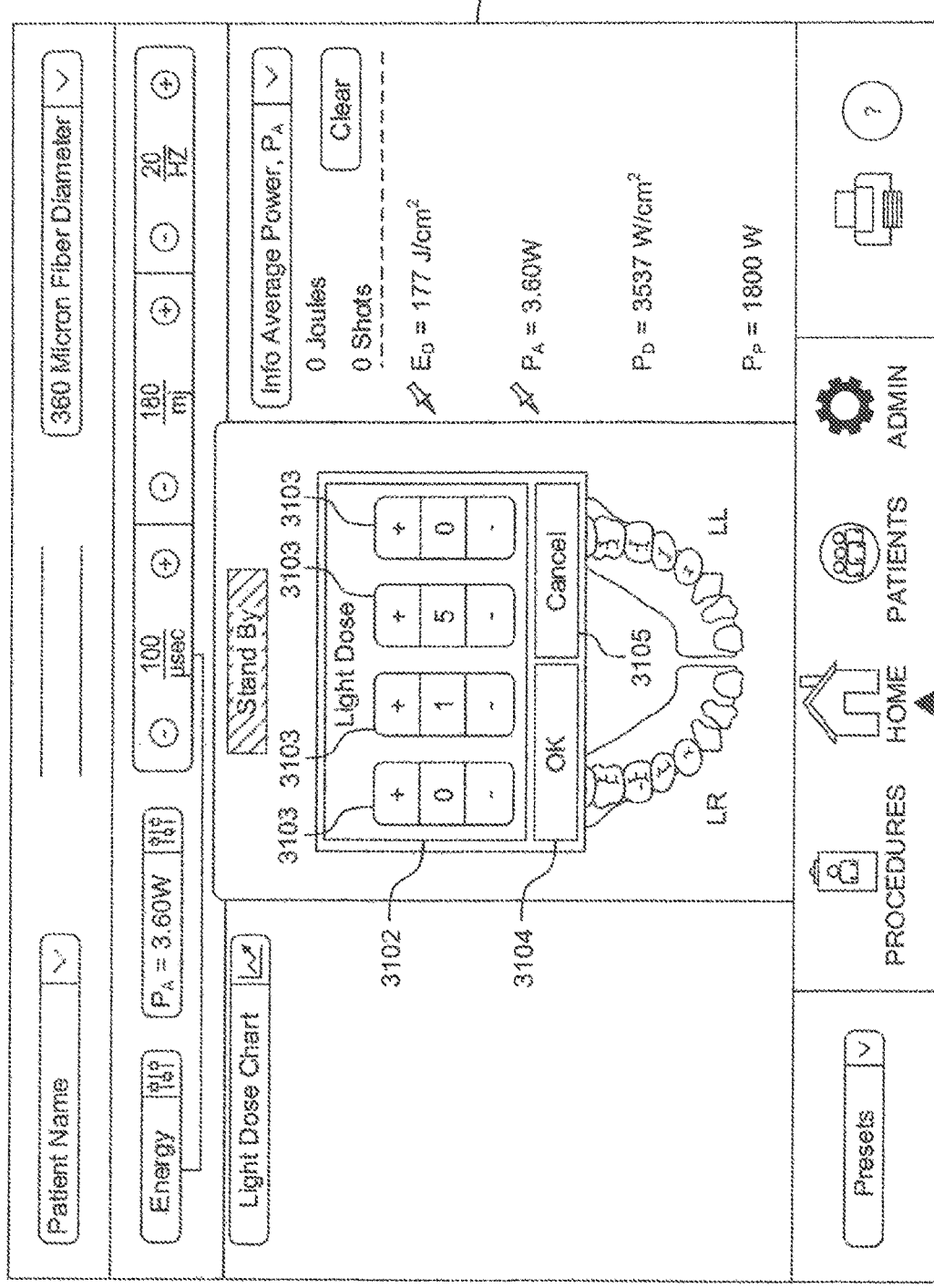

FIG. 30 displays a Light Dose Chart icon 3001, which looks like a chart with an upward pointing arrow, which may be displayed on a home screen. A user selects the Light Dose Chart icon to enable the Light Dose graphing feature.

Specifically, upon selecting icon 3001, a control surface such as control surface 3101 (depicted in FIG. 31) is displayed, with a pop-up window 3102 allowing a user to enter light dose values based on clinical judgment and training, by using the (+) and (−) near each digit 3103. Light dose settings permit an entry of up to four digits or 9,999 joules/mm pocket depth. After the user has selected the Light Dose entry, the user may select to cancel using cancel button 3105, or select the Ok button 3104, after which a Light Dose graph appears.

Figure 32:
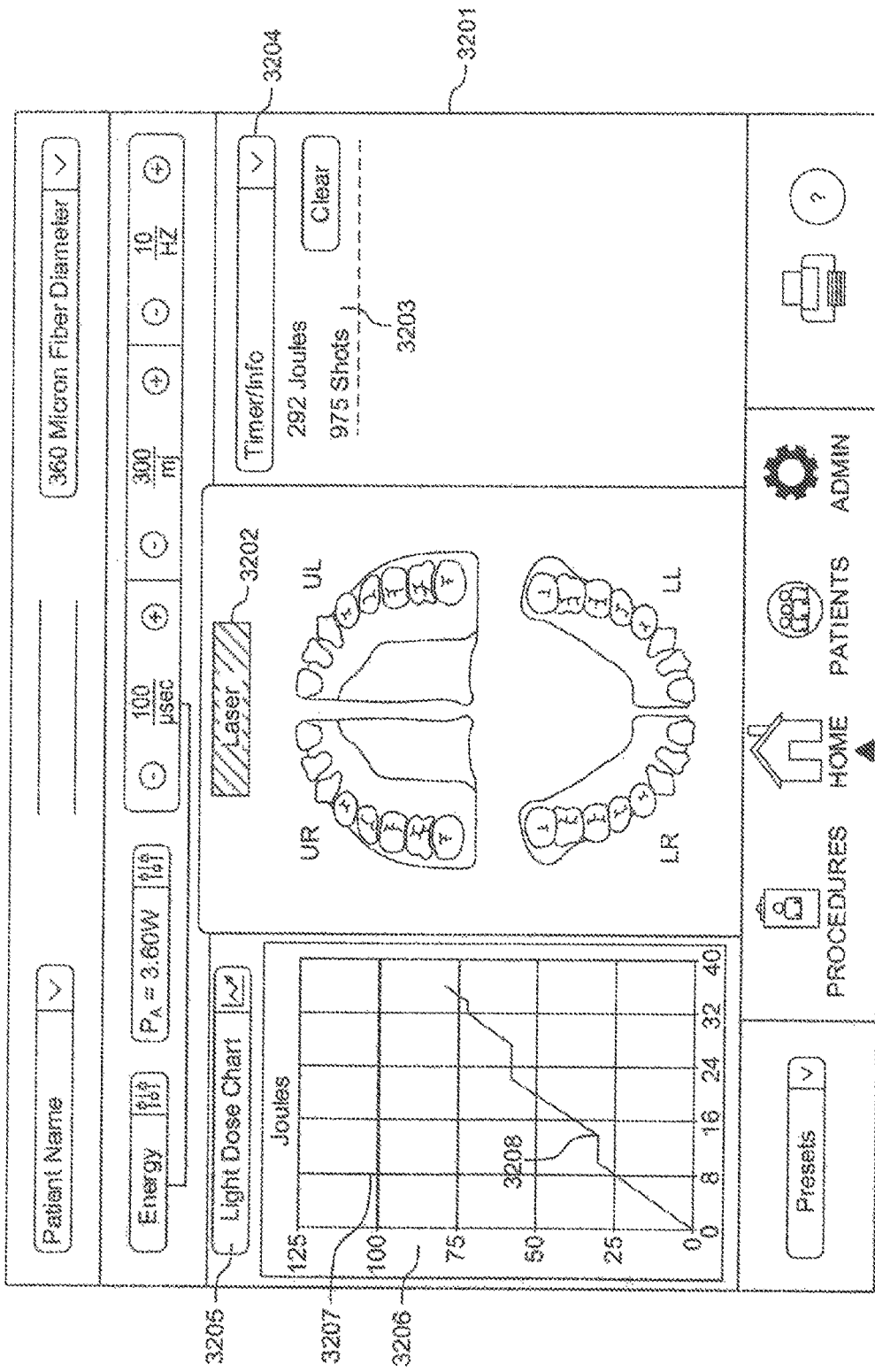

In particular FIG. 32 depicts a control surface 3201 with a light dose graph that changes as the laser is fired. In that regard, FIG. 32 shows a state in which the laser is currently being fired. Icon 3202 indicates that the laser is currently being fired. To do so, the user might toggle STANDBY to READY, depress footswitch 314, and fire the laser, and then observe the yellow laser warning light.

The light dose chart 3206 shows the amount of laser dosimetry applied so far during this active laser session (e.g., during an instance of pressing the footswitch), using a line 3208, in Joules/time(s). At the same time, a line 3207 shows the maximum allowable total joules which can safely or effectively be applied. This maximum allowable amount may change in dependence on, e.g., the procedure being performed. In that regard, additional lines may be displayed to show, for example, the maximum for particular phases of a multi-phase procedure, e.g., LANAP® Ablation or LANAP® Hemostasis.

The accumulation of Joules 3203 on the light dose graph is also displayed on the right side of the home screen under the Timer/Info icon bar 3204. The user may opt out of the light dose tracking by selecting the Light Dose Chart icon 3205 once more, after which the graph 3206 will disappear from the home screen.

Figure 33:
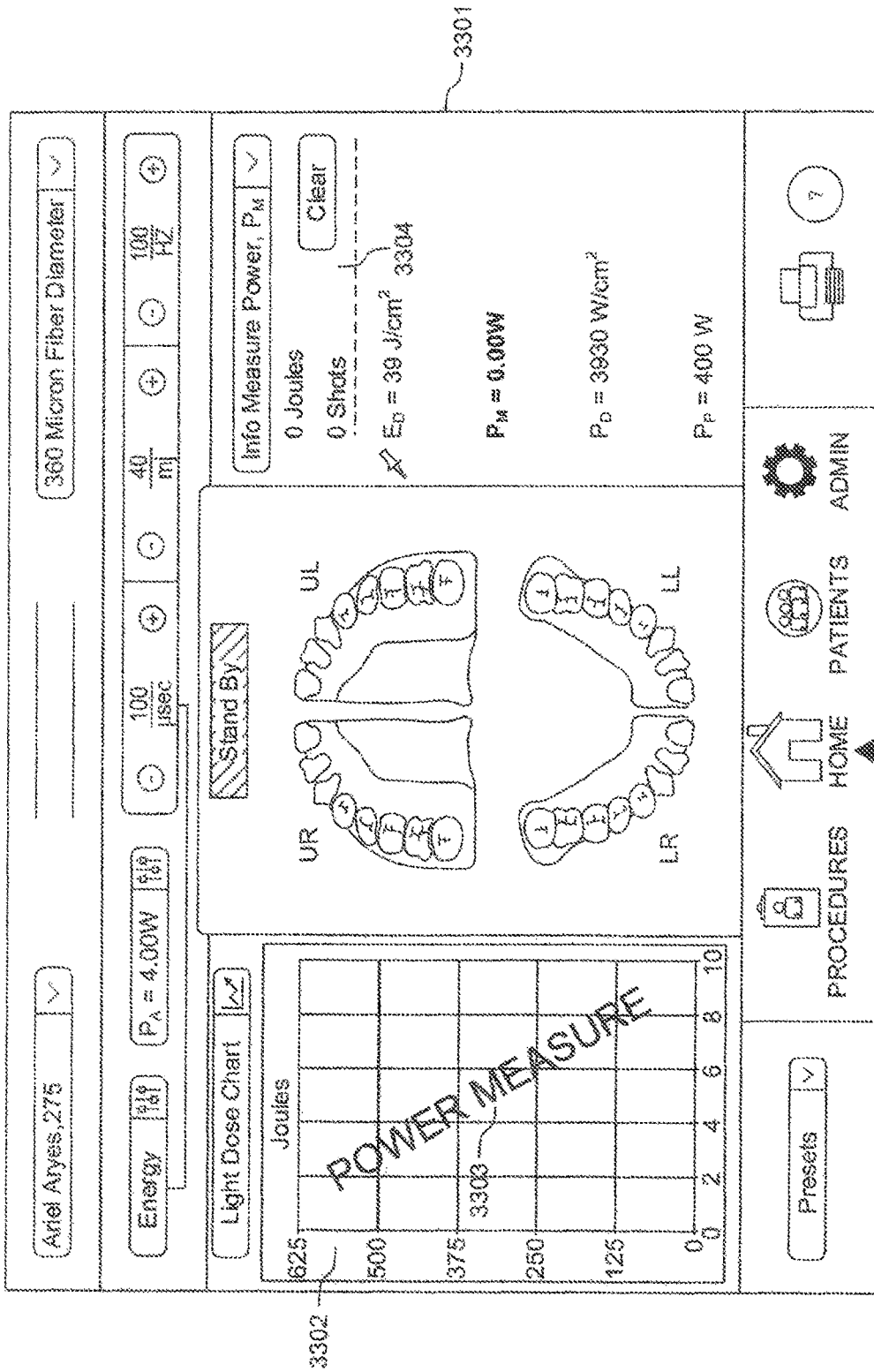

FIG. 33 shows a control surface 3301 including a Light Dose Chart 3302 in Measure Power (PM) Mode. While in the Measure Power, PM Mode, the system does not allow the user to record any patient data. Rather, it is a tool for the user to utilize for power measurement of main laser computer 300. If the Light Dose graph feature is still enabled and the chart appears on the home screen, a watermark 3303 may appear across the graph that will state Power Measurement Mode when the laser is firing and the footswitch is depressed. Meanwhile the power measurement display 3304 shows the measured power.

FIGS. 34 to 39 are views for explaining information displayed in association with an instance of laser firing according to example embodiments.

Figure 34:
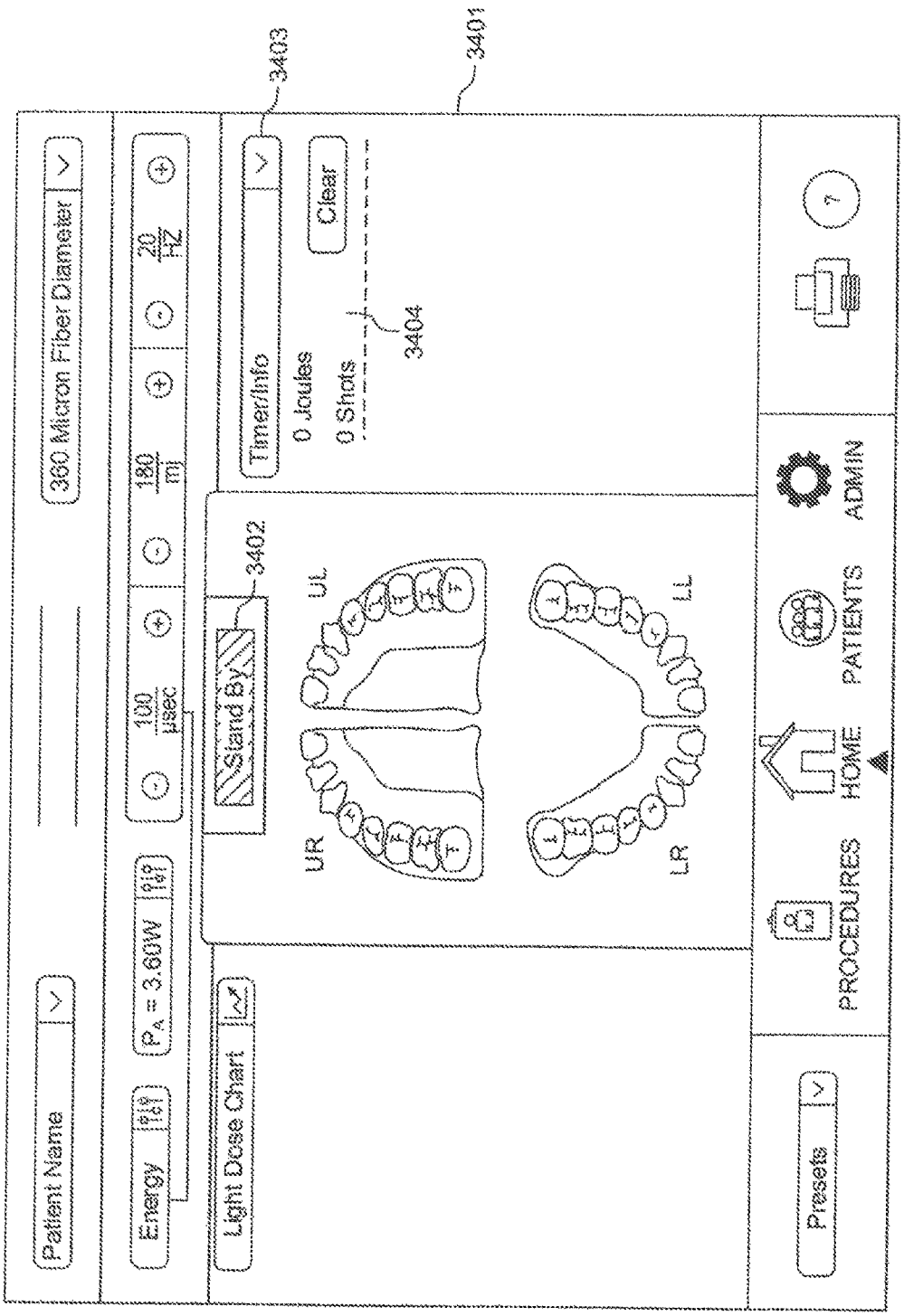

In particular, FIG. 34 indicates a control screen 3401 for a pre-firing standby state. Thus, as can be seen from FIG. 34, an icon 3402 indicates that the system is in standby mode, and, underneath the Timer/Info icon bar 3403, display 3404 indicates that an accumulation of Joules is at zero.

Figure 35:
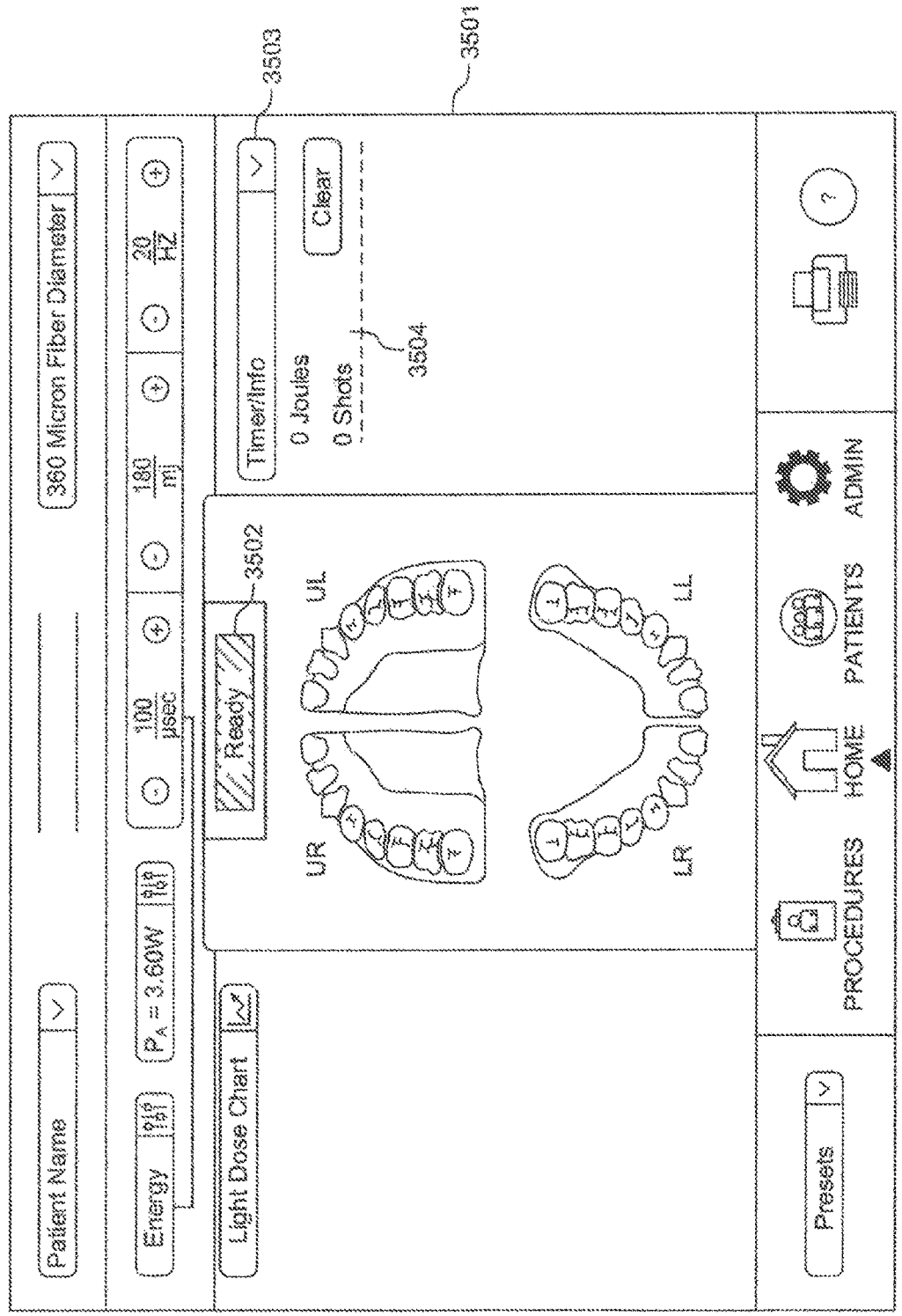

FIG. 35 shows a control screen 3501 for a state when a user toggles from standby to ready mode, just before firing (by depressing footswitch 314, firing the laser, etc.). An icon 3502 indicates the Ready mode. The accumulation of Joules 3504 on the dental arch will be displayed under the Info/Timer icon bar 3503. Laser energy will be transmitted in accordance with the therapeutic parameters selected via the optical fiber.

Figure 36:
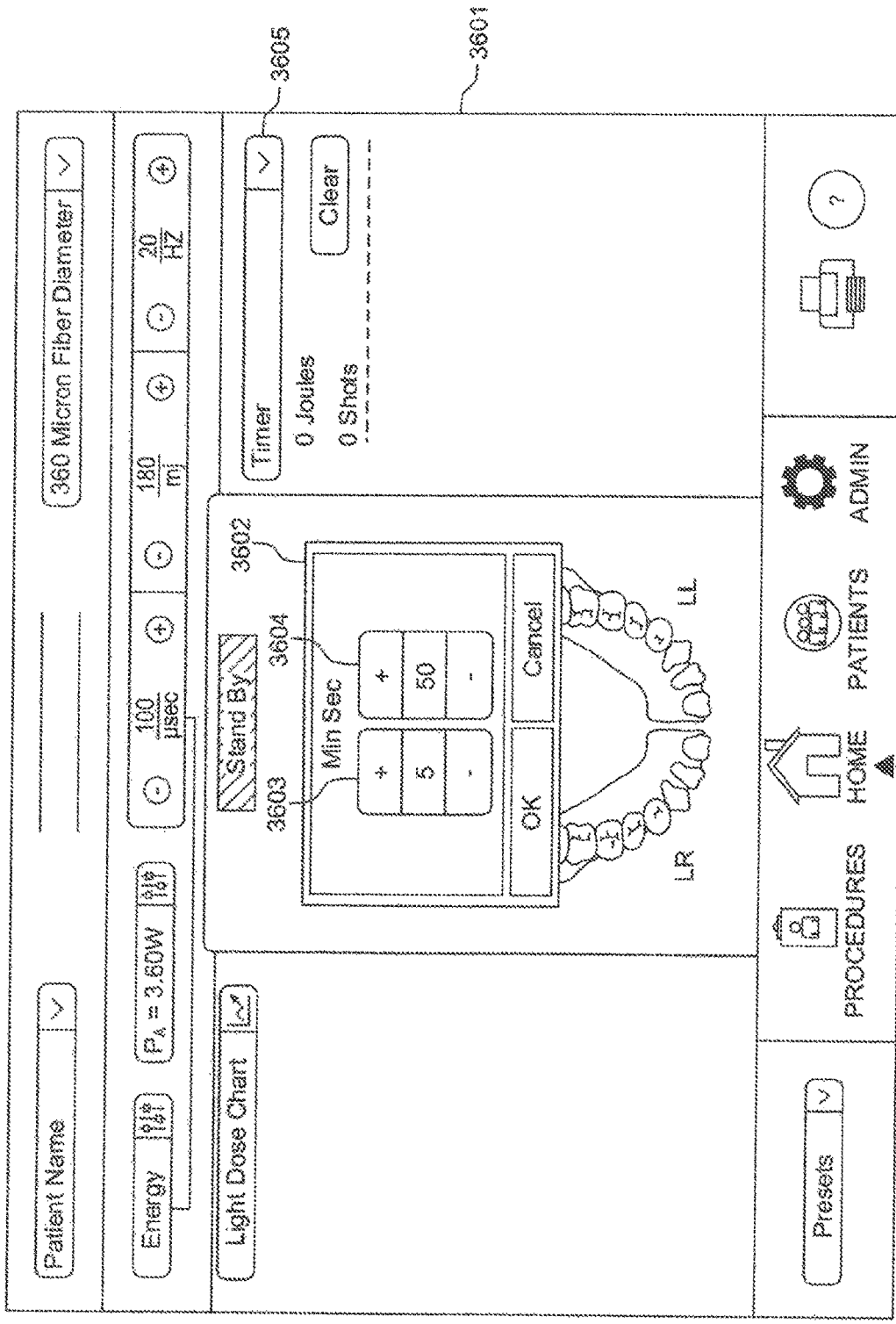

FIG. 36 illustrates a control surface 3601 for setting a timer. In particular, when the user selects "Timer" on the drop-down bar 3605, a separate pop-up box 3602 will appear showing the desired minutes 3603 and seconds 3604 to be entered by (+) and (−) symbols.

Figure 37:
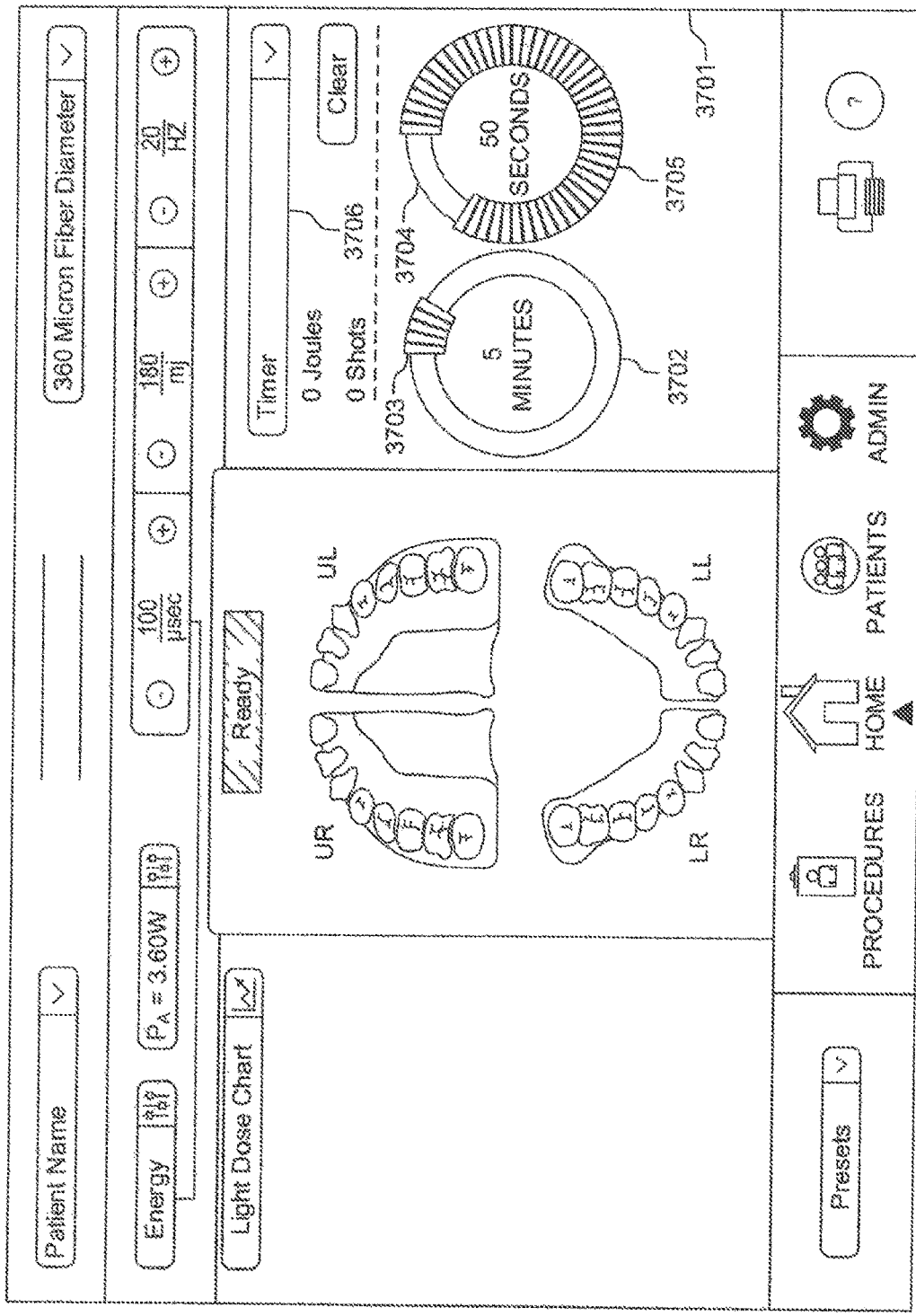

FIG. 37 shows a control screen 3701 after the selection of desired time, in which countdown timer indicators, such as minute wheel 3702 with ticks 3703 and second wheel 3704 with ticks 3705, will appear below the Timer icon bar 3706. When the footswitch 314 is depressed, the ticks on the appropriate timer will decrease according to the selected time. To exit from the countdown timer, the user may select the Timer icon bar 3706 once more.

Figure 38:
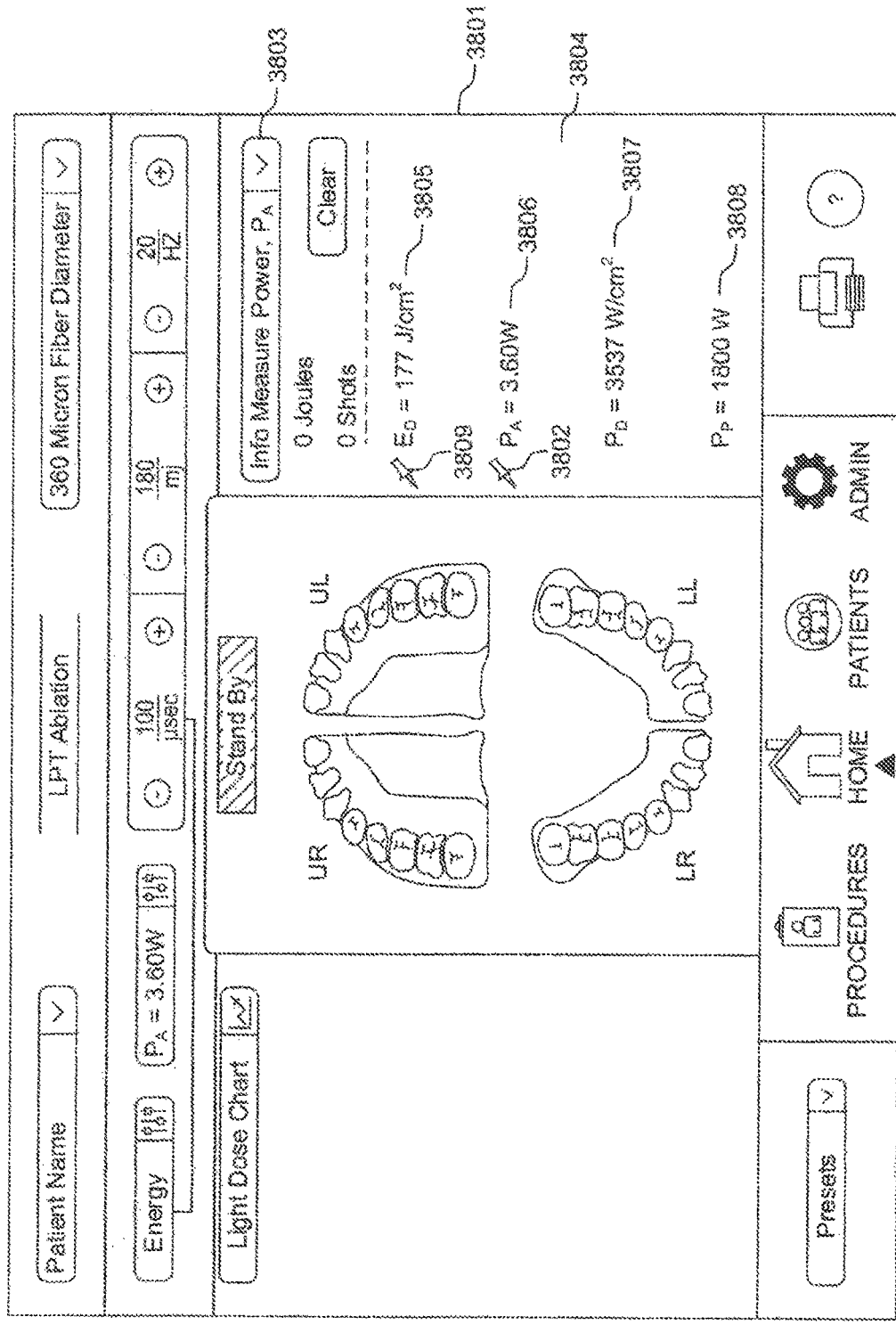

FIG. 38 illustrates a control screen 3801 for displaying various accumulated information according to an example embodiment. In particular, when a user selects Info/Average Power from the drop-down bar 3803, the laser parameters information table 3804 appears. These values in laser parameters information table 3804 may change when the fundamental laser parameters change and/or the selected fiber diameter is changed. On the other hand, thumbtack element 3802 allows the user to "pin" certain values such that other parameters are forced to change to fit.

The parameters in laser parameters information table 3804 include:

$E_D$, Energy Density (3805): $E_D$=Energy Density (depends on fiber and mJ settings only). $E_D$ is Joules/cm. $E_D$ may be held constant while the fiber diameter is changed and in fact by replacing the optical fiber on the front of the laser to the corresponding diameter value. There is a thumbtack pinning feature for Energy Density. The icon 3802 for this feature is located on the left side of $E_D$. Pinning $E_D$ changes the fundamental therapeutic parameter, mJ, to maintain (as close as possible) the energy density designated from the previous fiber diameter. Pinning $E_D$ and changing the fiber diameter will adjust mJ to keep $E_D$ approximately constant.

$P_A$, Average Power (3806): =Desired Average Power.

$P_D$, Power Density (3807): Average Power, Watts, per square millimeter of fiber diameter.

Pp, Peak Power (3808): =Peak Power each laser pulse (depends on μsec and mJ only).

Figure 39:
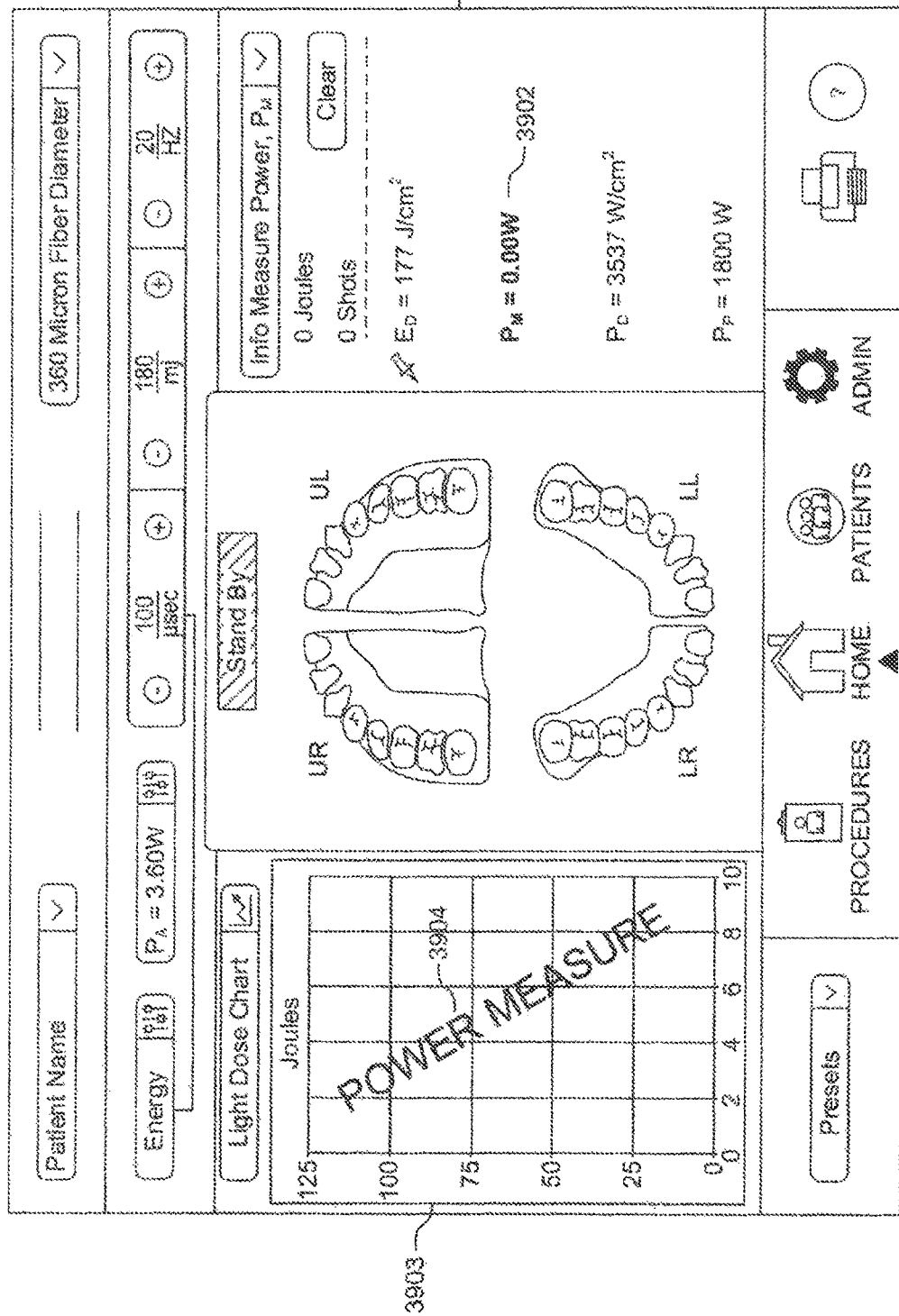

Turning to FIG. 39, when a user selects Info/Measure Power, ($P_M$) this activates the control screen 3901 in which the power measurement feature and the $P_M$ display 3902 is highlighted (e.g., displayed in red) to emphasize that this feature is activated. This allows the user to measure the power output of the main laser computer 300. In the $P_M$ mode the system does not write system data, like mJ, or Shots to the patient records. $P_M$ is a tool for the user to verify that the power settings made in the eGUI are realized at the distal end of the optical fiber nearest the surgical site. This is a comparison of the $P_A$ and $P_M$ values. If the Light Dose Chart 3903 pop-up window appears on the home screen, there will be a watermark 3904 that will appear across the graph that will state Power Measurement Mode when the footswitch is depressed, as illustrated in FIG. 39.

FIGS. 40 to 45 are views for illustrating selection of groups, areas or regions of a mouth for treatment and tracking thereof according to example embodiments.

Figure 40:
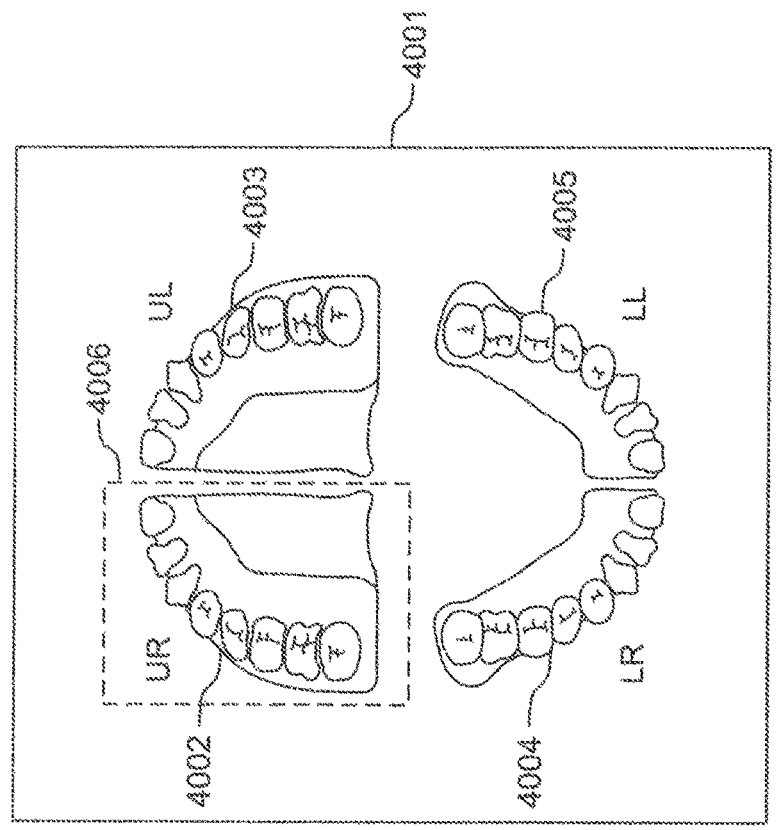

FIG. 40 illustrates a control surface 4001 for allowing a user to select a dental arch for which to record dosimetry. For example, a user may select and/or de-select the dental arch quadrant(s) labeled UR (4002), LR (4004), UL (4003), and LL (4005). When a specific quadrant is selected, the selected area will be highlighted on the HOME screen, as shown by indication box 4006, although this emphasis may also be displayed using, e.g., color in the selected area while displaying the other quadrant(s) as grayscale. When selected, as the UR quadrant shown here, Tx data is tagged with this location and will be available for analysis in the Patient Control Surface, Report Tab.

Figure 41:
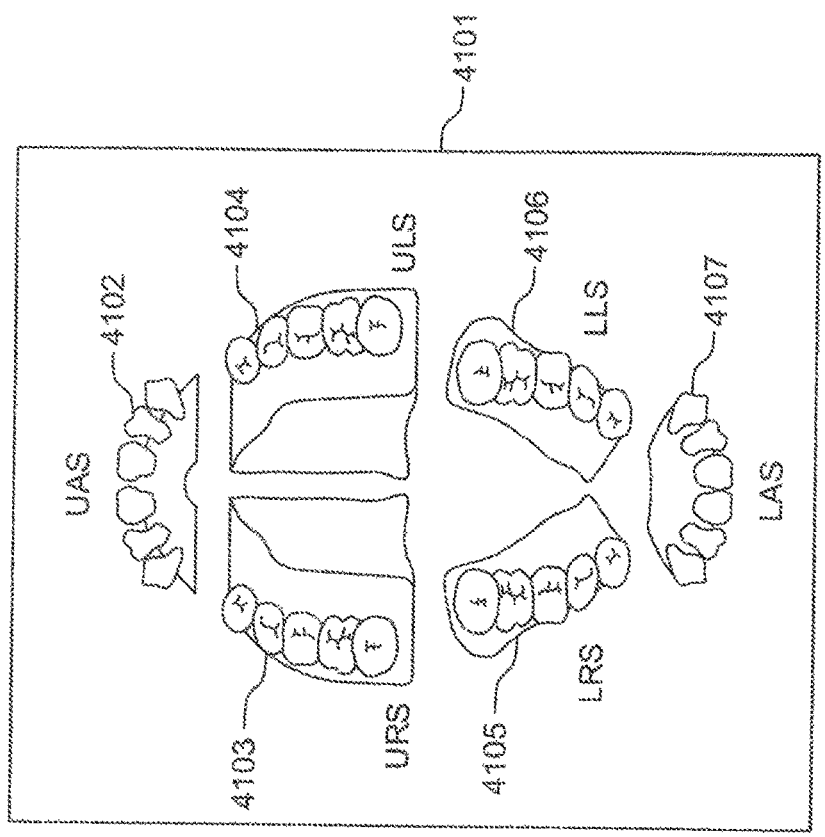
Figure 42:
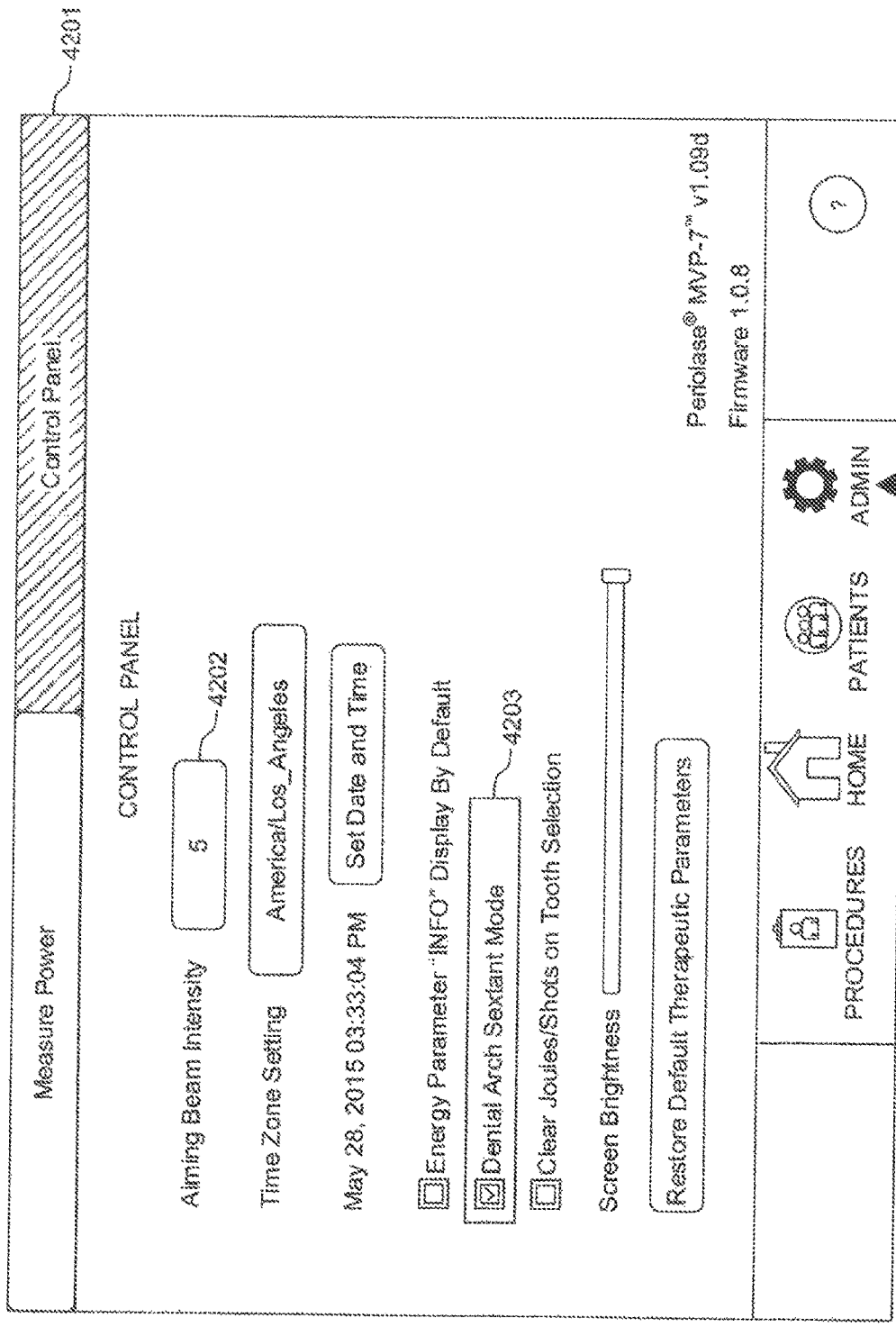

FIGS. 41 and 42 illustrate selection of a sextant. Specifically, there is an option for the user to select a different dental arch which is called a sextant. A display control surface 4101 indicates the different sextants labeled UAS (4102), URS (4103), ULS (4104), LRS (4105), LLS (4106), and LAS (4107). When a specific area of the dental arch sextant is selected, the selected area will be highlighted on the HOME screen.

Meanwhile, FIG. 42 illustrates one embodiment for changing to the sextant selection from an administration control surface 4201. In particular, the user selects or de-selects the Dental Arch Sextant Mode 4203 from the administration control surface, control panel tab 4202.

Figure 43:
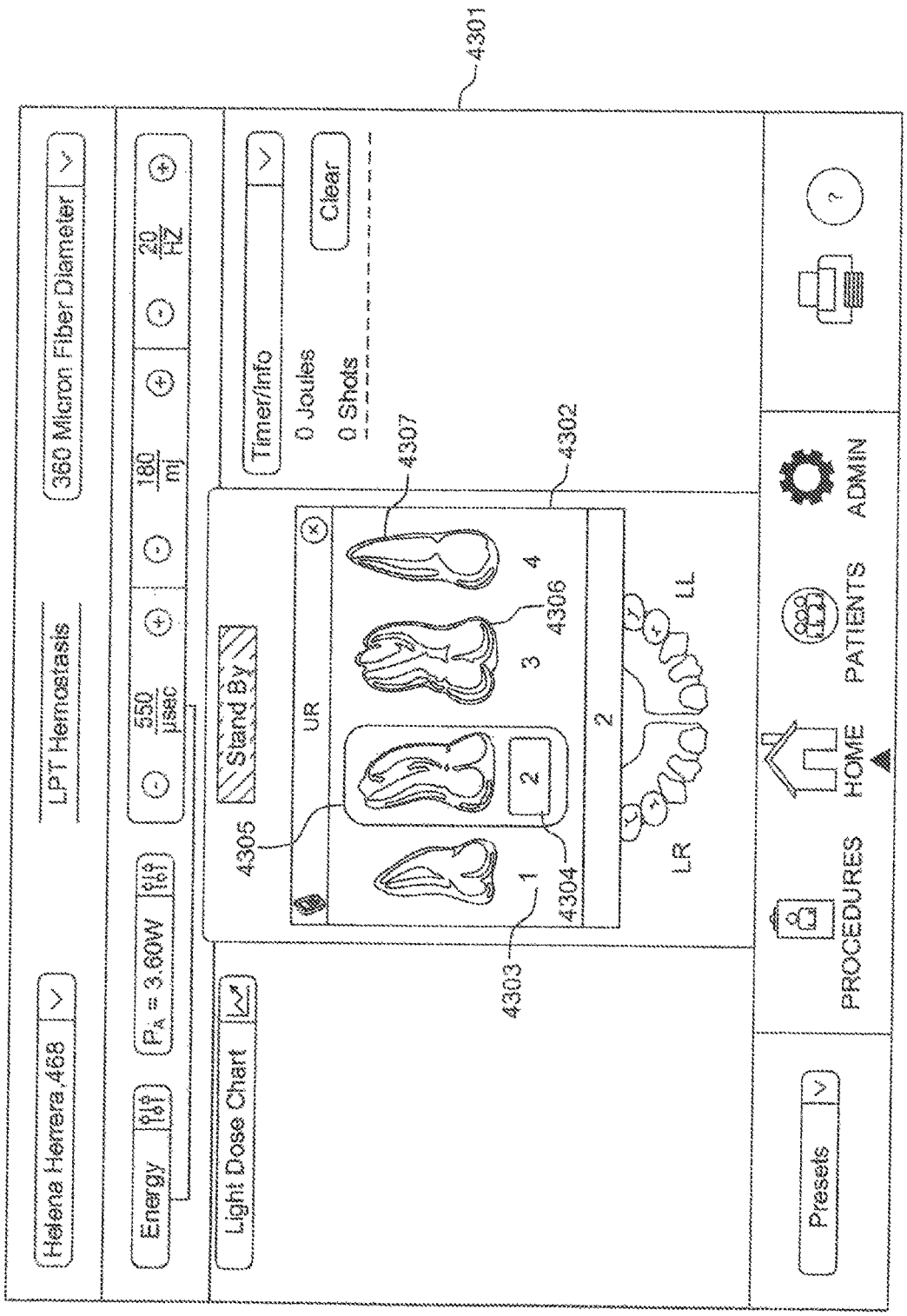
Figure 44:
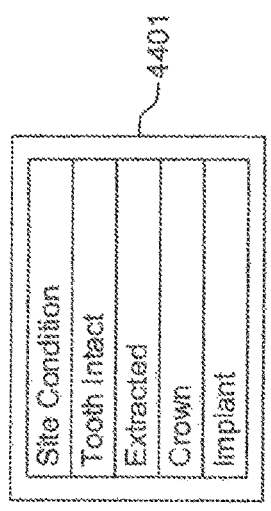

FIG. 43 illustrates a control surface 4301 by which a user is allowed to select a tooth location which can be denoted as an implant. In that regard, when recording information to the dental arch location, there are many options for additional specificity. Each of the teeth in the dental arch may be designated, individually or in ad hoc groupings of multiple teeth. Once designated, dosimetry data are labeled and recorded to these locations. There are options to select teeth individually or to select multi-tooth grouping options.

The individual tooth selection feature applies to either quadrant or sextant dental arches. To enable this feature, the user performs a long press on a particular quadrant/sextant. A pop-up box 4302 will appear with a tooth carousel including teeth 4303, 4304, 4306 and 4307. The selected tooth is highlighted with a red box 4305. The tooth carousel pop-up box has a left-right (LR) swipe functionality to allow the user to select the desired tooth.

When the user performs a long press on a specific individual tooth, a site condition designation window (FIG. 44) appears in a pop-up 4401 box with these options: Tooth Intact, Extracted, Crown, and Implant. The data for these site conditions will appear on the Reporting Control screen.

Figure 45:
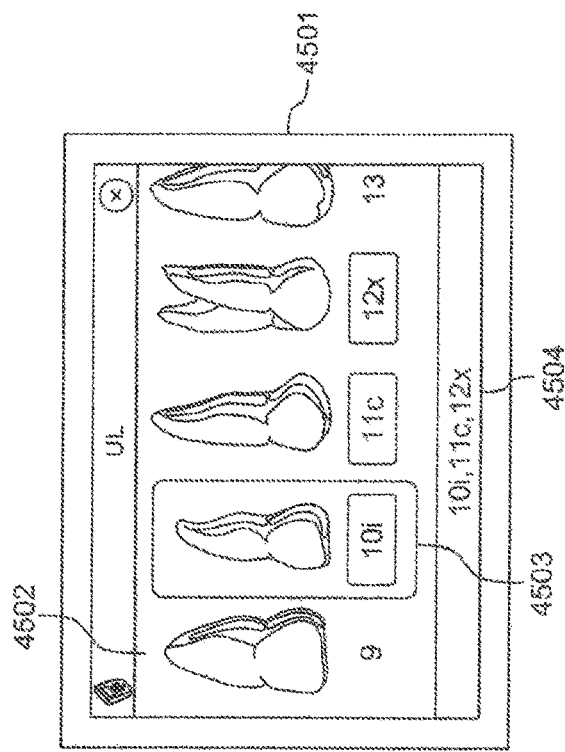

FIG. 45 illustrates a view of another tooth carousel 4501 for selecting single or multiple teeth (e.g., tooth 4502). In this example, selected teeth appear with rectangles such as rectangle 4503 (which may be colored, for example, red). Each tooth with a rectangle will appear in a treatment group on the reporting control surface. The home screen shows the tooth carousel multi-tooth feature with a display 4504 of 3 teeth selected from the upper left quadrant for this example. Teeth are labeled as follows: tooth 10i (tooth 10 selected with the site condition option Implant), tooth 11c (tooth 11 with the site condition option Crown), and 12x (tooth 12 with the site condition option Extracted). When the user toggles the standby to ready buttons and the laser is fired, the designated multi-tooth group is recorded in the database for use in reporting and analysis. If the user wishes to switch from one tooth to another, the user may simply select the other tooth by doing a short press on the tooth that was previously selected as part of the multi-tooth grouping.

Figure 46:
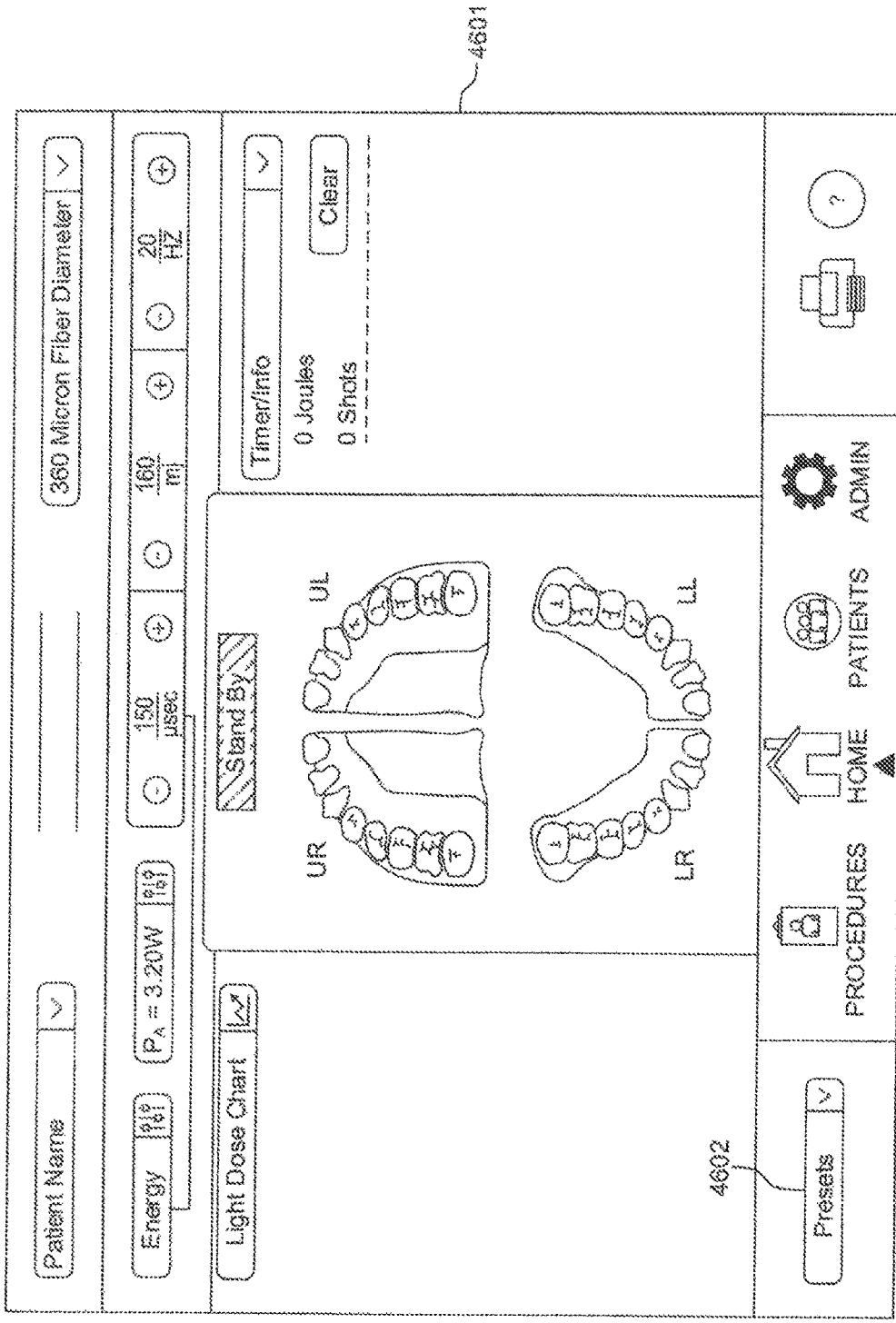
Figure 47:
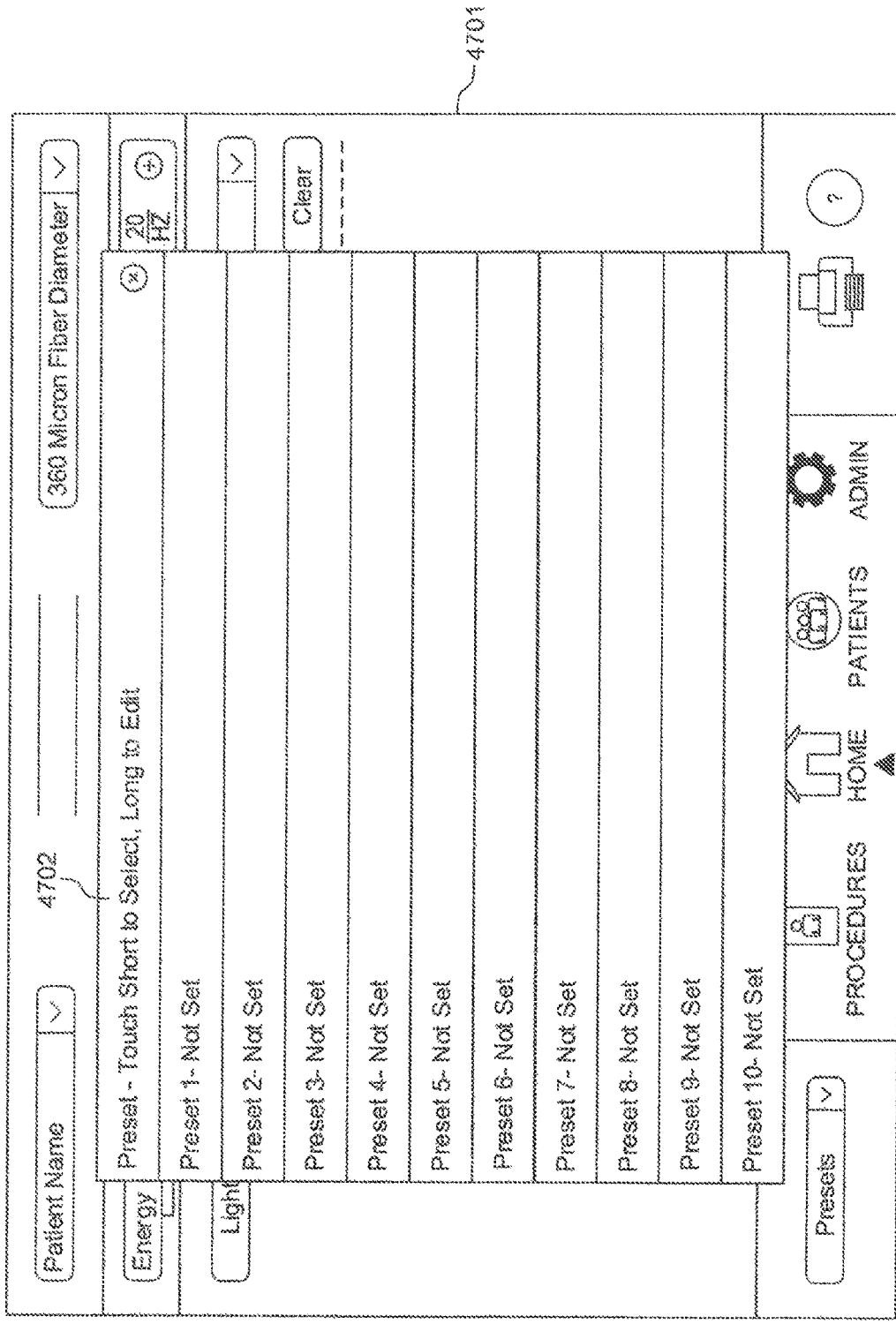
Figure 48:
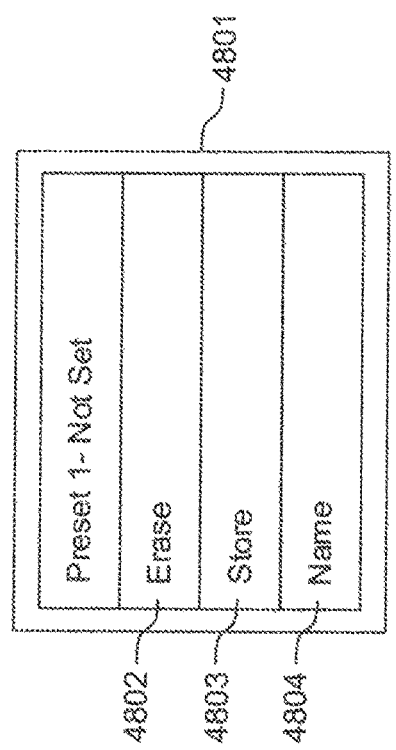

FIGS. 46 to 48 are views for explaining selection and adjustment of presets according to example embodiments.

In FIG. 46, the Presets icon bar 4602 is located at the lower left part of the home screen 4601. This feature enables the clinician to record and label all 3 of the fundamental therapeutic parameter settings (μsec, mJ, and Hz) which are presently set at the home screen. These can be recalled as needed.

FIGS. 47 and 48 depicts control screens which allow a user to name a preset with up to 8 alphanumerical characters, and to add new or select from previously named and saved preset parameters. When the user selects the Presets icon bar 4602, a separate pop-up box 4702 will appear on the updated control screen 4701, with options to save up to 10 or more presets. At the top of the presets pop-up box 4702, directions for use are indicated: Touch Short to Select, Long to Edit. When the user selects the option to touch short to select, then the selected preset will appear on the home screen at, e.g., in between the Patient Name and the Fiber Diameter icon bars.

When the user selects the option touch long to edit, a separate pop-up box 4801 as shown in FIG. 48 will appear, with 3 Preset options: which are to store (option 4803), name (option 4804), and erase (option 4802), as follows:

Option to Store: When the user selects the option to Store, the therapeutic parameter settings (or the energy icon) that are on the home screen will be saved as Preset 1. The user may go back to the home screen and change the therapeutic parameter settings by pressing the (+) and (−) icons, or by selecting the energy icon and selecting the therapeutic parameters that appear on the pop-up chart. The chart is separated in different columns from left to right, μsec, mJ, and Hz. After the user has made the appropriate changes in the energy settings, then the option to set the current settings prior to storage is selected. When the user wishes to store the energy settings that are currently on the home screen, the user must select the Presets icon bar.

Option to Name: The user selects a preset to name (e.g., Preset 3), then uses the option Touch Long to Edit. The user selects the option name and a box will appear so that the user can type in the name of the Preset to rename or personalize.

Option to Erase: The user selects a preset to erase, e.g., Preset 4), then uses the option Touch Long to Edit. The user selects Erase and observes if the chosen preset is erased from the Preset screen.

Figure 49:
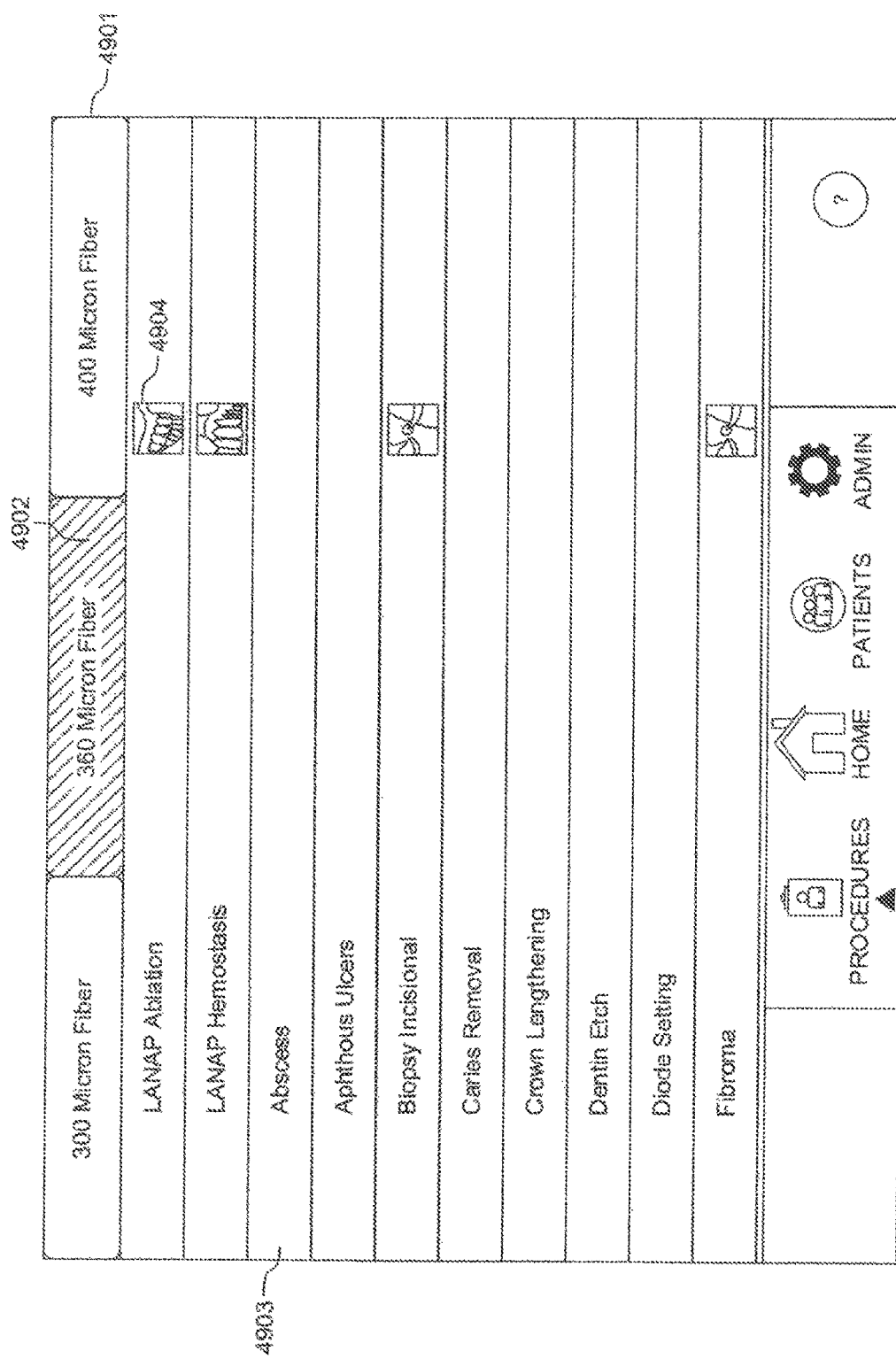
Figure 50:
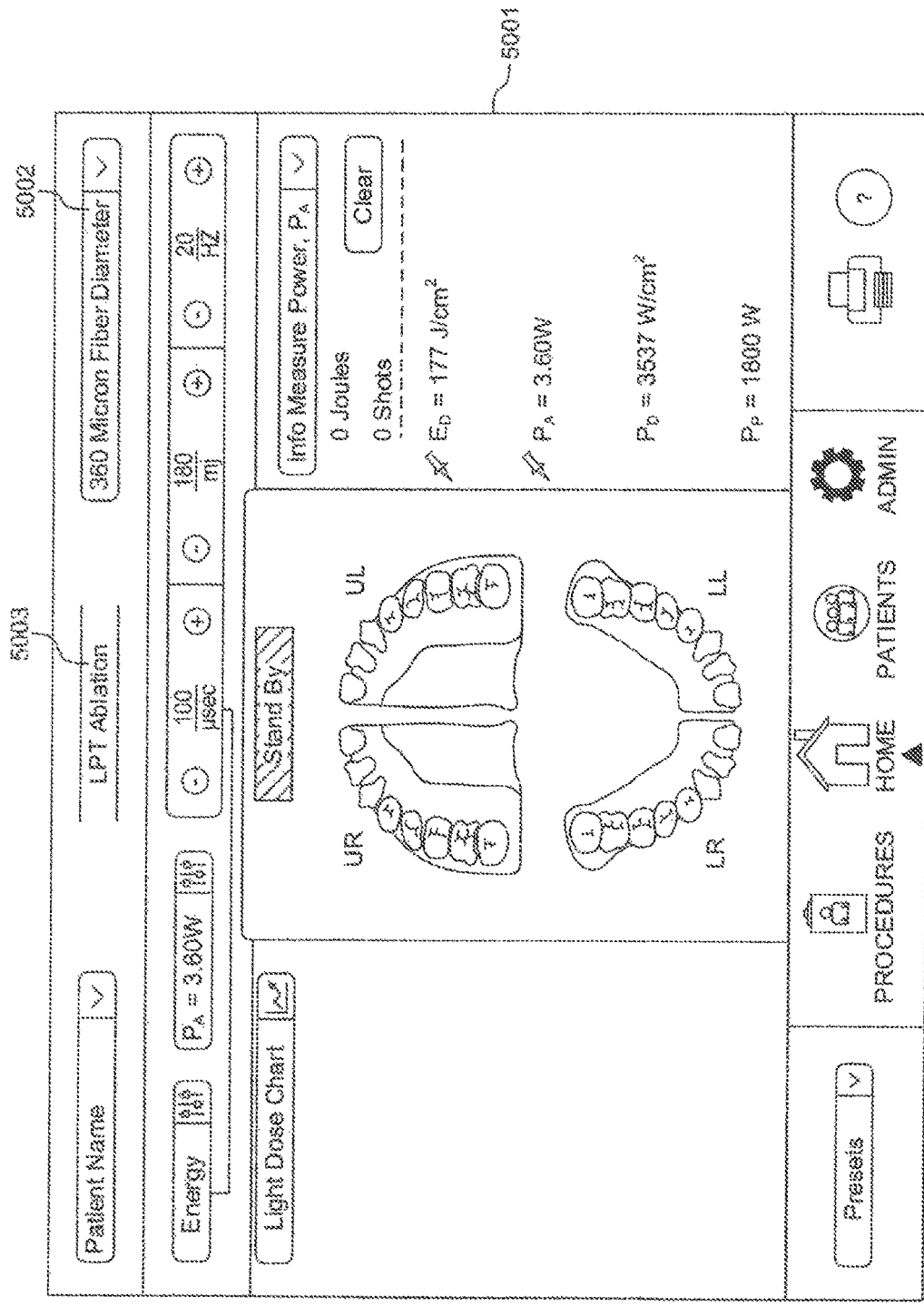

FIGS. 49 and 50 are views for illustrating a Treatment Preset Control Surface "Procedures" Screen 4901. The Preset Procedures screen 490 I has a list 4903 of patient treatment procedures that have the default therapeutic parameter settings according to the fiber diameter 4902 that the clinician has selected. An image 4904 may indicate that a video or photo tutorial is available for assistance on the corresponding procedure. Examples are shown below, according to the fiber diameter and the therapeutic parameter settings:

| 300 Micron Fiber Preset Procedures | 360 Micron Fiber Preset Procedures | 400 Micron Fiber Preset Procedures |
|---|---|---|
| LANAP Ablation | LANAP Ablation | LANAP Ablation |
| 100 μsec, 180 mJ, 20 Hz | 100 μsec, 120 mJ, 20 Hz | 100 μsec, 220 mJ, 20 Hz |
| Abscess | LANAP Hemostasis | LANAP Hemostasis |
| 150 μsec, 110 mJ, 20 Hz | 550 μsec, 180 mJ, 20 Hz | 550 μsec, 220 mJ, 20 Hz |
| Aphthous Ulcers | Abscess | Abscess |
| 150 μsec, 100 mJ, 20 Hz | 150 μsec, 160 mJ, 20 Hz | 150 μsec, 200 mJ, 20 Hz |
| Biopsy Incisional | Aphthous Ulcers | |
| 100 μsec, 30 mJ, 100 Hz | 150 μsec, 160 mJ, 20 Hz | |
| Caries Removal | Biopsy Incisional | Dentin Etch |
| 100 μsec, 210 mJ, 50 Hz | 100 μsec, 40 mJ, 100 Hz | Aphthous Ulcers |
| Crown Lengthening | Caries Removal | 150 μsec, 200 mJ, 20 Hz |
| 150 μsec, 40 mJ, 50 Hz | 100 μsec, 300 mJ, 100 Hz | |
| Dentin Etch | Crown Lengthening | Dentin Etch |
| 100 μsec, 170 mJ, 10 Hz | 150 μsec, 60 mJ, 50 Hz | 100 μsec, 250 mJ, 10 Hz |
| Diode Setting | Dentin Etch | Hemostasis |
| 100 μsec, 30 mJ, 100 Hz | 100 μsec, 250 mJ, 10 Hz | 550 μsec, 220 mJ, 20 Hz |
| Fibroma | Diode Setting | |
| 100 μsec, 30 mJ, 100 Hz | 100 μsec, 400 mJ, 100 Hz | |
| Frenectomy | Fibroma | Hygiene Curettage |
| 100 μsec, 30 mJ, 100 Hz | 100 μsec, 40 mJ, 100 Hz | 150 μsec, 120 mJ, 20 Hz |
| Gingivectomy | Frenectomy | |
| 100 μsec, 120 mJ, 20 Hz | 100 μsec, 40 mJ, 100 Hz | RCT Sterilization |
| Hygiene Curettage | Gingivectomy | 100 μsec, 180 mJ, 15 Hz |
| 150 μsec, 60 mJ, 20 Hz | 100 μsec, 180 mJ, 20 Hz | Sulcular Debridement |
| RCT Sterilization | Hemostasis | 150 μsec, 180 mJ, 20 Hz |
| 100 μsec, 100 mJ, 15 Hz | 550 μsec, 180 mJ, 20 Hz | |
| Sulcular Debridement | Hygiene Curettage | |
| 150 μsec, 100 mJ, 20 Hz | 150 μsec, 100 mJ, 20 Hz | |
| Tissue Recontouring | RCT Sterilization | |
| 100 μsec, 80 mJ, 50 Hz | 100 μsec, 150 mJ, 15 Hz | |
| Troughing | Sulcular Debridement | |
| 250 μsec, 120 mJ, 20 Hz | 150 μsec, 150 mJ, 20 Hz | |
| | Tissue Recontouring | |
| | 100 μsec, 110 mJ, 50 Hz | |
| | Troughing | |
| | 250 μsec, 180 mJ, 20 Hz | |

FIG. 50 illustrates a control surface 5001 after selection, including an indication 5002 of the selected fiber diameter, and an indication 5003 of the selected procedure.

Figure 51:
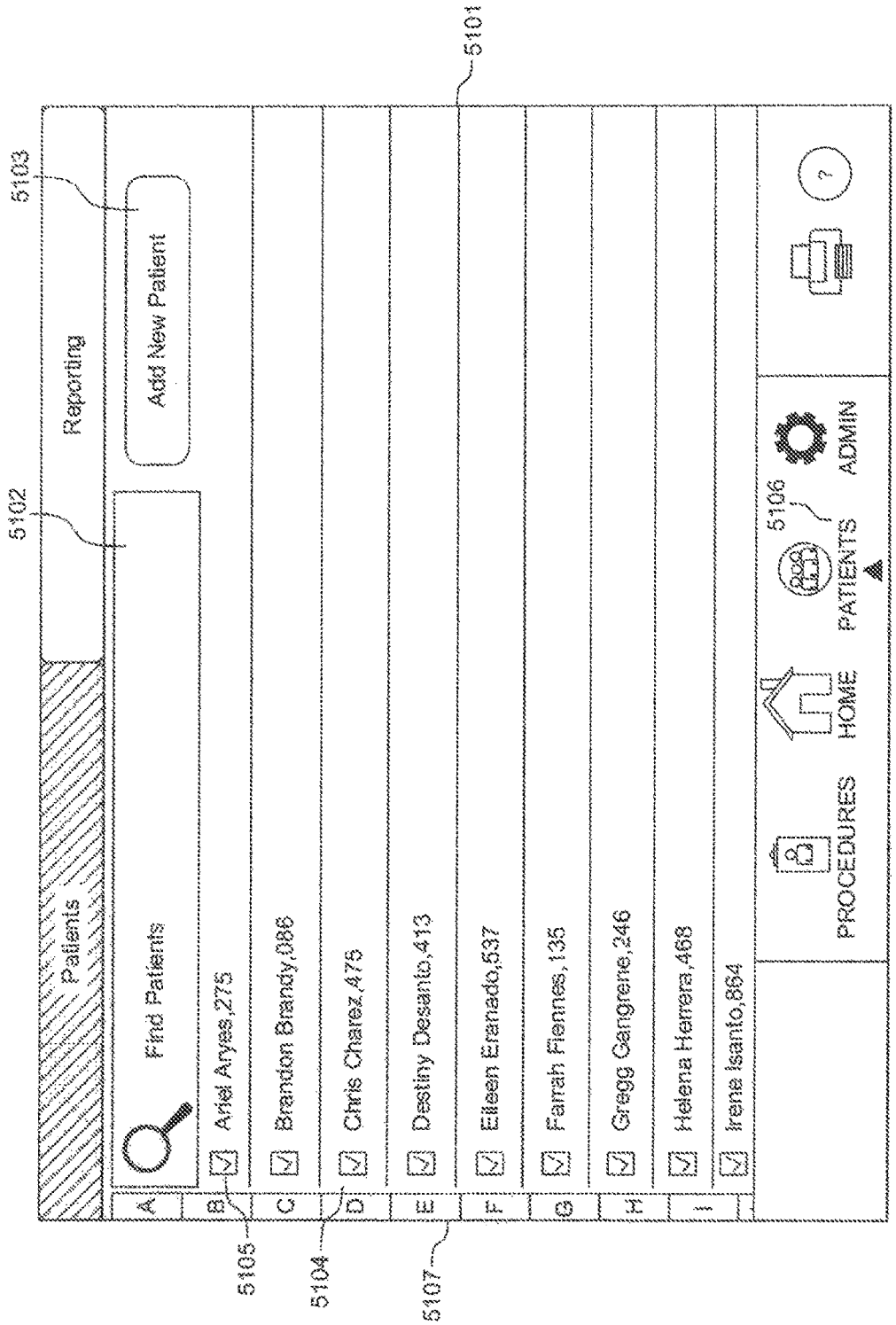
Figure 52:
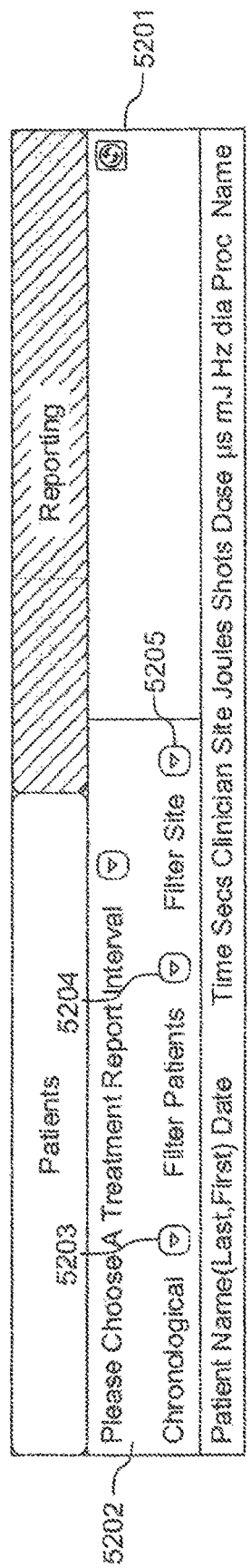

FIG. 51 illustrates an example Patients Control Surface 5101, which can be accessed by, e.g., clicking on "PATIENTS" icon 5106, and which may include two separate tabs: Patients and Reporting, as can be seen from the Patients tab (to the left of the screen) and the Reporting tab (to the right of the screen). As shown in FIG. 51, the "Patients" tab has been selected.

The Patients tab includes a Find Patients/Alphabetical Search Icon Bar 5102, where the user is able to find a patient by typing in the Patient's or Patients' name(s). The user is also given a control 5103 to select to add a new patient. An alphabet bar 5107 includes search functionality by which when the user presses on a particular letter of the alphabet bar (for example the letter A), then the patient names that are listed in list 5104 that have an A at the beginning of the first or last name (e.g., patient 5105) will be displayed.

In one example, if the user makes a mistake while entering patient data and has already chosen the option to press save, there is a way to delete or edit the entry. Once the user has found the patient entry that he/she would like to edit or delete, the user must long press on it for about 2-3 seconds and a box will appear with three different options: edit, delete, and select. When edit is selected, the user is able to make the appropriate changes. If the user selects delete then the entry will be deleted from the list. If the user chooses the option to select, then this will have the patient name show up on the drop-down list of the home screen.

If the user instead selects the "Reporting" tab from, e.g., Patients Control Surface 5101 in FIG. 51, a different series of displays may be generated, as explained with reference to FIGS. 52 to 59.

In that regard, the eGUI records comprehensive treatment information. Each time the footswitch 314 is activated (pressed), the main laser is fired and the date and time of the activation is recorded. In addition, there is recording of the Patient name, Quadrant/Sextant and or tooth/teeth selected, the diameter of the optical fiber in use, and the fundamental therapeutic parameters: μsec, mJ, and Hz. When the footswitch 314 is released, this data is recorded into the database for use and analysis on the Reporting Tab of the Patient control surface. The footswitch interval is the period between activation (when the footswitch is depressed) and release (when the footswitch is inactive). The totals of Joules and Laser Pulse "Shots" during the footswitch interval are also recorded and appended to the data element corresponding to the current treatment.

To generate a report, a user may select a report filter from the reporting control surface tab 5201, which is displayed when, e.g., the user selects the "Reporting" tab. As can be seen from FIG. 52, the reporting control surface tab 5201 has 4 main filters for the user to find patient data: Treatment Interval 5202, Chronological 5203, Filter Patients 5204, and Filter Site 5205. Each of these filters will be described in detail.

Figure 53:
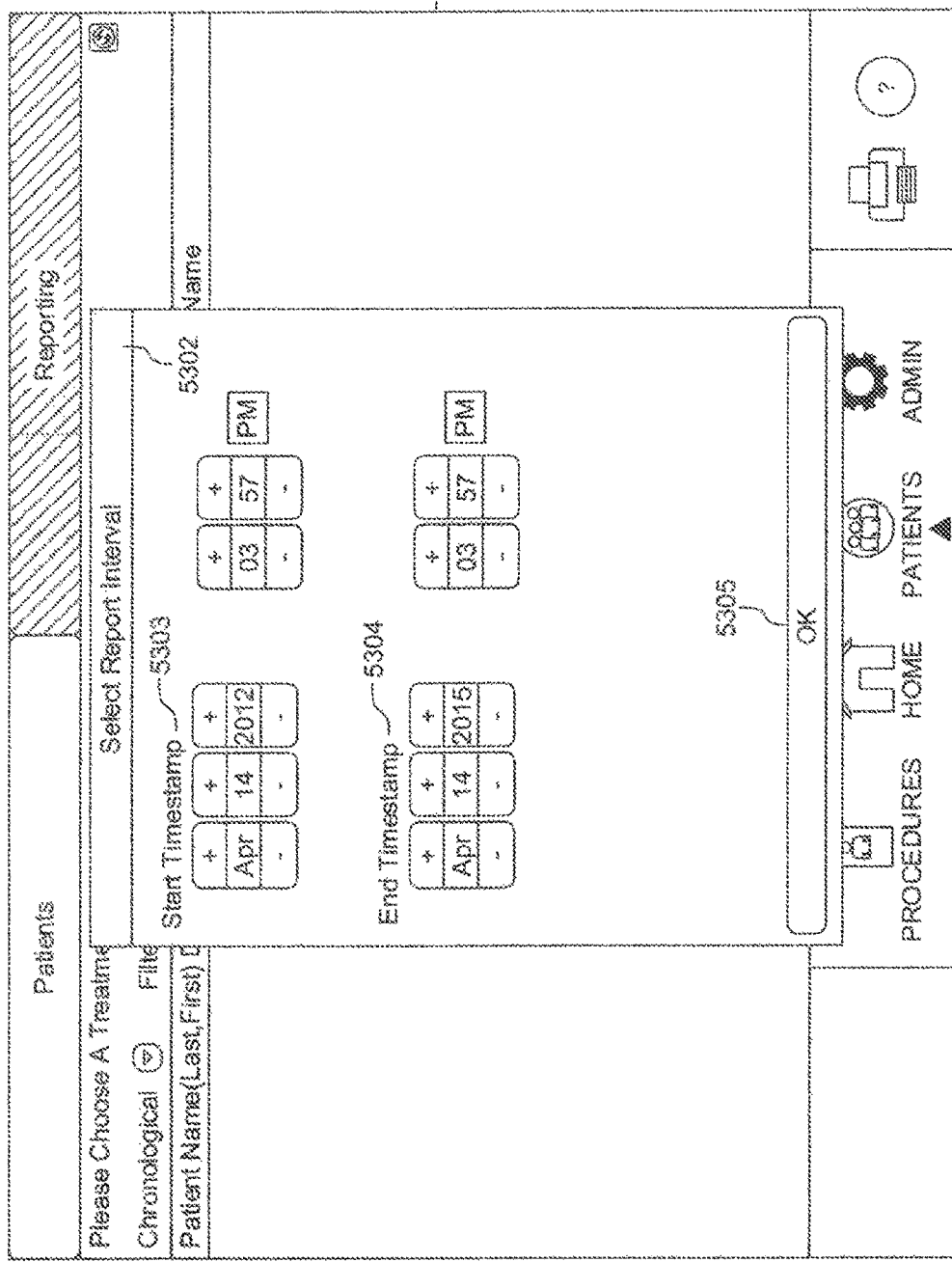

FIG. 53 illustrates a control surface 5301 for Filter 1, "Treatment Interval", which is essentially the date and time interval for the system data that one desires to examine. A window 5302 includes controls 5303 and 5304 for selecting the top date as the beginning date and the bottom date as the ending date for the treatment interval filter. The user selects Ok with icon 5305, and the treatment data is reported to the Reporting tab.

FIG. 54 illustrates a control surface 5401 for Filter 2, the "Chronological" tab. This tab provides several further filtering options via a "Select Report Options" control display 5402: Clinician option(s) displayed as element 5403 with the choice of Self or All, grouping options displayed as element 5404 with selections such as: None, Patient/chronological, and Patient Tx Site (Patient Treatment Site), and report detail options displayed as element 5405 with selections such as: Detail, Summary, or Both, along with an Ok button 5406 to confirm the selections made.

In more detail, insofar as clinician options, when the clinician chooses the filter option Self, then the patient data for the present login user is displayed. For example, when the clinician typed in the usemame mdt during the LOGIN procedure, then all the patient data for the mdt LOGIN credentials will appear on the Reporting Control Surface Screen. When the user chooses the filter option All, then all the patient data with all the LOGIN credentials (username(s) and password(s)) within the database will appear on the reporting control surface. This is useful in group practices where patients may be shared among clinicians.

Insofar as chronological grouping options, when the clinician chooses to filter the patient data by selecting the chronological grouping option None, this does not filter the patient data in any particular way. When the clinician chooses to filter the patient data by selecting the Pt:Chron grouping option, the patient data will appear alphabetically on the reporting control surface and then each record is sequenced by date and time. When the clinician chooses to filter the patient data by selecting the chronological grouping option Pt:Tx Site, then the patient data will appear by Patient Name, then by the treatment site, and finally by date and time within the treatment site.

Insofar as report detail options, option "Summary" shows joules and shots only, option "Detail" shows all recorded therapeutic parameters within each footswitch activation interval, and option "Both" provides for the report detail option, and cumulative summaries of the patient data.

Figure 55:
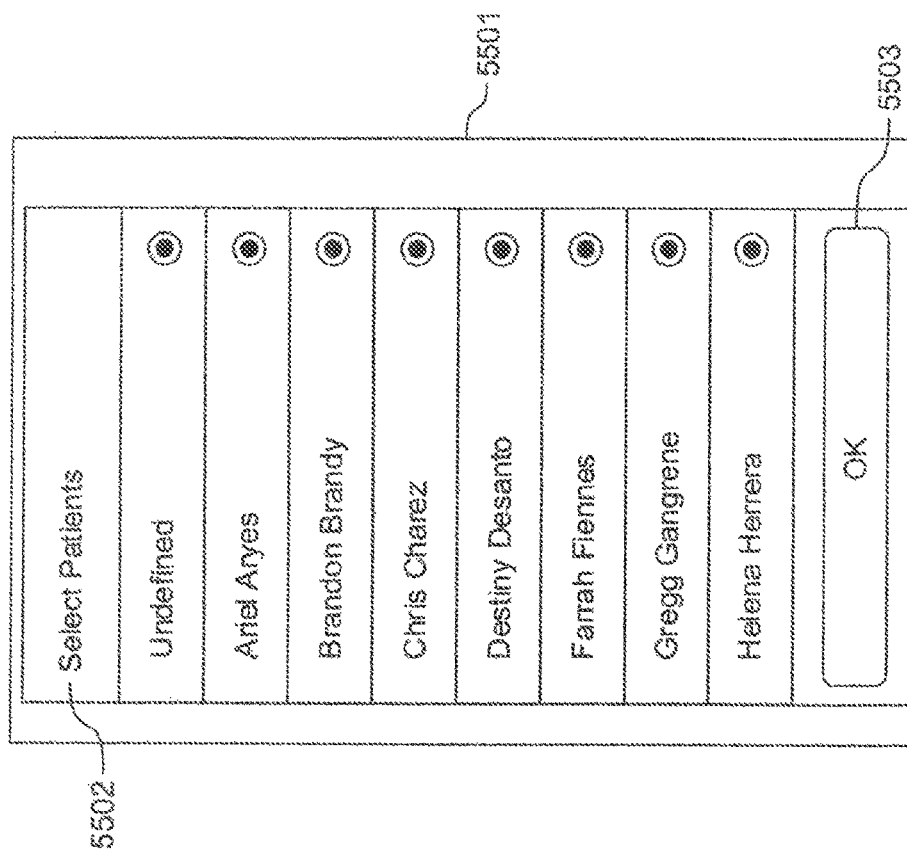

FIG. 55 illustrates a control surface 5501 for Filter 3, "Filter Patients". When selected, this filter displays a list 5502 including each of the names found in the database for the time interval selected using Filter 1. The user selects/checks a patient name or several patient names. To compare the selection of the patient names the user may press the Ok button 5503. The data only for those selected patients will appear on the reporting control tab. If there are no patient names to select from on the drop-down list of this filter then data for "undefined" which means no specific patient will be displayed after the user selects Ok. This means that no patient names were selected prior to the footswitch activation within the Filter 1 time interval. The default condition is all patient names.

Figure 56:
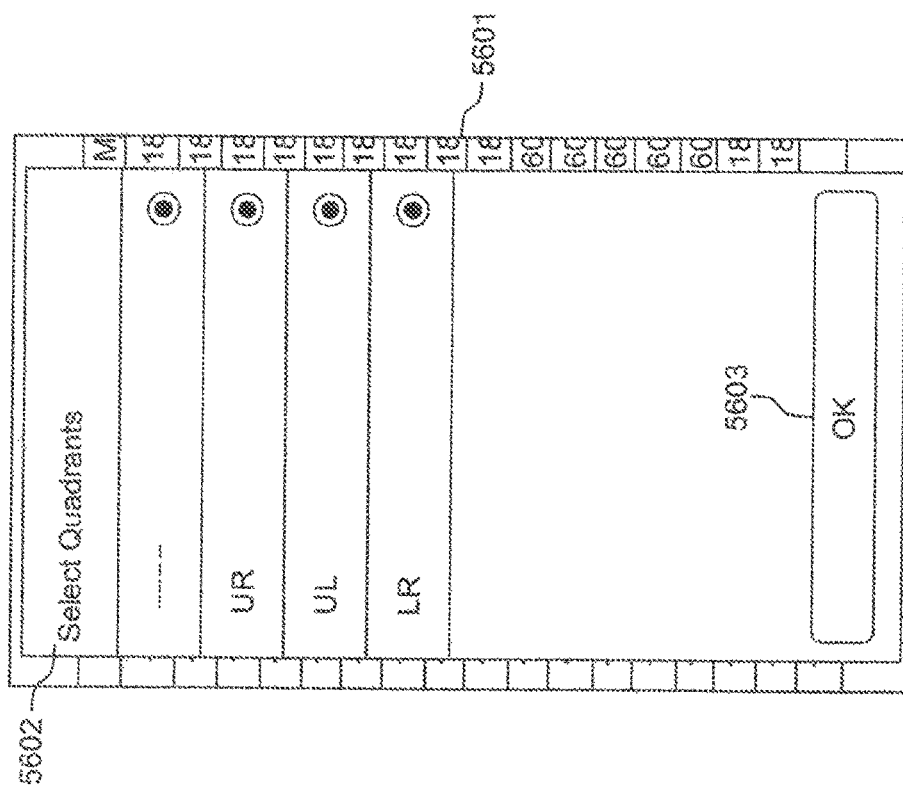

FIG. 56 illustrates a control surface 5601 for Filter 4, the "filter site" option. When selected there is a drop-down list 5602 titled Select Quadrants or Sextants. The drop-down list 5602 pertains to the clinicians' selection(s) of the Dental Arch options, whether Quadrant(s) or Sextant(s), which appear on the home screen. When the clinician selects one of the different filter sites (e.g., UR, UL and LR) for the clinician to be able to view the patient data, the patient data for those selected filter sites appears on the reporting control tab. The default condition is that all Quadrants/Sextants are displayed. The drop-down list also includes an Ok button 5603 for confirming selections.

Figure 57:
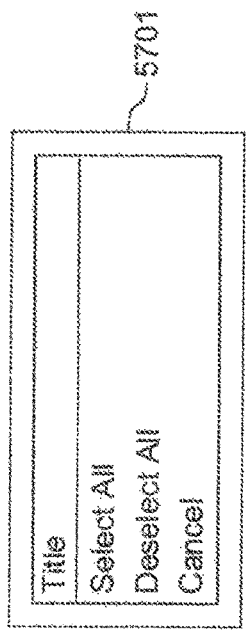

In one embodiment, a deliberate long touch on either of the drop-down lists of Filters 3 and 4 will activate a pop-up screen 5701 as shown in FIG. 57, with selections to Select All, Deselect All, or Cancel.

Figure 58:
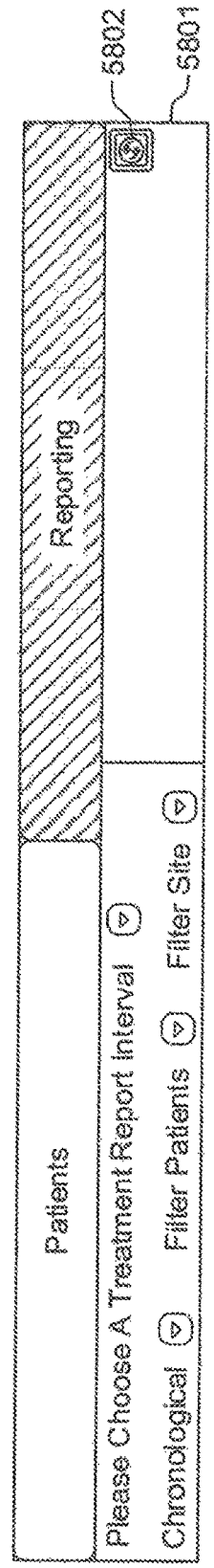

FIG. 58 is a view for illustrating a refresh button 5802 located toward the upper right side of the Reporting tab 5801 and, when selected, has the functionality of showing patient data.

Figure 59:
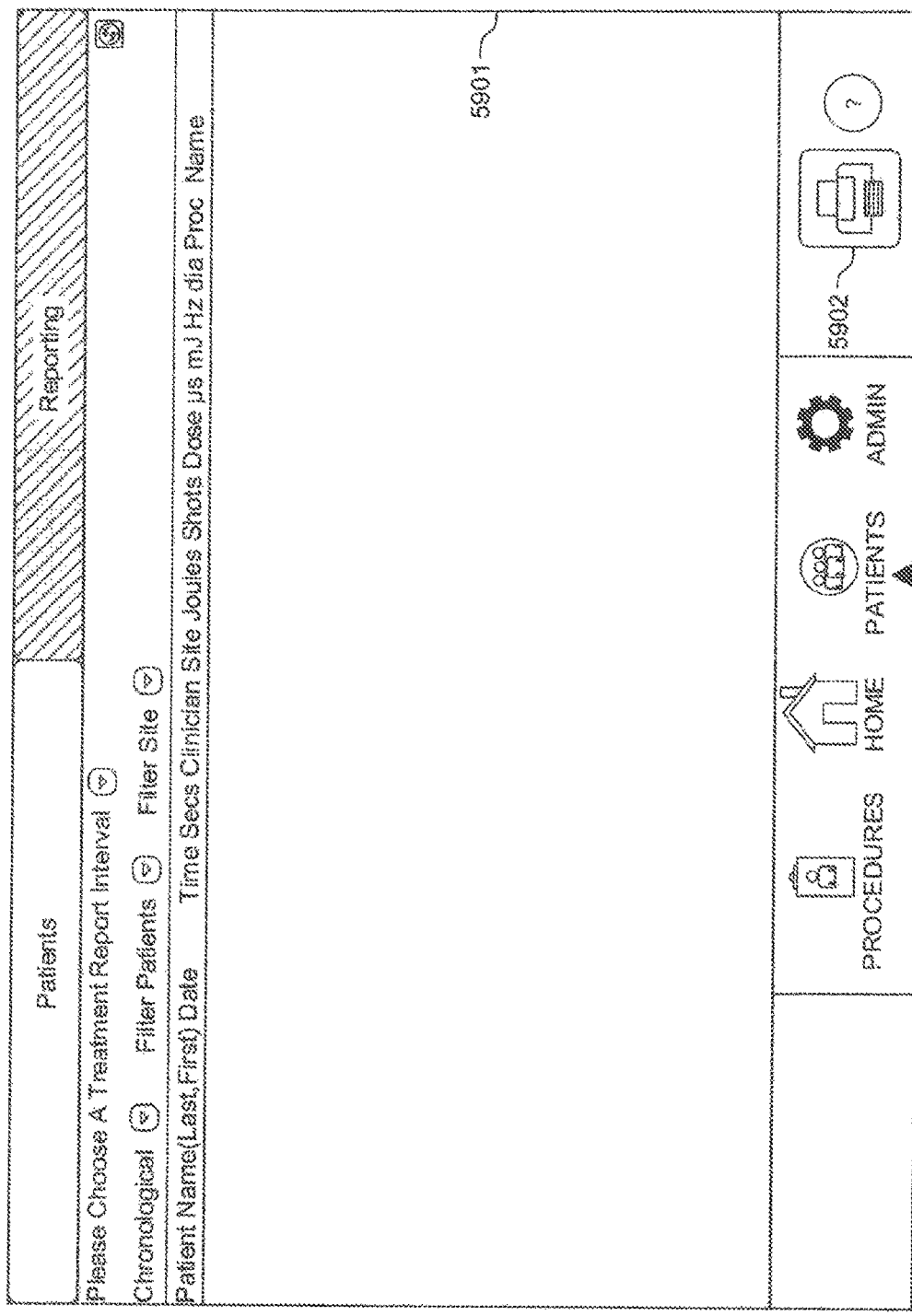

In FIG. 59, a control surface 5901 includes a print icon 5902: The print icon 5902 is configured with the main laser computer 300, tablet 400 (including, e.g., a tablet Bluetooth printing app), and a corresponding printer to print out patient data that appears on the reporting tab or the reporting control surface 5901. The printer icon 5902 is located toward the bottom right side of the home screen. This enables the user to be able to print out screen shots from the home screen as well as data from the Info/Timer icon bar and the 3 different options of features that can be accessed.

In one example, to use Bluetooth to print out patient data that is displayed on the Reporting tab (reporting control surface), the user selects the printer icon 5902 which is located toward the lower right side of the screen. Once the user has selected the printer icon 5902 on the reporting control surface (e.g., surface 5901), then the user will be brought to, e.g., a print mobile app screen, by which the user may select nearby Bluetooth printers. Once selected the print mobile app will do a device scan searching for Bluetooth printers and select a corresponding print icon so that the selected patient data will be printed out.

A sample report actually printed from the eGUI and the Bluetooth Printer might be arranged as follows:

| | | | | | | | | | | | | | |
|---|---|---|---|---|---|---|---|---|---|---|---|---|---|
| Treatment Interval Aug. 6, 2012 09:11:00 to Aug. 6, 2014 10:37:36 Patient-Both | | | | | | | | | | | | | |
| Patient Name (Last, First) | Date | Time | Secs | Clinician | Site | Joules | Shots | Dose | µS | mJ | Hz | dis | Proc Name |
| Yves, Yolanda | 08-06 | 10:23 | 11.0 | Boot Camp | 4 | 67.5 | 225 | — | 100 | 300 | 20 | 360 | Undefined |
| Yves, Yolanda | 08-06 | 10:22 | 12.0 | Boot Camp | 4 | 66.3 | 221 | — | 100 | 300 | 20 | 360 | Undefined |
| Yves, Yolanda | 08-06 | 10:22 | 5.0 | Boot Camp | UR | 35.1 | 117 | — | 100 | 300 | 20 | 360 | Undefined |
| Yves, Yolanda | 08-06 | 10:22 | 0.0 | Boot Camp | UR | 0.3 | 1 | — | 100 | 300 | 20 | 360 | Undefined |
| Yves, Yolanda Total | | | | | | 423.6 | 1412 | | | | | | |
| Oblanc, Othello | 08-06 | 09:35 | 0.0 | Boot Camp | LL | 0.7 | 17 | 100 | 100 | 40 | 100 | 360 | Undefined |
| Oblanc, Othello | 08-06 | 09:35 | 0.0 | Boot Camp | LL | 4.3 | 108 | 100 | 100 | 40 | 100 | 360 | Undefined |
| Oblanc, Othello | 08-06 | 09:35 | 0.0 | Boot Camp | LL | 1.0 | 24 | — | 100 | 40 | 100 | 360 | Undefined |
| Oblanc, Othello | 08-06 | 09:33 | 0.0 | Boot Camp | 20c | 20.4 | 511 | — | 100 | 40 | 100 | 360 | Undefined |

Treatment Interval Aug. 6, 2012 09:11:00 to
Aug. 6, 2014 10:37:36 Patient-Both

| Patient Name (Last, First) | Date | Time | Secs | Clinician | Site | Joules | Shots | Dose | µS | mJ | Hz | dis | Proc Name |
|---|---|---|---|---|---|---|---|---|---|---|---|---|---|
| Oblanc, Othello | 08-06 | 09:32 | 0.0 | Boot Camp | 20 | 22.5 | 562 | — | 100 | 40 | 100 | 360 | Undefined |
| Oblanc, Othello | 08-06 | 09:32 | 0.0 | Boot Camp | 31c | 30.0 | 751 | 110 | 100 | 40 | 100 | 360 | Undefined |
| Oblanc, Othello | 08-06 | 09:31 | 0.0 | Boot Camp | LR | 38.2 | 955 | 110 | 100 | 40 | 100 | 360 | Undefined |
| Oblanc, Othello | 08-06 | 09:31 | 0.0 | Boot Camp | LR | 59.2 | 1480 | 110 | 100 | 40 | 100 | 360 | Undefined |
| Oblanc, Othello | 08-06 | 09:30 | 0.0 | Boot Camp | LR | 25.2 | 631 | 110 | 100 | 40 | 100 | 360 | Undefined |
| Oblanc, Othello | | | | Total | | 201.6 | 5039 | | | | | | |

FIGS. 60 to 65 are views for explaining administration control screens according to example embodiments.

In one example, a main laser computer 300 "Admin" screen might include 2 separate tabs: a Measure Power tab and the Control Panel tab.

Figure 60:
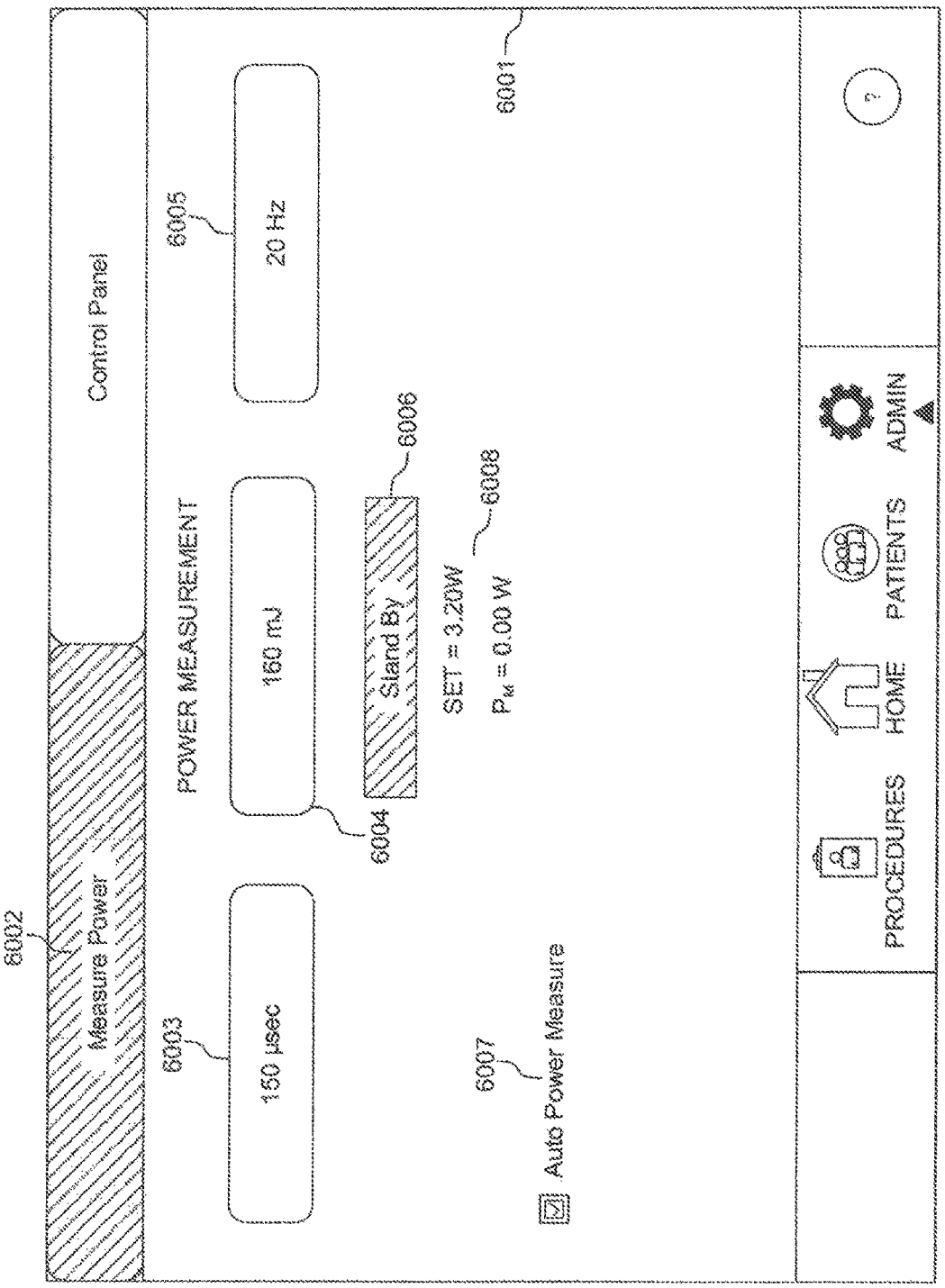
Figure 61:
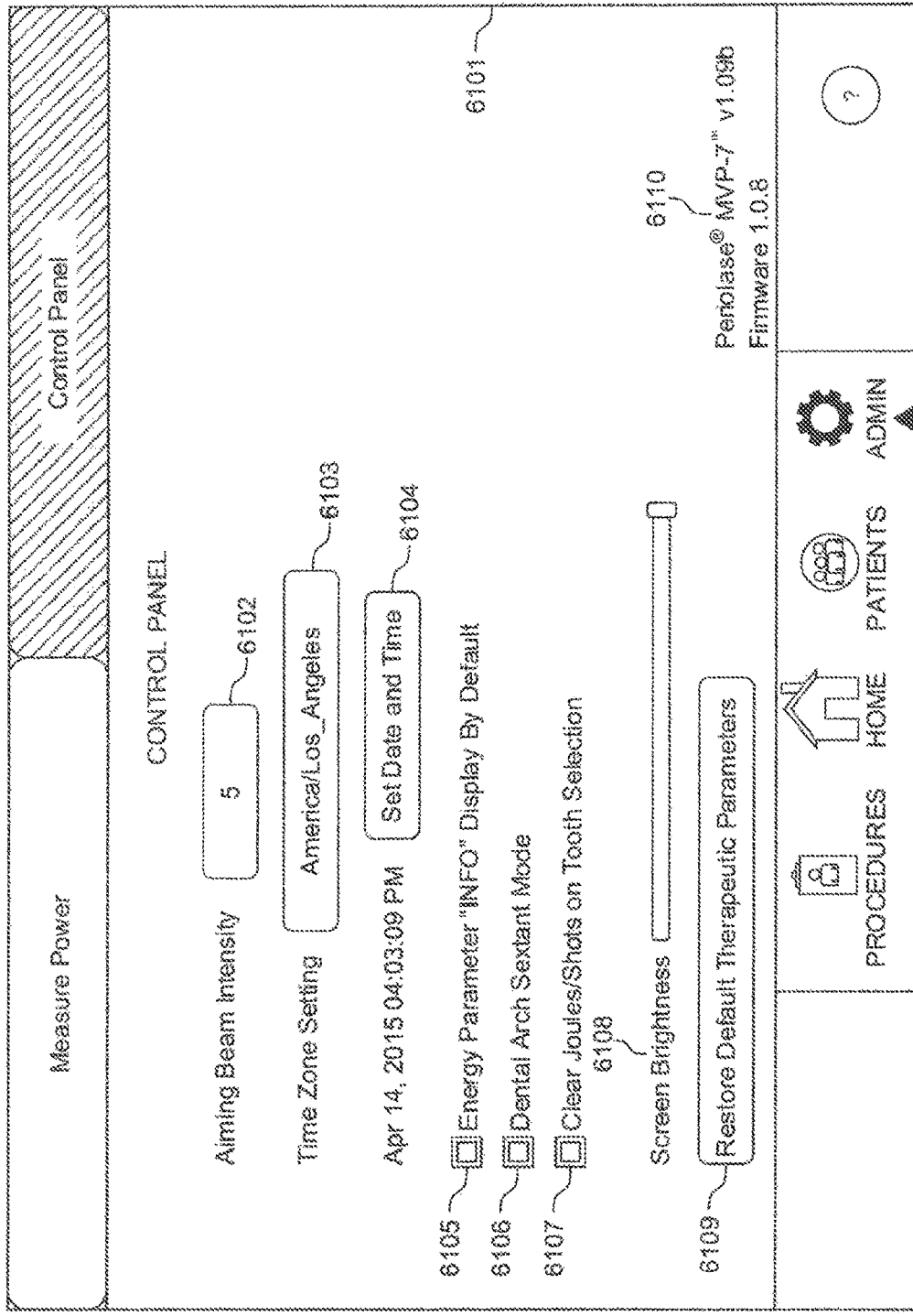

FIG. 60 depicts an example control screen 6001 in accordance with the Measure Power tab 6002. The Measure Power tab In one example, a main laser computer 300 "Admin" screen might include 2 separate tabs: a Measure Power tab and the Control Panel tab. 6002 has the same functionality as the $P_M$ (power measurement) mode under the Energy icon bar on the Home screen. This measures power output. The user adjusts the therapeutic parameter settings by clicking on µsec 6003, mJ 6004, and Hz 6005, then selecting the up and down arrows or clicking on the therapeutic parameter itself; a drop-down list of settings will appear. Therapeutic parameter settings that appear on the 3-column pop-up box of the Energy pop-up box (shown previously) with a red locked icon indicating that those set of therapeutic parameter settings cannot be changed. Control screen 6001 also includes an indicator 6006 that the laser is in standby mode, Auto Power Measure icon 6007 allowing for selection of the automatic power measure mode, and information display 6008 indicating the set power.

Figure 62:
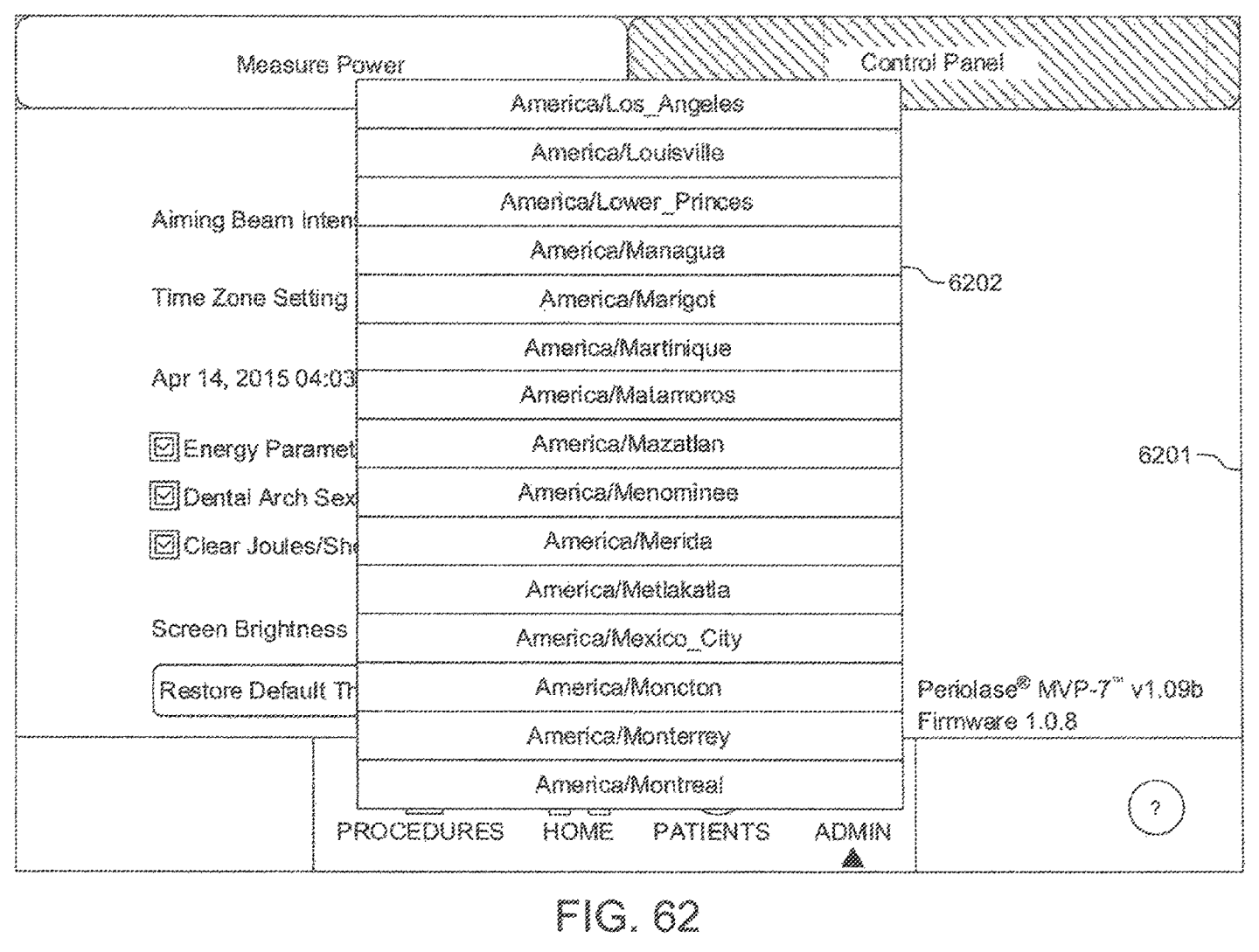

FIG. 6I is an example of a control screen 6101 displayed in accordance with the control panel tab. Control screen 6101 includes a control 6102 for selecting aiming beam intensity, with a default preferred setting of 5. Control screen 6103 also includes a time zone setting control 6103. In that regard, selection of the time zone setting control 6103 may cause a display of a pop-up list of selectable time zones, as shown in FIG. 62. In particular, as shown in FIG. 62, a control screen 6201 includes the displayed list 6202. The local time zone feature has a drop-down list of countries, cities and states that the user can choose from so that the time on the tablet will coincide with the user's local time zone.

Returning to FIG. 6I, a selectable icon 6104 may also allow a user to set the local date and time.

Start-up Configuration Checkbox Options 6105, 6106 and 6107 are features that can be accessed through the home screen of the tablet 400 when they are selected (checked). In particular, the options include option 6105 for Energy Parameter INFO Display By Default. When the user selects this check box, the Joules and Shots will appear by default on the home screen underneath the Timer/Info icon bar. Option 6106 for Dental Arch Sextant Mode provides that when the user selects this check box, the dental arch that will appear by default on the home screen will be the Sextant dental arch. Option 6107 for clear Joules/Shots on Tooth Selection provides that when the user selects this check box, the mJ on the home screen will clear to zero automatically when the user is accessing the Individual Tooth selection then decides to opt out of this feature on the home screen.

Screen Brightness control 6108 allows the user to control the screen brightness of the tablet by swiping from left to right. Restore Default Therapeutic Parameters control 6109, when selected, restores the default setting of the therapeutic parameter settings on any previously overwritten preset procedures.

Information display 6110 includes, e.g., a software and firmware version for main laser computer 300. This informs the user of what software of the tablet 400 is running and firmware version that the main laser computer 300 has installed. In this embodiment, the user should be able to read that the most up-to-date versions are: Software Main laser computer 300 MVP-7 v 1.09b and Firmware 1.0.8. If these versions are not up-to-date then the user can have the latest versions installed to ensure the eGUI interface can be utilized with all the current features for an enjoyable user experience.

Figure 63:
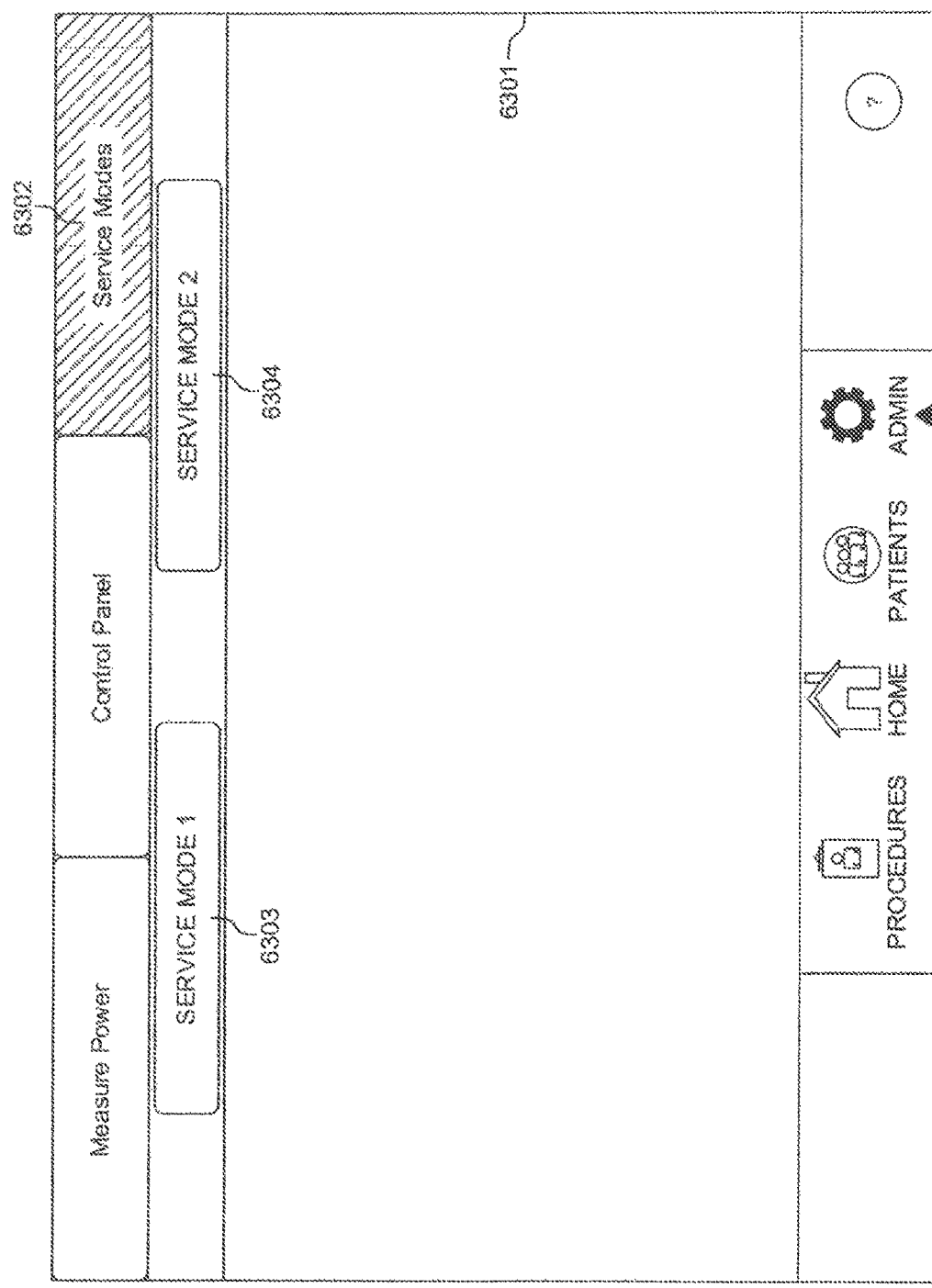
Figure 64:
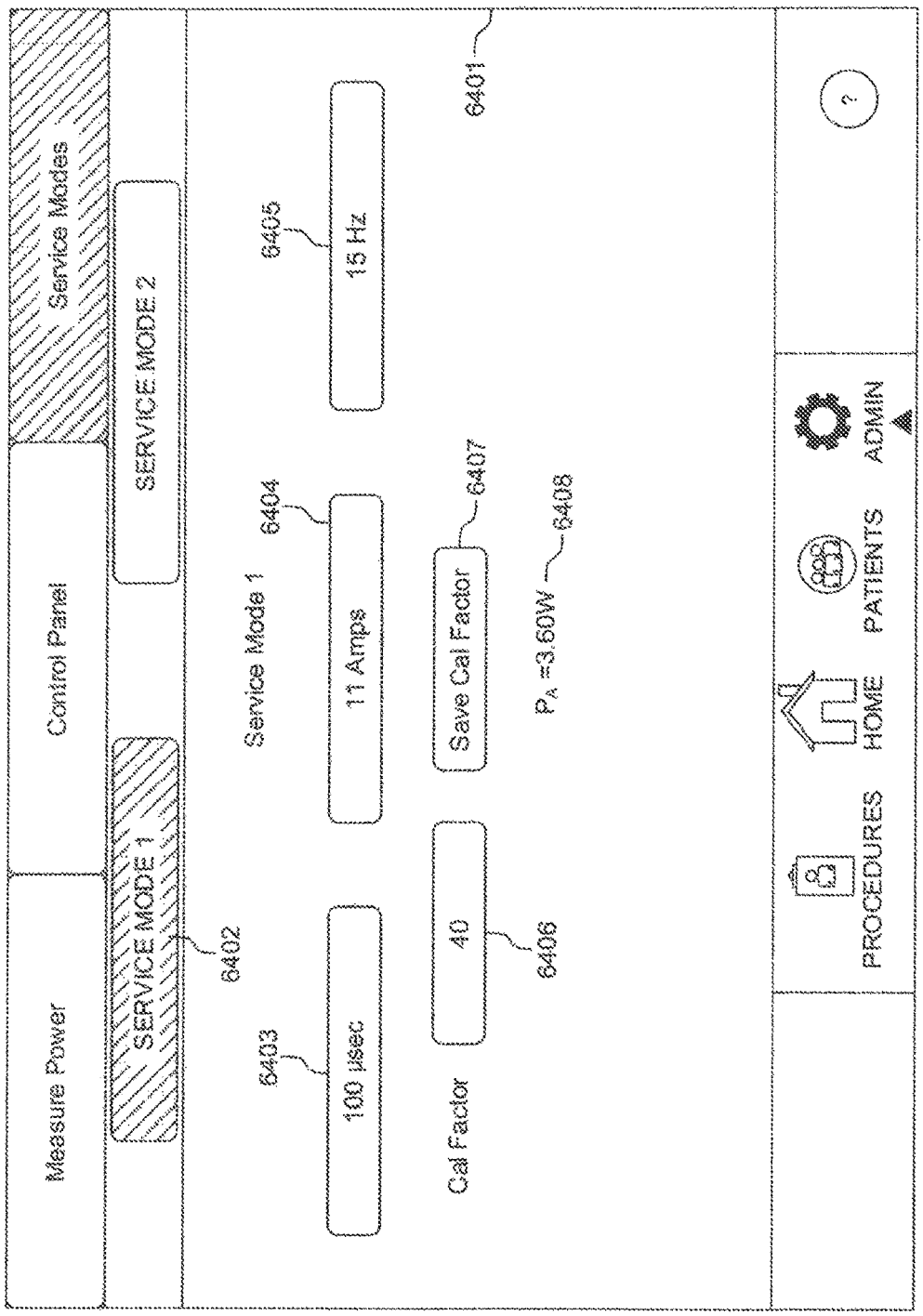
Figure 65:
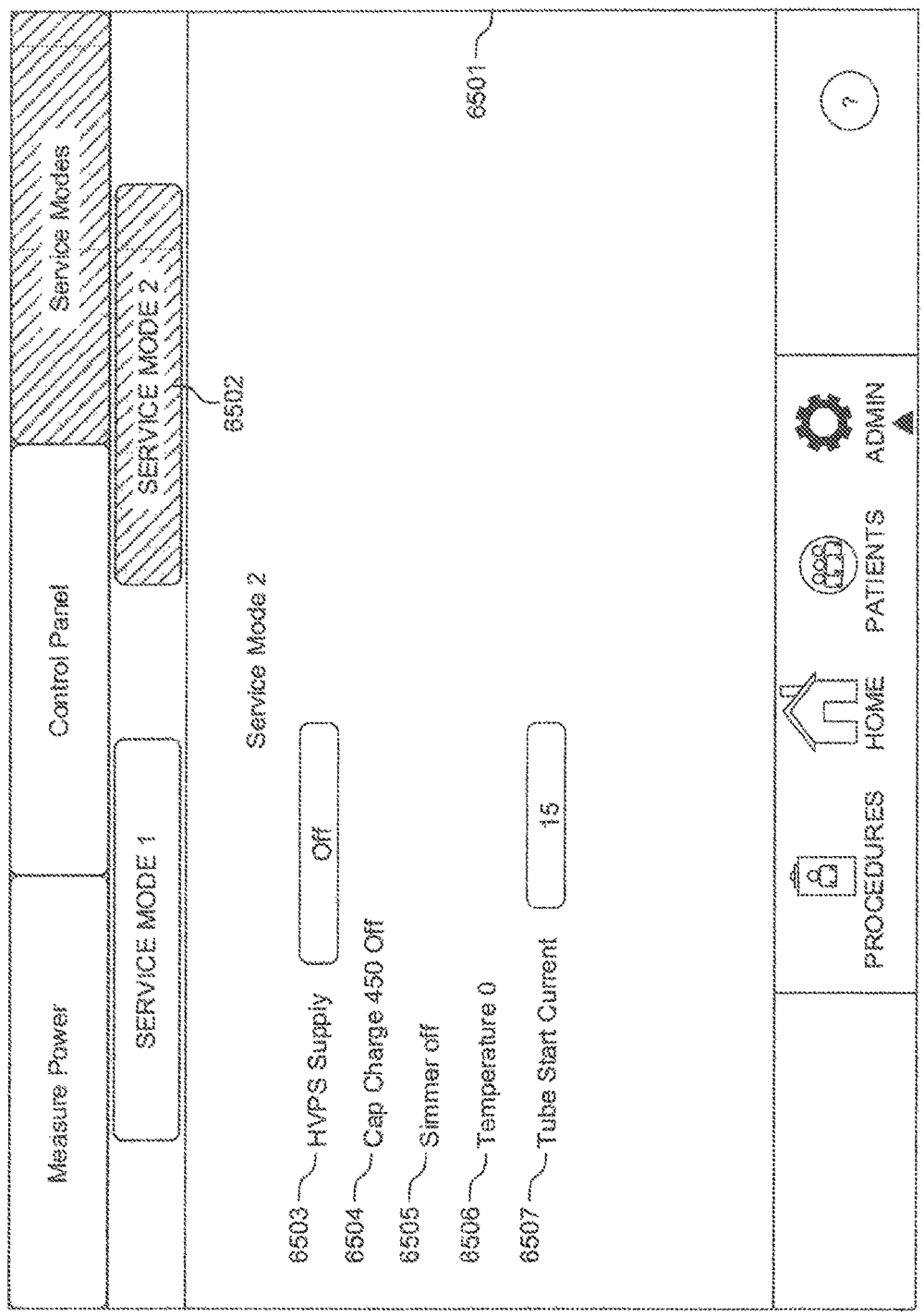

FIGS. 63 to 65 are views for explaining service mode screens.

FIG. 63 is a view of a control screen 6301 for selecting a service mode. In one embodiment, Service Mode is a feature that should be only accessible by a technician, rather than a clinician. This allows the user to have access to 4 separate TABS: Measure Power, Control Panel, and Service Mode tab 6302, which, when selected, displays buttons 6303 and 6304 for selection of service modes 1 and 2, respectively. In one example, in order to access the service mode feature, the user must login with service mode login credentials which are, e.g., "service" (all lowercase) for both username and password.

In that regard, the functionality of the measure power tab under the service mode credentials may have the same functionality as that of the Measure Power tab on the main laser computer 300 ADMIN Screen(s), and the functionality of the control panel tab under the service credentials may have the same functionality as that of the Measure Power tab on the main laser computer 300 ADMIN Screen(s).

FIG. 64 illustrates an example control screen 6401 when the SERVICE MODE 1 icon bar (6402) is selected. In one example, to access the service mode 1, the user selects a Service Modes tab from the Main laser computer 300 ADMIN screen. Once the Service Modes tab is selected, the user presses the SERVICE MODE 1 icon bar 6402 to be brought to the Service Mode 1 screen 6401. Service mode 1 allows operation of the laser at fixed current and pulse width, while monitoring the internal energy monitor. To adjust the μsec, Amps, and Hz settings, the user selects the corresponding parameter icon bars (6403, 6404 and 6405, respectively) and a drop-down list (not shown) will appear, after which the user may change the settings by using the (+) and (−) buttons or by selecting on the parameter itself and swiping up and down to select the desired individual parameter(s), after which a "SET" selection may save the parameters. The calibration factor can be changed with an icon bar 6406, to match the laser output to an external power meter and saved with an icon bar 6407. To change the calibration factor (cal factor), the user simply selects the Cal Factor icon bar 6406 and a drop-down list will appear. The user may swipe up and down to select a desired selection then press the Save Cal Factor icon bar 6407 to save the changes. Information display 6408 displays the measured power from the internal energy monitor, averaged over, e.g., 10 pulses. The footswitch fires the laser at the selected current, repetition rate and pulse width. The coolant pump will run, the READY lamp will light, and the aiming beam will turn on.

FIG. 65 illustrates an example control screen 6501 when the SERVICE MODE 2 icon bar (6502) is selected. In one example, to access the service mode 2, the user selects a Service Modes tab from the Main laser computer 300 ADMIN screen. Once the Service Modes tab is selected, the user presses the SERVICE MODE 2 icon bar 6502 to be brought to the service mode 2 screen 6501. Service mode 2 allows control of the HVPS supply using area 6503. Service mode 2 also allows testing of the capacitor charge (Cap Charge) and/or simmer circuits using controls 6504 and 6505, display of the coolant temperature 6506 and setting of the tube start current with control 6507. Service Mode 2 sets the tube start current and the default setting for this 15. The coolant pump will run.

During a charge and simmer test, a warning may be displayed as follows:

WARNING: High voltages are present when performing this service with the cover off Do not touch any wiring or components until power is disconnected and you are sure all capacitors have discharged.

Meanwhile, the measured coolant temperature may be shown in the timer display, in degrees C., for the user to confirm that the thermistor sense circuitry is functioning.

Figure 66:
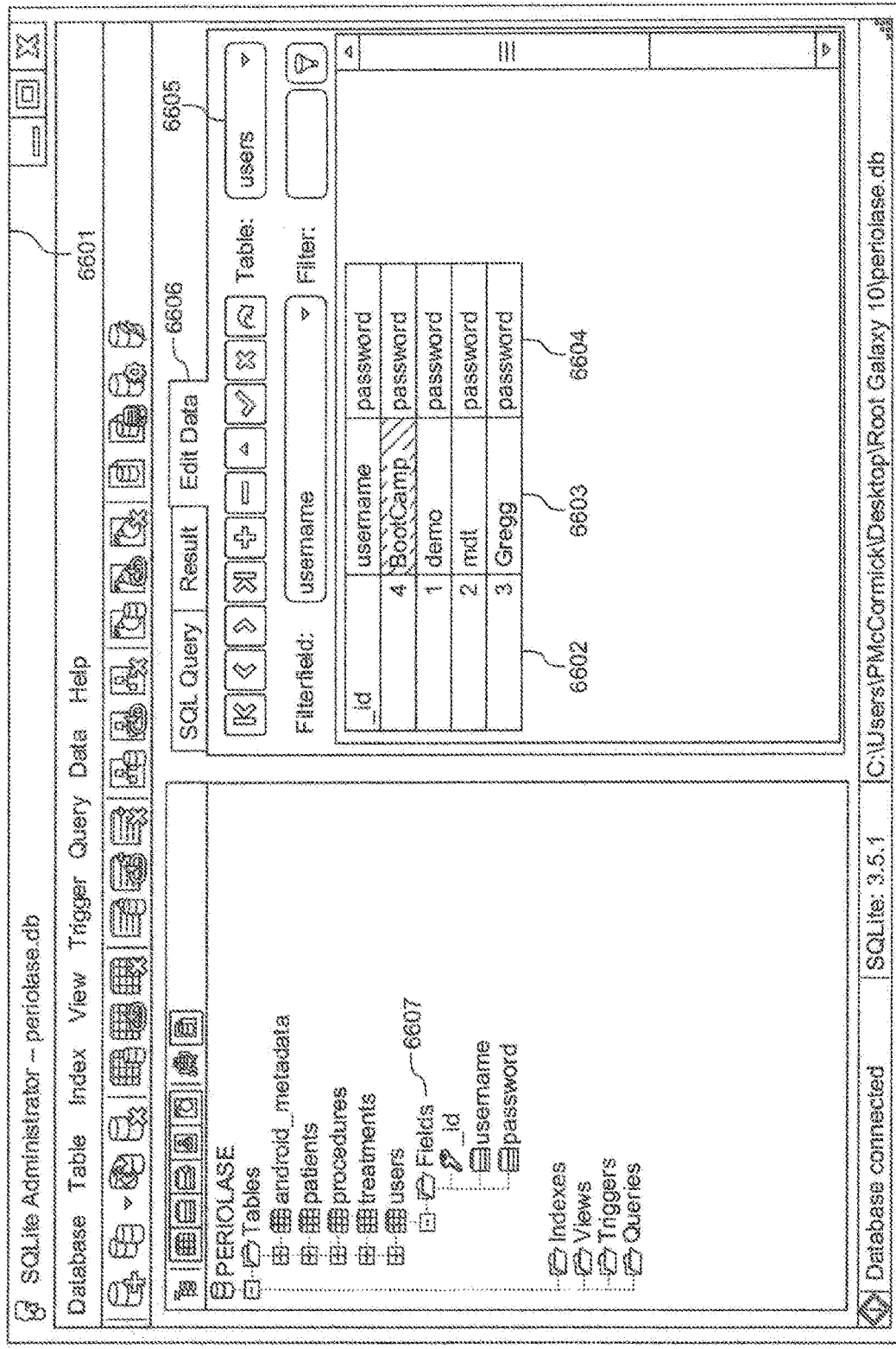

FIGS. 66 and 67 are views for explaining an example of users and procedures Database Administration. In particular, FIGS. 66 and 67 are views for using an SQL Lite database administrator console to manage users, user rights, procedures and images.

In that regard, FIG. 66 depicts an example of a first administration screen 6601. In this example, an administrator has selected a "fields" folder 6607 from a set of "users" on the left side, and selected an "Edit Data" tab 6606 on the right side. Drop-down list 6605 allows for display of other tables, but is currently set on "users". The editable users table includes column 6602 for a user id, column 6603 for a username, and column 6604 for a corresponding user password.

FIG. 67 depicts an example of another administration screen 6801, including detailed fields for a procedures table, including a column for procedure id 6802, a column for user id 6803, a column for a value indicating a level of access 6804, as discussed above, a column 6805 for procedure name, a column 6806 for a procedure image (if applicable or available), column 6807 for a pulse width corresponding to the procedure, column 6808 for an energy value corresponding to the procedure, column 6809 for a repetition rate corresponding to the procedure, and a column 6810 indicating the fiber diameter corresponding to each procedure id.

Treating Gingival Disease

Figure 70:
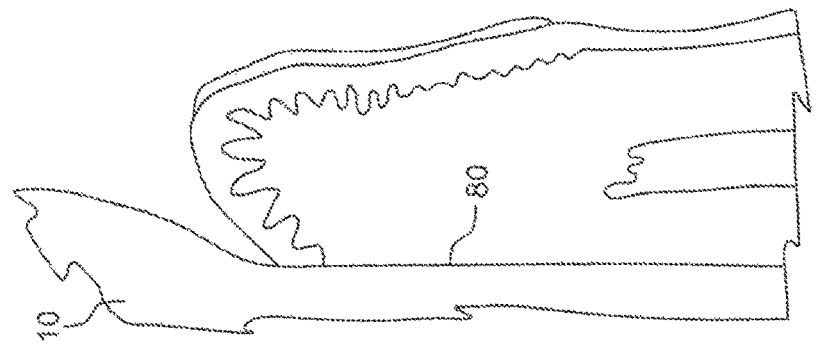
FIG. 70 is a section of the same gingival tissue as in FIG. 68 after completion of a laser-assisted periodontitis procedure according to an example embodiment.
Figure 69:
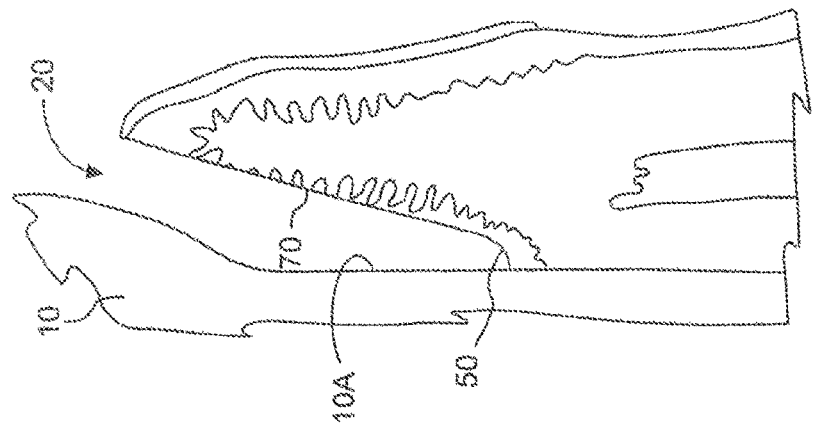
FIG. 69 is a section of the same gingival tissue as in FIG. 68 showing the position of surgical tissue severing according to an example embodiment.
Figure 68:
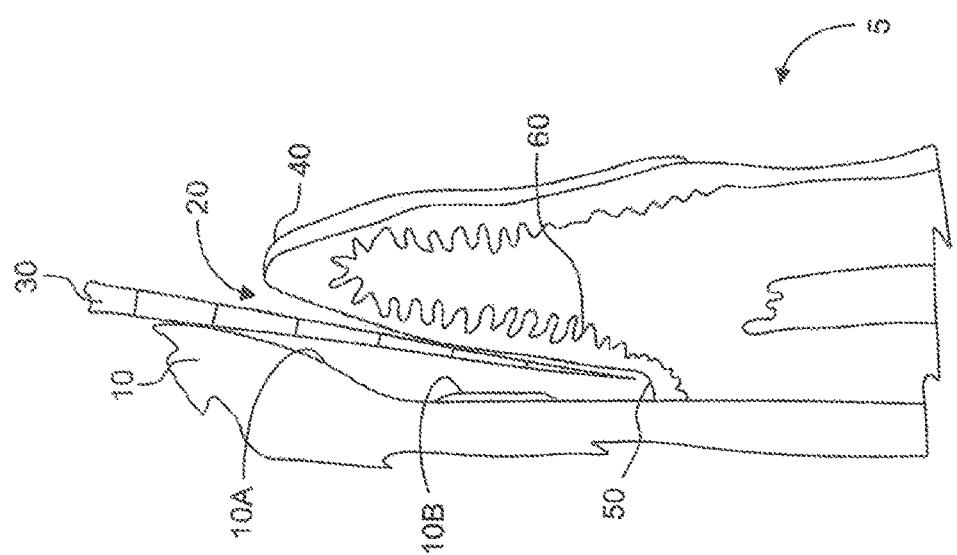
FIG. 68 is a section of a gingival tissue prior to the administration of a laser-assisted periodontitis procedure according to an example embodiment.

Aspects of the method for treating gingival disease will now be illustrated and described with respect to FIGS. 68 to 70.

In that regard, FIG. 68 is a section of a gingival tissue prior to the administration of a LANAP® procedure according to an example embodiment. FIG. 69 is a section of the same gingival tissue as in FIG. 68 showing the position of surgical tissue severing according to an example embodiment, and FIG. 70 is a section of the same gingival tissue as in FIG. 68 after completion of a LANAP® procedure according to an example embodiment.

Referring now to FIGS. 68 to 70, the LANAP® Procedure comprises a step-by-step approach. First, the gingival tissue 5 corresponding to a targeted tooth and root 10 is anesthetized. The depth of a pocket 20 in the gingival tissue is measured, preferably with a periodontal probe 30, taking at least six spaced-apart measurements around the tooth root 10. The pocket depth is defined as extending from the upper gingival margin 40 to the mucogingival junction 50. The interior epithelial lining 60 of the pocket 20 is then ablated and vaporized to the full depth of the pocket 20, preferably using a laser fiber having a preferred diameter of between 100 microns and 600 microns, the fiber preferably oriented parallel to the surface of the tooth root 10. This is completed on all sides of the tooth 10. This step generates and prepares a new pocket tissue surface 70. Preferably not more than 10 Watts of fiber output power is used, as measured at the distal end of the fiber, and a lasing frequency of not more than 100 hertz is preferably applied. Pulse duration range in this example may be 100 to 650 microseconds.

Next, the surface of the tooth and root 1OA is cleaned of all foreign matter 1OB, again (using, e.g., an ultrasonic handpiece as described above), to the depth of the pocket 20 on all sides of the tooth and root 10. In this example, this is followed by an irrigation of the pocket 20 with a bactericidal solution. Following that, the pocket 10 is lased to remove granulomatous tissue, and to disinfect, assist in hemostasis, cauterize free nerve endings, and seal lymphatics of the pocket tissue surface. Lasing also prepares the pocket tissue surface 70 for adhesion to the tooth and root surface.

Next, occlusal interferences and occlusal traumatic forces are eliminated (using, e.g., a high-speed handpiece). The new pocket tissue surface 70 is lased to adapt it for clot and tissue adhesion. The pocket tissue surface 70 is approximated with the tooth and root surface I OA preferably with finger pressure to hold the pocket tissue surface 70 in contact with the tooth and root surface I OA, preferably from 2 to 3 minutes, allowing a thin clot 80 to form between the pocket tissue surface 70 and the tooth and root surface I OA so as to advance and assure adhesion of these tissues. Finally, the body's natural immune system is enhanced by prescribed medications for outpatient use in preventing infection. This step is useful in order to protect against infection and reduce inflammation. The procedure preferably includes the further step of providing at least one subsequent occlusal equilibration examination.

Further example aspects of one embodiment of an example procedure are now described. In one example, the area of concern, usually two quadrants, is anesthetized. The procedure is applied independently to each tooth involved. Pocket depth is measured and recorded with a perio probe to determine the full depth of the diseased pocket. A contact laser fiber is oriented along the long axis of the tooth root and is used to create a gingival trough or flap by ablating the free gingival margin and the internal epithelial lining of the pocket, thereby exposing the tooth root surface. Appropriately cleaved contact laser fibers provide precise control of the laser energy, the physical placement of the laser energy, and the determination of the desired physical orientation of the laser to the tissue to be removed. A gingival trough or flap is used to expose the tooth root surface. Excision of the free gingival margin removes pathogens and pathologic proteins within the tissue of the free margin which are otherwise unremovable and provides hemostasis for better visualization. This step also defines the tissue margins preceding mechanical instrumentation and preserves the integrity of the mucosa. It also dissects-out the separation between the free gingival margin and the fibrous collagen matrix which holds the gingiva in position. This aids in the maintenance of the crest of the gingival margin. With the use of the "hot-tip" effect, further excision of the inner pocket epithelium around the entire tooth and root is completed, to the depth of the probe readings. Ordinarily, no attempt is made to break through the mucogingival junction with the optical fiber. The "hot-tip" effect (accumulated tissue proteins heated via conductivity secondary to the passage of laser energy through the fiber) provides the selective removal of sulcular and pocket epithelium and granulomatous tissue without removing substantially any connective fibrous tissue and does so circumferentially and radially. As necessary, the excised tissue that accumulates on the tip of the laser fiber is removed. Ultrasonic scaling of all tooth and root surfaces to the depth of pocket is completed. The intent is to remove all foreign structures and substance from the pocket to allow adhesion of the soft tissue to the clean tooth and root surface. Lasing of the pocket to remove remaining granulomatous tissue, disinfect tissue, assist in hemostasis, cauterize free nerve endings, seal lymphatics, prepare tissue for soft and fibrin clot adhesion to tooth and root surface is accomplished. Elimination of occlusal interferences and occlusal traumatic forces is completed using, e.g., a high-speed handpiece as described herein. For best results this step is helpful, since it allows the tissue to heal and the bone to regenerate. The laser modifies the tissue to allow new attachment to take place but if the trauma of malocclusion continues the tissue cannot withstand and begins to break down immediately. All treatment sites are irrigated to the deepest depth of the periodontal pockets with a bactericidal solution of a high tissue substantivity (e.g., chlorhexidine gluconate 0.12%). The irrigation aids the laser in the reduction of bacteria in the pocket and in removing debris. Approximation of the wound edges is completed. Lasing is further accomplished to control blood flow as needed. Healing of the wound edges is by secondary intention. The tissue is compressed with finger pressure for 1 to 3 minutes against the tooth and root from both a facial and lingual direction in order to permit only a thin clot to form between the tissue and the tooth and root.

Post-procedural steps include prescribing medications for home use and reviewing postoperative care with the patient. An anterior deprogrammer and dis-occluding occlusal splint may be used to provide anterior guidance, e.g., a "LANAP Splint" or anterior "jig". A thorough occlusal adjustment follow-up examination is required. This treatment should continue periodically until bone development is complete. Pocket-depth measurements are to be avoided for 12 months.

In another example embodiment, a laser-assisted gingivitis and complete periodontitis bone, periodontal ligament and cementum tissue complex true regeneration procedure uses a free-running pulsed neodymium yttrium aluminum garnet laser device with a 1,064-nanometer wavelength and duty cycles between 0.10 and 1.95 percent (100 to 650 microseconds at 10 to 30 hertz), average powers between 2.4 Watts and 6.0 Watts, energy levels between 80 millijoules and 600 millijoules, peak powers between 123 Watts/pulse and 6000 Watts/pulse, energy densities between 64 J/cm 2 and 849 J/cm2, power densities between 1910 Watts/cm 2 and 8488 Watts/cm 2 using preferably the free-running pulsed Nd:YAG PerioLase® MVP-7™ and includes steps of anesthetizing soft and hard tissues corresponding to a targeted tooth, quadrant or sextant of teeth of a patient, the tooth having a root and root surface, bone sounding using a periodontal probe and recording the depths of all bony defects in the soft tissue at 6 sites around the targeted tooth and root and to bone, from an upper gingival margin to the extent of the accessible bony defect, recording the sum total of all 6 probe depths/bone soundings and multiplying by a predesignated constant which in this example is 1 to 40, depending on soft tissue phenotype (biotype), LANAP® Periodontal Disease Case Type Classification I-V, and LANAP® Tooth Mobility Score 0-4 (representing a "light dose" of 1 to 40 Joules per millimeter pocket depth. Example: 6 probe depths of I 0 mm each=60 mm total×I=60 Joules of total light dose). The total light dose is applied such that the majority of the total light dose is applied during the LANAP® Ablation, while the remaining portion of the total light dose is delivered during the LANAP® Hemostasis setting. In this example, the total light dose is applied ⅔rds during the LANAP® Ablation, while the remaining ⅓rd of the energy is delivered during the LANAP® Hemostasis setting. In this example, 40 Joules are delivered during the LANAP® Ablation Step, and 20 Joules are delivered during the LANAP® Hemostasis Step. The example further uses a FiberFlex™ 300-, 320-, 360-, 400-micron (preferably a 360-micron) diameter quartz optical fiber fed through an anodized aluminum TrueFlex® handpiece and bendable cannula, photothermally rupturing, disassociating, separating, ablating, denaturing and vaporizing the inner diseased, inflamed, infected, bacteria-invaded, ulcerated epithelial lining of the pocket and granulomatous tissues, photothermally altering, disrupting, denaturing, dehydrating, and destroying hard calcified calculus and concrements on the tooth and root surface, to the soft tissue and hard tissue extent of the pocket and full bony defect, on all sides of the tooth and root to prepare the root surface of said tooth for a complete new regenerative tissue complex consisting of new alveolar bone, periodontal ligament and cementum, or long junctional epithelium, and includes lasing the tooth and root surface to destroy lipopolysaccharides (LPS) of gram-negative bacteria, irradiating tissue with blue light with energy densities between, but not limited to, 1 and 2500 J/cm2 and power densities between, but not limited to, 10 to 1200 mW/cm 2 for lethal effect on bacteria, using a laser and/or preferentially LANAP® PiezoSonic piezo-electric ultrasonic device with water lavage and 20,000 to 30,000 hertz, and specialized LANAP Piezo ultrasonic tips, operating at 8 to 10 Watts, used in sequence for cleaning the tooth and root surface of all foreign matter, bacterial smear layer covering and included in soft and hard calcification, calculus, concrements, cement on the tooth and root surface to the full depth of the pocket on all sides of the tooth and root surfaces from crestal margin to bony defect base, decorticating the crestal and marginal ridge bone to perform an osteotomy and/or ostectomy and to initiate angiogenesis, irrigating the pocket with a bactericidal solution, preferably chlorhexidine 0.12%, and using the laser within the full parameter range. In this example embodiment, the laser is used with average powers of 2.4 to 6.0 Watts, 10 to 30 hertz repetition rate, and 100 to 650 microsecond pulse duration, preferably with Duty Cycles between 0.1 percent and 1.95 percent. At 100 microsecond pulse duration (in this example): Average Power of 2.4 Watts, Energy Level of 120 millijoules, Peak Power of 1200 Watts/pulse, Energy Density of 118 J/cm 2, Power Density of 2358 Watts/cm 2 and Duty Cycle of 0.20 percent; to an Average Power of 6.0 Watts, Energy Level of 300 millijoules, Peak Power of 3000 Watts/pulse, Energy Density of 295 J/cm2, Power Density of 5894 Watts/cm 2 and Duty Cycle of 0.2 percent; to 650 microsecond pulse duration: Average Power of 2.4 Watts, Energy Level of 120 millijoules, Peak Power of 184 Watts/pulse, Energy Density of 118 J/cm 2, Power Density of 2358 Watts/cm 2 and Duty Cycle of 1.0 percent; to an Average Power of 6.0 Watts, Energy Level of 300 millijoules, Peak Power of 461 Watts/pulse, Energy Density of 295 J/cm2, Power Density of 5894 Watts/cm 2 and Duty Cycle of 1.0 percent.

In one aspect, the procedure further includes using a FiberFlex™ 300-, 320-, 360-, 400-micron (preferably a 360-micron) diameter quartz optical fiber fed through an anodized aluminum TrueFlex® handpiece and bendable cannula; lasing to intentionally irradiate the bone at the base of the bony defect in the 6 separate pocket depth measurement locations to initiate hemostasis from the medullary bone; stimulate and upregulate the release of growth factors (e.g., IGF-1 and IGF-11, TGF-beta 1, TGF-beta 2, BMP-2); stimulate and upregulate fibroblasts and stem cells; warm the blood in the pocket to thermolytically cleave fibrinogen thereby converting the blood into fibrin (thrombin catalyzes the conversion of fibrinogen to fibrin), create a stable fibrin clot, and create angiogenesis; remove and/or denature any remaining, residual granulomatous tissue and inflamed, infected and diseased epithelial lining, intentionally leaving granulation tissue in place (inclusive of stem cells, capillaries, fibroblasts), but disinfected; disinfect, assist in hemostasis, cauterize free nerve endings, and seal lymphatics of the pocket tissue surface; and prepare the pocket tissue surface for adhesion; lasing the pocket tissue surface to adapt the pocket tissue surface for tissue adhesion; approximating the pocket tissue surface with the tooth and root surface; maintaining the pocket tissue surface in contact with the tooth and root surface to advance adhesion; and eliminating occlusal interferences and occlusal traumatic forces. In one aspect, the depth measuring is completed with a periodontal probe taking at least six spaced-apart measurements around the tooth root. In another aspect, the ablating, vaporizing, and lasing are completed with a laser fiber oriented parallel to the surface of the tooth root. In still another aspect, the procedure includes a step of providing a free-running pulsed Nd:YAG, 1,064-nanometer wavelength laser, preferably the PerioLase® MVP-7™, wherein the ablating, denaturing and vaporizing is completed with not more than 6.00 Watts of average output power from the laser, as measured at the distal end of the fiber, and with a lasing frequency of not more than 100 Hz. In yet another aspect, the laser fiber is of a diameter between approximately 200 and 600 microns. In still another aspect, the method includes firm pressure to hold the pocket tissue surface in contact with the tooth and root surface for 1 to 3 minutes allowing a thin clot to form between the pocket tissue surface and the tooth and root surface.

In these examples, the TrueFlex® handpiece is fabricated from anodized aluminum, but in other examples the handpiece may be fabricated from stainless steel, plastic, Delrin®, titanium and so forth, and not necessarily anodized aluminum.

It should be understood that the body's natural immune system is enhanced by prescribed medications for outpatient use in helping to prevent infection. This step may be important or necessary in order to protect against infection and reduce inflammation. The procedure preferably includes the further step of providing at least one subsequent occlusal equilibration examination.

II. LENAP+eGUI

According to another embodiment herein, a method for removing deep gingival pockets, e.g., a laser excisional new attachment procedure/protocol (LENAP), provides for excise of disease while providing for reconnection of the tissue-tooth connection. Steps in the process include creating a gingival trough in the pocket with a contact laser fiber, excising the pocket epithelium while selectively removing sulcular and pocket epithelium and granulation tissue fully around the targeted tooth to the full depth without breaking through the mucogingival junction, scaling the root surfaces to the full depth ultrasonically, lasing the pocket to remove granulation tissue and to disinfect the tissue, assist in hemostatis, cauterize free nerve endings, seal lymphatics, prepare the tissue for welding and desensitize the tooth, and compressing the tissue against the tooth until adhesion is achieved.

The eGUI can assist the clinician in performing the laser delivery steps of the LENAP protocol by providing procedure presets consistent with the level of clinician training proficiency and certification, as described above with respect to, e.g., FIGS. 4, 7, 48, 49, 66 and 67.

The eGUI also assists the clinician in performing the laser delivery steps of the LENAP protocol by providing instructional and patient educational videos and photos, as described above with respect to, e.g., FIGS. 14, 49 and 50.

The eGUI further assists the clinician in performing the laser delivery steps of the LENAP protocol by providing use of individually selectable Pulse Duration, Energy, Repetition Rate, and intuitive Average Power groupings within a safe therapeutic treatment window, as described above with respect to, e.g., FIGS. 3, 4, 16 to 26, 38, 47, 48, 60 and 61.

The eGUI additionally assists the clinician in performing the laser delivery steps of the LENAP protocol by providing display of measured power contrasted with average power settings to help ensure delivered power matches the intended amount, as described above with respect to, e.g., FIGS. 30 to 39.

The eGUI further assists the clinician in performing the laser delivery steps of the LENAP protocol by providing the ability to hold average power constant as repetition rate or energy settings are individually adjusted, as described above with respect to, e.g., FIGS. 27 to 29.

The eGUI also assists the clinician in performing the laser delivery steps of the LENAP protocol by communicating with a smart connector that identifies the diameter of the optical energy delivery system (e.g., a diameter of fiber 502) in order to adjust laser parameters accordingly, as described above with respect to, e.g., FIGS. 3, 13, 14, 16, 21, 38, 49, 50 and 67.

The eGUI additionally assists the clinician in performing the laser delivery steps of the LENAP protocol by providing ability to hold energy density constant when optical fiber diameters are changed, as described above with respect to, e.g., FIGS. 3, 13, 14, 16, 21, 38, 39, 49, 50 and 67.

The eGUI also assists the clinician in performing the laser delivery steps of the LENAP protocol by providing a display of Joules, Shots, Energy Density, Power Density and Peak Power settings to determine laser beam intensity, impact, and overall effect on tissue, as described above with respect to, e.g., FIGS. 3, 4, 13 to 39, 43, 50, 52, 54, 60, 61 and 67.

The eGUI further assists the clinician in performing the laser delivery steps of the LENAP protocol by providing synchronization with electronic records plus tissue phenotype exemplar photographs to aid in accurate recording, saving and computing parameters and light dose, as described above with respect to, e.g., FIGS. 4, 11, 14, 30 to 33 and 49 to 59.

The eGUI also assists the clinician in performing the laser delivery steps of the LENAP protocol by providing a presentation of light dose to the clinician for approval or adjustment, as described above with respect to, e.g., FIGS. 4, 30 to 33 and 39.

The eGUI additionally assists the clinician in performing the laser delivery steps of the LENAP protocol by providing conversion of average probe depth diagnostics into J/mm average pocket depth and then to light dose, as described above with respect to, e.g., FIGS. 7 and 30.

The eGUI further assists the clinician in performing the laser delivery steps of the LENAP protocol by providing an intuitive chart display of energy delivery progression of photobiomodulation and LENAP light dose delivery that is visually tracked with reference bands corresponding to dosage for first and second pass and managed with a countdown timer according to energy delivery rates and thermal-relaxation criteria, and following the LENAP protocol formula for the first and second laser pass, as described above with respect to, e.g., FIGS. 36 to 39.

In that regard, each of the foregoing features provided by the eGUI promote safety, effectiveness and efficiency of the LENAP protocol for the benefit of the patient.

For purposes of efficiency in description of the LENAP protocol herein, reference may be made again to FIGS. 68 to 70.

In that regard, this embodiment relates generally to surgical procedures, and more particularly to an improved surgical method for eliminating a condition of deep gingival pockets and the disease associated with this condition.

Specifically, periodontal diseases are caused by certain types of bacteria in plaque. These bacteria create toxins which irritate the gums and result in a breakdown of the attachment of the gum tissues to the teeth. Over time, these toxins can destroy gum tissues, and allowing the infection to progress, can result in bone loss. There are many forms of gingival and periodontal diseases, the most common types being gingivitis and adult periodontitis. Gingivitis is the earliest stage and affects only the gum tissue. At this stage, the disease is still reversible. If not treated, however, it may lead to a more severe condition called periodontitis. The gums, bone and other structures that support the teeth become damaged. Teeth can become loose and may have to be removed. At this stage, the disease may require more complex treatment to prevent tooth loss. With healthy gingiva (gum tissue), the teeth are firmly anchored in place. Gingivitis develops as toxins in plaque irritate the gums, making them red, tender, swollen and likely to bleed easily. Periodontitis occurs when toxins destroy the tissues that anchor them in the bone. Gums become detached from the teeth, forming pockets that fill with more plaque. Tooth roots are exposed to plaque and become susceptible to decay and sensitive to cold and touch. Advanced periodontitis is present when the teeth lose more attachment because the supporting bone is destroyed. Unless treated, the affected tooth frequently become loose and may fall out. The method of treatment of periodontal diseases depends upon the type of disease and how far the condition has progressed. The first step is usually a thorough cleaning which may include scaling to remove plaque and calculus deposits beneath the gum line. The tooth roots may also be planed to smooth the root surface so that the gingiva may heal next to the teeth. Surgery may be required when deeper pockets, usually over 4 to 6 mm, are found. It is difficult for the dentist or hygienist to thoroughly remove plaque and calculus from deep pockets. Patients can seldom keep them clean and free of plaque. Allowing pockets to remain may invite infection and bone destruction. When pockets are deep and bone has been destroyed, flap surgery may be necessary to provide access to the roots of the teeth in order to thoroughly remove calculus, plaque and any diseased tissue, and to recontour the bone to a more favorable architecture. In this technique, the gum is lifted away and is then sutured back into place or into a new position that will be easier to keep clean. Some methods teach the use of surgical debridement of the root surface and the removal of granulation tissue following the resection of the soft tissue flap. Aesthetic modifications of this approach have been reported under the title of open flap curettage, reverse bevel flap surgery, Widman flap surgery and modifications of Widman flap surgery and apically positioned flap osseous surgery, guided tissue regeneration.

The embodiment relates to the removal of the deep gingival pocket, elimination of disease and reattachment of the gingiva to the tooth surface.

By virtue of this embodiment, it is ordinarily possible to treat gingivitis or gum disease, and to eliminate gingival pockets by establishing a new connective tissue attachment to the tooth at, or near, the coronal level by producing a long junctional epithelium. The inflamed sulcular and pocket epithelium is excised without substantially removing any connective tissue. The procedure, as described, is indicated when there is a moderate-to-deep, as probed pocket depth of 5 mm or greater, as measured from the coronal to the mucogingival junction, and when any of the following is present: bony defects visible and/or probable, infection in the gingival tissue, mobility of the dentition, and/or aesthetic considerations.

A laser, such as provided by Millennium Dental Technologies, Inc. "PerioLase® MVP-7™" including eGUI, operating at a wavelength of, e.g., between 400 and 12,000 nanometers (in one example, preferably 1064 nanometers), is used to create an initial excisional trough at the marginal gingiva using between one and one hundred Watts, preferably 2.4-6.0 Watts of fiber output power (measured at the distal end of the fiber), and frequencies between one hertz and three hundred megahertz, preferably 10-30 Hertz.

In that regard, although this procedure is described with respect to a specific device (PerioLase® MVP-7™ including eGUI), it should be understood that the procedure is not limited to this device, and can be performed by other devices capable of laser dosimetry, such as an original MVP-7™ type laser without the eGUI.

In one example, the laser device has a 1,064-nanometer wavelength and operates over a preferred parameter range which includes duty cycles between 0.10 and 1.95 percent (100 to 650 microseconds at 10 to 30 hertz); average powers between 2.4 Watts and 6.0 Watts; energy levels between 80 millijoules and 600 millijoules; peak powers between 123 Watts/pulse and 6000 Watts/pulse; energy densities between 64 J/cm2 and 849 J/cm2; and power densities between 1910 Watts/cm 2 and 8488 Watts/cm 2.

According to the embodiment, the method includes excising the inner pocket epithelium around the entire tooth to a depth equal to an initial probe reading of the inner pocket. The eGUI assists the clinician in performing the laser delivery steps of the LENAP protocol by providing: procedure presets consistent with the level of clinician training proficiency and certification; instructional and patient educational videos and photos; use of individually selectable Pulse Duration, Energy, Repetition Rate, and intuitive Average Power groupings within a safe therapeutic treatment window; display of measured power contrasted with average power settings to help ensure delivered power matches the intended amount; ability to hold average power constant as repetition rate or energy settings are individually adjusted; a smart connector that identifies the diameter of the optical energy delivery system in order to adjust laser parameters accordingly; ability to hold energy density constant when optical fiber diameters are changed; a display of Joules, Shots, Energy Density, Power Density and Peak Power settings to determine laser beam intensity, impact, and overall effect on tissue; synchronization with electronic records plus tissue phenotype exemplar photographs to aid in accurate recording, saving and computing parameters and light dose; presentation of light dose to the clinician for approval or adjustment; conversion of average probe depth diagnostics into J/mm average pocket depth and then to light dose; and an intuitive chart display of energy delivery progression of photobiomodulation and LENAP light dose delivery that is visually tracked with reference bands corresponding to dosage for first and second pass and managed with a countdown timer according to energy delivery rates and thermal-relaxation criteria, and following the LENAP protocol formula for the first and second laser pass—all of which promote safety, effectiveness and efficiency of the LENAP protocol for the benefit of the patient.

The excising is followed by an ultrasonic scaling of root surfaces and root planing and scaling of all cementum. The procedure further includes cleaning steps and a lasing of the pocket in preparation for tissue welding. The eGUI assists the clinician in these steps by providing: procedure presets consistent with the level of clinician training proficiency and certification; instructional and patient educational videos and photos; use of individually selectable Pulse Duration, Energy, Repetition Rate, and intuitive Average Power groupings within a safe therapeutic treatment window; display of measured power contrasted with average power settings to help ensure delivered power matches the intended amount; an ability to hold average power constant as repetition rate or energy settings are individually adjusted; a smart connector that identifies the diameter of the optical energy delivery system in order to adjust laser parameters accordingly; ability to hold energy density constant when optical fiber diameters are changed; a display of Joules, Shots, Energy Density, Power Density and Peak Power settings to determine laser beam intensity, impact, and overall effect on tissue; synchronization with electronic records plus tissue phenotype exemplar photographs to aid in accurate recording, saving and computing parameters and light dose; presentation of light dose to the clinician for approval or adjustment; conversion of average probe depth diagnostics into J/mm average pocket depth and then to light dose; and an intuitive chart display of energy delivery progression of photobiomodulation and LENAP light dose delivery that is visually tracked with reference bands corresponding to dosage for first and second pass and managed with a countdown timer according to energy delivery rates and thermal-relaxation criteria, and following the LENAP protocol formula for the first and second laser pass—all of which promote safety, effectiveness and efficiency of the LENAP protocol for the benefit of the patient.

The procedure is categorized as a Gingival Flap Procedure and limited or complete occlusal adjustment. Treatment time of 120 minutes is reasonable to perform two quadrants. Treatment is followed by a coronal polishing/prophylaxis and an occlusal equilibration follow-up and a postoperative check of the area treated. In one example, the lasing steps comprise application of the remaining ⅓ of the total light dose using a 300-, 320-, 360-, 400-micron-diameter (preferably 360-micron-diameter) quartz optical FiberFlex™ fiber fed through a TrueFlex® handpiece and bendable cannula, while operating the FR Nd:YAG laser device within the preferred parameter range.

In one example, a topically placed anesthetic is used to anesthetize the area. For example, a clinician may begin with 4% Prilocaine Plain, using a 30-gauge needle. This anesthetic is perceived by the patient as painless, due to its unique ability to anesthetize soft tissue without stinging. The clinician may inject the anesthetic very slowly into the area, allowing several minutes for the Prilocaine Plain to take effect. The clinician may then continue using a 30-gauge needle and follow this procedure with a suitable longer-acting anesthetic. However, an exception would be made if health reasons caused the anesthetic to be contraindicated. The area of concern usually involves two opposing quadrants and then the other two opposing quadrants some days later, or alternatively, full-mouth treatment in one appointment. Anesthesia is routinely used in every procedure for the reasons set forth below:
  a) aiding in accurate measurement of the full-depth of the diseased pocket;
  b) allowing the doctor to be aggressive in the root planing and scaling of all surfaces of the tooth;
  c) allowing the patient to be as comfortable as possible during the treatment, thereby minimizing the patient's endogenous adrenaline production, and in turn achieve the optimal therapy results;
  d) maximizing the doctor's ability to concentrate on the procedure; and
  e) optimizing the use of ultrasonic probes at frequencies between one hertz and three hundred thousand hertz.

In one example, the anesthetization is performed via a nerve block or by infiltration.

The pocket depths should then be recorded with a periodontal probe with six areas recorded around each tooth. This will allow a determination of the full depth of the diseased pocket. The eGUI may assist the clinician in this regard by providing instructional and patient educational videos and photos; synchronization with electronic records plus tissue phenotype exemplar photographs to aid in accurate recording, saving and computing parameters and light dose; presentation of light dose to the clinician for approval or adjustment; and conversion of average probe depth diagnostics into J/mm average pocket depth and then to light dose, all of which promote safety, effectiveness and efficiency of the LENAP protocol for the benefit of the patient. In one aspect, the conversion from probe depths/bone soundings to the total light dose estimation comprises multiplying by 1 to 40, depending on soft tissue phenotype (biotype), LANAP® Periodontal Disease Case Type Classification 1-V, and LANAP® Tooth Mobility Score 0-4.

Additionally, the appropriate application of intermittent or simultaneous water spray should be used for tissue cooling. A contact laser fiber with a fiber diameter of between 100 mu (microns) and 1000 mu (microns), preferably 300-400 microns should be used, in an orientation along the long axis of the tooth, to create a gingival trough by excising the free gingival margin and the internal epithelial lining of the pocket, thus exposing the root surface and removing all internal epithelial from the gingival pocket. The eGUI may assist the clinician by providing: procedure presets consistent with the level of clinician training proficiency and certification; instructional and patient educational videos and photos; use of individually selectable Pulse Duration, Energy, Repetition Rate, and intuitive Average Power groupings within a safe therapeutic treatment window; display of measured power contrasted with average power settings to help ensure delivered power matches the intended amount; ability to hold average power constant as repetition rate or energy settings are individually adjusted; a smart connector that identifies the diameter of the optical energy delivery system in order to adjust laser parameters accordingly; ability to hold energy density constant when optical fiber diameters are changed; a display of Joules, Shots, Energy Density, Power Density and Peak Power settings to determine laser beam intensity, impact, and overall effect on tissue; synchronization with electronic records plus tissue phenotype exemplar photographs to aid in accurate recording, saving and computing parameters and light dose; presentation of light dose to the clinician for approval or adjustment; conversion of average probe depth diagnostics into J/mm average pocket depth and then to light dose; and an intuitive chart display of energy delivery progression of photobiomodulation and LENAP light dose delivery that is visually tracked with reference bands corresponding to dosage for first and second pass and managed with a countdown timer according to energy delivery rates and thermal-relaxation criteria, and following the LENAP protocol formula for the first and second laser pass—all of which promote safety, effectiveness and efficiency of the LENAP protocol for the benefit of the patient.

Appropriately cleaved contact laser fibers are used for the precise control of the laser energy, the physical placement of the laser energy, and the determination of the desired orientation of the laser to the tissue desired to be removed. Orientation along the long axis of the tool defines the direction of the laser fiber for the proper initial excision. The root surface is then opened by gingival troughing for viewing.

Excising the free gingival margin with the laser energy removes accretions and pathogens within the tissue of the free margin, which otherwise would not be removable. Additionally, this procedure provides hemostasis for better visualization and further defines the tissue margins preceding mechanical instrumentation. The integrity of the mucosa is also preserved by releasing tissue tension around the tooth prior to mechanical manipulation, thereby dissecting the separation between the free gingival margin and the fibrous collagen matrix, which holds the gingiva in position. Maintenance of the crest of the gingival margin is aided in that the healing of the fibrous collagen matrix will maintain the gingival crest at, or better, than the presurgical level. The eGUI assists the clinician in that regard by providing: procedure presets consistent with the level of clinician training proficiency and certification; instructional and patient educational videos and photos; use of individually selectable Pulse Duration, Energy, Repetition Rate, and intuitive Average Power groupings within a safe therapeutic treatment window; display of measured power contrasted with average power settings to help ensure delivered power matches the intended amount; ability to hold average power constant as repetition rate or energy settings are individually adjusted; a smart connector that identifies the diameter of the optical energy delivery system in order to adjust laser parameters accordingly; ability to hold energy density constant when optical fiber diameters are changed; a display of Joules, Shots, Energy Density, Power Density and Peak Power settings to determine laser beam intensity, impact, and overall effect on tissue; synchronization with electronic records plus tissue phenotype exemplar photographs to aid in accurate recording, saving and computing parameters and light dose; presentation of light dose to the clinician for approval or adjustment; conversion of average probe depth diagnostics into J/mm average pocket depth and then to light dose; and an intuitive chart display of energy delivery progression of photobiomodulation and LENAP light dose delivery that is visually tracked with reference bands corresponding to dosage for first and second pass and managed with a countdown timer according to energy delivery rates and thermal-relaxation criteria, and following the LENAP protocol formula for the first and second laser pass—all of which promote safety, effectiveness and efficiency of the LENAP protocol for the benefit of the patient.

By use of the "hot-tip" effect (accumulated tissue proteins heated via conductivity secondary to the passage of laser energy through the fiber), the clinician may continue to excise the inner pocket epithelium around the entire tooth to the depth of the probed reading (while not breaking through the mucogingival junction). This effect provides the selective removal of sulcular, pocket epithelium and granulation tissue without removing any substantial connective fibrous tissue and does so circumferentially, as long as the area is not allowed to become dry during surgery. As necessary, the clinician may remove the excised tissue that accumulates on the tip of the laser fiber. The eGUI assists the clinician in these aspects by providing: procedure presets consistent with the level of clinician training proficiency and certification; instructional and patient educational videos and photos; use of individually selectable Pulse Duration, Energy, Repetition Rate, and intuitive Average Power groupings within a safe therapeutic treatment window; display of measured power contrasted with average power settings to help ensure delivered power matches the intended amount; ability to hold average power constant as repetition rate or energy settings are individually adjusted; a smart connector that identifies the diameter of the optical energy delivery system in order to adjust laser parameters accordingly; ability to hold energy density constant when optical fiber diameters are changed; a display of Joules, Shots, Energy Density, Power Density and Peak Power settings to determine laser beam intensity, impact, and overall effect on tissue; synchronization with electronic records plus tissue phenotype exemplar photographs to aid in accurate recording, saving and computing parameters and light dose; presentation of light dose to the clinician for approval or adjustment; conversion of average probe depth diagnostics into J/mm average pocket depth and then to light dose; and an intuitive chart display of energy delivery progression of photobiomodulation and LENAP light dose delivery that is visually tracked with reference bands corresponding to dosage for first and second pass and managed with a countdown timer according to energy delivery rates and thermal-relaxation criteria, and following the LENAP protocol formula for the first and second laser pass—all of which promote safety, effectiveness and efficiency of the LENAP protocol for the benefit of the patient.

Next, the clinician may ultrasonically scale all root surfaces to the depth of the pocket. The intent is to remove all foreign structures and substances from the pocket, thereby allowing adhesion of the lased soft tissue to the clean tooth surface. Next, the clinician may carefully root plane and scale all cementum. This can be augmented by the use of the well-known, small "spoon-like" bone files which clean the surface on the cementum exceptionally well.

Between one and one hundred Watts of fiber output power and a frequency between one hertz and three hundred megahertz, preferably 10-30 Hz, will then be used in the deep periodontal pockets for optimal bacterial destruction without causing bacterial injection into the periodontal tissues. This will minimize a soft tissue cellulitis. By using the laser fiber, the clinician may explore for remaining calculus and/or root roughness. These small fibers are very adept at detection of any surface irregularities. The clinician may continue or repeat, if necessary, any or all of the steps above, as needed, to achieve a smooth and clean root surface.

Again, the laser is used in the pocket to remove large areas of granulation tissue, disinfect tissue, assist in hemostasis, cauterize free nerve endings, seal lymphatics and prepare tissue for welding and desensitizing teeth. The eGUI assists the clinician in this regard by providing: procedure presets consistent with the level of clinician training proficiency and certification; instructional and patient educational videos and photos; use of individually selectable Pulse Duration, Energy, Repetition Rate, and intuitive Average Power groupings within a safe therapeutic treatment window; display of measured power contrasted with average power settings to help ensure delivered power matches the intended amount; ability to hold average power constant as repetition rate or energy settings are individually adjusted; a smart connector that identifies the diameter of the optical energy delivery system in order to adjust laser parameters accordingly; ability to hold energy density constant when optical fiber diameters are changed; a display of Joules, Shots, Energy Density, Power Density and Peak Power settings to determine laser beam intensity, impact, and overall effect on tissue; synchronization with electronic records plus tissue phenotype exemplar photographs to aid in accurate recording, saving and computing parameters and light dose; presentation of light dose to the clinician for approval or adjustment; conversion of average probe depth diagnostics into J/mm average pocket depth and then to light dose; and an intuitive chart display of energy delivery progression of photobiomodulation and LENAP light dose delivery that is visually tracked with reference bands corresponding to dosage for first and second pass and managed with a countdown timer according to energy delivery rates and thermal-relaxation criteria, and following the LENAP protocol formula for the first and second laser pass—all of which promote safety, effectiveness and efficiency of the LENAP protocol for the benefit of the patient. The area should be rinsed with water to remove any residue, calculus or blood clots; also, the laser may be used for touch-up if needed.

Elimination of all occlusal prematurities and interferences, centric working and balancing is done to allow healing of the tissue and bone regeneration. An occlusal splint is necessary when trauma-induced periodontal disease is manifest, i.e., occlusal trauma in the presence of bacteria-induced periodontal disease. Master impressions for an anterior deprogrammer and dis-occluding occlusal splint are taken. The splint is designed to provide anterior guidance, i.e., a "LANAP Splint" is the appliance of choice. In one example, the splint is delivered at an appointment that is scheduled one week after the postoperative appointment. At this time it can be adjusted accordingly for tooth stabilization.

All treatment sites are irrigated to the deepest depth of the periodontal pockets with a bactericidal solution consisting of a high tissue substantivity (e.g., chlorhexidine gluconate 0.12%). The irrigation aids the laser in the reduction of bacteria in the pocket and in removing debris.

In one example, cleaning comprises application of a piezo-electric ultrasonic device with water lavage and 20,000 to 30,000 hertz and use of appropriate tips operating at 8 to 10 Watts.

The clinician may approximate the wound edges and, using the laser, control oozing as needed. Healing of the wound edges by secondary intention is imperative.

The tissues should be compressed with wet gauze for two to three minutes against the tooth from both a facial and lingual direction, permitting only a thin clot to form between the tissue and the tooth.

Medications should be prescribed for home use, and a review of postoperative care should be discussed with the patient. A postoperative appointment should be scheduled within seven to ten days. Perform a through occlusal equilibration follow-up.

This treatment should be continued periodically until bone development is complete. Appointments should continue for one full year.

The procedure will now be described in further detail. As mentioned above, for purposes of efficiency reference may be made again to FIGS. 68 to 70.

To reiterate, FIG. 68 is a section of a gingival tissue prior to the administration of a LANAP® procedure according to an example embodiment. FIG. 69 is a section of the same gingival tissue as in FIG. 68 showing the position of surgical tissue severing according to an example embodiment. FIG. 70 is a section of the same gingival tissue as in FIG. 68 after completion of a LANAP® procedure according to an example embodiment.

The above-described figures illustrate a method for treating gingival disease. An excisional new attachment procedure comprises a step-by-step approach. First, the gingival tissue 5 corresponding to a targeted tooth 10 is anesthetized. The depth of a pocket 20 in the gingival tissue is measured, preferably with a periodontal probe 30, taking at least six spaced-apart measurements around the tooth 10. The pocket depth is defined as extending from the upper gingival margin 40 to the mucogingival junction 50. The eGUI assists the clinician in this regard by providing: instructional and patient educational videos and photos; synchronization with electronic records plus tissue phenotype exemplar photographs to aid in accurate recording, saving and computing parameters and light dose; presentation of light dose to the clinician for approval or adjustment; and conversion of average probe depth diagnostics into J/mm average pocket depth and then to light dose, all of which promote safety, effectiveness and efficiency of the LENAP protocol for the benefit of the patient.

The interior epithelial lining 60 of the pocket 20 is then ablated and vaporized to the full depth of the pocket 20, preferably using a laser fiber having a preferred diameter of between 100 microns and 1000 microns, the fiber preferably held oriented with the axis of the tooth 10. This is completed and on all sides of the tooth 10. This step generates and prepares a new pocket tissue surface 70. Preferably not more than 100 Watts of fiber output power is used, as measured at a distal end of the fiber, and a lasing frequency of not more than 300 megahertz is preferably applied. Preferably, water is sprayed into the pocket 20 for cooling during the ablating and vaporizing step. The eGUI may assist the clinician in this process by providing: procedure presets consistent with the level of clinician training proficiency and certification; instructional and patient educational videos and photos; use of individually selectable Pulse Duration, Energy, Repetition Rate, and intuitive Average Power groupings within a safe therapeutic treatment window; display of measured power contrasted with average power settings to help ensure delivered power matches the intended amount; ability to hold average power constant as repetition rate or energy settings are individually adjusted; a smart connector that identifies the diameter of the optical energy delivery system in order to adjust laser parameters accordingly; ability to hold energy density constant when optical fiber diameters are changed; a display of Joules, Shots, Energy Density, Power Density and Peak Power settings to determine laser beam intensity, impact, and overall effect on tissue; synchronization with electronic records plus tissue phenotype exemplar photographs to aid in accurate recording, saving and computing parameters and light dose; presentation of light dose to the clinician for approval or adjustment; conversion of average probe depth diagnostics into J/mm average pocket depth and then to light dose; and an intuitive chart display of energy delivery progression of photobiomodulation and LENAP light dose delivery that is visually tracked with reference bands corresponding to dosage for first and second pass and managed with a countdown timer according to energy delivery rates and thermal-relaxation criteria, and following the LENAP protocol formula for the first and second laser pass—all of which promote safety, effectiveness and efficiency of the LENAP protocol for the benefit of the patient.

In one example, ablating and vaporizing comprises application of ⅔ of the total light dose using a 360-micron-diameter quartz FiberFlex™ optical fiber fed through a TrueFlex® handpiece and a bendable cannula, while operating the FR Nd:YAG laser device within the preferred parameter range.

Next, the surface of the tooth 10A is cleaned of all foreign matter 10B, again, to the depth of the pocket 20 on all sides of the tooth 10. Next, the pocket 10 is lased to remove granulation tissue, and to disinfect, assist in hemostatis, cauterize free nerve endings, and seal lymphatics, of the pocket tissue surface. Lasing also prepares the pocket tissue surface 70 for welding, and also desensitizes the tooth. The eGUI can assist the clinician by providing: procedure presets consistent with the level of clinician training proficiency and certification; instructional and patient educational videos and photos; use of individually selectable Pulse Duration, Energy, Repetition Rate, and intuitive Average Power groupings within a safe therapeutic treatment window; display of measured power contrasted with average power settings to help ensure delivered power matches the intended amount; ability to hold average power constant as repetition rate or energy settings are individually adjusted; a smart connector that identifies the diameter of the optical energy delivery system in order to adjust laser parameters accordingly; ability to hold energy density constant when optical fiber diameters are changed; a display of Joules, Shots, Energy Density, Power Density and Peak Power settings to determine laser beam intensity, impact, and overall effect on tissue; synchronization with electronic records plus tissue phenotype exemplar photographs to aid in accurate recording, saving and computing parameters and light dose; presentation of light dose to the clinician for approval or adjustment; conversion of average probe depth diagnostics into J/mm average pocket depth and then to light dose; and an intuitive chart display of energy delivery progression of photobiomodulation and LENAP light dose delivery that is visually tracked with reference bands corresponding to dosage for first and second pass and managed with a countdown timer according to energy delivery rates and thermal-relaxation criteria, and following the LENAP protocol formula for the first and second laser pass—all of which promote safety, effectiveness and efficiency of the LENAP protocol for the benefit of the patient. All debris is then rinsed from the pocket 20. This is followed by an irrigation of the pocket 20 with a bactericidal solution.

Next, occlusal interferences are eliminated. The new pocket tissue surface 70 is lased to adapt it for tissue welding. The eGUI may assist the clinician by providing: procedure presets consistent with the level of clinician training proficiency and certification; instructional and patient educational videos and photos; use of individually selectable Pulse Duration, Energy, Repetition Rate, and intuitive Average Power groupings within a safe therapeutic treatment window; display of measured power contrasted with average power settings to help ensure delivered power matches the intended amount; ability to hold average power constant as repetition rate or energy settings are individually adjusted; a smart connector that identifies the diameter of the optical energy delivery system in order to adjust laser parameters accordingly; ability to hold energy density constant when optical fiber diameters are changed; a display of Joules, Shots, Energy Density, Power Density and Peak Power settings to determine laser beam intensity, impact, and overall effect on tissue; synchronization with electronic records plus tissue phenotype exemplar photographs to aid in accurate recording, saving and computing parameters and light dose; presentation of light dose to the clinician for approval or adjustment; conversion of average probe depth diagnostics into J/mm average pocket depth and then to light dose; and an intuitive chart display of energy delivery progression of photobiomodulation and LENAP light dose delivery that is visually tracked with reference bands corresponding to dosage for first and second pass and managed with a countdown timer according to energy delivery rates and thermal-relaxation criteria, and following the LENAP protocol formula for the first and second laser pass—all of which promote safety, effectiveness and efficiency of the LENAP protocol for the benefit of the patient.

The pocket tissue surface 70 is approximated with the tooth surface 10A preferably using wet gauze to hold the pocket tissue surface 70 in contact with the tooth surface 10A, preferably from 2 to 3 minutes allowing a thin clot 80 to form between the pocket tissue surface 70 and the tooth surface 10A so as to advance and assure adhesion of these tissues. Finally, the body's natural immune system is enhanced by prescribed medications for outpatient use in preventing infection. This important step is necessary in order to protect against infection and reduce inflammation. The procedure preferably includes the further step of providing at least one subsequent occlusal equilibration examination.

A recapitulation of the above description with further details follows:

The area of concern, usually two quadrants, is anesthetized. The procedure is applied independently to each tooth involved. Pocket depth is measured and recorded with a perio probe to determine the full depth of the diseased pocket. A contact laser fiber is oriented along the long axis of the tooth and is used to create a gingival trough by excising the free gingival margin and the internal epithelial lining of the pocket, thereby exposing the root surface. Appropriately cleaved contact laser fibers provide precise control of the laser energy, the physical placement of the laser energy, and the determination of the desired physical orientation of the laser to the tissue to be removed. Gingival troughing is used to access the root surface. Excision of the free gingival margin removes accretions and pathogens within the tissue of the free margin which are otherwise unremovable and provides hemostasis for better visualization. This step also defines the tissue margins preceding mechanical instrumentation and preserves the integrity of the mucosa by releasing tissue tension. It also dissects-out the separation between the free gingival margin and the fibrous collagen matrix which holds the gingiva in position. This aids in the maintenance of the crest of the gingival margin. With the use of the "hot-tip" effect, further excision of the inner pocket epithelium around the entire tooth is completed, to the depth of the probe readings. No attempt is made to break through the mucogingival junction. The "hot-tip" effect (accumulated tissue proteins heated via conductivity secondary to the passage of laser energy through the fiber) provides the selective removal of sulcular and pocket epithelium and granulation tissue without removing substantially any connective fibrous tissue, and does so circumferentially. As necessary, the excised tissue that accumulates on the tip of the laser fiber is removed. The eGUI assists the clinician in performing the laser delivery steps of the LENAP protocol by providing: procedure presets consistent with the level of clinician training proficiency and certification; instructional and patient educational videos and photos; use of individually selectable Pulse Duration, Energy, Repetition Rate, and intuitive Average Power groupings within a safe therapeutic treatment window; display of measured power contrasted with average power settings to help ensure delivered power matches the intended amount; ability to hold average power constant as repetition rate or energy settings are individually adjusted; a smart connector that identifies the diameter of the optical energy delivery system in order to adjust laser parameters accordingly; ability to hold energy density constant when optical fiber diameters are changed; a display of Joules, Shots, Energy Density, Power Density and Peak Power settings to determine laser beam intensity, impact, and overall effect on tissue; synchronization with electronic records plus tissue phenotype exemplar photographs to aid in accurate recording, saving and computing parameters and light dose; presentation of light dose to the clinician for approval or adjustment; conversion of average probe depth diagnostics into J/mm average pocket depth and then to light dose; and an intuitive chart display of energy delivery progression of photobiomodulation and LENAP light dose delivery that is visually tracked with reference bands corresponding to dosage for first and second pass and managed with a countdown timer according to energy delivery rates and thermal-relaxation criteria, and following the LENAP protocol formula for the first and second laser pass—all of which promote safety, effectiveness and efficiency of the LENAP protocol for the benefit of the patient.

Ultrasonic scaling of all root surfaces to the depth of pocket is completed. The intent is to remove all foreign structures and substance from the pocket to allow adhesion of the soft tissue to the clean tooth surface. Careful root planing and scaling of all cementum is completed. This can be augmented by the use of small, spoon-like bone files, which are highly effective in cleaning the surface of the cementum. The laser fiber is used to explore for remaining calculus and/or root roughness. These small fibers are very adept at detection of any surface irregularities. Lasing of the pocket to remove large areas of granulation tissue, disinfect tissue, assist in hemostasis, cauterize free nerve endings, seal lymphatics, prepare tissue for welding and desensitize those teeth that are sensitive is accomplished. The eGUI can assist the clinician in this regard by providing: procedure presets consistent with the level of clinician training proficiency and certification; instructional and patient educational videos and photos; use of individually selectable Pulse Duration, Energy, Repetition Rate, and intuitive Average Power groupings within a safe therapeutic treatment window; display of measured power contrasted with average power settings to help ensure delivered power matches the intended amount; ability to hold average power constant as repetition rate or energy settings are individually adjusted; a smart connector that identifies the diameter of the optical energy delivery system in order to adjust laser parameters accordingly; ability to hold energy density constant when optical fiber diameters are changed; a display of Joules, Shots, Energy Density, Power Density and Peak Power settings to determine laser beam intensity, impact, and overall effect on tissue; synchronization with electronic records plus tissue phenotype exemplar photographs to aid in accurate recording, saving and computing parameters and light dose; presentation of light dose to the clinician for approval or adjustment; conversion of average probe depth diagnostics into J/mm average pocket depth and then to light dose; and an intuitive chart display of energy delivery progression of photobiomodulation and LENAP light dose delivery that is visually tracked with reference bands corresponding to dosage for first and second pass and managed with a countdown timer according to energy delivery rates and thermal-relaxation criteria, and following the LENAP protocol formula for the first and second laser pass—all of which promote safety, effectiveness and efficiency of the LENAP protocol for the benefit of the patient.

The areas are rinsed with water to remove any residue, calculus and blood clots. Elimination of all occlusal interferences, centric, working and balancing, is completed. For best results this step is imperative since it allows the tissue to heal and the bone to regenerate. The laser modifies the tissue to allow new attachment to take place but if the trauma of malocclusion continues the tissue cannot withstand and begins to break down immediately. All treatment sites are irrigated to the deepest depth of the periodontal pockets with a bactericidal solution of a high tissue substantivity (e.g., chlorhexidine gluconate 0.12%). The irrigation aids the laser in the reduction of bacteria in the pocket and in removing debris. Approximation of the wound edges is completed. Lasing is further accomplished to control oozing as needed. Healing of the wound edges by secondary intention is imperative. The eGUI assists the clinician in performing the laser delivery steps of the LENAP protocol by providing: procedure presets consistent with the level of clinician training proficiency and certification; instructional and patient educational videos and photos; use of individually selectable Pulse Duration, Energy, Repetition Rate, and intuitive Average Power groupings within a safe therapeutic treatment window; display of measured power contrasted with average power settings to help ensure delivered power matches the intended amount; ability to hold average power constant as repetition rate or energy settings are individually adjusted; a smart connector that identifies the diameter of the optical energy delivery system in order to adjust laser parameters accordingly; ability to hold energy density constant when optical fiber diameters are changed; a display of Joules, Shots, Energy Density, Power Density and Peak Power settings to determine laser beam intensity, impact, and overall effect on tissue; synchronization with electronic records plus tissue phenotype exemplar photographs to aid in accurate recording, saving and computing parameters and light dose; presentation of light dose to the clinician for approval or adjustment; conversion of average probe depth diagnostics into J/mm average pocket depth and then to light dose; and an intuitive chart display of energy delivery progression of photobiomodulation and LENAP light dose delivery that is visually tracked with reference bands corresponding to dosage for first and second pass and managed with a countdown timer according to energy delivery rates and thermal-relaxation criteria, and following the LENAP protocol formula for the first and second laser pass—all of which promote safety, effectiveness and efficiency of the LENAP protocol for the benefit of the patient. The tissue is compressed with wet gauze for 2 to 3 minutes against the tooth from both a facial and lingual direction in order to permit only a thin clot to form between the tissue and the tooth.

Post-procedural steps include prescribing medications for home use and reviewing postoperative care with the patient. Master impressions for an anterior deprogrammer and disoccluding occlusal splint are taken. The splint is designed to provide anterior guidance, i.e., a "LANAP Splint" is the appliance of choice. This will be delivered at the postoperative appointment and adjusted as needed for tooth/teeth stabilization. A thorough occlusal equilibration follow-up examination is required. This treatment should continue periodically until bone development is complete. Pocket-depth readings at 60, 120 and 180 days during continuing care appointments are desirable.

Thus, according to this example embodiment, an excisional new attachment procedure includes a) anesthetizing a gingival tissue corresponding to a targeted tooth of a patient the tooth having a tooth surface, b) measuring a depth of a pocket in the gingival tissue, from an upper gingival margin to a mucogingival junction, and c) ablating and vaporizing an interior epithelial lining of the pocket, to the depth of the pocket on all sides of the tooth to prepare a new pocket tissue surface. The procedure further includes d) cleaning the tooth surface of all foreign matter, to the depth of the pocket on all sides of the tooth, and e) lasing the pocket to remove granulation tissue, and to: disinfect, assist in hemostatis, cauterize free nerve endings, and seal lymphatics of the pocket tissue surface, and to prepare the pocket tissue surface for welding, and to desensitize the tooth. In addition, the procedure includes f) rinsing the pocket to remove debris, g) irrigating the pocket with a bactericidal solution, h) eliminating occlusal interferences, and i) lasing the pocket tissue surface to adapt the pocket tissue surface for tissue welding. The procedure also includes j) approximating the pocket tissue surface with the tooth surface, and k) maintaining the pocket tissue surface in contact with the tooth surface to advance adhesion.

The eGUI can assist the clinician in the above by using instructional and patient educational videos and photos stored on the device to promote safety, effectiveness and efficiency using the laser. The eGUI can further assist the clinician by using procedure presets on the device consistent with the level of clinician training proficiency and certification to promote safety, effectiveness and efficiency. Moreover, the eGUI can assist the clinician by using individually selectable Pulse Duration, Energy, Repetition Rate, and intuitive Average Power groupings within a safe therapeutic treatment window available and programmed on the device to promote safety, effectiveness and efficiency. The eGUI can display measured power contrasted with average power settings to help ensure delivered power matches the intended amount to promote safety, effectiveness and efficiency. Further, the eGUI can assist the clinician by providing the ability to hold average power constant as repetition rate or energy settings are individually adjusted to promote safety, effectiveness and efficiency. The eGUI can also assist the clinician by using (and communicating with) a smart connector that identifies the diameter of the optical energy delivery system in order to adjust laser parameters accordingly to promote safety, effectiveness and efficiency. Moreover, the eGUI enhances this aspect by holding energy density constant when optical fiber diameters are changed to promote safety, effectiveness and efficiency. Additionally, the eGUI can assist the clinician by displaying Joules, Shots, Energy Density, Power Density and Peak Power settings to determine laser beam intensity, impact, and overall effect on tissue to promote safety, effectiveness and efficiency. Additionally, the eGUI can assist the clinician by using device synchronization with electronic records, plus tissue phenotype exemplar photographs on the device to aid in accurate recording, saving and computing parameters and light dose to promote safety, effectiveness and efficiency. The eGUI can further assist by presenting a light dose to the clinician for approval or adjustment to promote safety, effectiveness and efficiency. In addition, the eGUI can assist the clinician by conversion of average probe depth diagnostics into J/mm average pocket depth and then to light dose to promote safety, effectiveness and efficiency. The eGUI can also assist the clinician by an intuitive chart display of energy delivery progression of photobiomodulation and LENAP light dose delivery that is visually tracked with reference bands corresponding to dosage for the first and second pass and managed with a countdown timer according to energy delivery rates and thermal-relaxation criteria, and following the LENAP protocol formula for the first and second laser pass to promote safety, effectiveness and efficiency.

In one aspect, the ablating and vaporizing, and the lasing is completed with a laser fiber held oriented with the axis of the tooth. The eGUI can assist the clinician in this regard by using instructional and patient educational videos and photos stored on the device to promote safety, effectiveness and efficiency using the laser. The eGUI can further assist the clinician by using procedure presets on the device consistent with the level of clinician training proficiency and certification to promote safety, effectiveness and efficiency. Moreover, the eGUI can assist the clinician by using individually selectable Pulse Duration, Energy, Repetition Rate, and intuitive Average Power groupings within a safe therapeutic treatment window available and programmed on the device to promote safety, effectiveness and efficiency. The eGUI can display measured power contrasted with average power settings to help ensure delivered power matches the intended amount to promote safety, effectiveness and efficiency. Further, the eGUI can assist the clinician by providing the ability to hold average power constant as repetition rate or energy settings are individually adjusted to promote safety, effectiveness and efficiency. The eGUI can also assist the clinician by using (and communicating with) a smart connector that identifies the diameter of the optical energy delivery system in order to adjust laser parameters accordingly to promote safety, effectiveness and efficiency. Moreover, the eGUI enhances this aspect by holding energy density constant when optical fiber diameters are changed to promote safety, effectiveness and efficiency. Additionally, the eGUI can assist the clinician by displaying Joules, Shots, Energy Density, Power Density and Peak Power settings to determine laser beam intensity, impact, and overall effect on tissue to promote safety, effectiveness and efficiency. Additionally, the eGUI can assist the clinician by using device synchronization with electronic records, plus tissue phenotype exemplar photographs on the device to aid in accurate recording, saving and computing parameters and light dose to promote safety, effectiveness and efficiency. The eGUI can further assist by presenting a light dose to the clinician for approval or adjustment to promote safety, effectiveness and efficiency. In addition, the eGUI can assist the clinician by conversion of average probe depth diagnostics into J/mm average pocket depth and then to light dose to promote safety, effectiveness and efficiency. The eGUI can also assist the clinician by an intuitive chart display of energy delivery progression of photobiomodulation and LENAP light dose delivery that is visually tracked with reference bands corresponding to dosage for the first and second pass and managed with a countdown timer according to energy delivery rates and thermal-relaxation criteria, and following the LENAP protocol formula for the first and second laser pass to promote safety, effectiveness and efficiency.

In another aspect, the depth measuring is completed with a periodontal probe taking at least six spaced-apart measurements around the tooth. The eGUI can assist the clinician in this regard by using instructional and patient educational videos and photos stored on the device to promote safety, effectiveness and efficiency.

In yet another aspect, the method includes providing the laser, and the ablating and vaporizing is completed with not more than 100 Watts of output power from the laser, as measured at a distal end of a laser fiber of the laser, and with a lasing frequency of not more than 300 megahertz. The eGUI can assist the clinician in this regard by using instructional and patient educational videos and photos stored on the device to promote safety, effectiveness and efficiency using the laser. The eGUI can further assist the clinician by using procedure presets on the device consistent with the level of clinician training proficiency and certification to promote safety, effectiveness and efficiency. Moreover, the eGUI can assist the clinician by using individually selectable Pulse Duration, Energy, Repetition Rate, and intuitive Average Power groupings within a safe therapeutic treatment window available and programmed on the device to promote safety, effectiveness and efficiency. The eGUI can display measured power contrasted with average power settings to help ensure delivered power matches the intended amount to promote safety, effectiveness and efficiency. Further, the eGUI can assist the clinician by providing the ability to hold average power constant as repetition rate or energy settings are individually adjusted to promote safety, effectiveness and efficiency. The eGUI can also assist the clinician by using (and communicating with) a smart connector that identifies the diameter of the optical energy delivery system in order to adjust laser parameters accordingly to promote safety, effectiveness and efficiency. Moreover, the eGUI enhances this aspect by holding energy density constant when optical fiber diameters are changed to promote safety, effectiveness and efficiency. Additionally, the eGUI can assist the clinician by displaying Joules, Shots, Energy Density, Power Density and Peak Power settings to determine laser beam intensity, impact, and overall effect on tissue to promote safety, effectiveness and efficiency. Additionally, the eGUI can assist the clinician by using device synchronization with electronic records, plus tissue phenotype exemplar photographs on the device to aid in accurate recording, saving and computing parameters and light dose to promote safety, effectiveness and efficiency. The eGUI can further assist by presenting a light dose to the clinician for approval or adjustment to promote safety, effectiveness and efficiency. In addition, the eGUI can assist the clinician by conversion of average probe depth diagnostics into J/mm average pocket depth and then to light dose to promote safety, effectiveness and efficiency. The eGUI can also assist the clinician by an intuitive chart display of energy delivery progression of photobiomodulation and LENAP light dose delivery that is visually tracked with reference bands corresponding to dosage for the first and second pass and managed with a countdown timer according to energy delivery rates and thermal-relaxation criteria, and following the LENAP protocol formula for the first and second laser pass to promote safety, effectiveness and efficiency.

In still another aspect, the method includes spraying water onto the pocket tissue surface for cooling the pocket tissue surface during the ablating and vaporizing step. The eGUI can assist the clinician in this regard by using (e.g., displaying) instructional and patient educational videos and photos stored on the device to promote safety, effectiveness and efficiency.

In yet another aspect, the laser fiber is of a diameter of between approximately 100 microns and 1000 microns. The eGUI can assist the clinician in this regard by using instructional and patient educational videos and photos stored on the device to promote safety, effectiveness and efficiency using the laser. The eGUI can further assist the clinician by using procedure presets on the device consistent with the level of clinician training proficiency and certification to promote safety, effectiveness and efficiency. Moreover, the eGUI can assist the clinician by using individually selectable Pulse Duration, Energy, Repetition Rate, and intuitive Average Power groupings within a safe therapeutic treatment window available and programmed on the device to promote safety, effectiveness and efficiency. The eGUI can display measured power contrasted with average power settings to help ensure delivered power matches the intended amount to promote safety, effectiveness and efficiency. Further, the eGUI can assist the clinician by providing the ability to hold average power constant as repetition rate or energy settings are individually adjusted to promote safety, effectiveness and efficiency. The eGUI can also assist the clinician by using (and communicating with) a smart connector that identifies the diameter of the optical energy delivery system in order to adjust laser parameters accordingly to promote safety, effectiveness and efficiency. Moreover, the eGUI enhances this aspect by holding energy density constant when optical fiber diameters are changed to promote safety, effectiveness and efficiency. Additionally, the eGUI can assist the clinician by displaying Joules, Shots, Energy Density, Power Density and Peak Power settings to determine laser beam intensity, impact, and overall effect on tissue to promote safety, effectiveness and efficiency. Additionally, the eGUI can assist the clinician by using device synchronization with electronic records, plus tissue phenotype exemplar photographs on the device to aid in accurate recording, saving and computing parameters and light dose to promote safety, effectiveness and efficiency. The eGUI can further assist by presenting a light dose to the clinician for approval or adjustment to promote safety, effectiveness and efficiency. In addition, the eGUI can assist the clinician by conversion of average probe depth diagnostics into J/mm average pocket depth and then to light dose to promote safety, effectiveness and efficiency. The eGUI can also assist the clinician by an intuitive chart display of energy delivery progression of photobiomodulation and LENAP light dose delivery that is visually tracked with reference bands corresponding to dosage for the first and second pass and managed with a countdown timer according to energy delivery rates and thermal-relaxation criteria, and following the LENAP protocol formula for the first and second laser pass to promote safety, effectiveness and efficiency.

In another aspect, maintaining the pocket tissue surface in contact with the tooth surface includes using wet gauze to hold the pocket tissue surface in contact with the tooth surface from 2 to 3 minutes allowing a thin clot to form between the pocket tissue surface and the tooth surface. The eGUI can assist the clinician in this regard by using instructional and patient educational videos and photos stored on the device to promote safety, effectiveness and efficiency.

In one aspect, the method may further include prescribing medications for outpatient use in preventing infection. The eGUI can assist the clinician in this regard by using instructional and patient educational videos and photos stored on the device to promote safety, effectiveness and efficiency.

In another aspect, the method may further include providing at least one subsequent occlusal equilibration examination. Again, the eGUI can assist the clinician in this regard by using instructional and patient educational videos and photos stored on the device to promote safety, effectiveness and efficiency.

In another aspect, the method may further include enhancing the patient's natural immune system to protect against infection and reduce inflammation. Yet again, the eGUI can assist the clinician in this regard by using instructional and patient educational videos and photos stored on the device to promote safety, effectiveness and efficiency.

Relational Database

Figure 71:
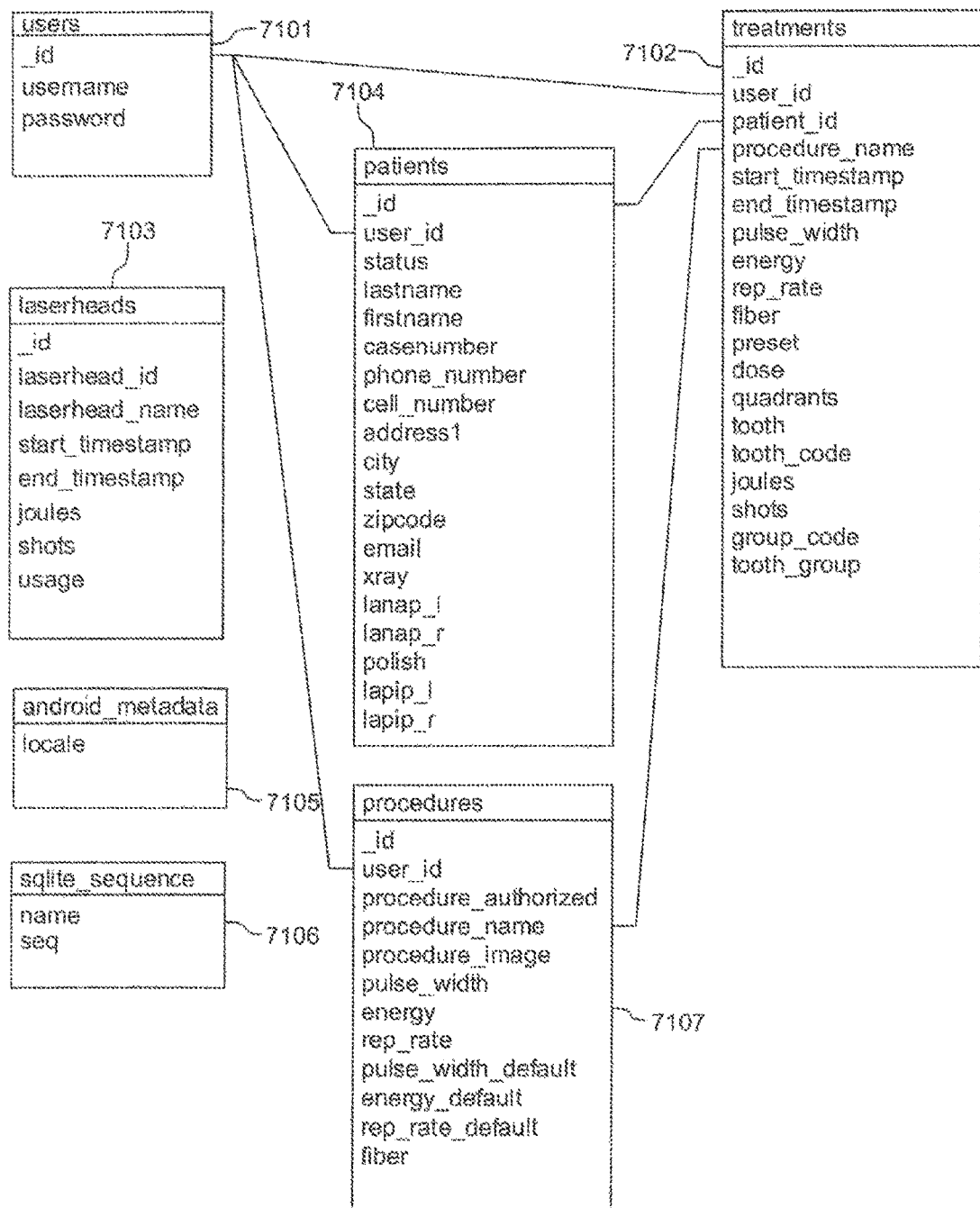
FIG. 71 is a view for explaining a relational database for storing patient and user data according to an example embodiment.

FIG. 71 is a view for explaining a relational database according to an example embodiment. The relational database may be stored in, for example, non-volatile memory 411 in tablet 400. In an alternative embodiment, this information might be stored at main laser computer 300, or at data appliance 427.

In that regard, the database contains data that is recorded and used as a durable data archive. The database may be transportable, i.e., it can be extracted and reinstalled in another device for (a) duplicate archive or (b) analytical purposes. The database can be installed on alternate devices running disparate operating systems including UNIX and Windows. In addition, the database can be synchronized with electronic medical (dental) records. Synchronized data can be operated upon by algorithms to determine recommended treatments of laser dosimetry.

As shown in FIG. 71, sets of data include users 7101, patients 7104, treatments 7102, procedures 7107, laserheads 7103, android_metadata 7105, and sqlite_sequence 7106.

Users 7101 includes information about the user of the laser (e.g., a clinician or dentist) and includes, for example, an ID, a username, and a password. The ID links to patients in patients 7104 associated with the user, treatments 7102 associated with the user such as treatments performed by the user, and procedures 7107 such as those which are authorized for that user's level of training. For example, users 7101 may include a record of user_ids, usernames, and passwords. The _id record is a key field and is linked to the user_id record in the tables for patients (7104), procedures (7107) and treatments (7102). In one example, username and password fields are used to authenticate user login credentials.

Patients 7104 includes information about patients associated with a user, including, for example, name, phone number, address, and information concerning LANAP® and LAPIP® procedures which may have been performed on the patient. Data recorded by a particular user_id may be listed for archival purposes. Standard patient master record information is included here including names, addresses, case number (file number), etc.

Treatments 7102 includes information about treatments performed with the laser, including, e.g., laser parameters such as a pulse width and energy and information concerning tooth groups or implants which are treated. To that end, treatments 7102 links to an ID of the user in users 7101, the patient in patients 7104, and a procedure name in procedures 7107 associated with the treatment.

More specifically, treatments 7102 (i.e., the treatments table) is a record of therapeutic laser light dosimetry administered to a specific patient at a specific location in the mouth, recorded by date, time and duration of laser light application.

In that regard, the specific location in the mouth may be described by the dental arch quadrant or sextant, tooth location by number, tooth characteristic such as missing, implant or crown at the numbered location. Ad hoc groupings of teeth within a quadrant or sextant can be designated by the user id (clinician) and recorded in the database. The laser light dosimetry is characterized by the pulse width (μsec), energy (joules) and pulse repetition rate (Hz) of the laser energy administered during the duration of the laser light application. These three values are collectively "therapeutic parameters". The joules and number of laser pulses or "shots" accumulated for the duration of the laser light application are recorded. Some combinations of therapeutic parameters are given Procedural Names such as "LANAP Ablation". Other combinations of therapeutic parameters can be named by the clinician to aid his/her memory. Procedural Names or clinician-named therapeutic parameters when selected are also recorded in the database.

Procedures 7107 includes information about the procedures for which treatment is performed, such as ablation, hemostasis and the like. For example, procedures 7107 includes default parameters and procedure names, and also includes authorized procedures for a user (who is identified by a corresponding user ID in users 7101). In that regard, in one embodiment, procedural names for therapeutic parameters stored in procedures 7107 are authorized for each user id. Laser light dosimetry administered to a specific patient and stored in treatments 7102 may also include the user_id of the clinician performing the procedure.

In one example, data elements or fields include the user_id of the clinician authorized to perform the procedure. This is keyed to the training program with advanced procedures being authorized via upgraded passwords as the clinical training and qualifications of the user progress. In that regard, in the procedures table 7107, the procedure authorized field may be a tristate variable, i.e., it assumes one of three values: 0: =procedure not authorized for this user_id, 1: =procedure authorized but may not be overwritten by this user_id, and 2: =procedure authorized and may be overwritten by this user id.

Other data elements of procedures 7107 may include the procedure name, a clinical photograph or motion picture illustrating the clinical procedure techniques and expected clinical outcomes, the therapeutic parameters, the diameter of the optical fiber used for the intended procedure, and the factory settings for the procedure in the event the user_id performs a therapeutic parameter overwrite and would like to recover (restore) the recommended settings.

Laserheads 7103 includes identifying and maintenance information about the laser head, such as an ID, name, and usage information. For example, laserheads 7103 may store the historical record for total time used and total energy output during laser operation. This is used by repair and manufacturing facilities for evaluating mean time between failures and the operational stress exposure of critical components. The serial number of the laser head may also be recorded here, and new laser head serial numbers can be added as the laserheads are replaced during service.

Android metadata 7105 includes metadata associated with tablet 400 such as, for example, locale information identifying where the tablet is being used.

Sqlite_sequence 7106 includes, e.g., information for managing the relational database.

The database can be operated upon by select and update queries. Select queries can be used to extract and format report data using filters deployed on the display subsystem and other devices. Update queries assist with data synchronization and archiving across platforms. Select queries make data filters and include parameters such as the beginning and ending values of a time interval, for a specific or all user_ids. The listing within the time interval can be: (1) chronological, (2) by patient and then chronological or (3) by patient and chronological within treatment site locations. These data can be further filtered to show detailed data, summary data, and a combination of both detailed and summary data.

In one example, two "smart filters" are provided: "Filter Patients" indicates a listing limited to those patient names found within the time interval and user_id selections, where the user may select or deselect patient names to formulate the most useful report, and "Filter Site", which is a smart filter showing those treatment site quadrants or sextants which have been treated during the time interval and user_ids selected. Again, the user may select or deselect treatment sites to formulate the most useful report.

Footswitch

Figure 72:
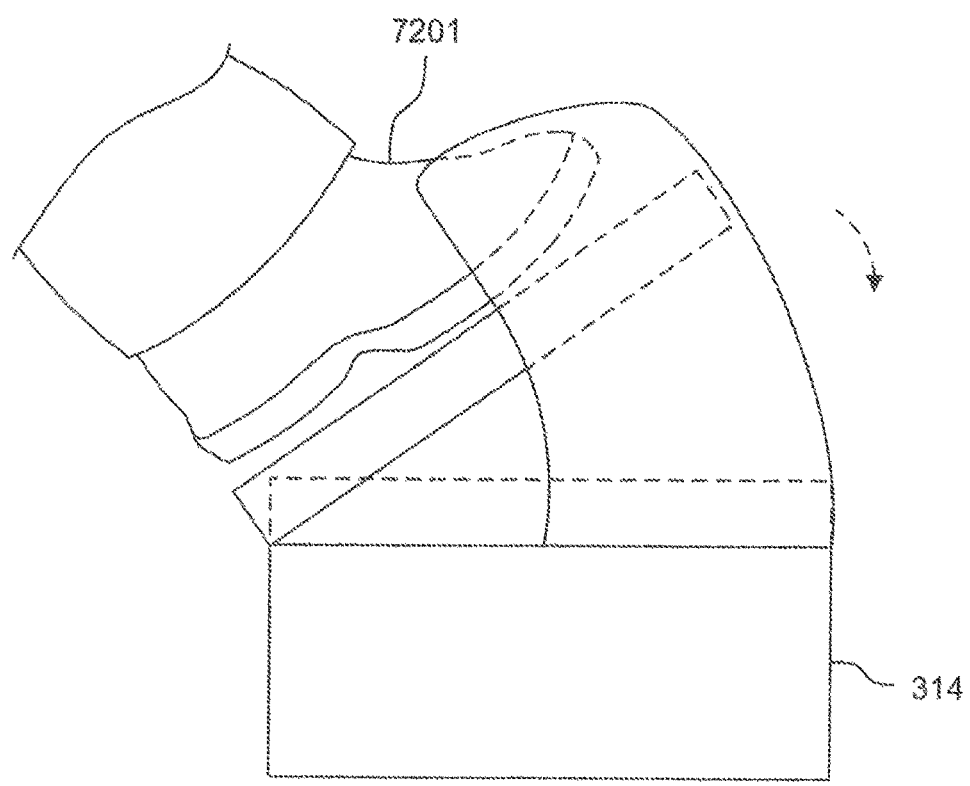
FIG. 72 is a view for explaining a footswitch for operating a laser according to an example embodiment.

FIG. 72 is a view for explaining operation of a footswitch, e.g., footswitch 314. In particular, as shown in FIG. 72, a user operates the laser by pressing down with a foot 7201 on footswitch 314. The physical nature of footswitch 314 may vary. For example, footswitch 314 might also be a raised disc on a circular platform. In addition, footswitch 314 might include a footswitch guard, and might be configured to perform wireless communication with other elements of the system.

Laser Cavity

Figure 73:
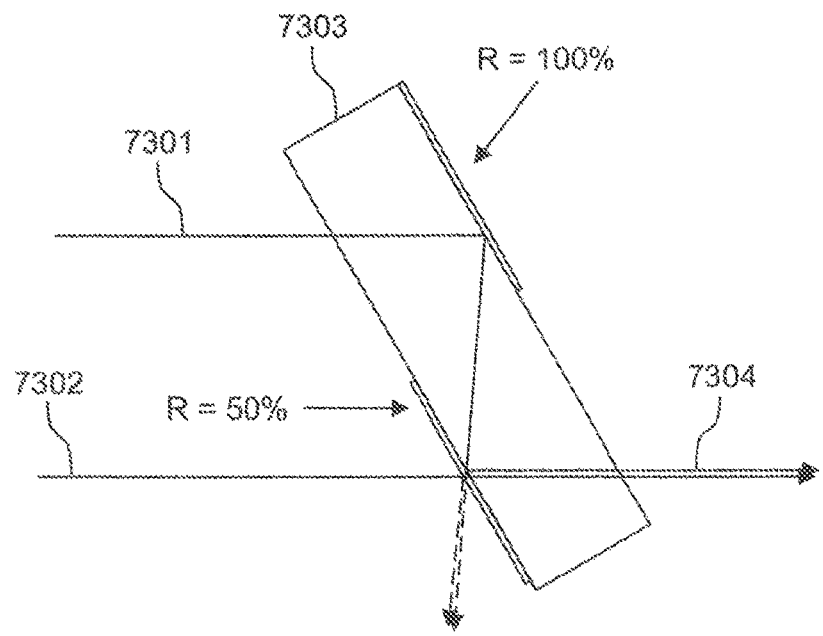
FIG. 73 is a view for explaining delivery of a laser light through a laser cavity.
Figure 74:
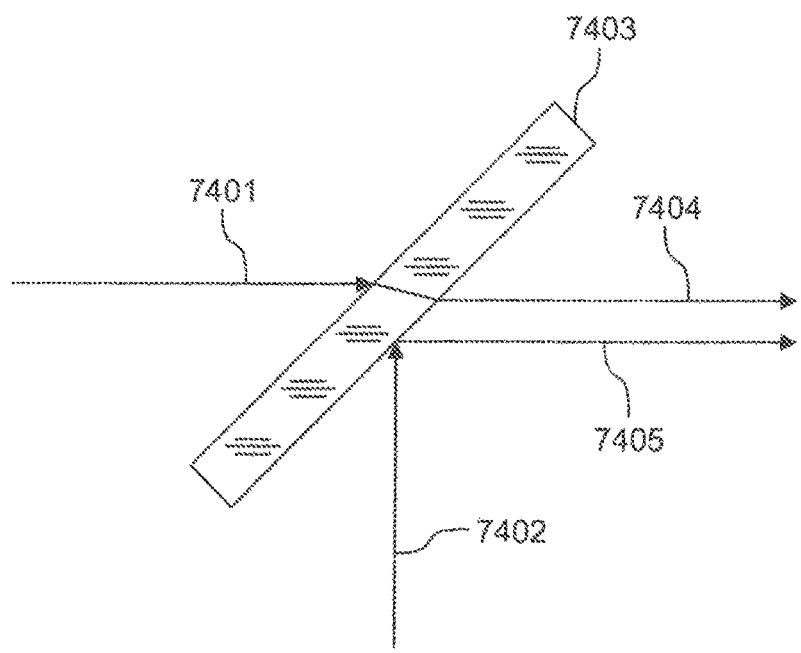
FIG. 74 is another view for explaining delivery of a laser light through a laser cavity.

FIGS. 73 and 74 are views for explaining delivery of laser light through a laser cavity. For example, these structures may be used to deliver both a) pulsed energy from a laser device such as a Nd:YAG laser and b) blue light from a blue light device with wavelength emission in the range of 400 to 520 nm, such as a diode laser, Ti:sapphire laser, argon ion laser, light-emitting diode, superluminescent diode, halogen, plasma-arc curing (PAC), or other light source. In that regard, some handpieces (e.g., a handpiece laser such as laser 103) may have compact and/or different dimensions and arrangements, and therefore additional features are added to guide types of light through the device.

For example, FIG. 73 depicts one example embodiment in which Nd:YAG laser light beam 7301 or blue laser light 7302 are input into a reflector element 7303. Reflector element 7303 uses mirrors or other reflective material to direct either beam into an output beam 7304. A common laser delivery system 103 is used to transmit either wavelength. The reflectance (R) values of reflector element 7303 are designed to allow this beam management to occur.

Meanwhile, FIG. 74 depicts an example embodiment using a beam combiner. In FIG. 74, an invisible infrared Nd:YAG beam 7401 and a visible aiming beam 7402 are input to a reflector. The infrared beam is allowed to pass through as transmitted beam 7404, whereas the aiming beam 7402 is reflected as a reflected beam 7405. The two beams may be delivered simultaneously and coaxially through common delivery system 103. The aiming beam 7402 is used to indicate the location of the emitted invisible infrared beam 7404. The aiming beam 7402 may be activated prior to the activation of the 7401 beam to assist the clinician in locating and predicting the path of the 7401 beam when it is activated to perform the clinical procedures.

OTHER EMBODIMENTS

According to other embodiments contemplated by the present disclosure, example embodiments may include a computer processor such as a single core or multi-core central processing unit (CPU) or micro-processing unit (MPU), which is constructed to realize the functionality described above. The computer processor might be incorporated in a stand-alone apparatus or in a multi-component apparatus or might comprise multiple computer processors which are constructed to work together to realize such functionality. The computer processor or processors execute a computer-executable program (sometimes referred to as computer-executable instructions or computer-executable code) to perform some or all of the above-described functions. The computer-executable program may be pre-stored in the computer processor(s), or the computer processor(s) may be functionally connected for access to a non-transitory computer-readable storage medium on which the computer-executable program or program steps are stored. For these purposes, access to the non-transitory computer-readable storage medium may be a local access such as by access via a local memory bus structure or may be a remote access such as by access via a wired or wireless network or Internet. The computer processor(s) may thereafter be operated to execute the computer-executable program or program steps to perform functions of the above-described embodiments.

According to still further embodiments contemplated by the present disclosure, example embodiments may include methods in which the functionality described above is performed by a computer processor such as a single core or multi-core central processing unit (CPU) or micro-processing unit (MPU). As explained above, the computer processor might be incorporated in a stand-alone apparatus or in a multi-component apparatus or might comprise multiple computer processors which work together to perform such functionality. The computer processor or processors execute a computer-executable program (sometimes referred to as computer-executable instructions or computer-executable code) to perform some or all of the above-described functions. The computer-executable program may be pre-stored in the computer processor(s), or the computer processor(s) may be functionally connected for access to a non-transitory computer-readable storage medium on which the computer-executable program or program steps are stored. Access to the non-transitory computer-readable storage medium may form part of the method of the embodiment. For these purposes, access to the non-transitory computer-readable storage medium may be a local access such as by access via a local memory bus structure or may be a remote access such as by access via a wired or wireless network or Internet. The computer processor(s) is/are thereafter operated to execute the computer-executable program or program steps to perform functions of the above-described embodiments.

The non-transitory computer-readable storage medium on which a computer-executable program or program steps are stored may be any of a wide variety of tangible storage devices which are constructed to retrievably store data, including, for example, any of a flexible disk (floppy disk), a hard disk, an optical disk, a magneto-optical disk, a compact disc (CD), a digital versatile disc (DVD), microdrive, a read-only memory (ROM), random-access memory (RAM), erasable programmable read-only memory (EPROM), electronically erasable programmable read-only memory (EEPROM), dynamic random-access memory (DRAM), video RAM (VRAM), a magnetic tape or card, optical card, nanosystem, molecular memory integrated circuit, redundant array of independent disks (RAID), a non-volatile memory card, a flash memory device, a storage of distributed computing systems and the like. The storage medium may be a function expansion unit removably inserted in and/or remotely accessed by the apparatus or system for use with the computer processor(s).

This disclosure has provided a detailed description with respect to particular representative embodiments. It is understood that the scope of the appended claims is not limited to the above-described embodiments and that various changes and modifications may be made without departing from the scope of the claims.

What is claimed is:

1. A laser assisted new attachment and regeneration procedure using a laser device algorithm comprising:
    connecting a main laser computer to a laser containing a laser delivery system, wherein the main laser computer interfaces with a laser controller;
    presenting for selection on a user interface a limited subset of laser parameters within a group of possible operating ranges for performing a procedure for regenerating periodontal tissues;
    obtaining a set of selected laser parameters;
    providing the laser controller with the selected laser parameters including a pulse duration, a pulse energy, and a pulse repetition rate;
    activating the laser in a first pass to remove a diseased interior epithelial lining to a full depth of a periodontal pocket and to remove at least one bony defect around a tooth root;
    removing granulomatous tissue to prepare a new pocket tissue surface;
    debriding of the tooth root's root surface and the at least one bony defect of foreign matter to the full depth of the periodontal pocket on each side of the tooth root;
    irrigating the periodontal pocket with a bactericidal solution;
    activating the laser in a second pass on a tooth pocket interior to the full depth of the periodontal pocket to stimulate and upregulate fibroblasts and stem cells, and to establish thermogenic hemostasis which forms a stable fibrin clot within each wall of the at least one bony defect and up to a gingival crest;
    stabilizing the full depth of the periodontal pocket and the tooth root complex by eliminating occlusal interferences;
    approximating the periodontal pocket tissue with the tooth surface to create a thin film thickness of a blood clot to form the stable fibrin clot; and
    maintaining the periodontal pocket tissue surface in contact with the tooth surface to advance tissue adhesion and periodontal regeneration.

2. The procedure of claim 1 further comprising:
    adjusting an electrical current to match a measured laser energy to a selected laser energy, wherein adjusting the electrical current occurs as the laser is fired.

3. The procedure of claim 2, wherein a calibration factor is set during a calibration process, wherein the calibration factor is used in establishing a relationship between the measured laser energy and the selected laser energy.

4. The procedure of claim 1 further comprising:
    preventing frequent laser lamp starts by delaying laser lamp deactivation.

5. The procedure of claim 1, wherein the laser in the first pass uses the pulse repetition rate between 10 and 100 Hz.

6. The procedure of claim 1, further comprising:
    displaying on the user interface a plurality of settings for each operator-controlled laser parameter, wherein the plurality of settings is provided by the laser controller.

7. The procedure of claim 6, wherein at least one of lasing steps is preceded by the controller locking a set of the plurality of settings, wherein the remaining plurality of settings provided by the laser controller form an unlocked plurality of settings that is available for selection.

8. The procedure of claim 7, wherein the unlocked plurality of settings available for selection provides a safe and a therapeutic laser treatment for at least one of the lasing steps.

* * * * *